(12) United States Patent
Berkland et al.

(10) Patent No.: US 8,906,392 B2
(45) Date of Patent: *Dec. 9, 2014

(54) NANOCLUSTER COMPOSITIONS AND METHODS

(75) Inventors: Cory J. Berkland, Lawrence, KS (US);
Lianjun Shi, Bridgewater, NJ (US);
Nashwa El Gendy, Cairo (EG); Carl Plumley, Little Rock, AR (US); Mark Bailey, Mountain View, CA (US)

(73) Assignee: University of Kansas, Lawrence, KS (US)

( * ) Notice: Subject to any disclaimer, the term of this patent is extended or adjusted under 35 U.S.C. 154(b) by 48 days.

This patent is subject to a terminal disclaimer.

(21) Appl. No.: 12/954,509

(22) Filed: Nov. 24, 2010

(65) Prior Publication Data

US 2011/0223203 A1 Sep. 15, 2011

Related U.S. Application Data

(60) Continuation-in-part of application No. PCT/US2009/050565, filed on Jul. 14, 2009, and a continuation-in-part of application No. 12/261,907, filed on Oct. 30, 2008, now abandoned, and a continuation-in-part of application No. 12/261,873, filed on Oct. 30, 2008, now abandoned, which is a division of application No. 11/610,986, filed on Dec. 14, 2006, now Pat. No. 7,651,770.

(60) Provisional application No. 60/751,172, filed on Dec. 16, 2005, provisional application No. 61/081,034, filed on Jul. 15, 2008, provisional application No. 61/081,037, filed on Jul. 16, 2008.

(51) Int. Cl.
| | | |
|---|---|---|
| *A61K 9/00* | (2006.01) | |
| *A61K 9/16* | (2006.01) | |
| *B82Y 30/00* | (2011.01) | |
| *A61K 9/51* | (2006.01) | |
| *A61K 9/14* | (2006.01) | |

(52) U.S. Cl.
CPC ............ *A61K 9/1688* (2013.01); *A61K 9/1647* (2013.01); *A61K 9/5123* (2013.01); *B82Y 30/00* (2013.01); *A61K 9/14* (2013.01); *A61K 9/145* (2013.01); *A61K 9/5192* (2013.01); *A61K 9/1617* (2013.01); *A61K 9/5153* (2013.01); *A61K 9/5115* (2013.01); *A61K 9/0075* (2013.01); *A61K 9/1611* (2013.01)

USPC .............. 424/400; 514/44; 514/174; 514/3.1; 514/563; 514/172; 514/653; 514/304; 514/300; 424/1.81; 424/184.1

(58) Field of Classification Search
CPC ....... A61K 9/14; A61K 9/145; A61K 9/1611; B82Y 30/00
See application file for complete search history.

(56) References Cited

U.S. PATENT DOCUMENTS

| | | | |
|---|---|---|---|
| 5,362,729 | A | 11/1994 | Cozzi et al. |
| 6,441,025 | B2 | 8/2002 | Li et al. |
| 2005/0019270 | A1 * | 1/2005 | Finlay et al. ..................... 424/46 |
| 2005/0143361 | A1 * | 6/2005 | Happonen et al. ............ 514/171 |
| 2007/0172653 | A1 | 7/2007 | Berkland et al. |

OTHER PUBLICATIONS

Lenfers, et al., Substantial Activity of Budesonide in Patents with Irinotecan (CPT-11) and 5-Fluorouracil Induced Diarrhea and Failure of Loperamide Treatment; Annals of Oncology, 1999, vol. 10: 1251-1253, summary; p. 1251, col. 2, para 3-4; p. 1253, col. 1, para 3-4.

Alabaster, et al., Metabolic Modification by Insulin Enhances Methotrexate Cytotoxicity in MCF-7 Human Breast Cancer Cells; Eur J Cancer Clin Oncol, 1981, vol. 17, No. 1, pp. 1223-1228, abstract; fig 1, p. 1223, col. 2, para 3; p. 1225, col. 2, para 4; p. 1228, col. 2, para 2.

Thews, et al., Nifedipine Improves Blood Flow and Oxygen Supply, but not Steady-State Oxygenation of Tumours in Perfusion Pressure Controlled Isolated Limb Perfusion; British Journal of Cancer, 2002, vol. 97, pp. 1462-1469; abstract; p. 1463, col. 1, para 2-3; p. 1463, col. 2, para 2.

Lieberman, et al., Pharmaceutical Dosage Forms—Disperse Systems; Informa Health Care, 1996, vol. 2, Ed 2, Fig 3, Table 4; p. 18, para 7; p. 19, para 1-2; p. 29, para 3; p. 166, para 1-3; p. 288, para 3.

International Search Report for PCT/US2009/050565 dated Sep. 8, 2009.

International Preliminary Report on Patentability for PCT/US2009/050565 dated Jan. 18, 2011.

* cited by examiner

*Primary Examiner* — Suzanne Ziska
(74) *Attorney, Agent, or Firm* — Reed Smith LLP; Robert R. Riddle

(57) ABSTRACT

Compositions, methods of making, and methods of using nanoclusters in which the nanoclusters comprise a plurality of nanoparticles having a core of nanoparticles arranged such that the surfaces of the nanoparticles contact adjacent nanoparticles, the nanoparticles comprise an active ingredient, and the nanocluster has a mass median aerodynamic diameter of from about 0.25 μm to about 20 μm.

9 Claims, 69 Drawing Sheets

FIG. 10
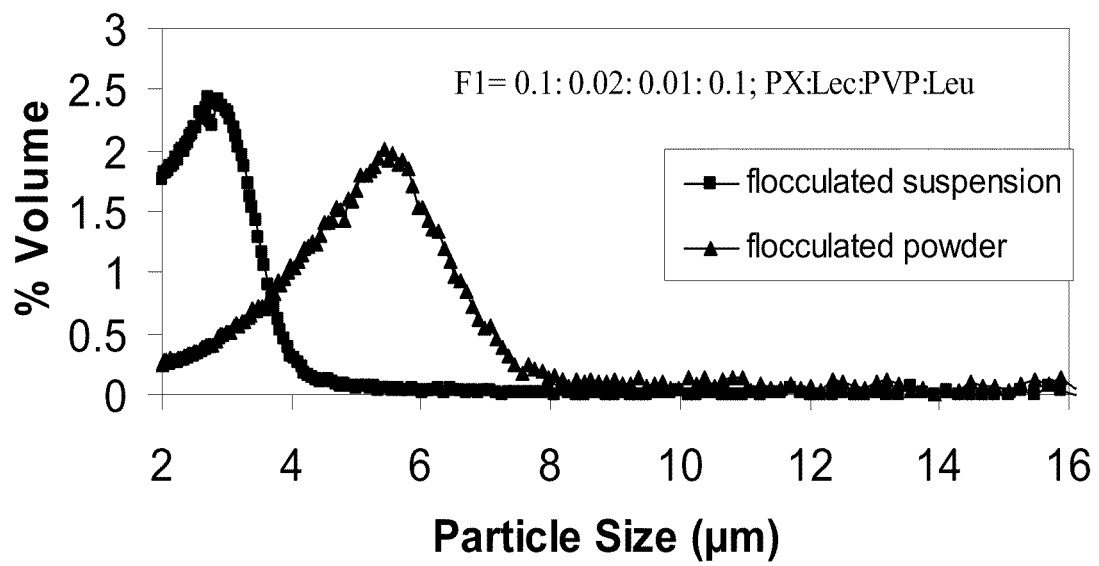
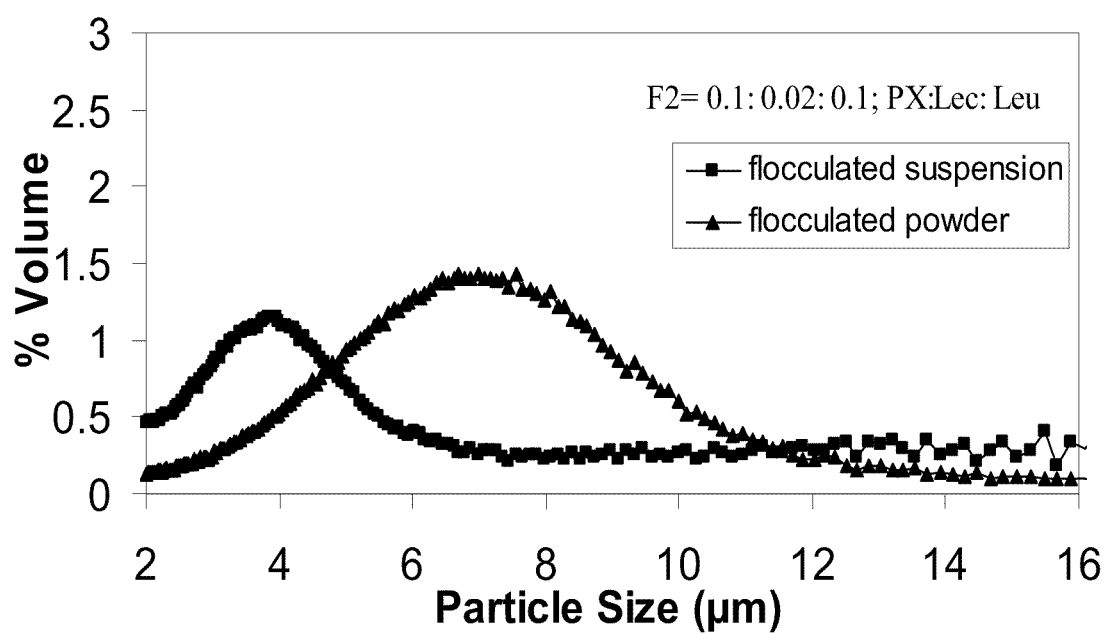

FIG. 11

FIG. 12

F1 = 0.1: 0.02:0.01: 0.1;PX: Lec: PVP: Leu
F2 = 0.1: 0.02: 0.1; PX: Lec:Leu
PX: Paclitaxel powder as received

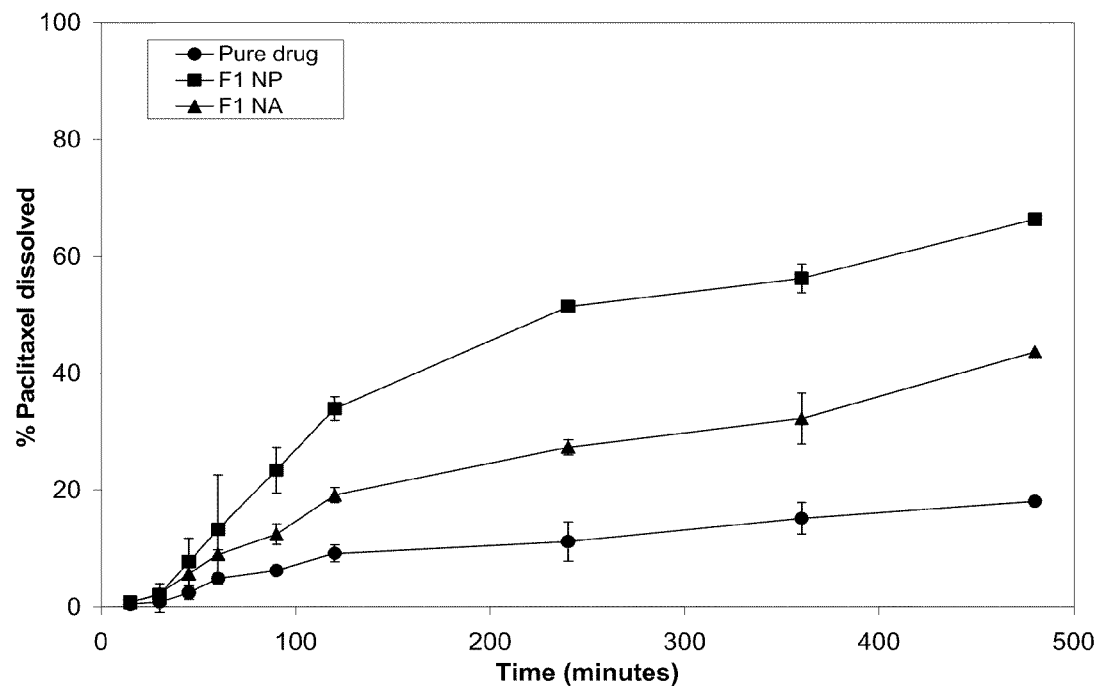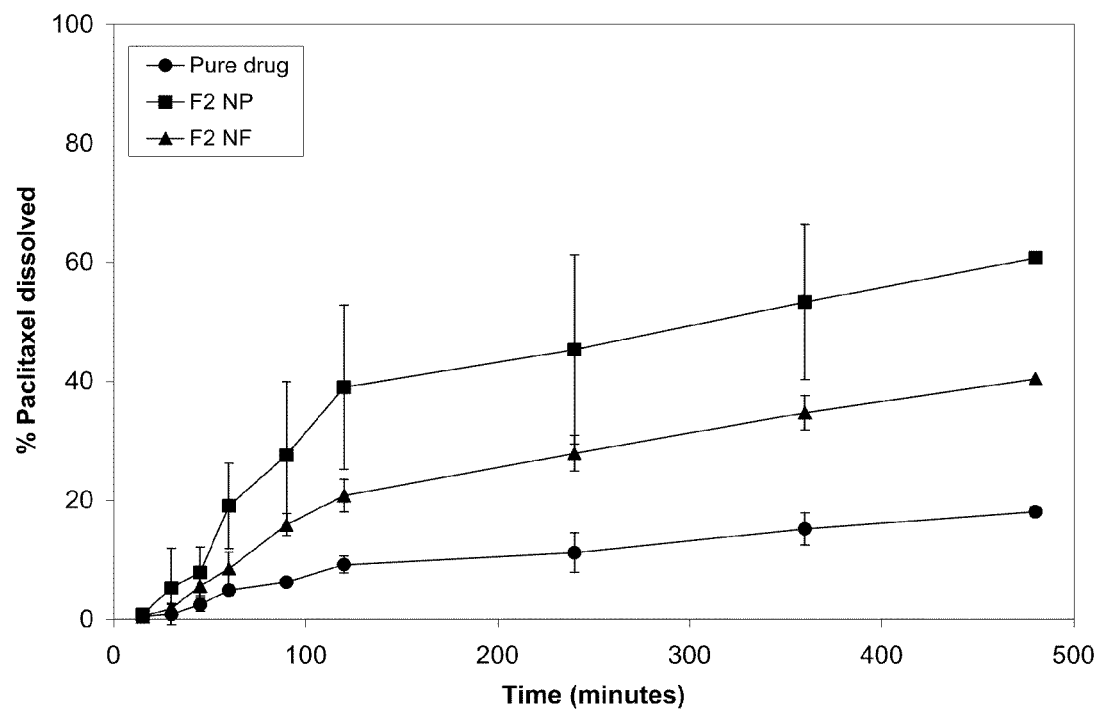
FIG. 13

FIG. 14

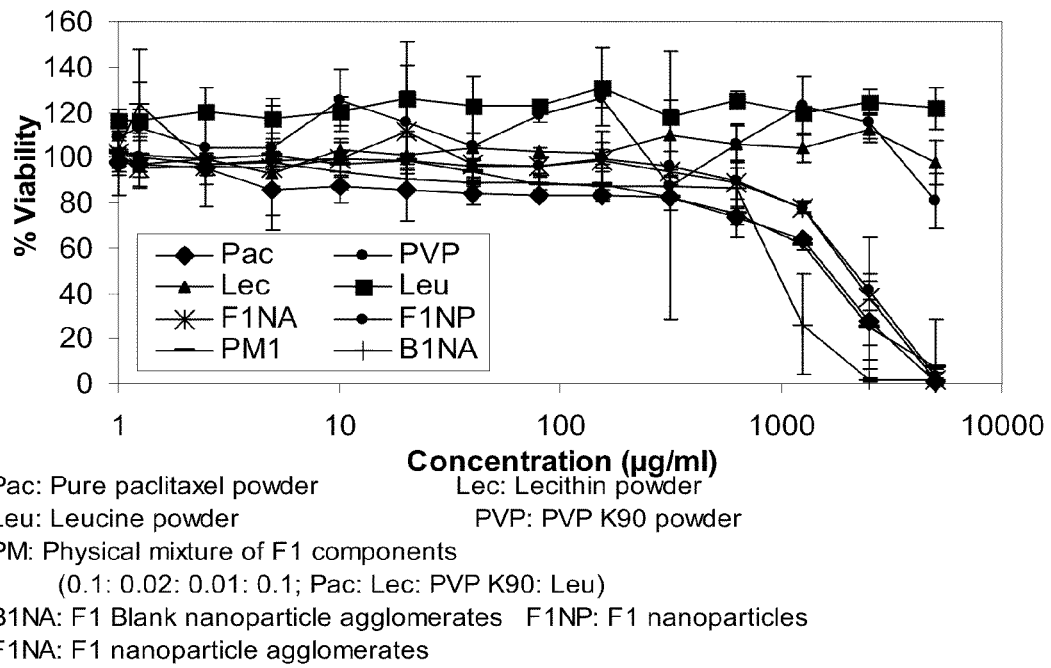

Pac: Pure paclitaxel powder   Lec: Lecithin powder
Leu: Leucine powder   PVP: PVP K90 powder
PM: Physical mixture of F1 components
  (0.1: 0.02: 0.01: 0.1; Pac: Lec: PVP K90: Leu)
B1NA: F1 Blank nanoparticle agglomerates   F1NP: F1 nanoparticles
F1NA: F1 nanoparticle agglomerates

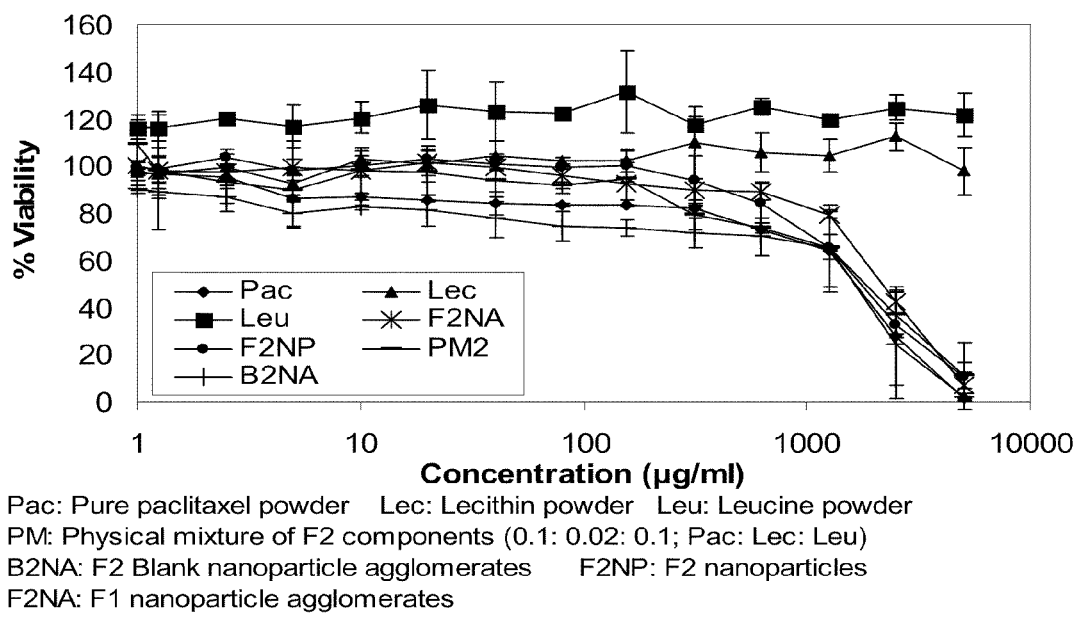

Pac: Pure paclitaxel powder   Lec: Lecithin powder   Leu: Leucine powder
PM: Physical mixture of F2 components (0.1: 0.02: 0.1; Pac: Lec: Leu)
B2NA: F2 Blank nanoparticle agglomerates   F2NP: F2 nanoparticles
F2NA: F1 nanoparticle agglomerates FIG. 15
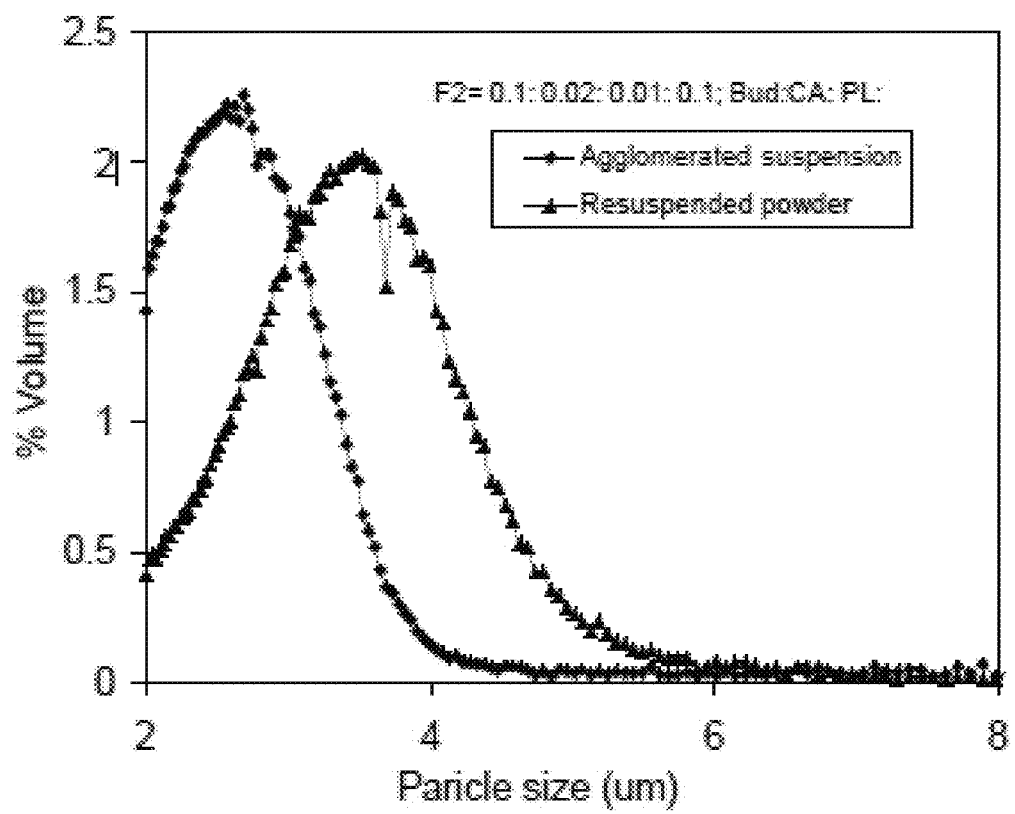
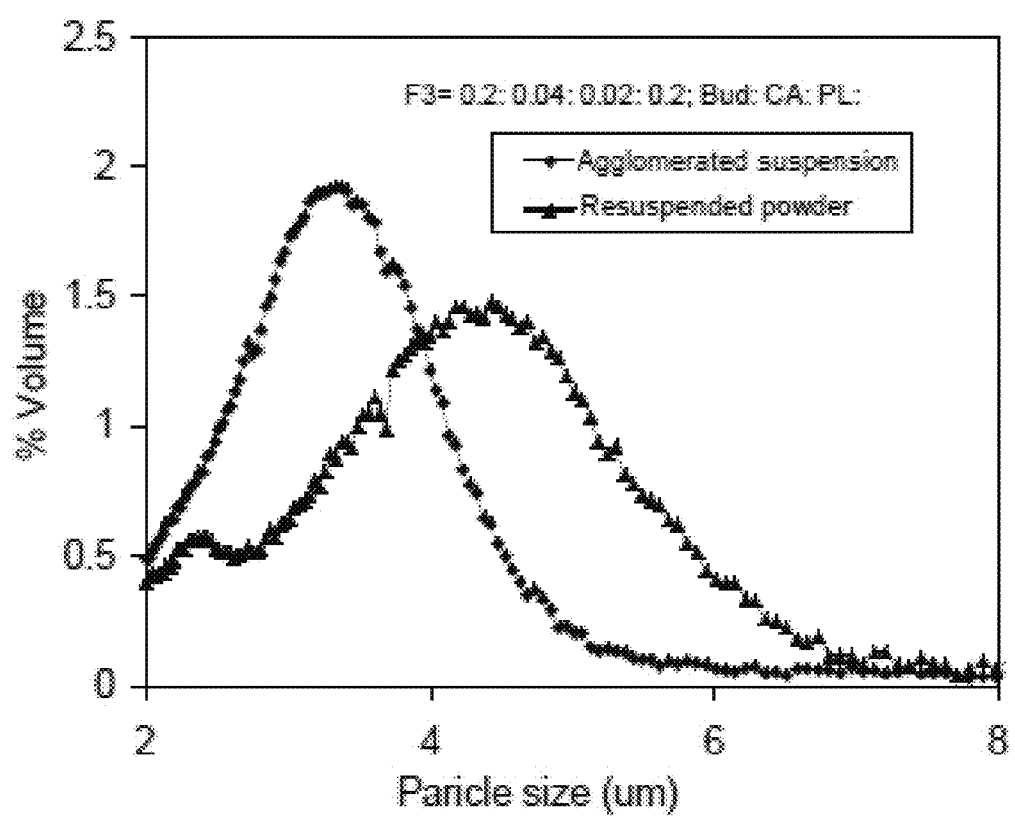

FIG. 16
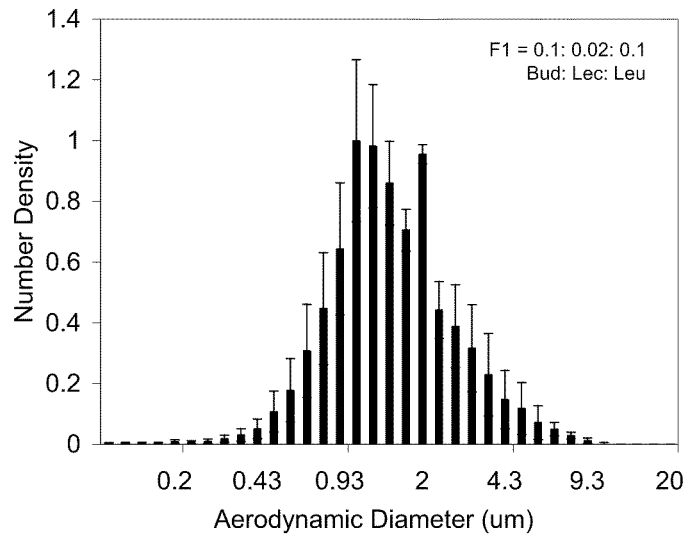
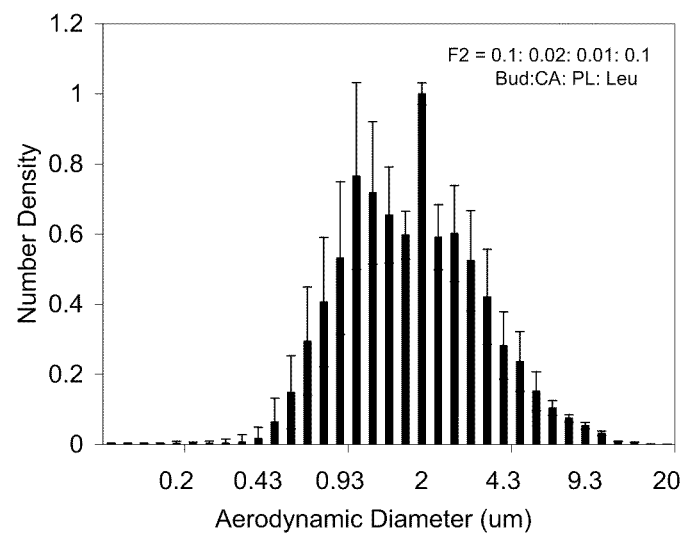
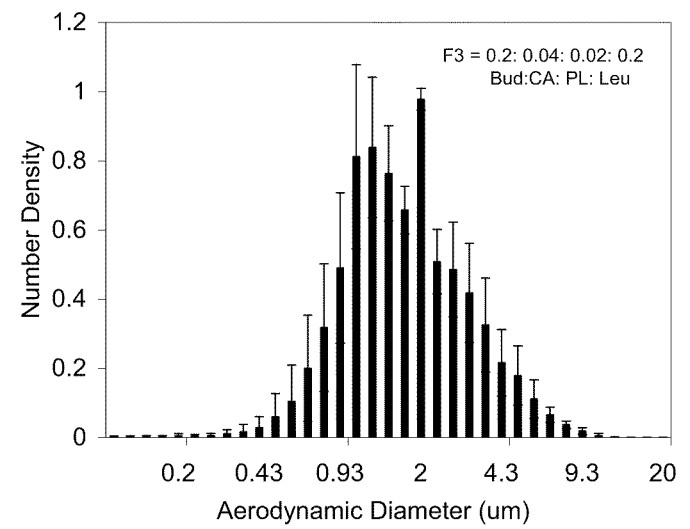

FIG. 17
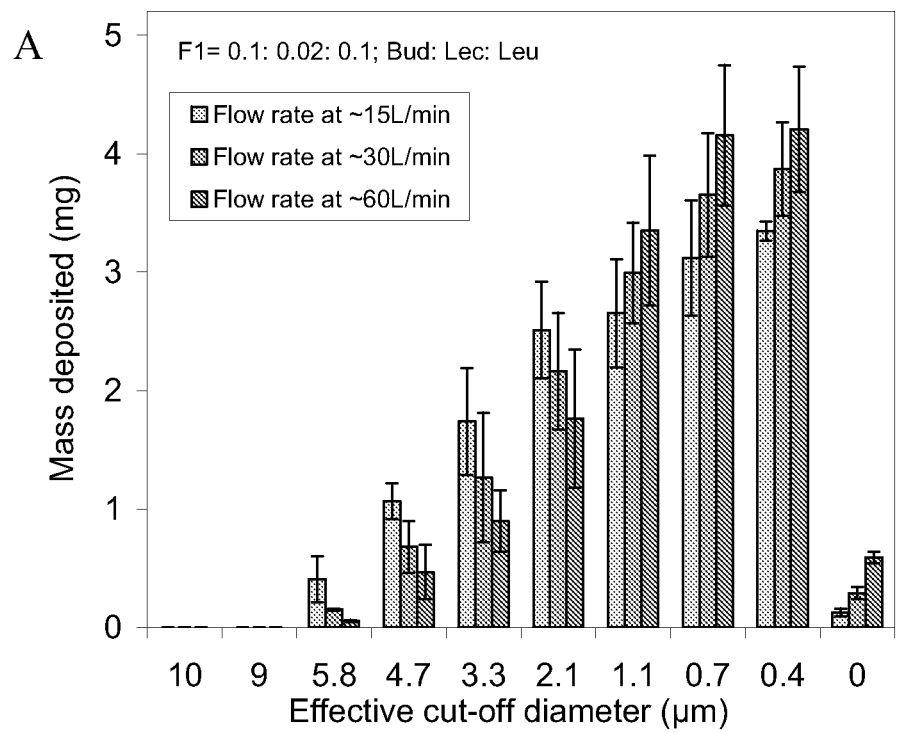
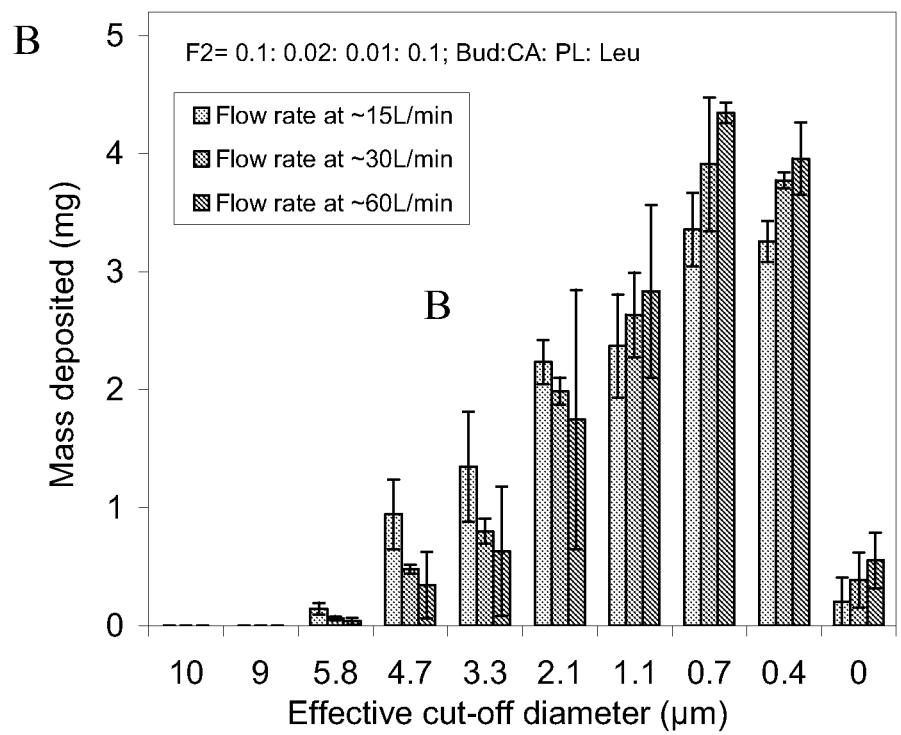

FIG. 17 (cont.)

Figure 22:
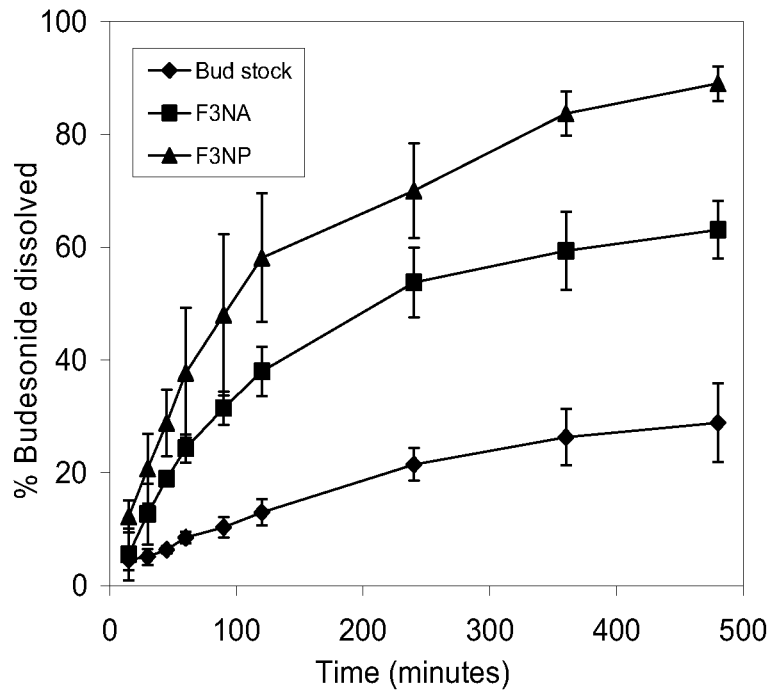

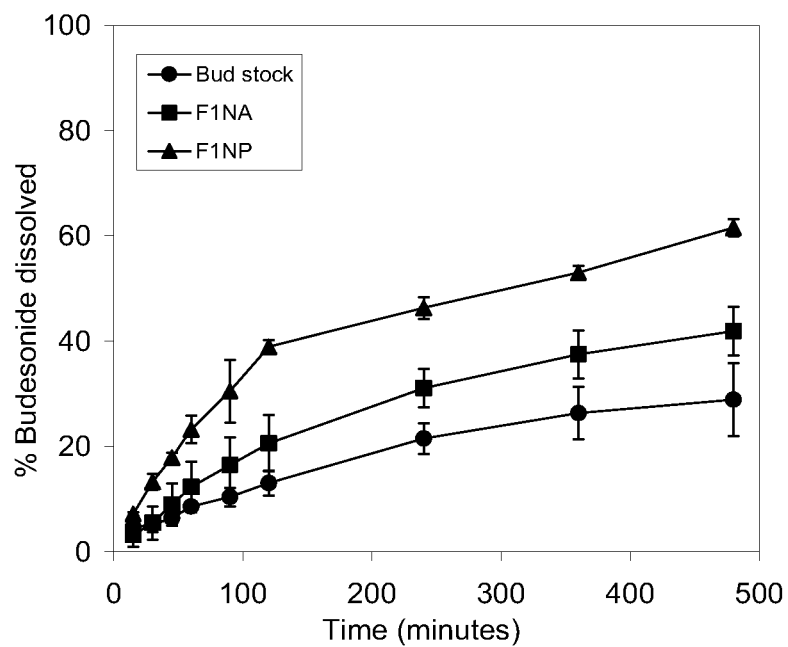
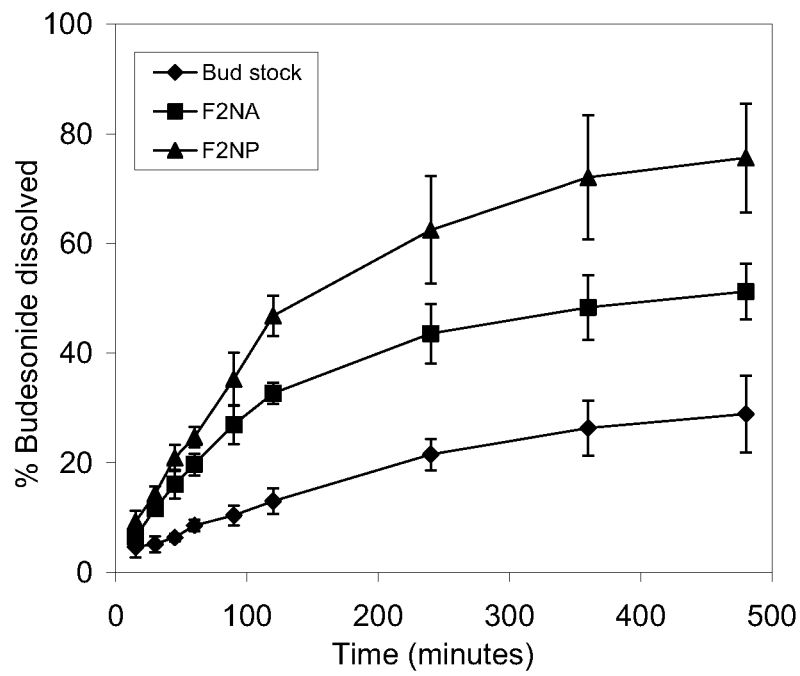
FIG. 22

FIG. 35
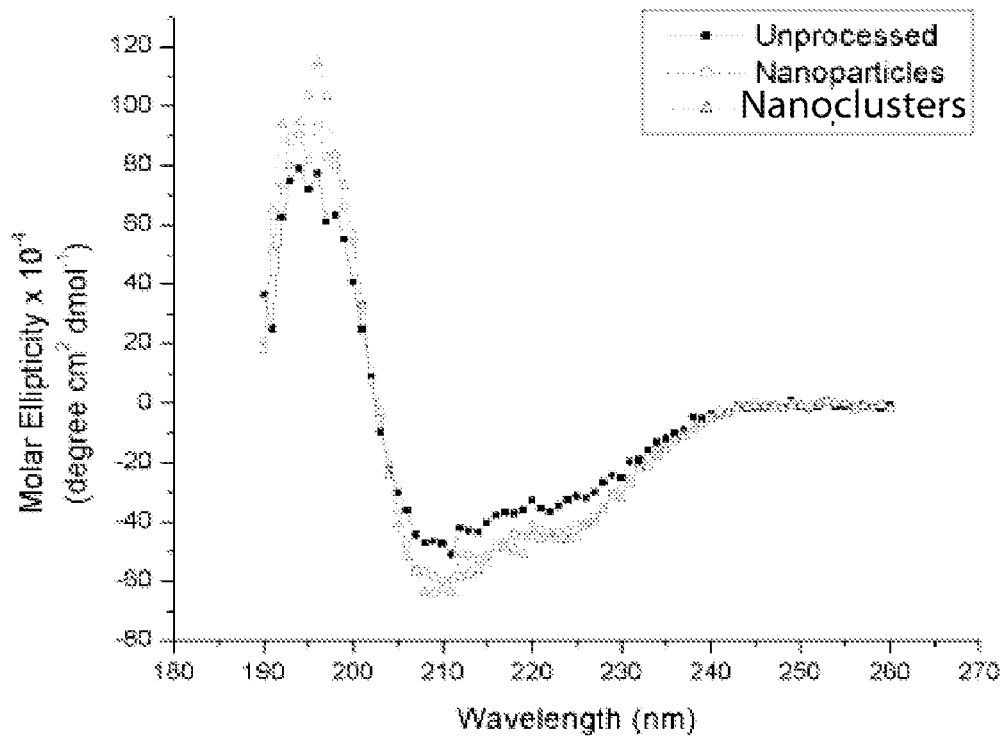
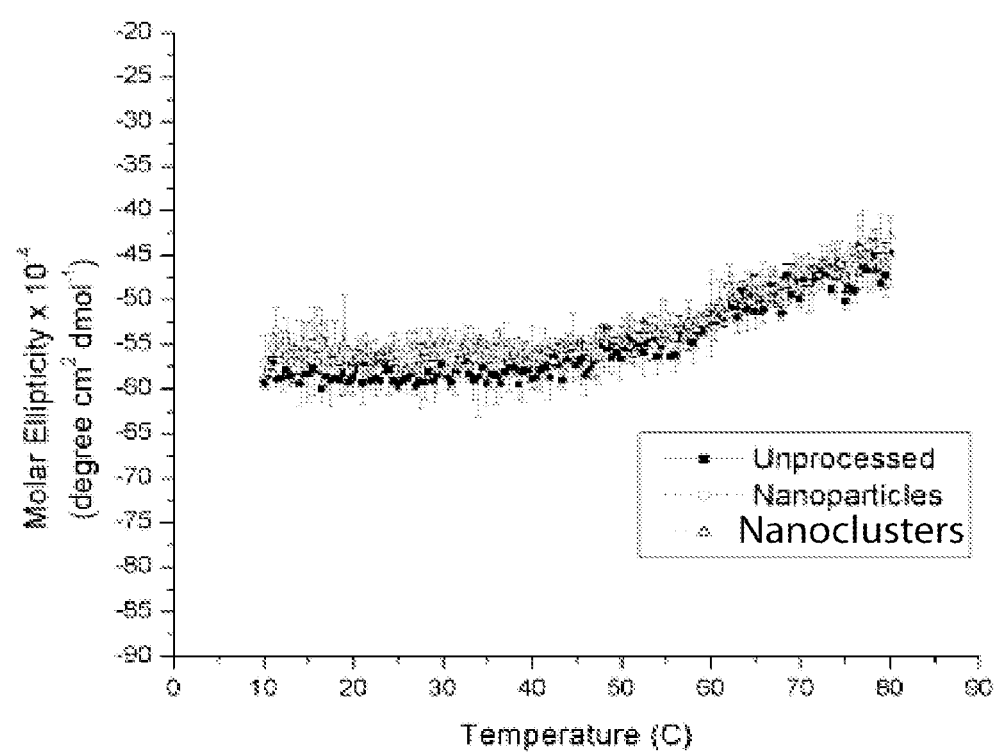

FIG. 39
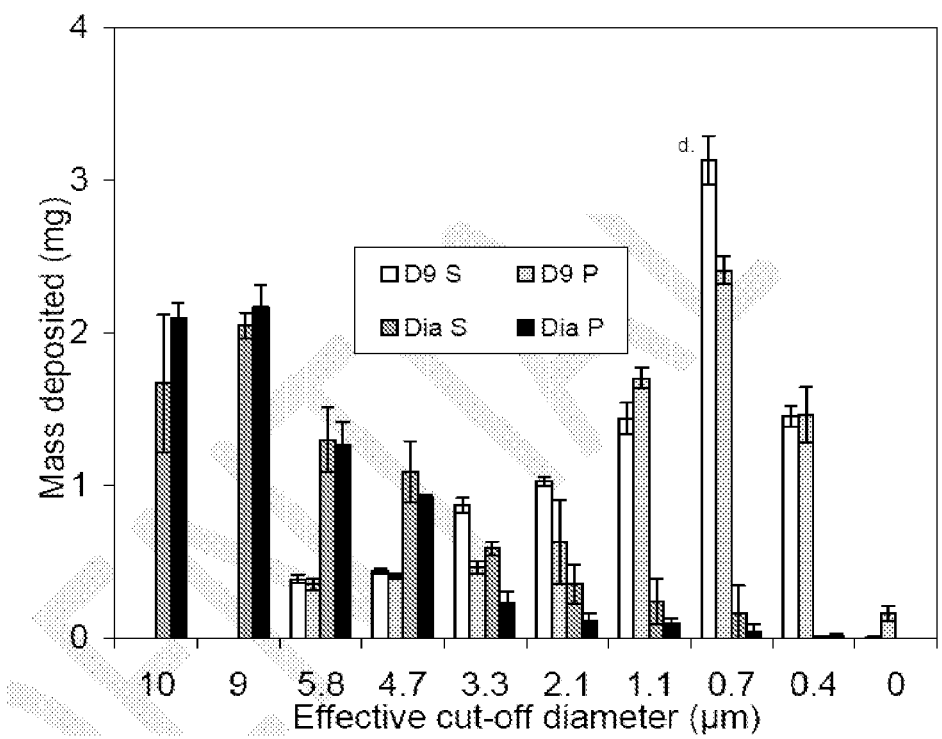
FIG. 40
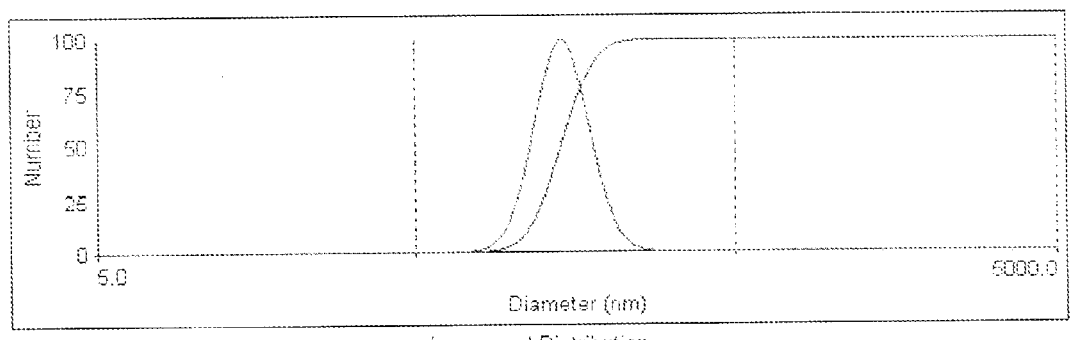
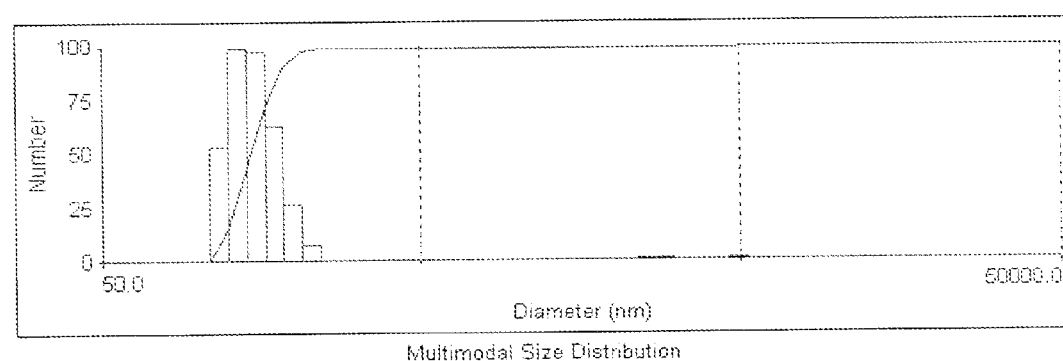

FIG. 46
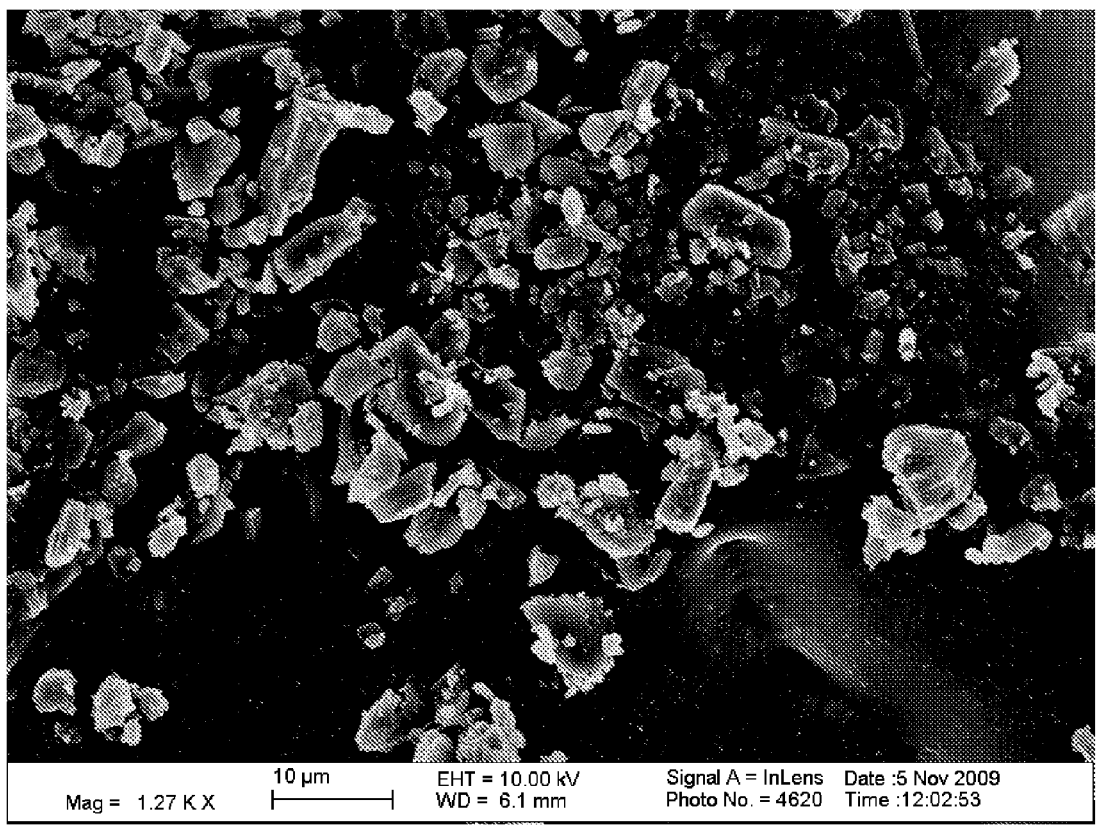
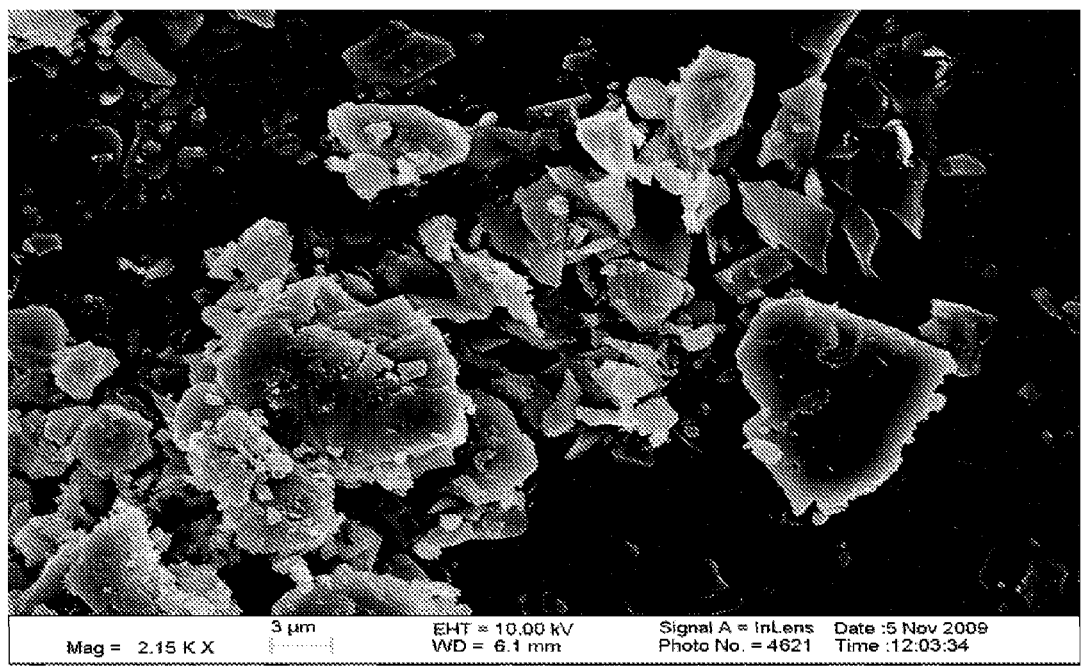

FIG. 57
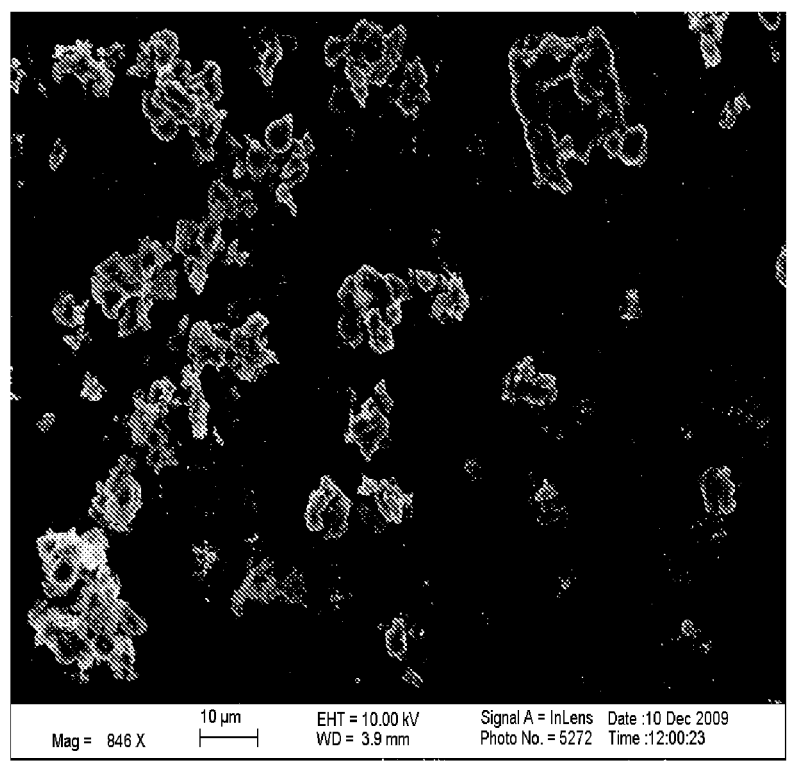
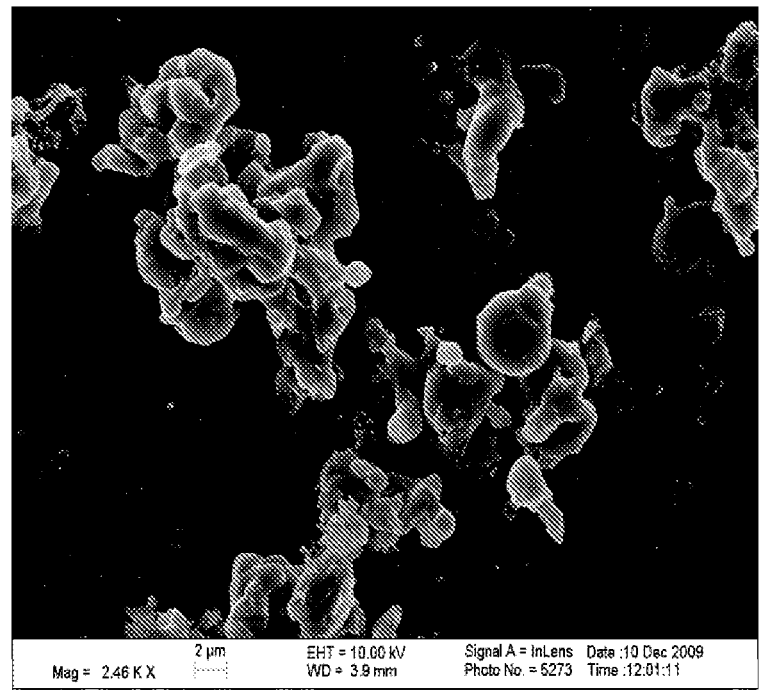

FIG. 58
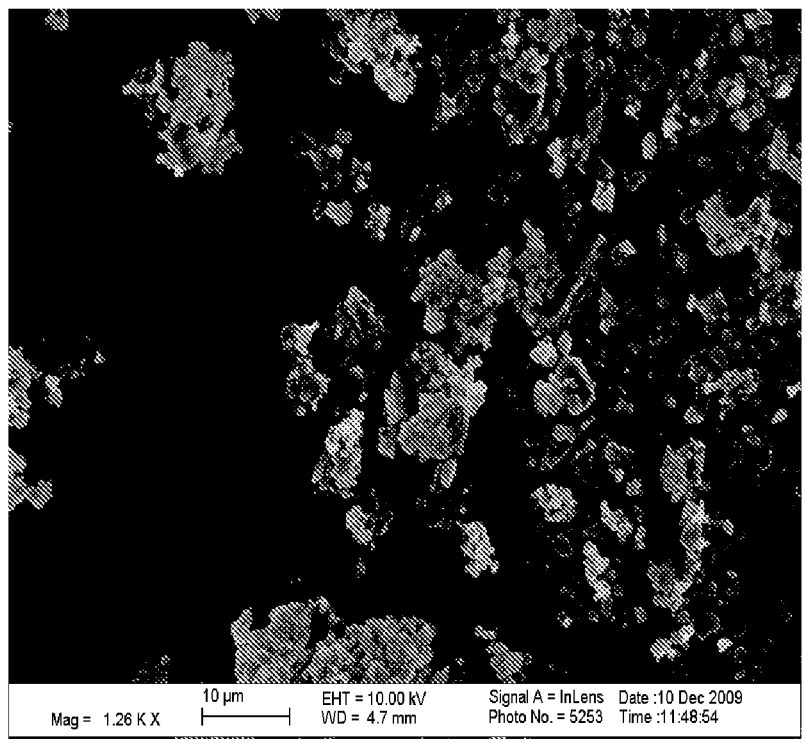
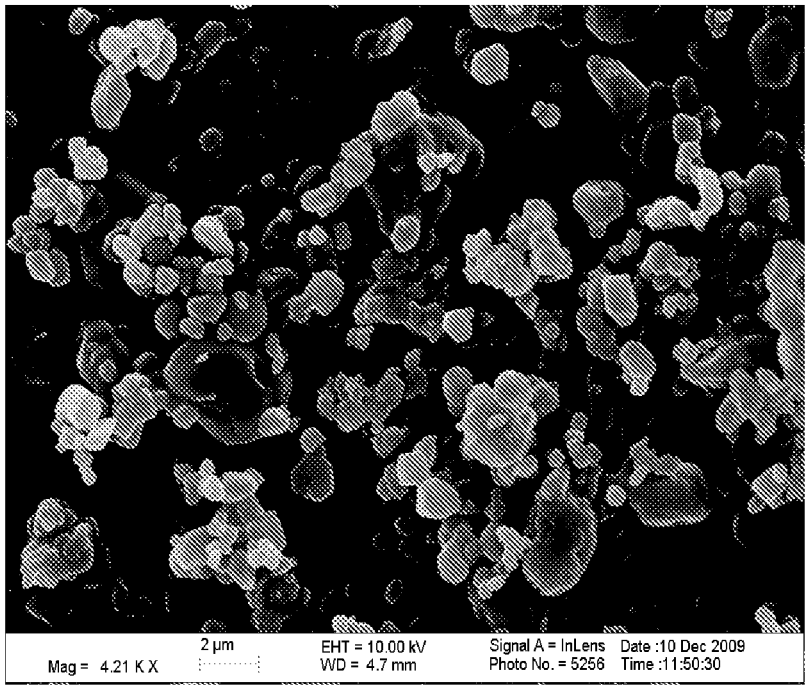

FIG. 59
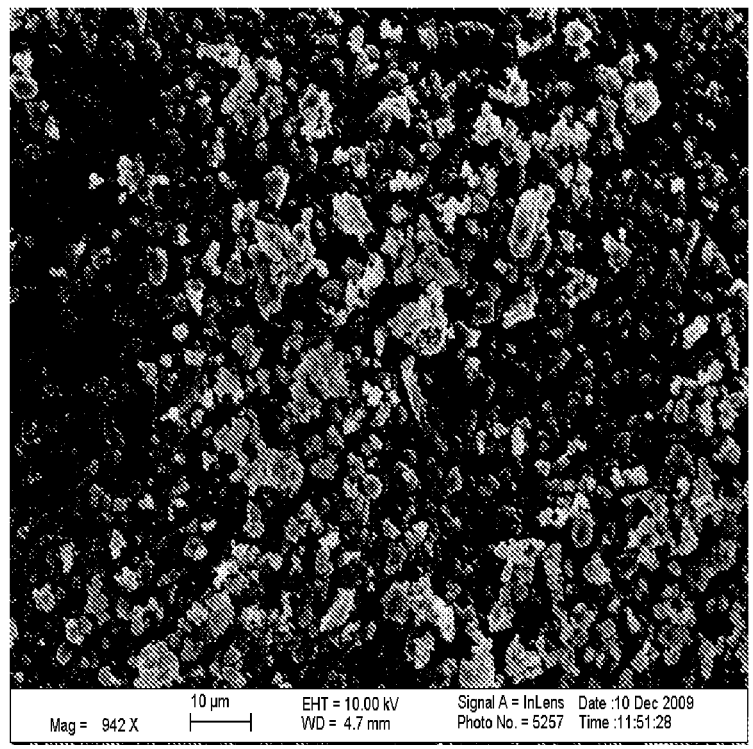
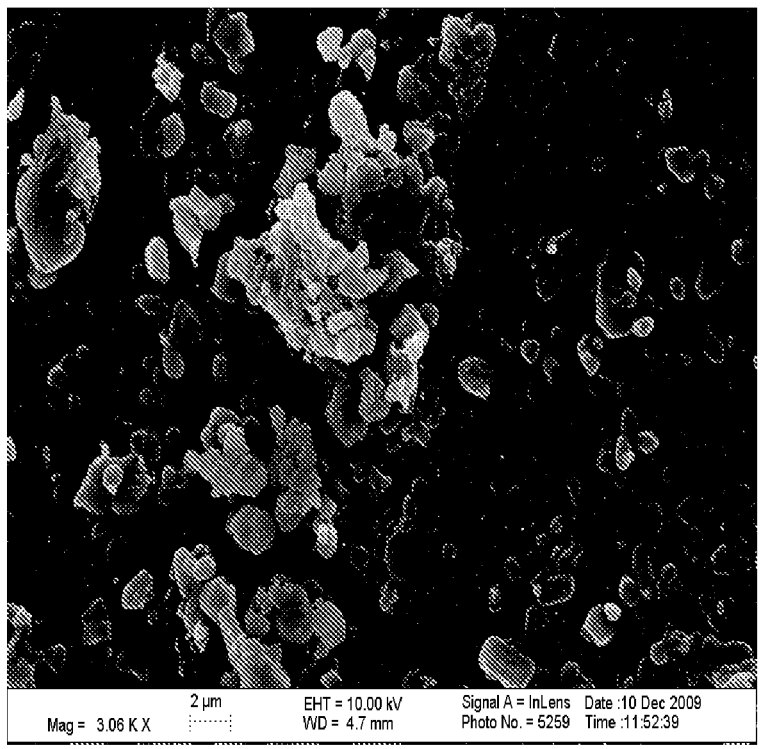

FIG. 61
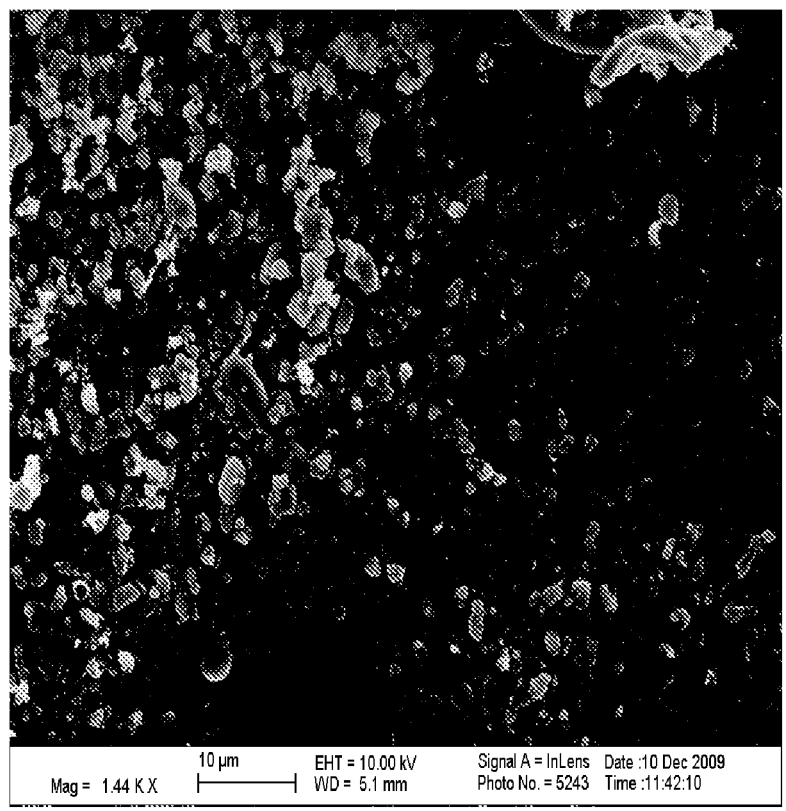
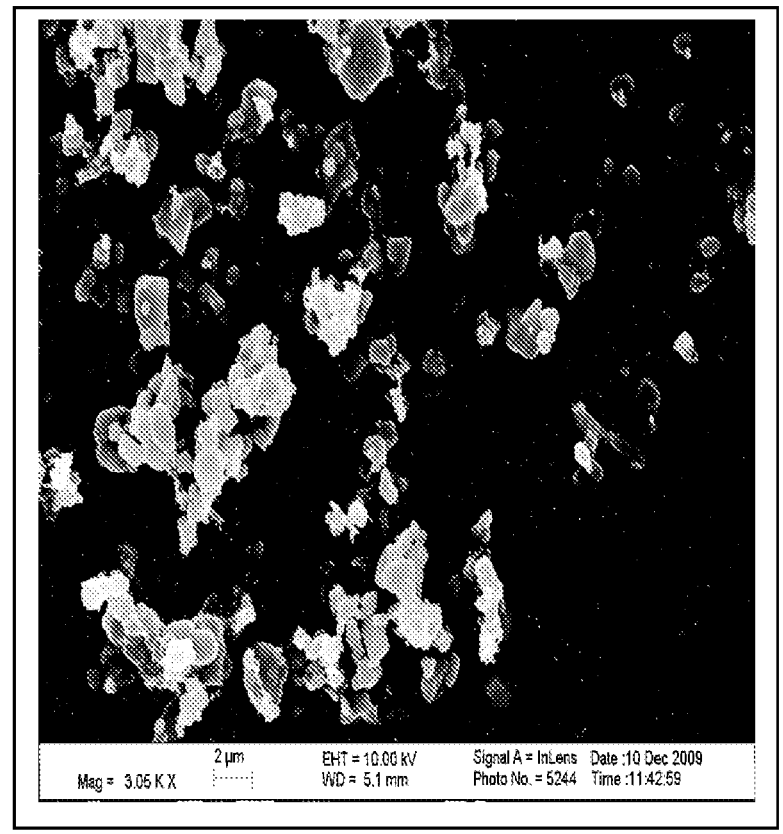

FIG. 62
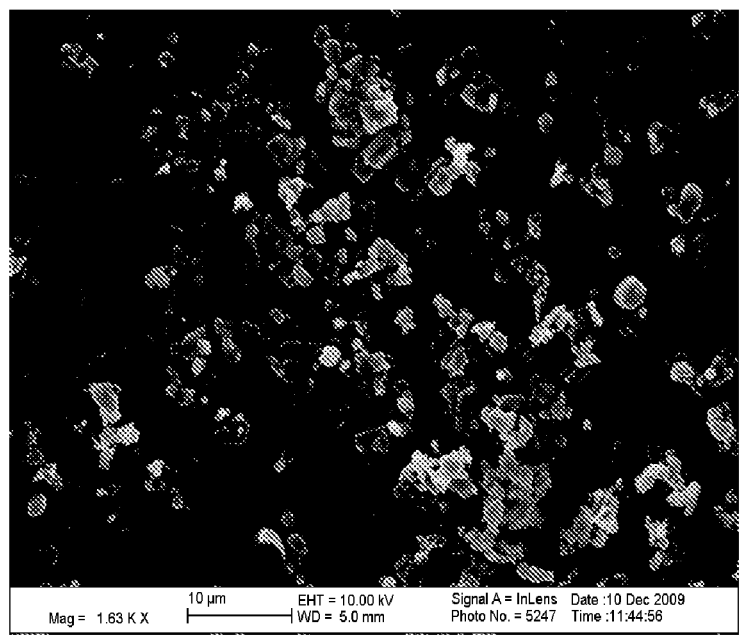
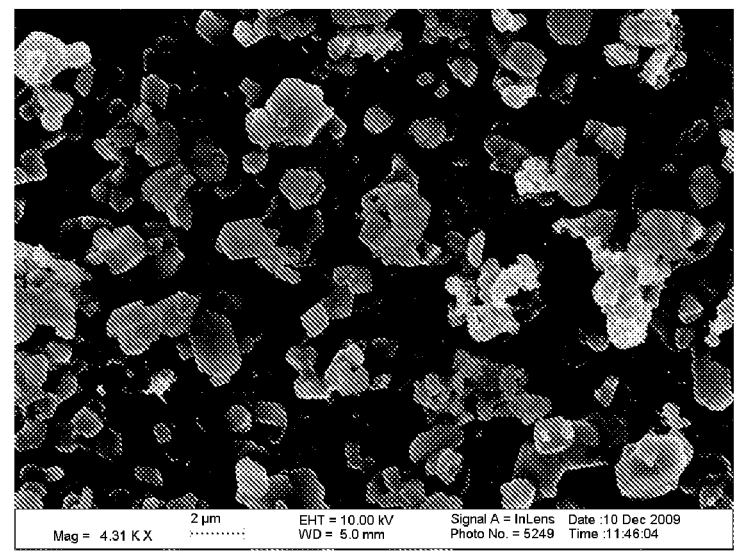

FIG. 63
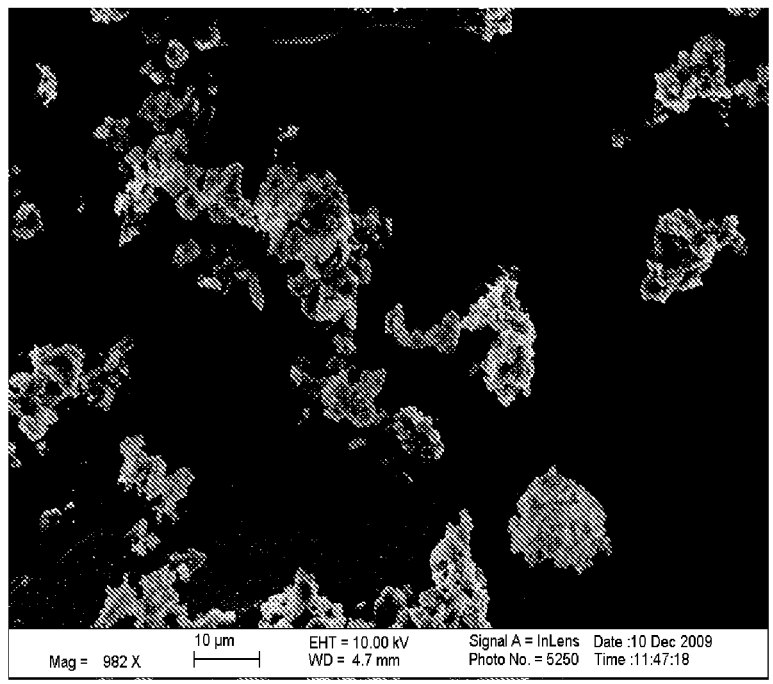
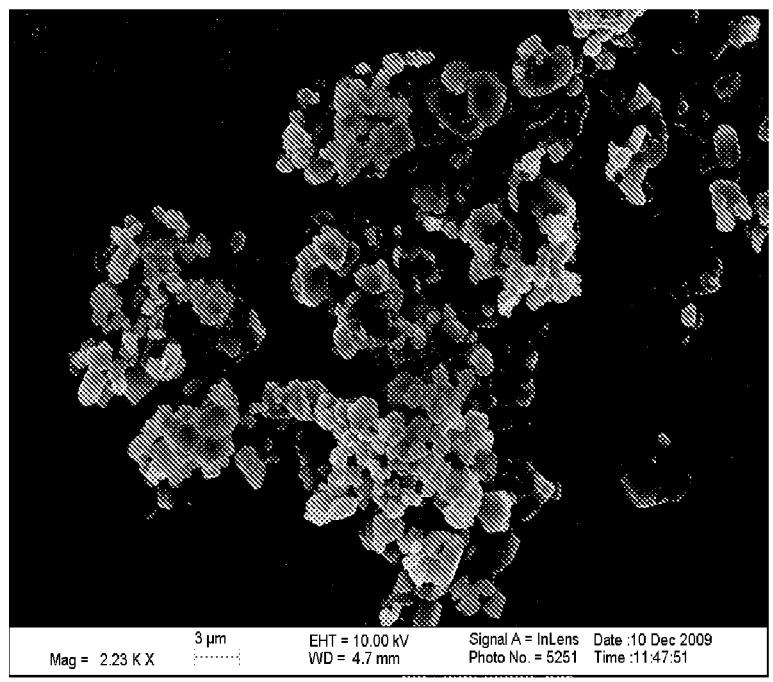

FIG. 66
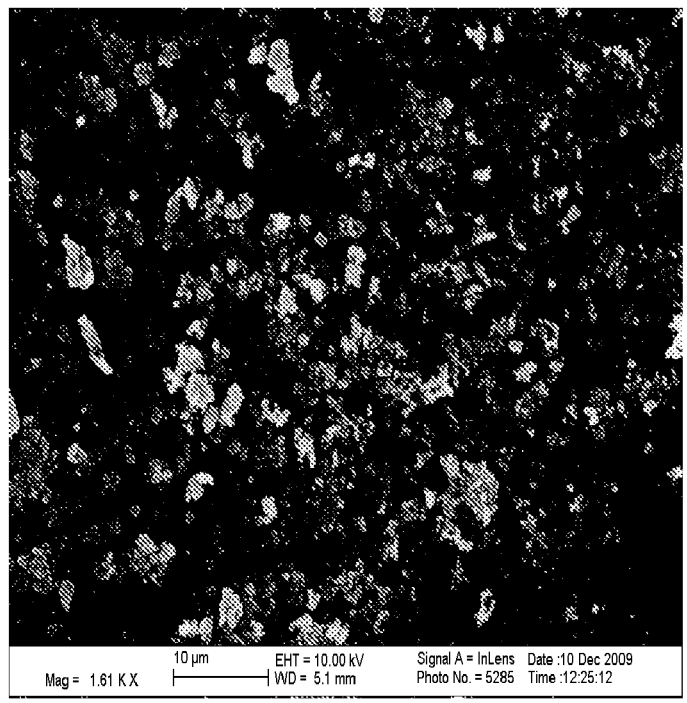
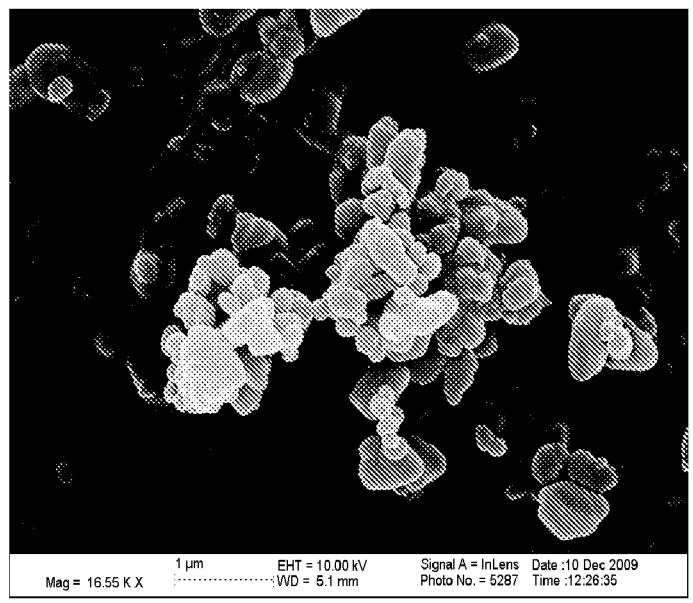

FIG. 79
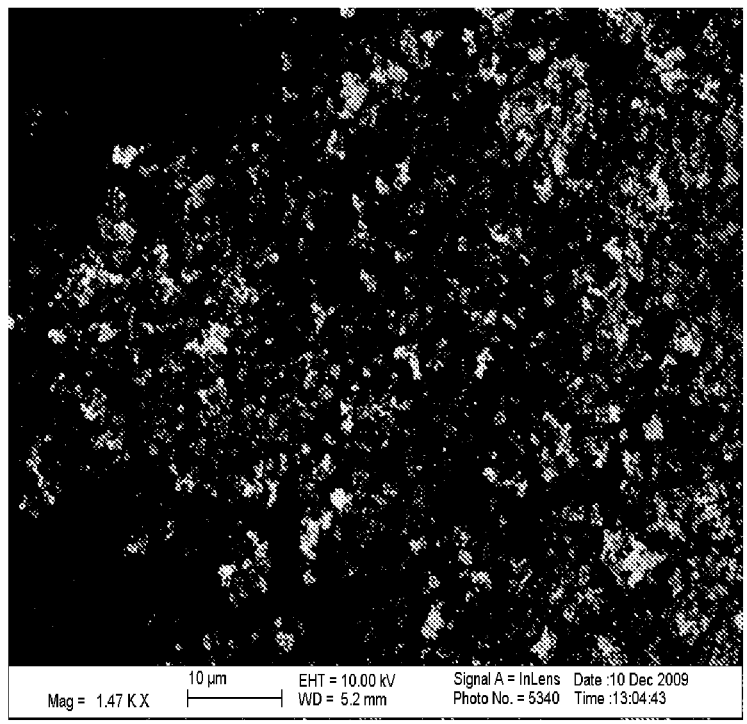
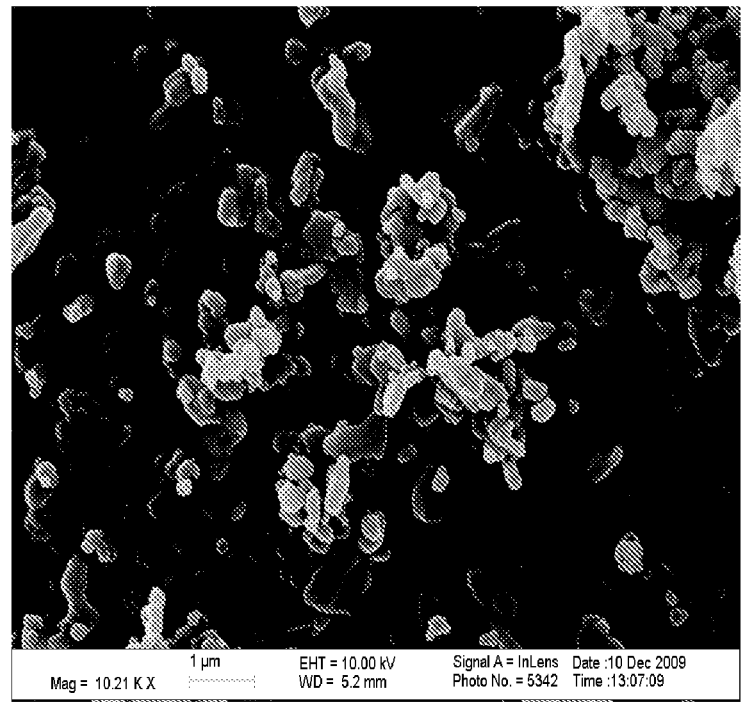

FIG. 81
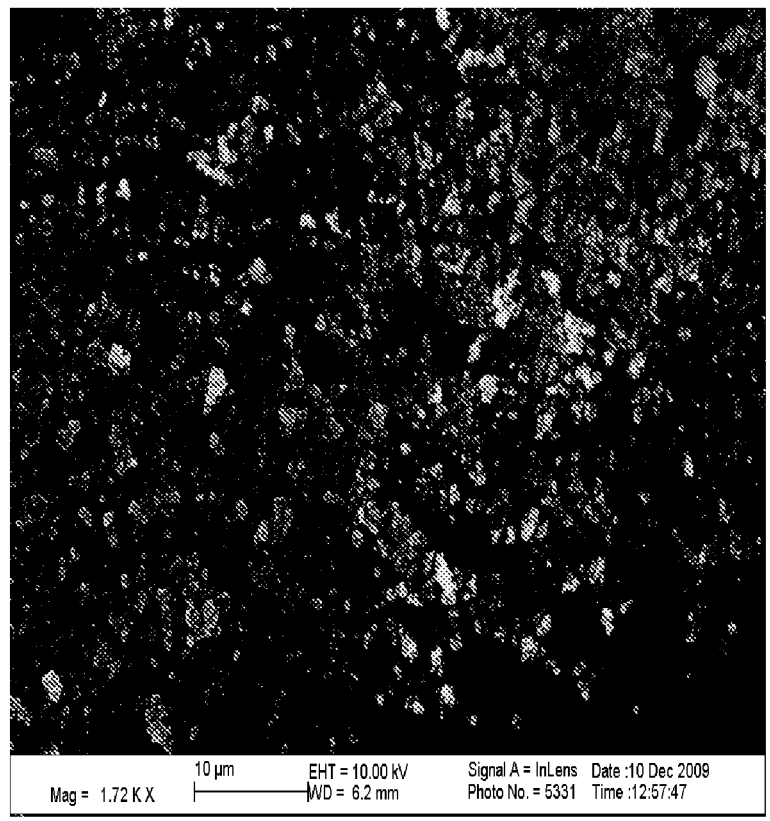
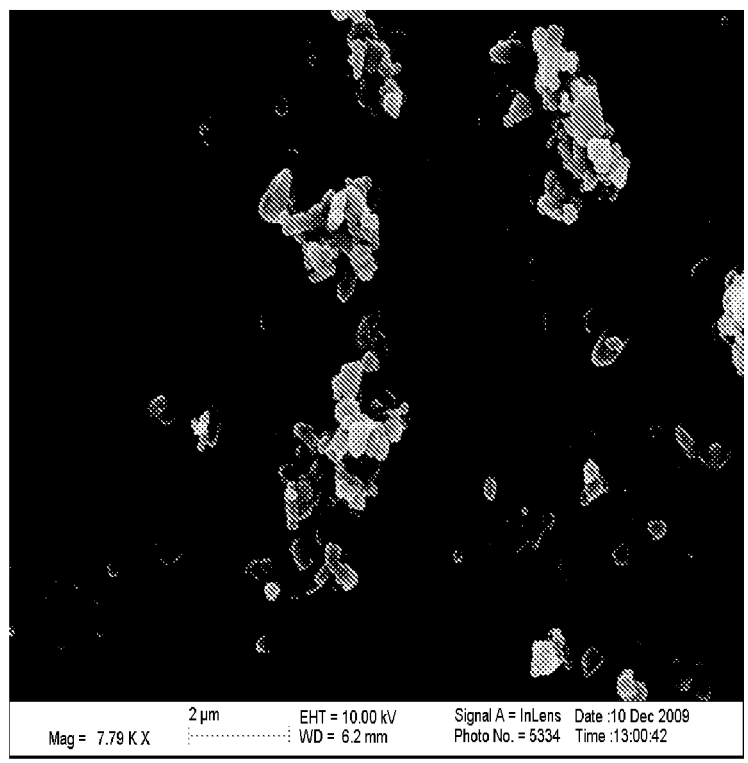

FIG. 82
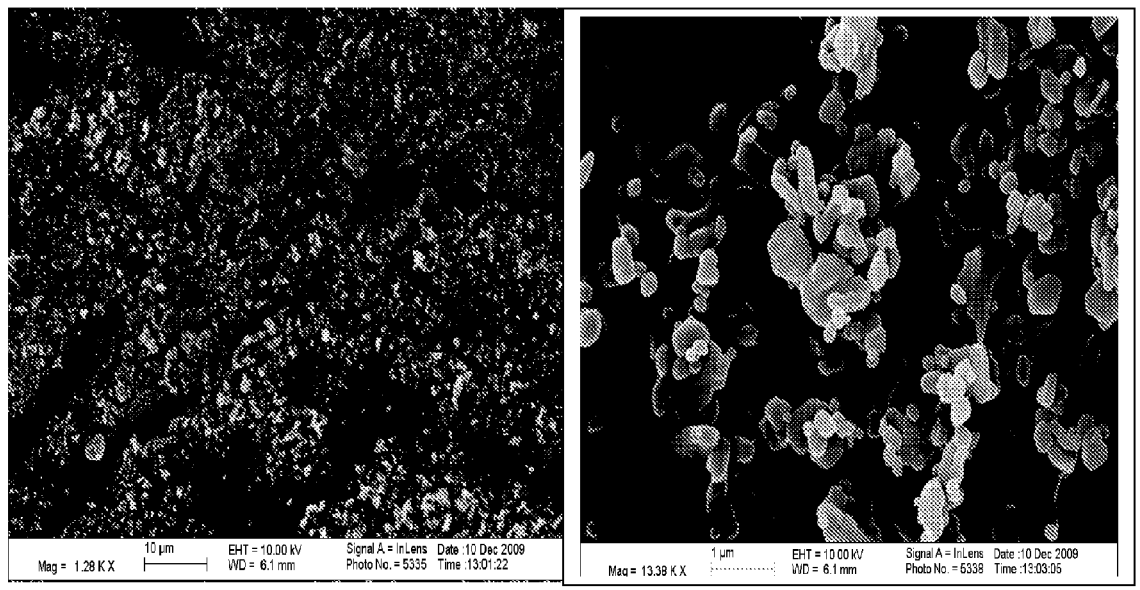
FIG. 83
Budesonide NCs
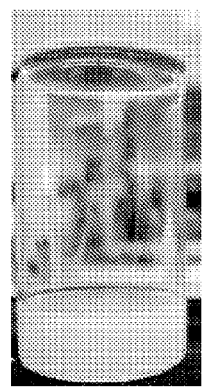
Budesonide milled
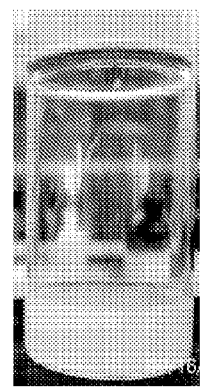

FIG. 84
Budesonide NCs  Budesonide milled
 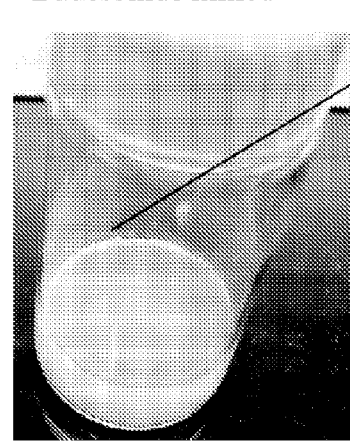 → Creaming
FIG. 85
Budesonide NCs  Budesonide milled
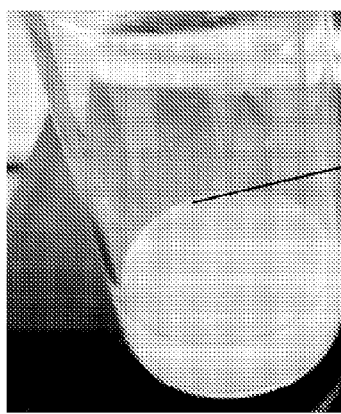 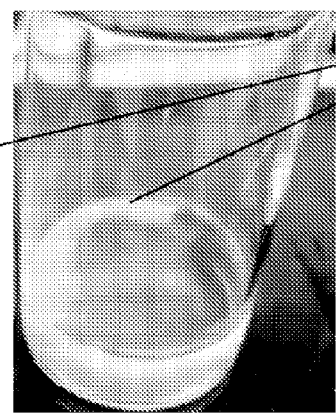 → Creaming FIG. 86
Budesonide NCs
Budesonide milled
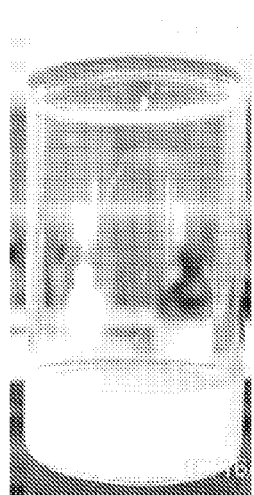
FIG. 87
Budesonide NCs
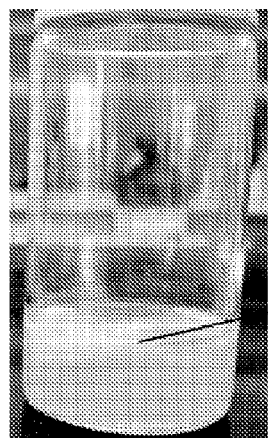
Budesonide milled
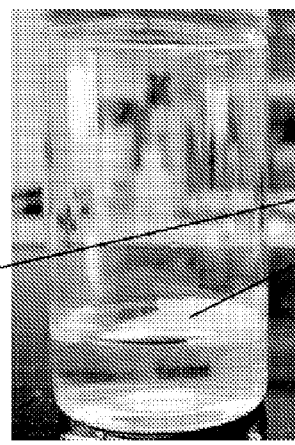
→ Creaming

NANOCLUSTER COMPOSITIONS AND METHODS

CROSS-REFERENCE TO RELATED APPLICATIONS

This application is a continuation-in-part of PCT/US/09/50565, entitled "Nanoclusters for Delivery of Poorly Water Soluble Drug Nanoparticles," filed on Jul. 14, 2009, which claims the benefit of Provisional application Nos. 61/081,034, filed on Jul. 15, 2008 and 61/081,037, filed on Jul. 16, 2008, and also a continuation-in-part of U.S. patent application Ser. No. 12/261,907, entitled "Nanoclusters for Delivery of Therapeutics," filed on Oct. 30, 2008 now abandoned, and also a continuation-in-part of U.S. patent application Ser. No. 12/261,873, entitled "Nanoclusters for Delivery of Therapeutics," filed on Oct. 30, 2008 now abandoned, both of which are divisionals of U.S. patent application Ser. No. 11/610,986, filed on Dec. 14, 2006 now U.S. Pat. No. 7,651,770, which claims the benefit of Provisional application No. 60/751,172 filed Dec. 16, 2005, all of which are incorporated by reference.

BACKGROUND

Millions of people worldwide suffer from a wide variety of diseases or conditions that would benefit from the effective delivery of therapeutic or diagnostic agents. Examples of these diseases or conditions include pulmonary diseases, circulatory diseases, muscular diseases, bone diseases, and cancers.

Current drug delivery treatment options can often be ineffective due to inefficient delivery of an active ingredient to a targeted site. The use of nanoparticles as drug delivery vehicles has been employed for a variety of indications. Nanoparticles, for example, have been shown to improve the dissolution of poorly water-soluble drugs and enhance the transport of drugs both intra- and paracellularly. In addition, literature indicates that plasmid DNA can be effectively delivered by polycationic polymers that form nanoparticles when mixed with DNA resulting in enhanced gene expression. Although nanoparticles offer several advantages for delivering drugs (e.g. improved dissolution of low solubility API, intracellular and transcellular transport, etc.), the use of nanoparticles, for example, can be hindered by the inability to deliver nanoparticles to the site of drug action (e.g. dried nanoparticles are too small to deposit efficiently in the lungs, can avoid detection by APCs, etc.). In addition, nanoparticles are often difficult to handle at an industrial scale.

SUMMARY

The present disclosure relates to the delivery of therapeutic and diagnostic agents, and more particularly, in certain embodiments, to a nanocluster drug delivery platform.

The present disclosure provides, according to certain embodiments, nanoclusters comprising a plurality of nanoparticles having a core of nanoparticles arranged such that the surfaces of the nanoparticles contact adjacent nanoparticles, the nanoparticles comprise active ingredient, and the nanocluster has a mass median aerodynamic diameter of from about 0.25 µm to about 20 µm.

The present disclosure provides, according to certain embodiments, methods comprising forming a nanocluster comprised of a core of nanoparticles arranged such that the surface of the nanoparticles contact one another, the nanoparticles comprise an active ingredient, wherein the nanocluster has a mass median aerodynamic diameter of from about 0.25 µm to about 20 µM.

The present disclosure provides, according to certain embodiments, methods comprising administering to a subject a nanocluster comprised of a core of nanoparticles arranged such that the surface of the nanoparticles contact one another, the nanoparticles comprise an active ingredient, wherein the nanocluster has a mass median aerodynamic diameter of from about 0.25 µm to about 20 µm.

The present disclosure provides, according to certain embodiments, compositions comprising a nanocluster, the nanocluster comprises a plurality of nanoparticles having a core of nanoparticles arranged such that the surfaces of the nanoparticles contact adjacent nanoparticles, the nanoparticles comprise an active ingredient, and the nanocluster has a mass median aerodynamic diameter of from about 0.25 µm to about 20 µm.

The features and advantages of the present disclosure will be readily apparent to those skilled in the art upon a reading of the description of the embodiments that follows

DRAWINGS

Some specific example embodiments of the disclosure may be understood by referring, in part, to the following description and the accompanying drawings.

Figure 1:
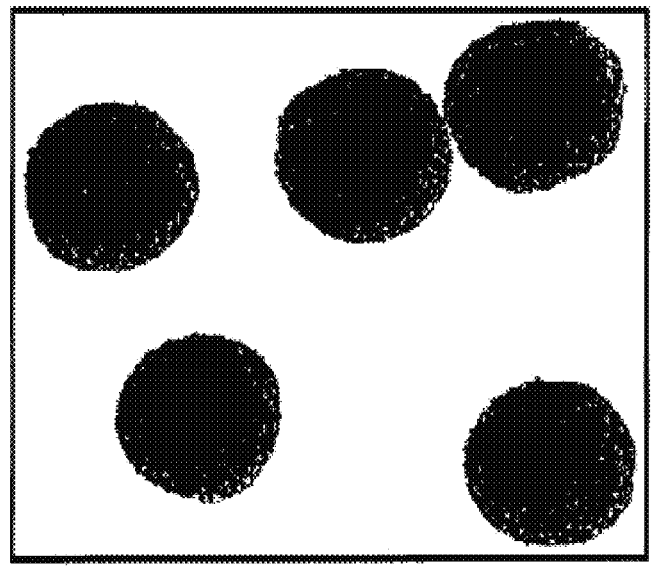

FIG. 1. Uniform (~75 µm) nanoclusters composed of polystyrene nanoparticles.

Figures 2A, 2B:
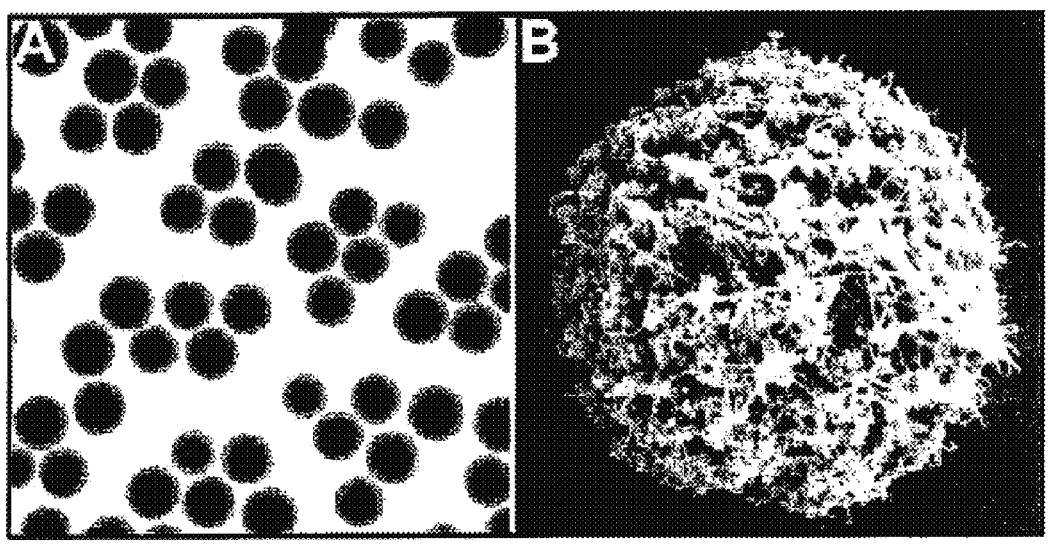

FIG. 2. Electron micrographs of (A) 225 nm silica nanoparticles coated with a dispersion material (light gray corona) and (B) a 9 µm nanocluster of the silica nanoparticles coated with dispersion material.

FIG. 3. The dispersion of nanoclusters over time composed of nanoparticles coated with a hydrolysable polymer was a function of pH as determined by (A) absorption of light at 480 nm and (B) visual inspection. (C) Size analysis of the dispersion shows polydisperse agglomerates are liberated from the nanoclusters, which then break down into monodisperse nanoparticles.

Figures 4A, 4B, 4C:
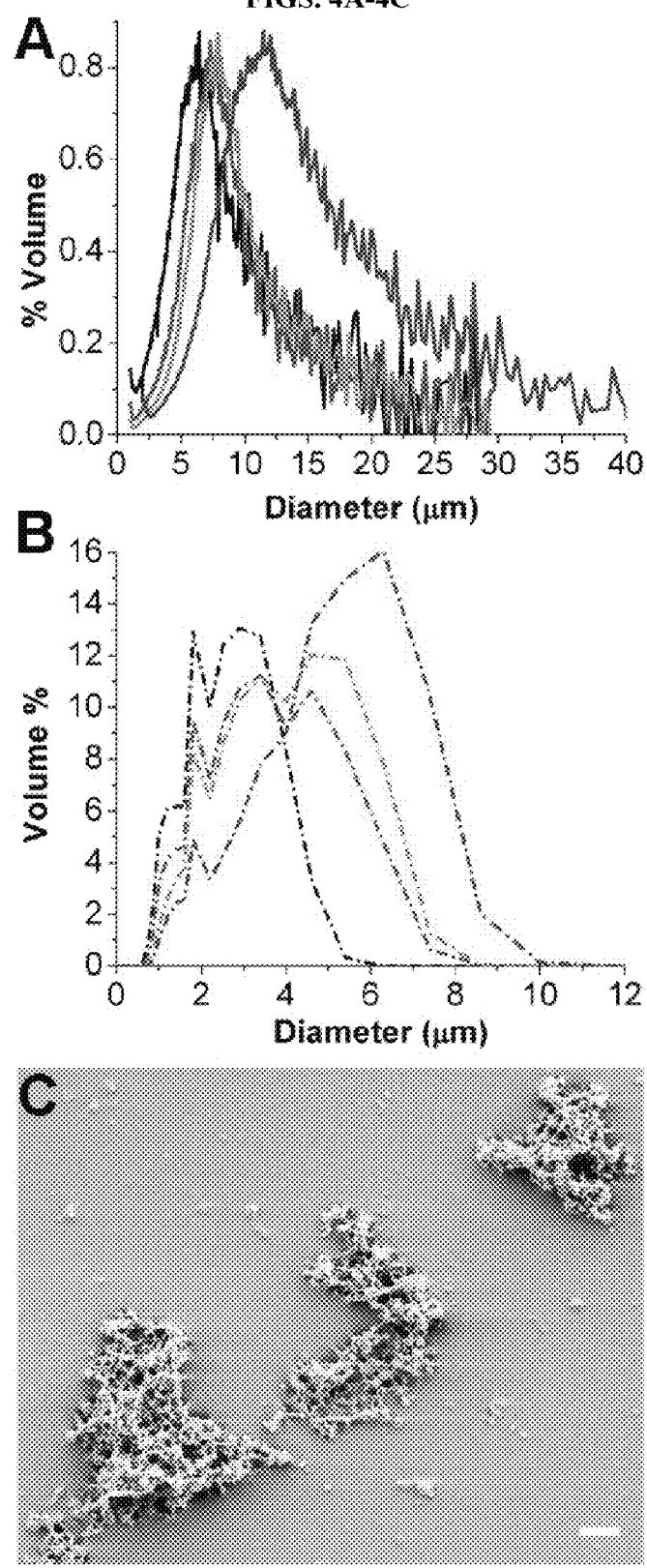

FIG. 4A, FIG. 4B, FIG. 4C. The (FIG. 4A) geometric and (FIG. 4B) aerodynamic size distributions of PLGA nanoclusters produced by increasing the concentration of nanoparticles (black=0.68 mg/ml, red=1.36 mg/ml, green=2.16 mg/ml, blue=2.72 mg/ml). FIG. 4C Scanning electron micrograph of nanocluster structure. Scale bar=5 µm.

Figures 5A, 5B, 5C, 5D, 5E, 5F:
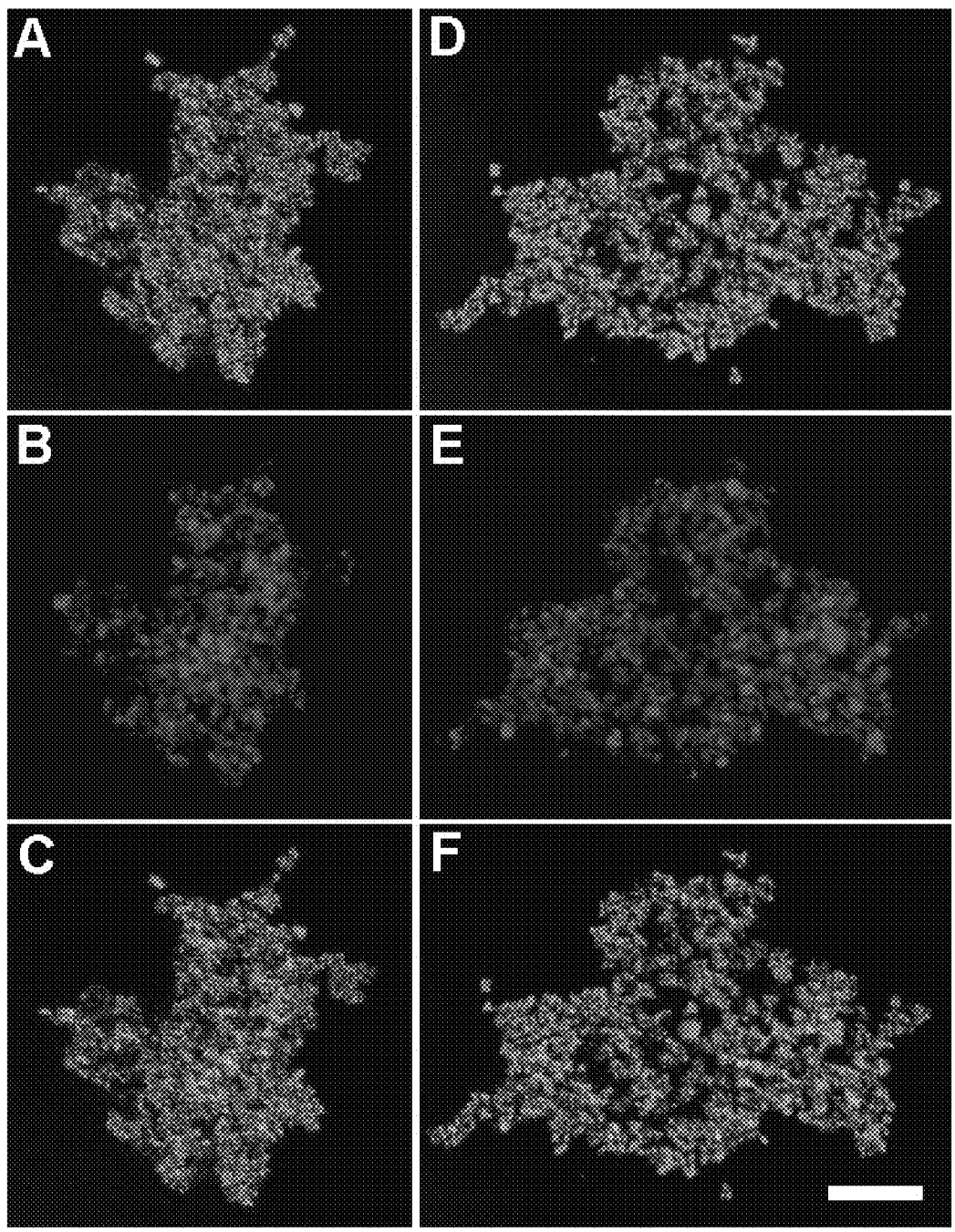

FIG. 5A, FIG. 5B, FIG. 5C, FIG. 5D, FIG. 5E, FIG. 5F. Laser scanning confocal micrographs of PLGA nanoparticle nanoclusters. FITC-labeled PVAm-coated nanoparticles (FIG. 5A and FIG. 5D) and rhodamine-labeled PEMA-coated nanoparticles (FIG. 5B and FIG. 5E) are both identified within the nanocluster structure. FIG. 5C and FIG. 5F Overlays of the micrographs reveal the diffuse structure of the nanoclusters. Scale bar=5 µm.

Figure 6:
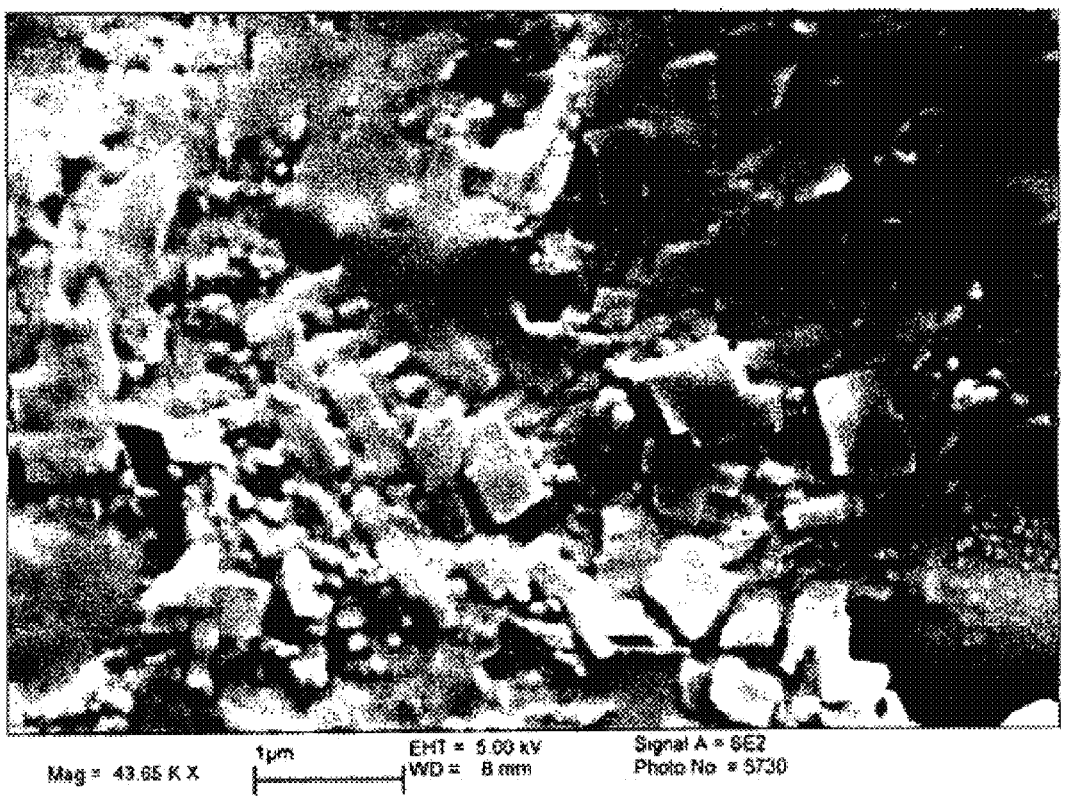

FIG. 6. Scanning electron microscope (SEM) image of a population of nifedipine nanoparticles.

Figure 7:
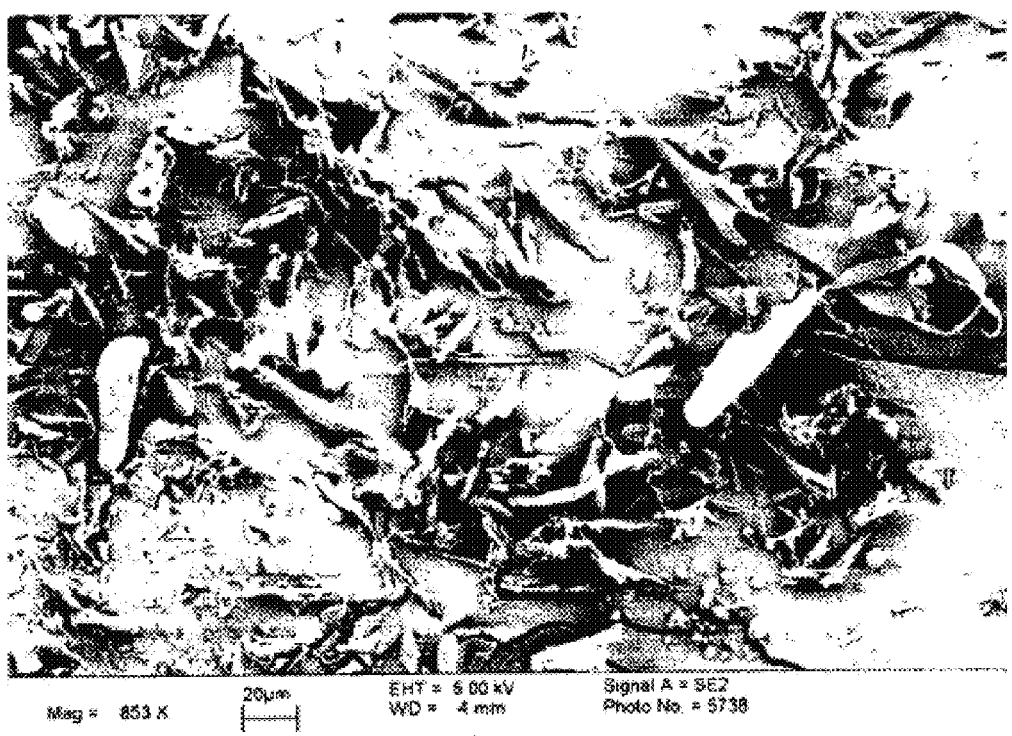

FIG. 7. SEM image of nifedipine nanoparticle clusters.

Figure 8:
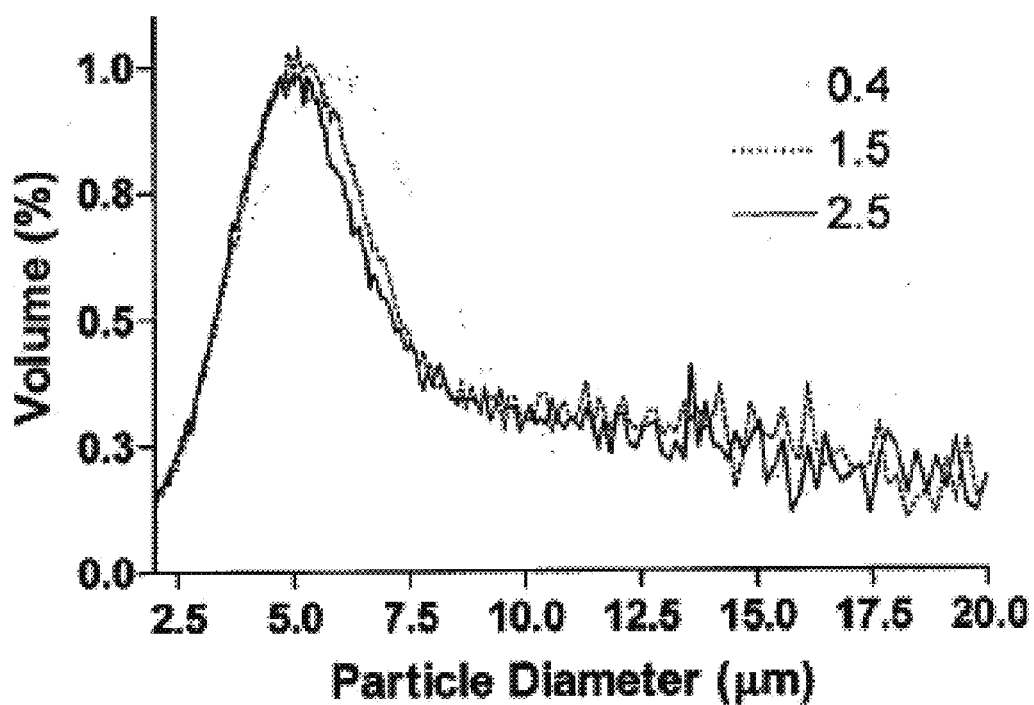

FIG. 8 Illustration of the geometric diameter of the nanoclusters comprising DOTAP/PLGA nanoparticles and ovalbumin.

Figure 9:
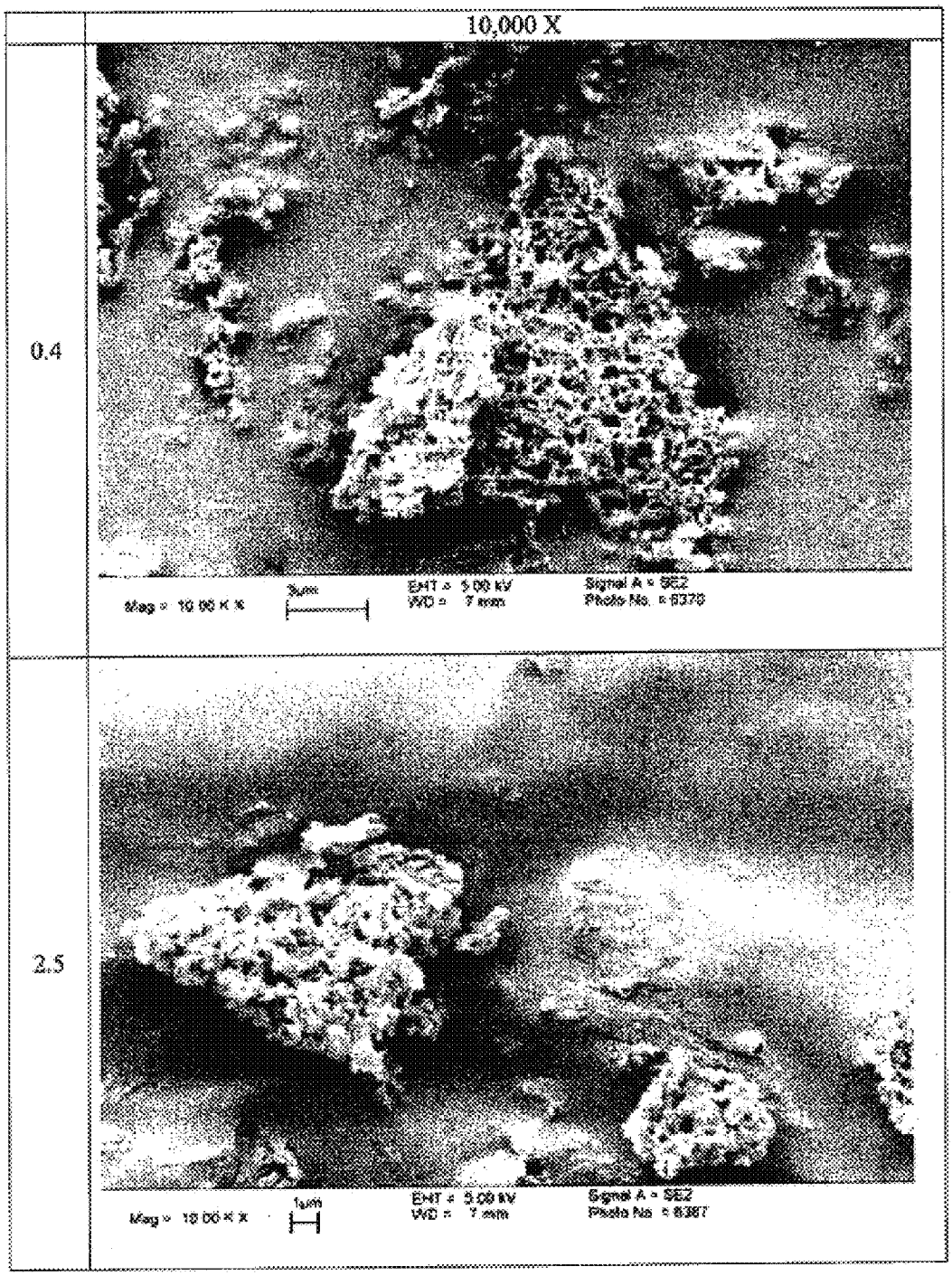

FIG. 9. SEM images of the nanoclusters comprising DOTAP/PLGA nanoparticles and ovalbumin.

FIG. 10. The particle size distributions of paclitaxel nanoparticle agglomerates in suspension after agglomeration and resuspended after lyophilization.

Figure 11:
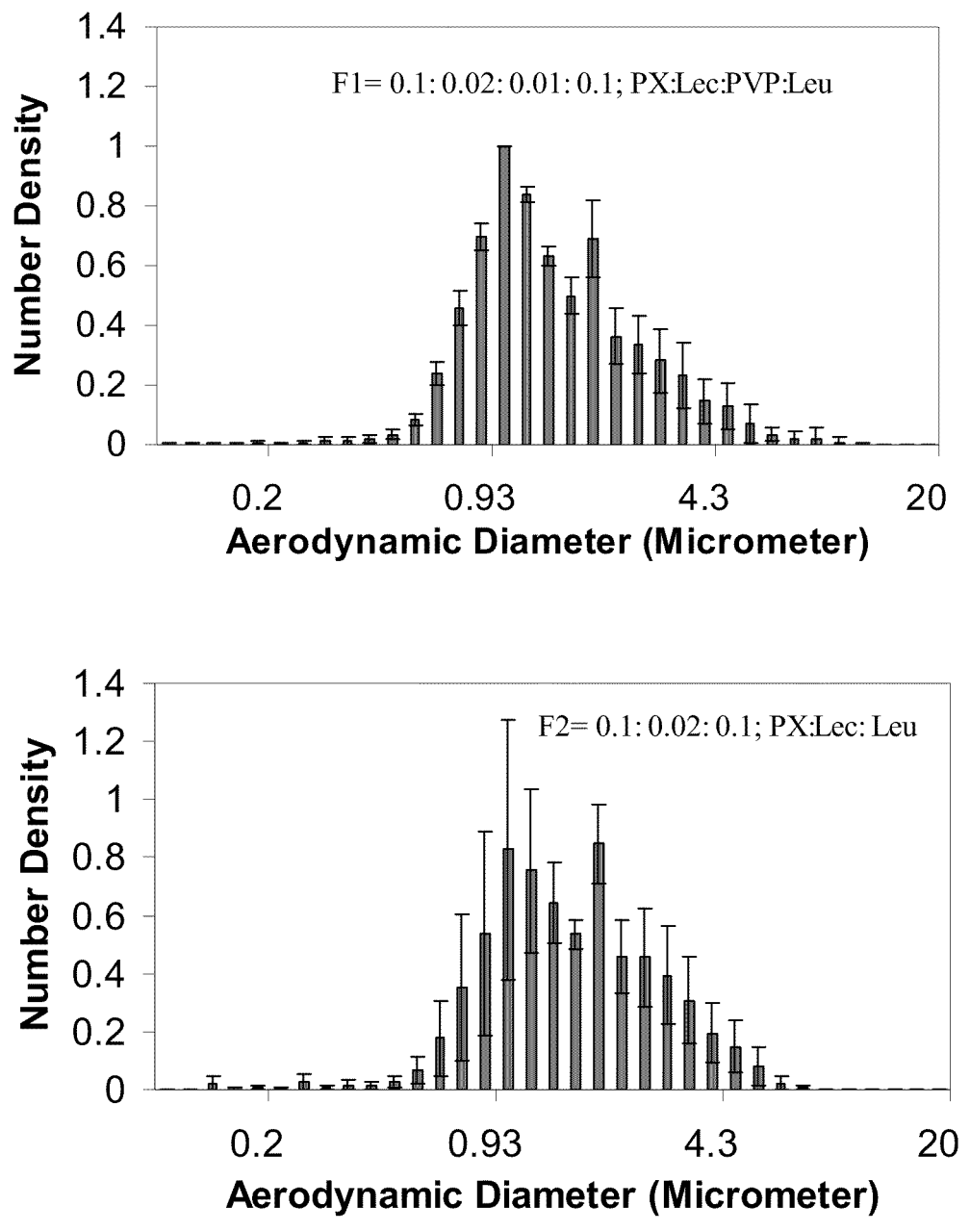

FIG. 11. Aerodynamic size distributions of paclitaxel nanoparticle agglomerates after lyophilization.

FIG. 12. The distribution of paclitaxel powder as received and nanoparticle agglomerate formulations deposited on the stages of a cascade impactor at a flow rate of ~30 L/min.

FIG. 13. In-vitro dissolution profiles of paclitaxel in PBS (pH 7.4) from pure paclitaxel powder and two different nanoparticle (NP) and nanoparticle agglomerate formulations (NA).

FIG. 14. Viability of A549 cells in the presence of formulation components as determined by an MTS assay.

FIG. 15. The particle size distributions of budesonide nanoparticle agglomerates in suspension after agglomeration and resuspended after lyophilization.

FIG. 16. Aerodynamic size distributions of budesonide nanoparticle agglomerates after lyophilization.

FIG. 17. The distribution of budesonide nanoparticle agglomerate formulations (A) F1, (B) F2, and (C) F3 deposited on the stages of a cascade impactor. (D) Formulations were compared with stock budesonide at a flow rate of ~30 L/min.

Figure 18:
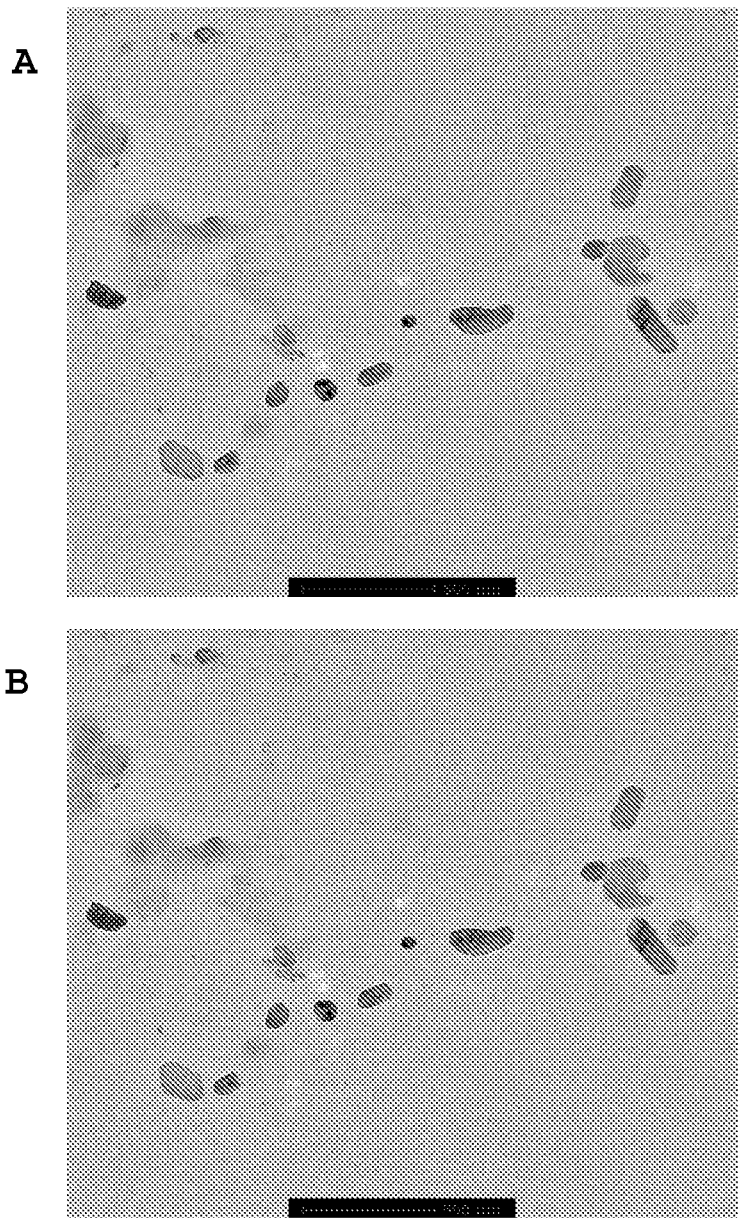

FIG. 18. Transmission electron micrographs of A) F1 nanoparticles and B) F1 nanoparticle agglomerates.

Figure 19:
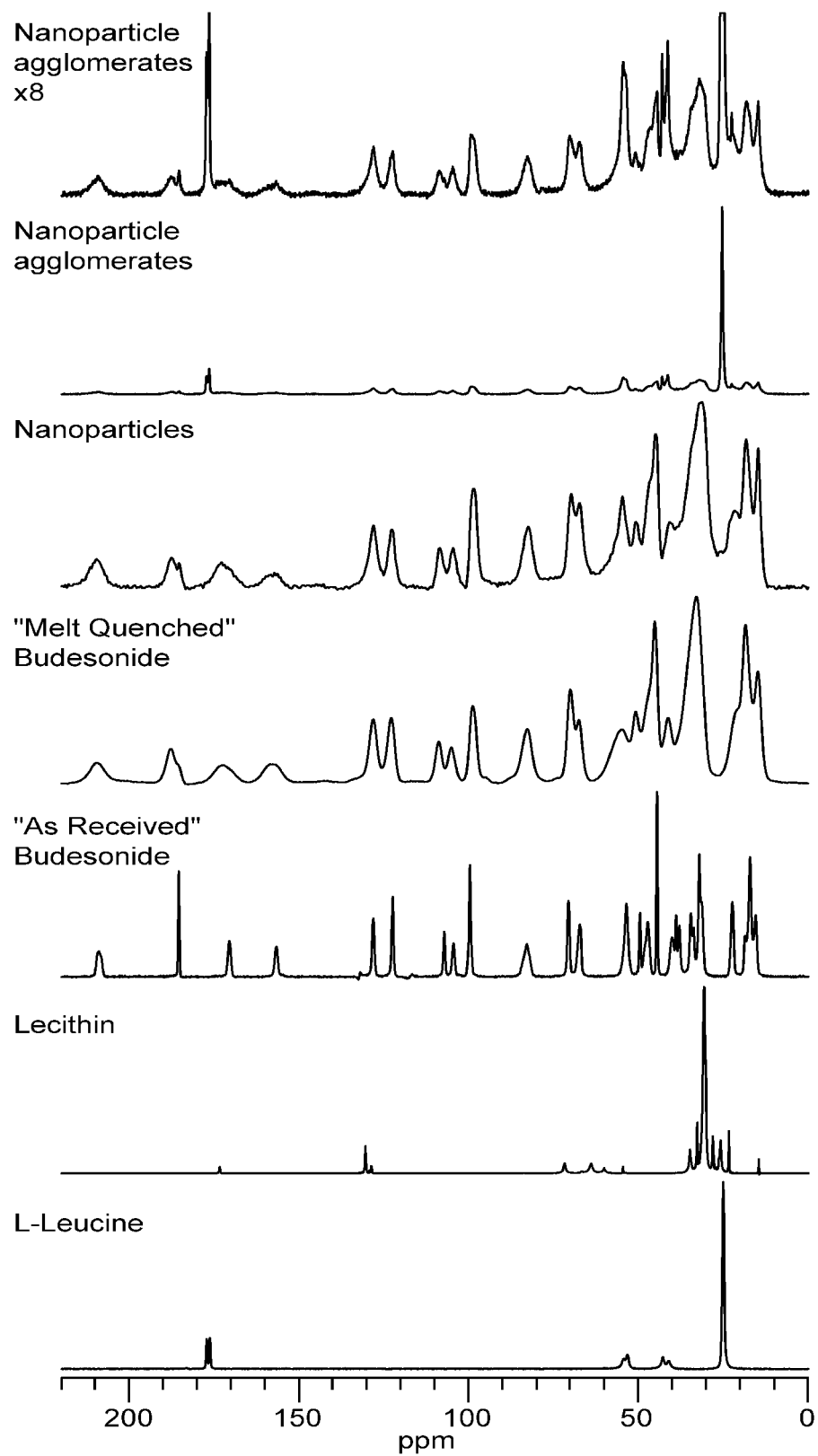

FIG. 19. 13C CP/MAS spectra of budesonide, excipients, and budesonide formulations. The nanoparticle agglomerates spectrum was expanded 8 times vertically to produce the nanoparticle agglomerates ×8 spectrum to aid the interpretation of the budesonide peaks.

Figure 20:
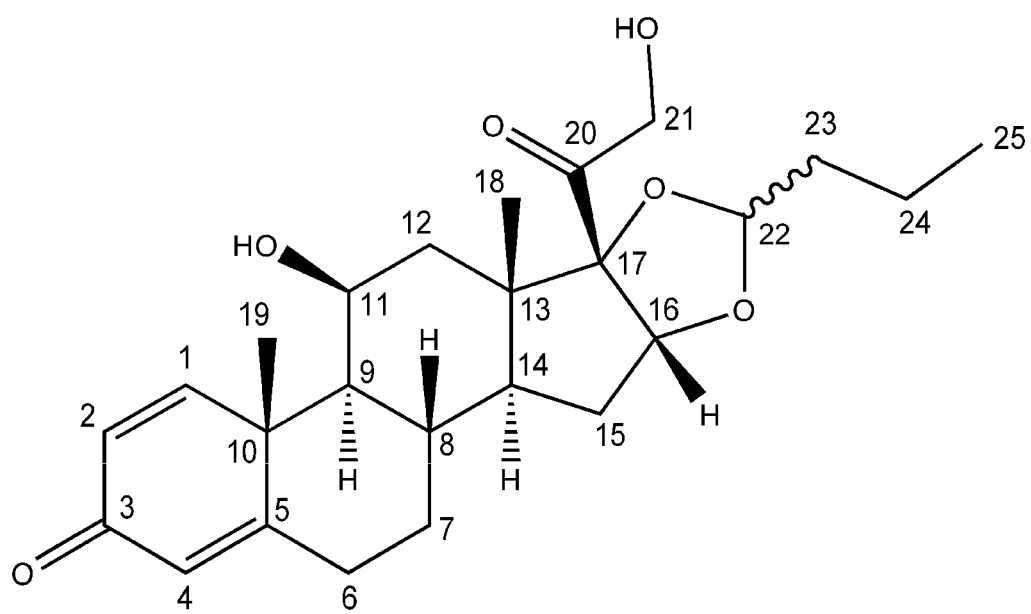

FIG. 20. Structure of budesonide with carbon numbering.

Figure 21:
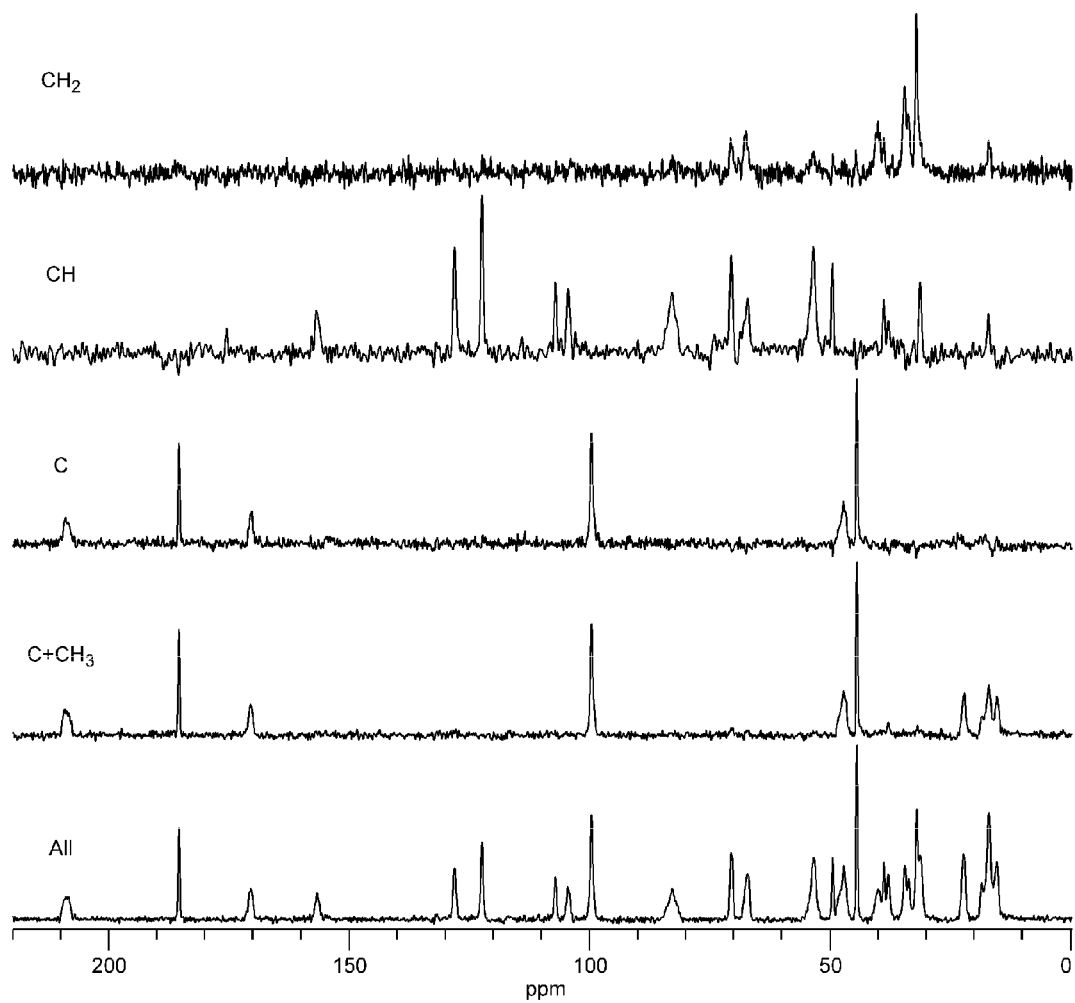

FIG. 21. 13C CP/MAS spectra from spectral editing experiment. All=all carbon types are shown, C+CH3=only unprotonated and methyl carbons are shown, C=only unprotonated carbons are shown, CH=only methine carbons are shown, and CH2=only methylene carbons are shown.

FIG. 22. In-vitro dissolution profiles of budesonide in PBS (pH 7.4) from budesonide stock and three different nanoparticle (NP) and nanoparticle agglomerate formulations (NA).

Figure 23:
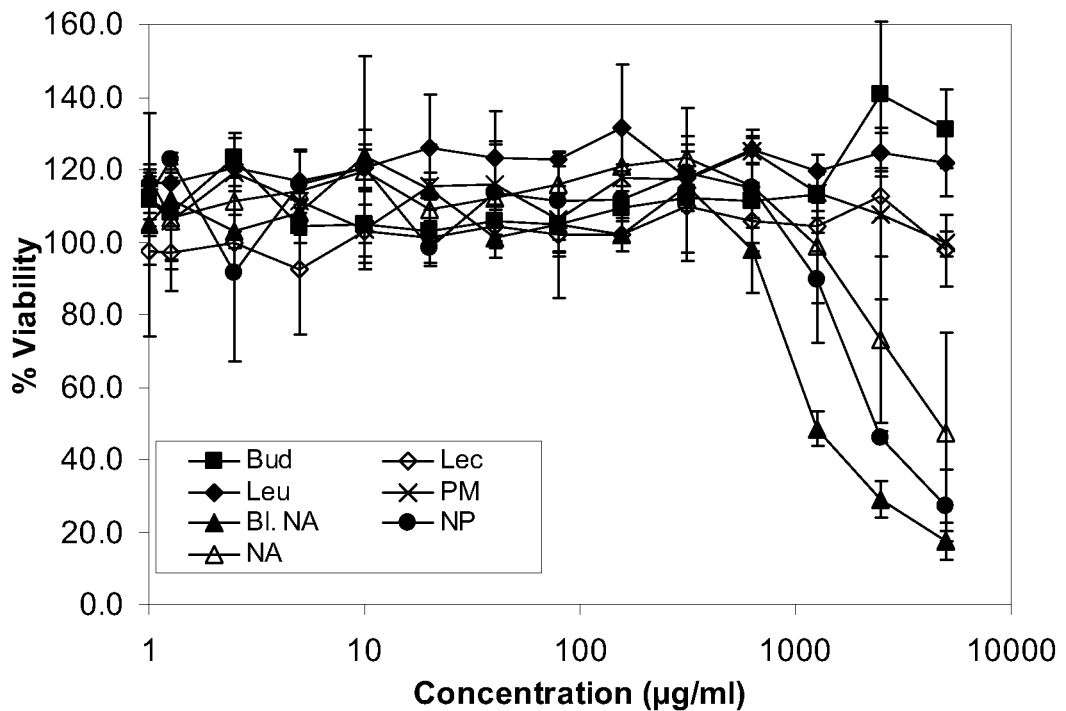

FIG. 23. Viability of A549 cells in the presence of formulation components as determined by an MTS assay. Bud: budesonide; Lec: Lecithin stock; Leu: Leucine stock; PM: Physical mixture of F1 components (0.1:0.02:0.1; Bud:Lec: Leu); B1. NA: F1 Blank nanoparticle agglomerates; NP: F1 nanoparticles; NA: F1 nanoparticle agglomerates.

Figure 24:
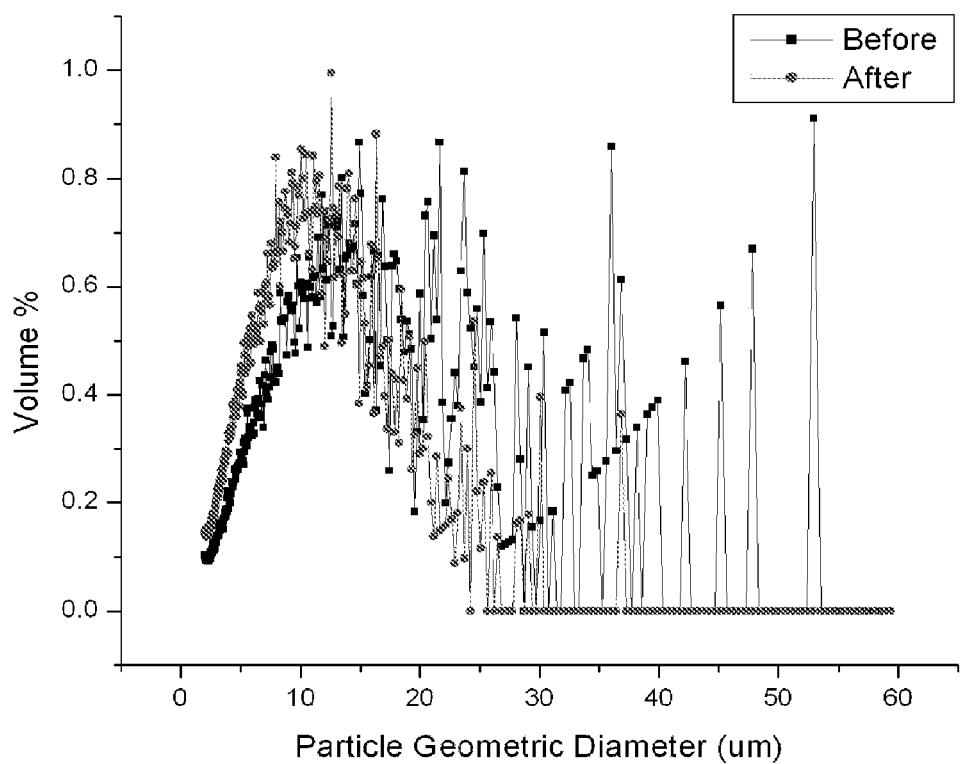

FIG. 24. Percent volume as a function of particle diameter for a agglomerated solution of NIF/SA nanoparticles in water (421.7+/−26.2 nm, −32.16+/−3.75 mV) after addition of NaCl to 0.1M. Also shown is the same solution after homogenization at 25000 RPM for 30 seconds.

Figure 25:
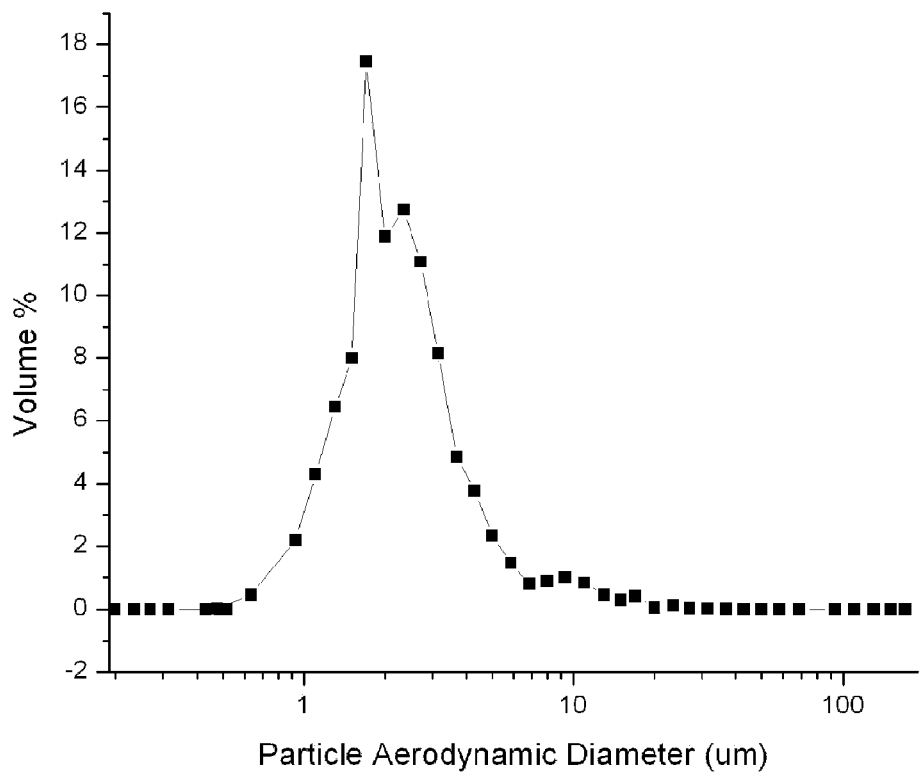

FIG. 25. Aerodynamic Diameter size distribution for the sample of nanoparticle agglomerates.

Figure 26:
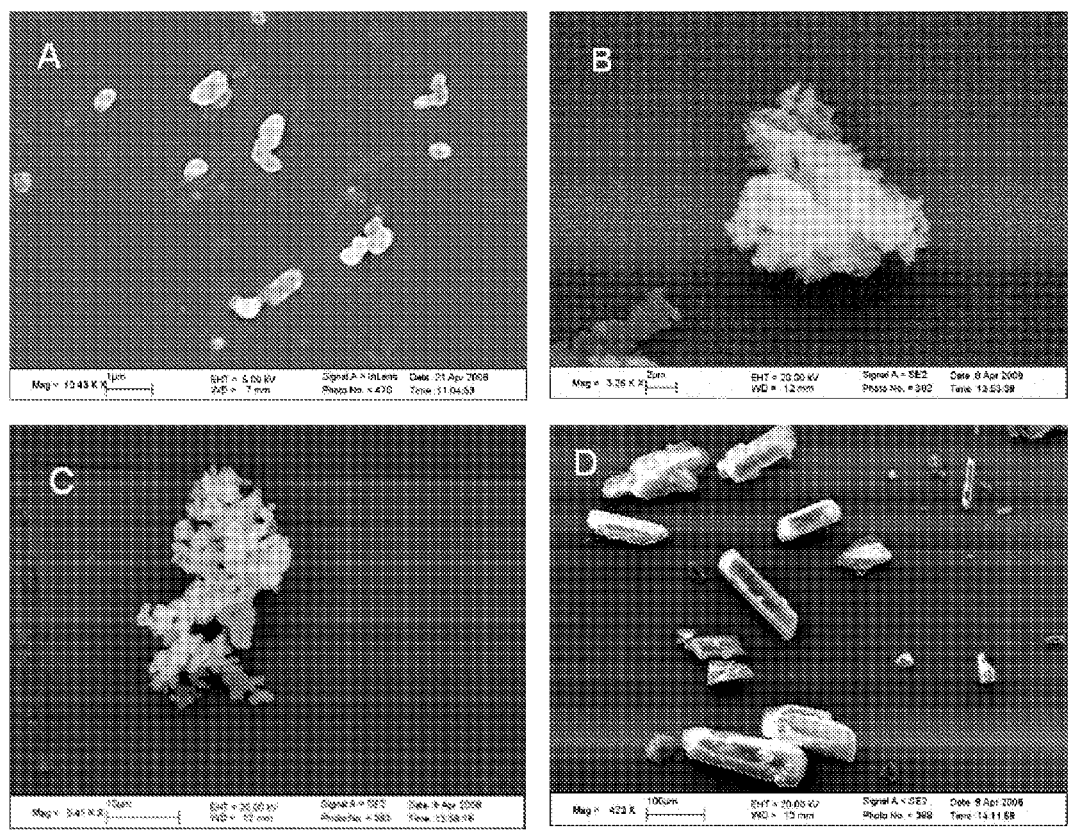

FIG. 26. A collection of SEM images for nanoparticles directly after sonication (A), newly prepared agglomerates (B), agglomerate powders after residing under room conditions and devoid of light for 1 month (C), and pure nifedipine crystals as received (D).

Figure 27:
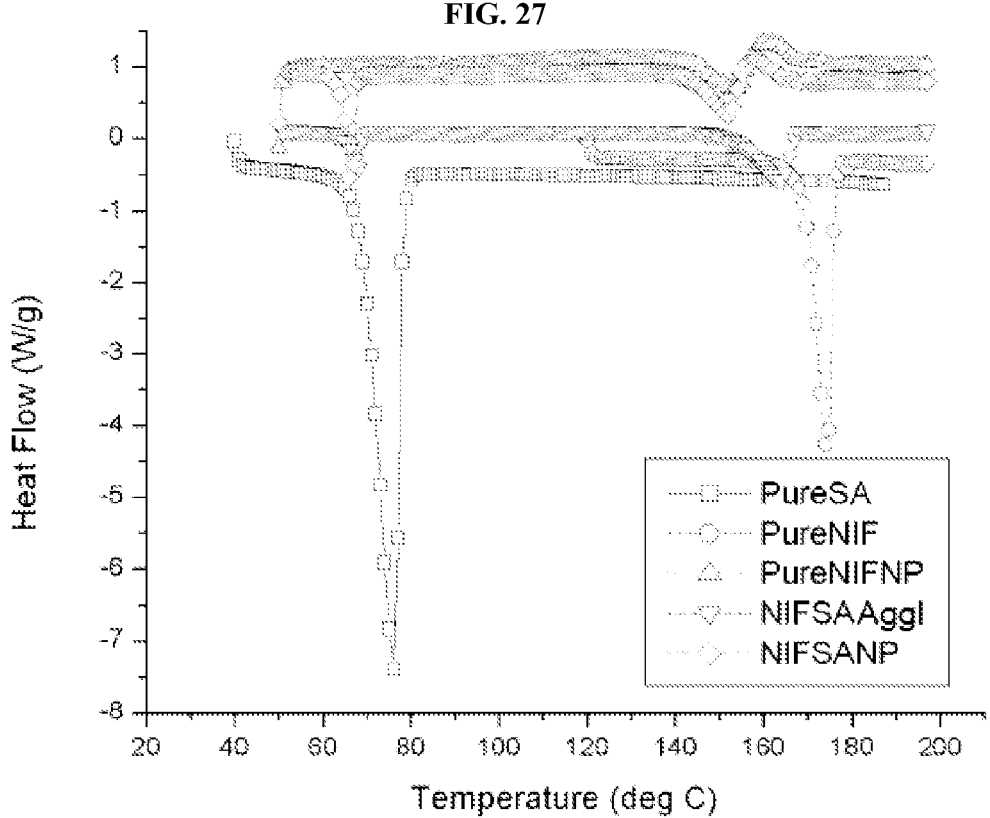

FIG. 27. DSC outputs for the optimal formulation of nanoparticles, pure nifedipine, and agglomerated nanoparticles.

Figure 28:
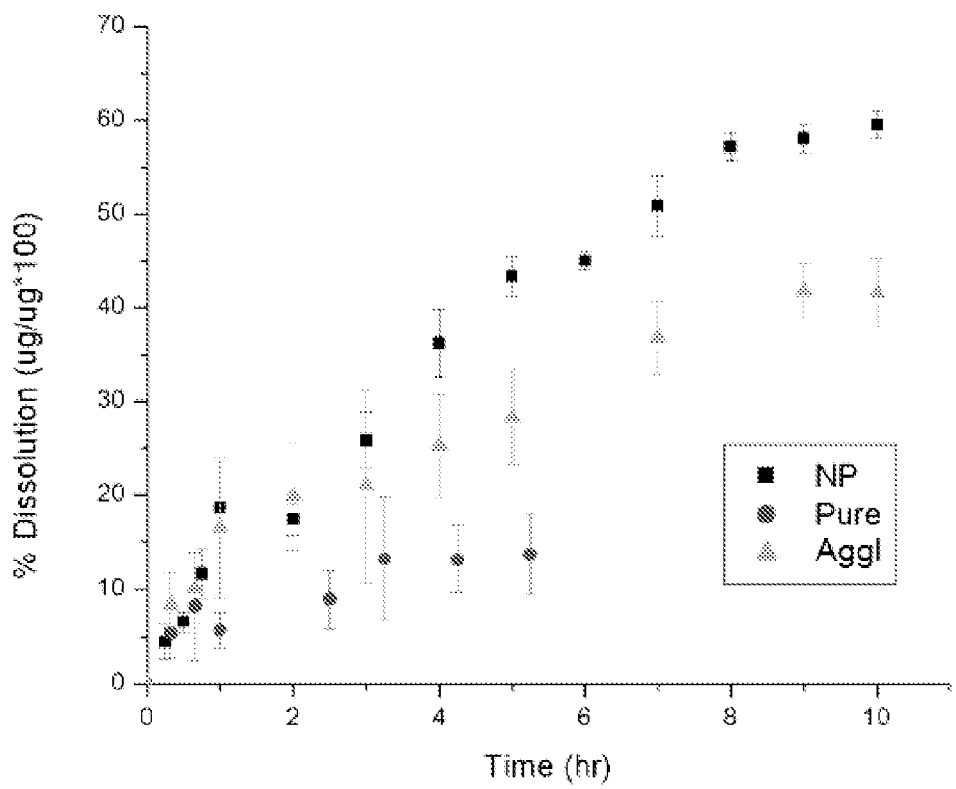

FIG. 28. Percent drug dissolution vs. Time as deduced via HPLC UV spectroscopy for the nifedipine/stearic acid nanoparticles, agglomerates, and the drug in pure crystalline form.

Figure 29:
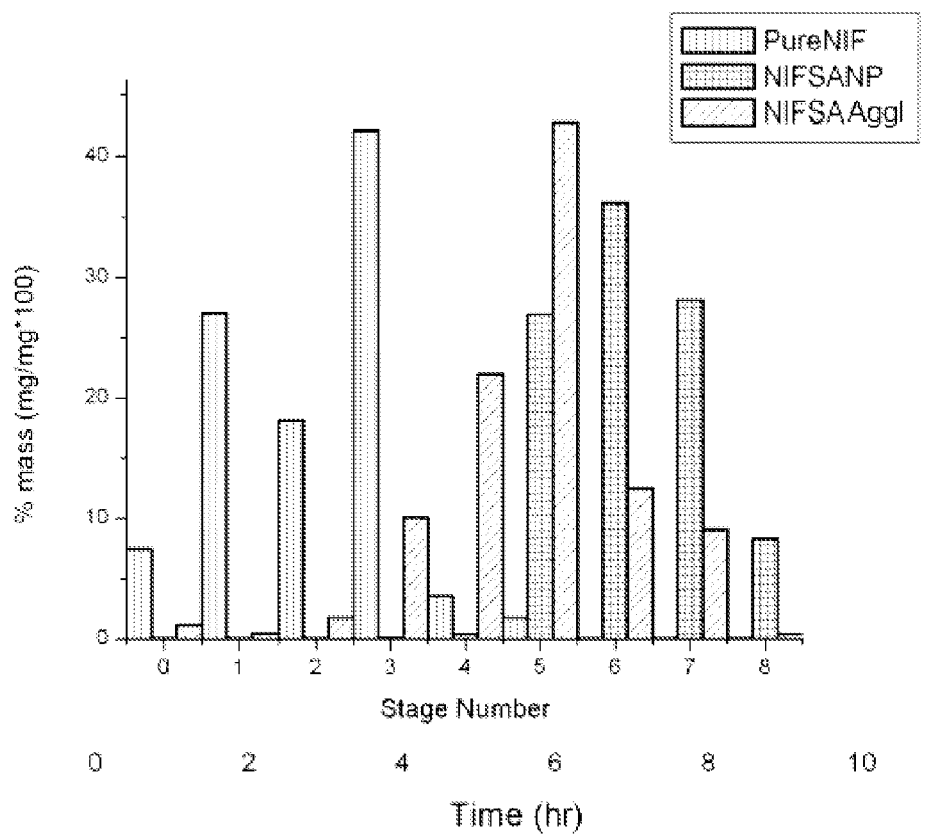

FIG. 29. Cascade impactor readings for nifedipine/stearic acid nanoparticles, agglomerates, and drug as received in pure form.

Figure 30:
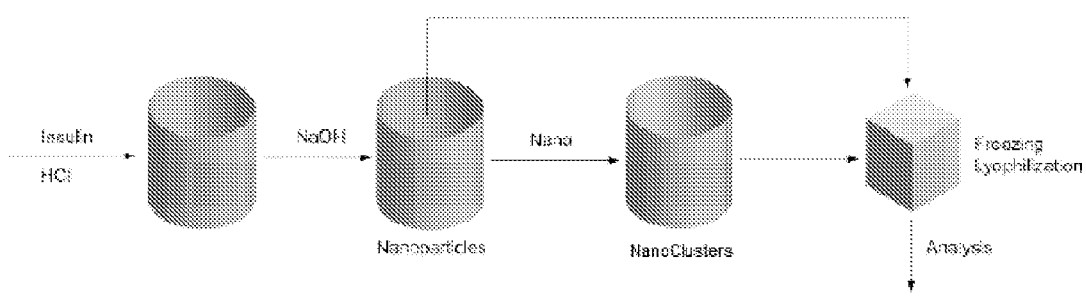

FIG. 30. Outline of insulin processing method.

Figure 31:
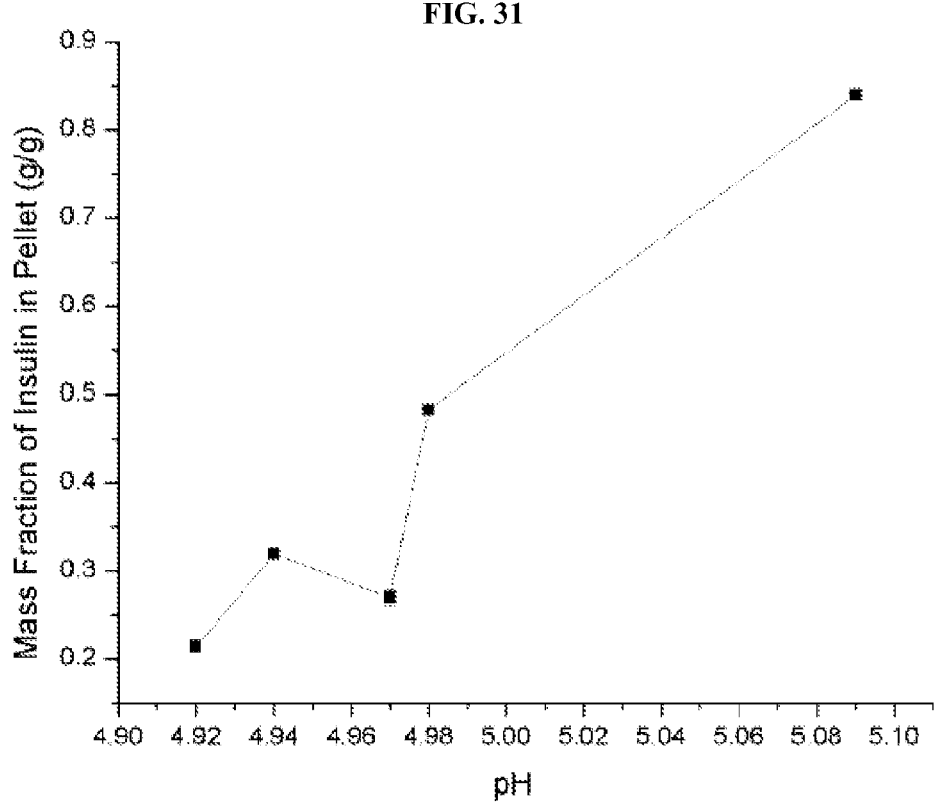

FIG. 31. Mass fraction of insulin in pellet vs. PH. Each value represents mean±standard deviation of three experiments.

Figure 32:
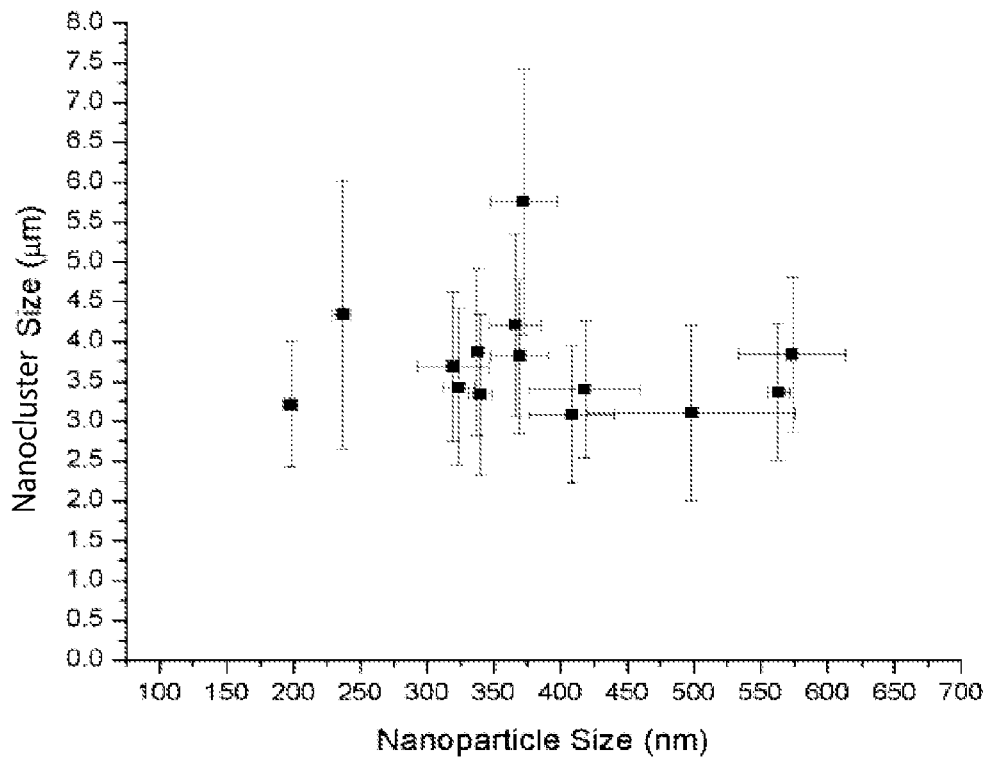

FIG. 32. Nanocluster size vs. Nanoparticle size. Each value represents mean±standard deviation of three experiments.

Figure 33:
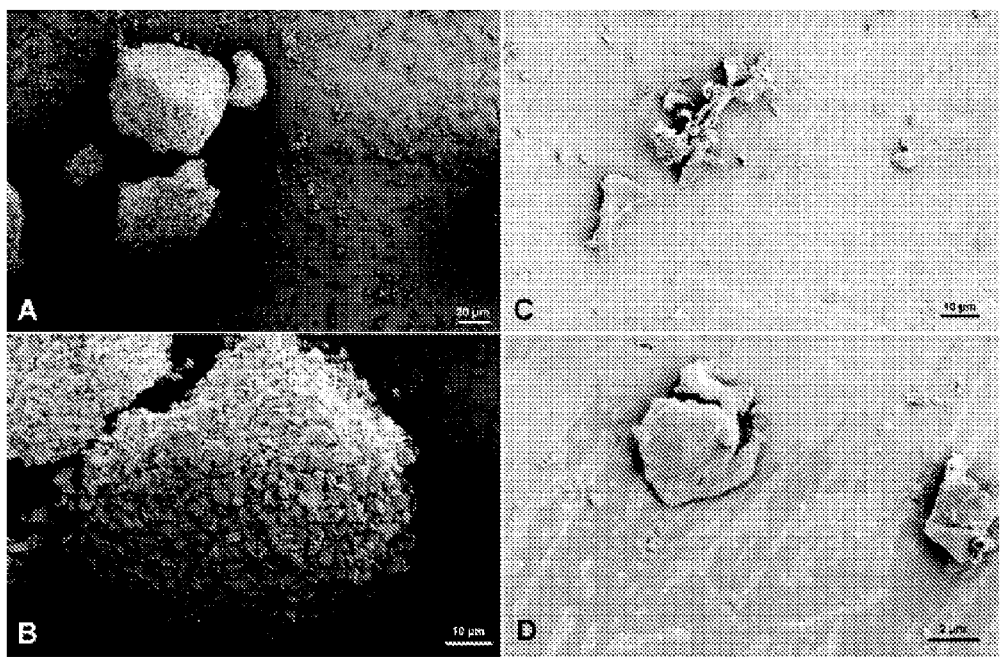

FIG. 33. SEM micrographs of insulin particles; (A) and (B) are unprocessed insulin particles (scale bars 30 pm and 10 pm, respectively); (C) and (D) are insulin nanoclusters after processing (scale bars 10 pm and 2 pm, respectively).

Figure 34:
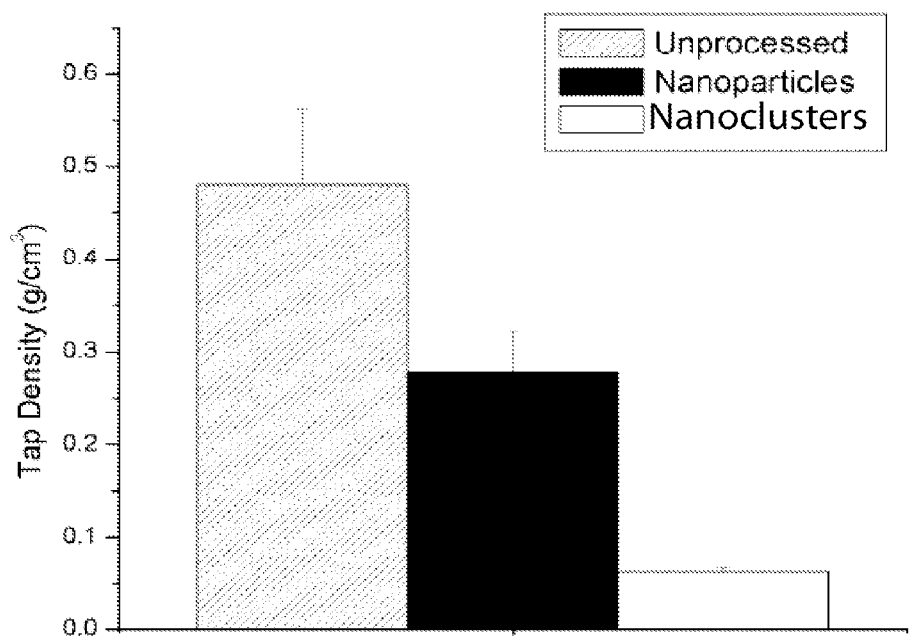

FIG. 34. Tap density of insulin powders. Each bar shows mean±standard deviation of three experiments.

FIG. 35. Circular dichroism of dissolved insulin powders. The top panel shows isothermal spectra, and the bottom panel shows variable temperature scan at a wavelength of 210 nm. Each value of the variable temperature scan represents mean±standard deviation of three experiments.

Figure 36:
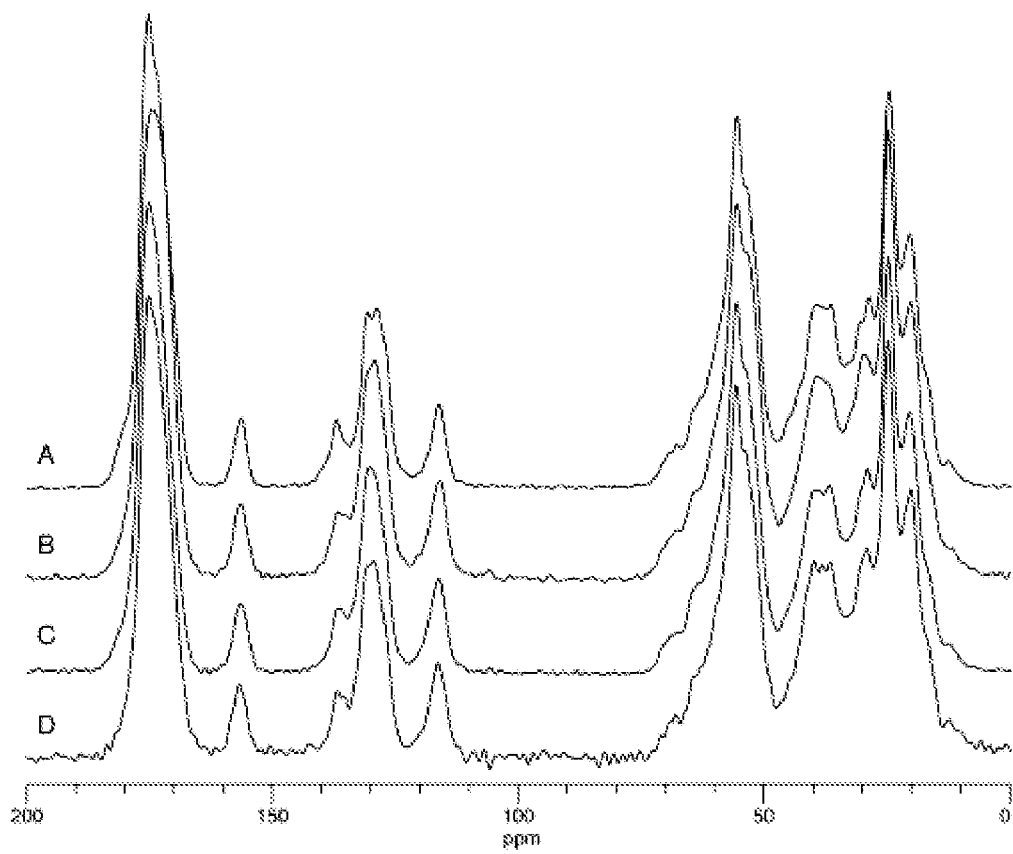

FIG. 36. 13C CP/MAS NMR spectra for insulin powders; (A) Unprocessed; (B)

Insulin nanoclusters; (C) Lyophilized insulin nanoparticles; (D) Centrifuged and dried insulin nanoparticles.

Figure 37:
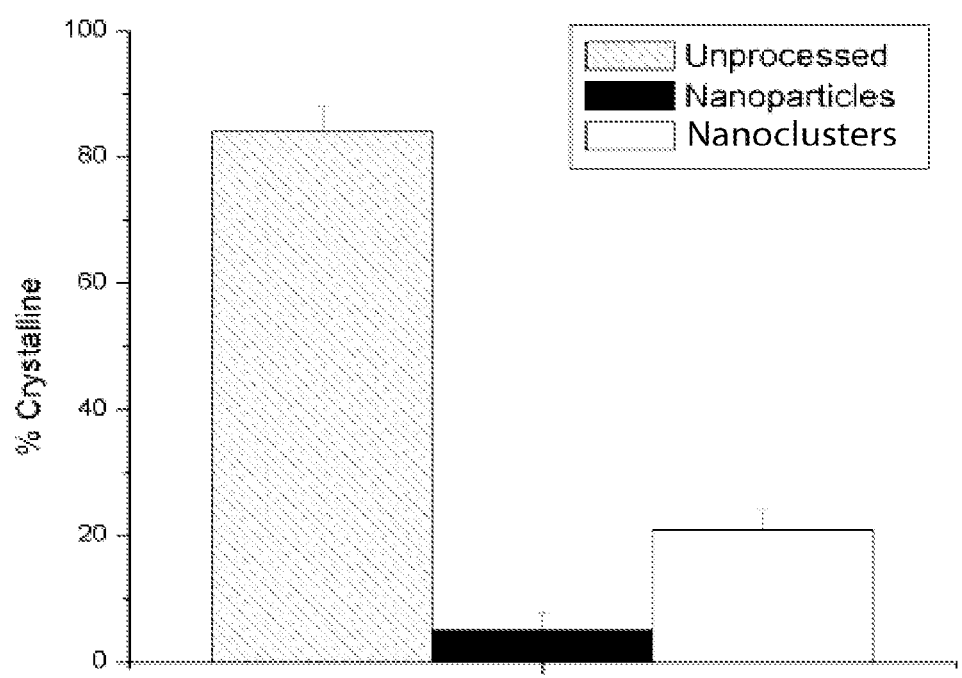

FIG. 37. Percent crystallinity of insulin particles, as determined by the HPLC dissolution method described in the U.S. Pharmacopeia and National Formulary. Each bar shows mean±standard deviation of three experiments.

Figure 38:
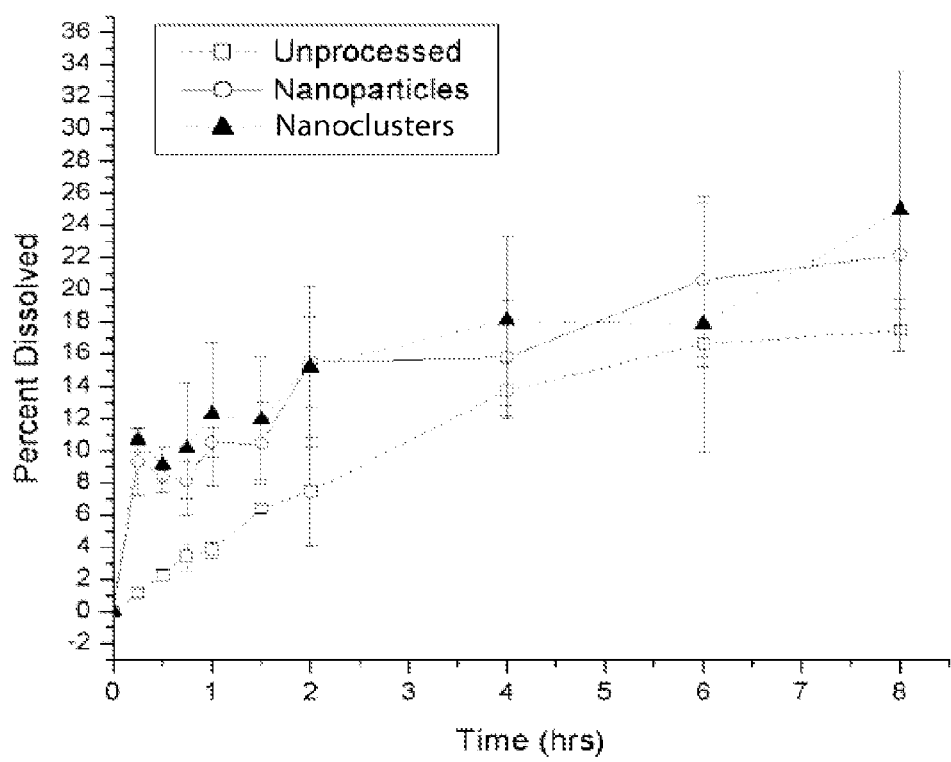

FIG. 38. Dissolution of insulin powders over time. Each value represents mean±standard deviation of three experiments.

FIG. 39. The distribution of diatrizoic acid powder as received as well as nanoparticle agglomerate. D9 S: Resuspended Diatrizoic acid nanoparticle agglomerates; D9 P: Diatriazoic acid nanoparticle agglomerated dry powder; Dia S: Resuspended Diatrizoic acid powder as received; Dia P: Diatrizoic acid powder as received.

FIG. 40. Size distribution of moxifloxacin nanoparticles suspension M5.

Figure 41:
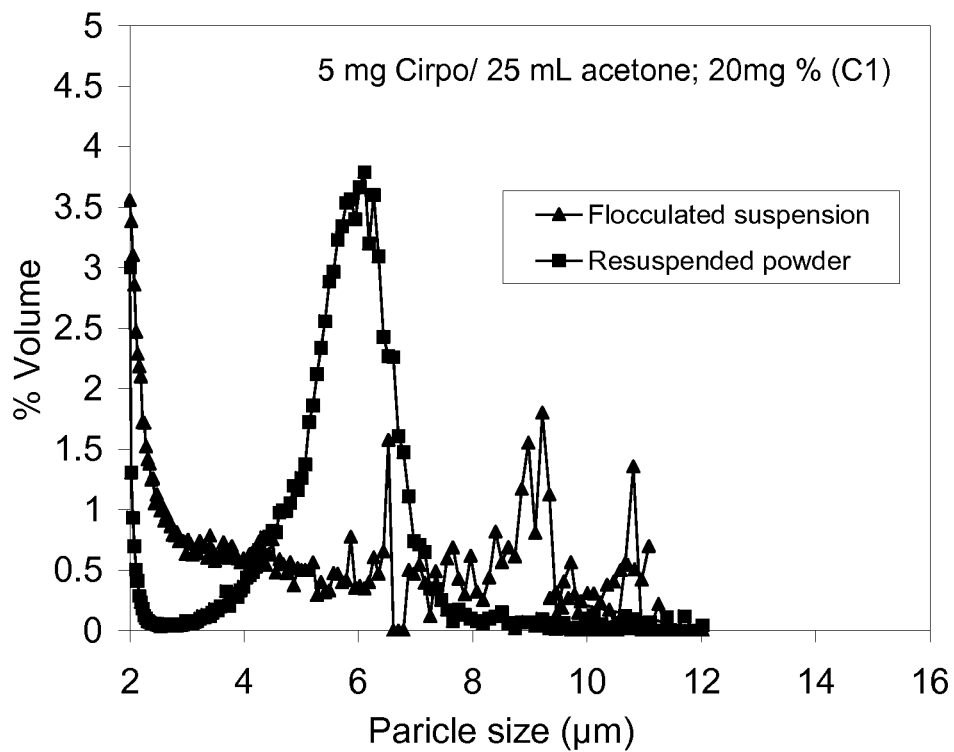

FIG. 41. The particle size distributions of Ciprofloxacin nanoparticle agglomerates C1 after flocculation and resuspended after lyophilization.

Figure 42:
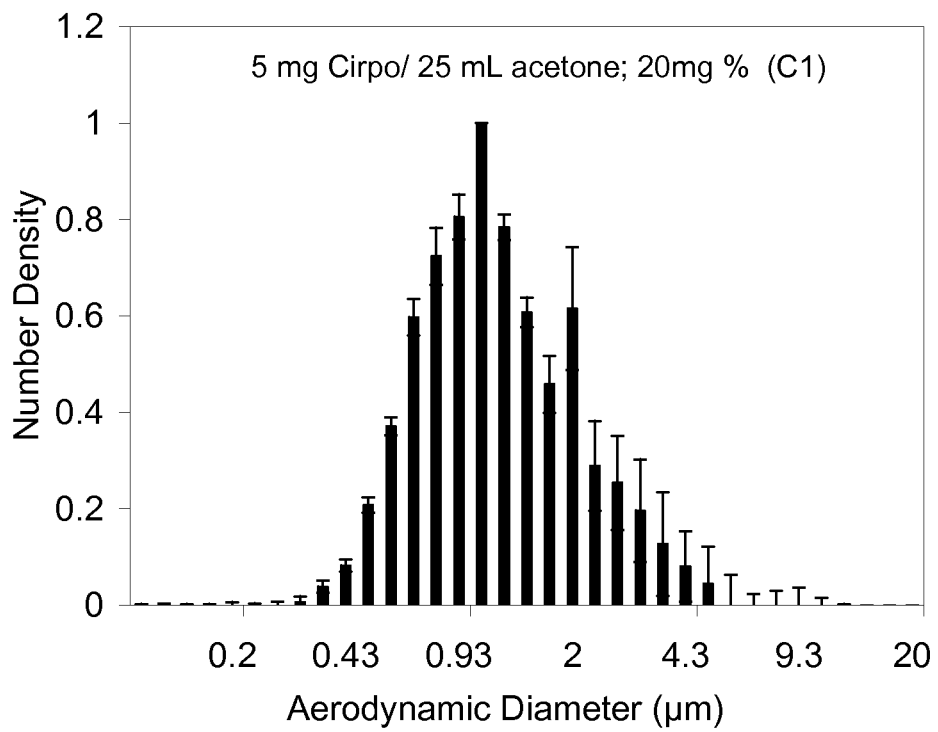

FIG. 42. Aerodynamic size distributions of Ciprofloxacin nanoparticle agglomerates C1 after lyophilization.

Figure 43:
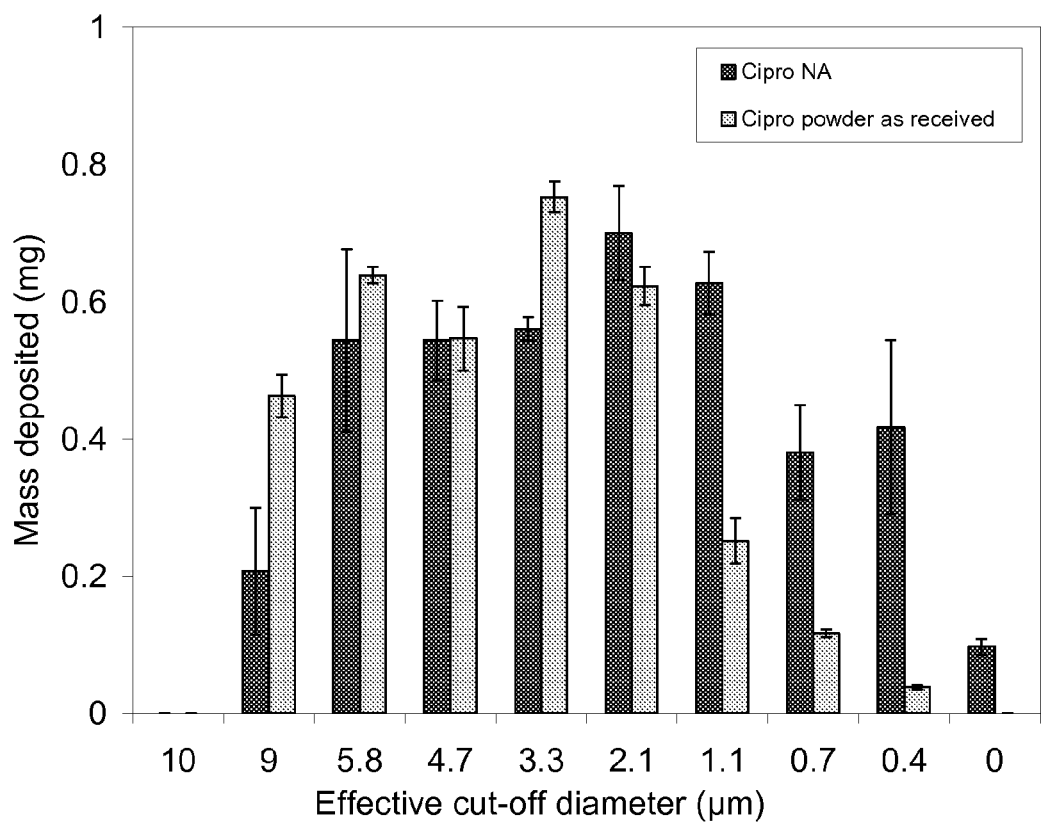

FIG. 43. The distribution of Ciprofloxacin powder as received as well as nanoparticle agglomerate formulation (C1) deposited on the stages of a cascade impactor at a flow rate of ~30 L/min.

Figure 44A:
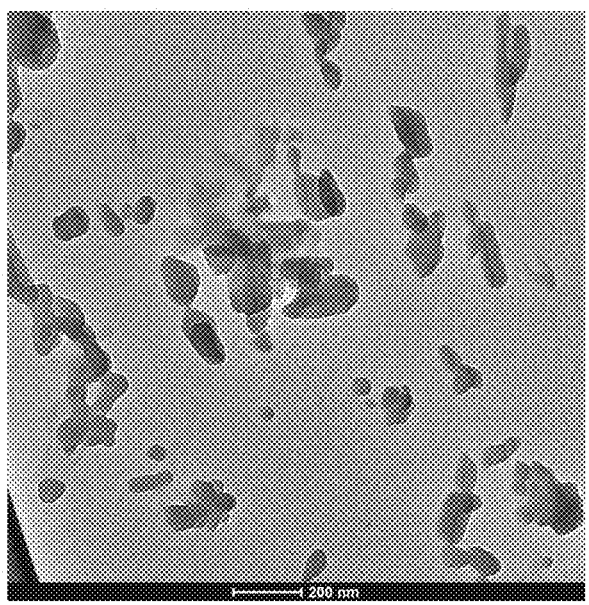

FIG. 44A/B. Transmission electron micrographs of diatrizoic acid A) D1 nanoparticles and B) D1 nanoparticle agglomerates.

Figure 45:
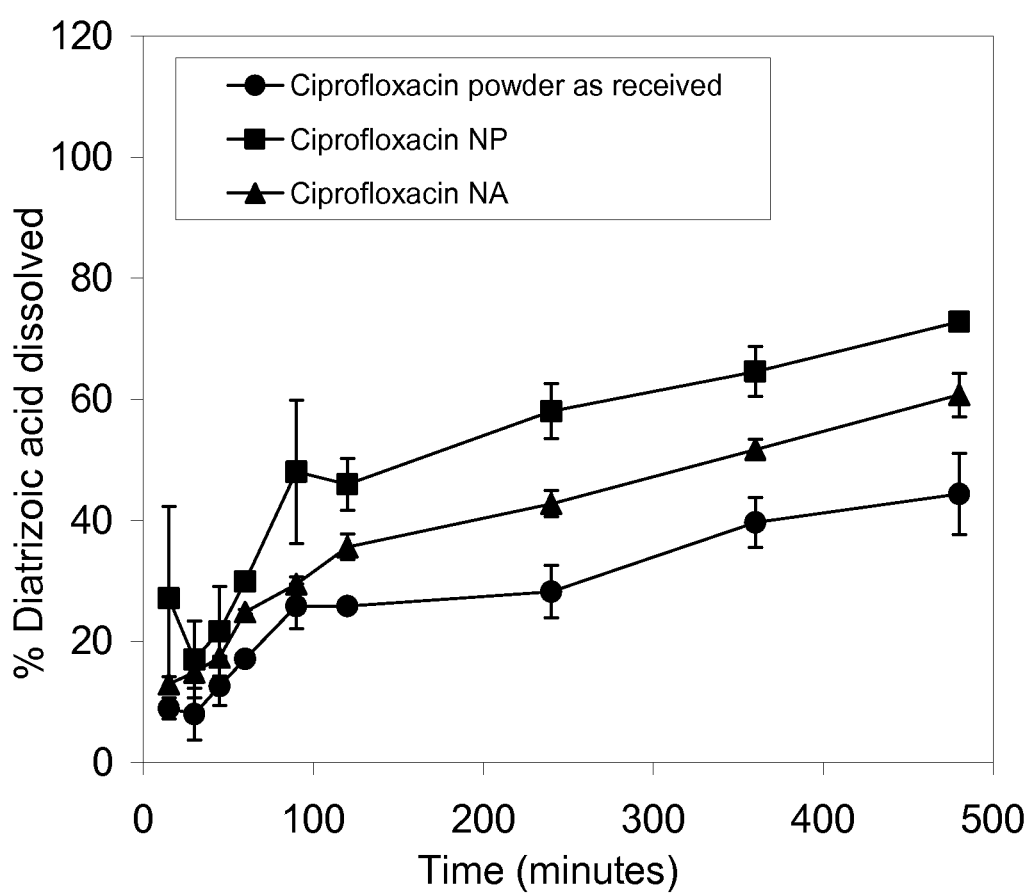

FIG. 45. Dissolution profiles of Ciprofloxacin in PBS (pH 7.4) from Ciprofloxacin powder as received as well as the prepared C1 nanoparticle (NP) and nanoparticle agglomerate formulation (NA).

Figure 47:
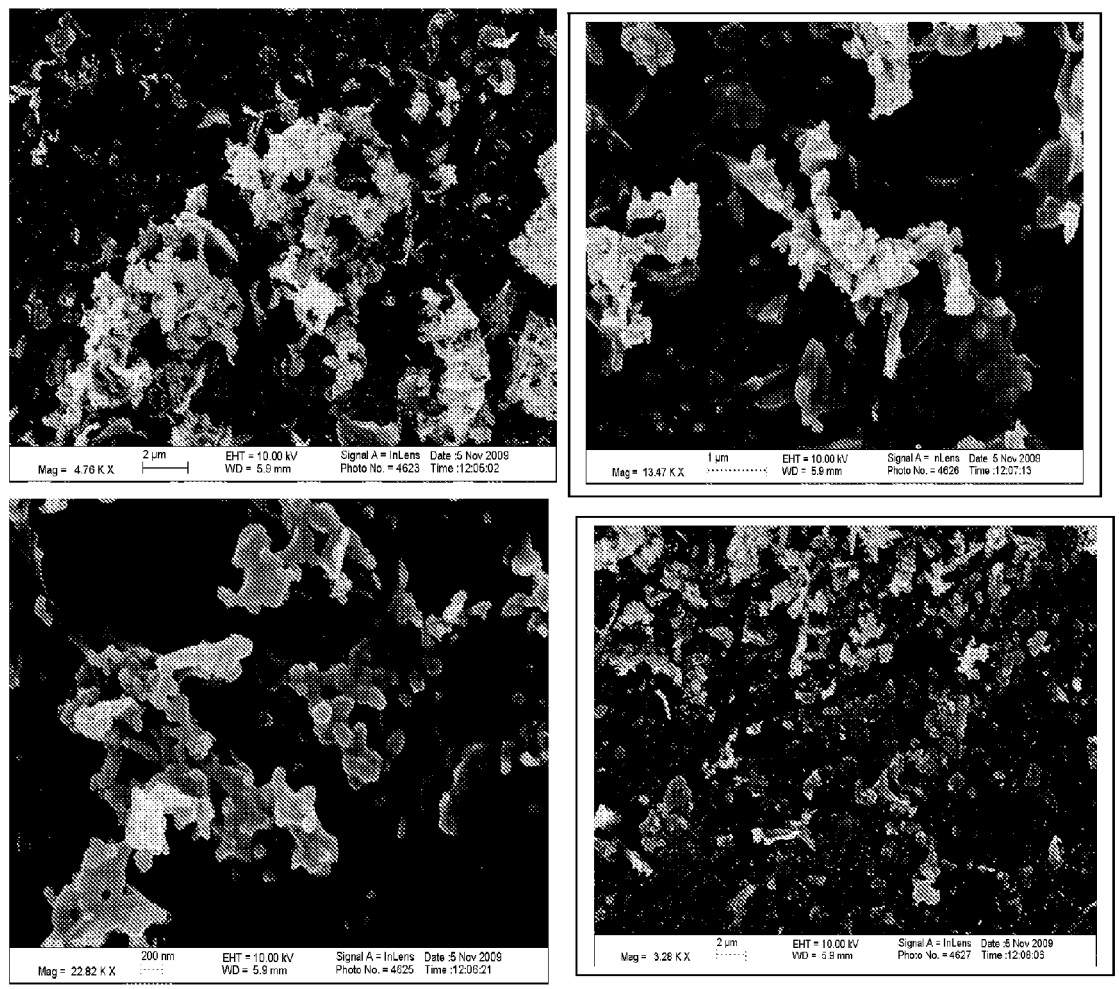
Figure 48:
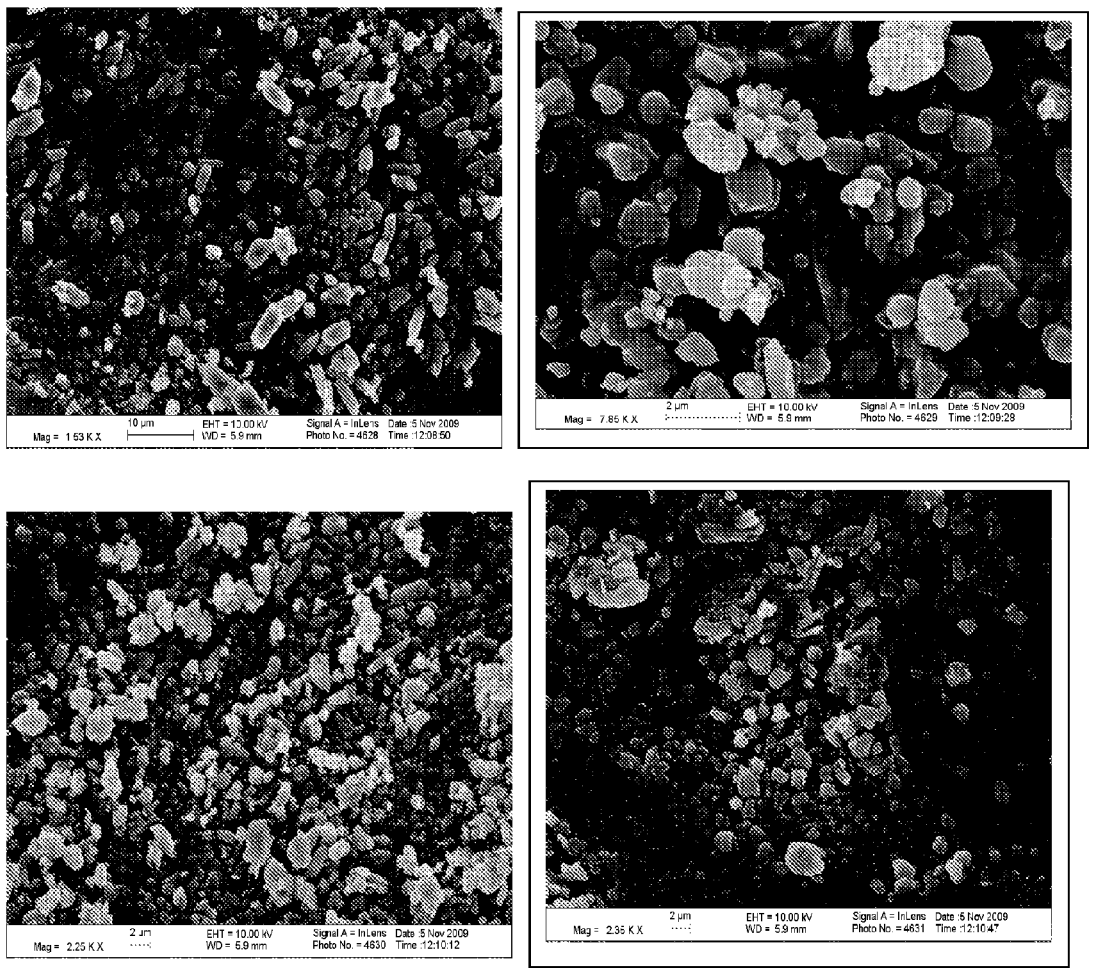
Figure 49:
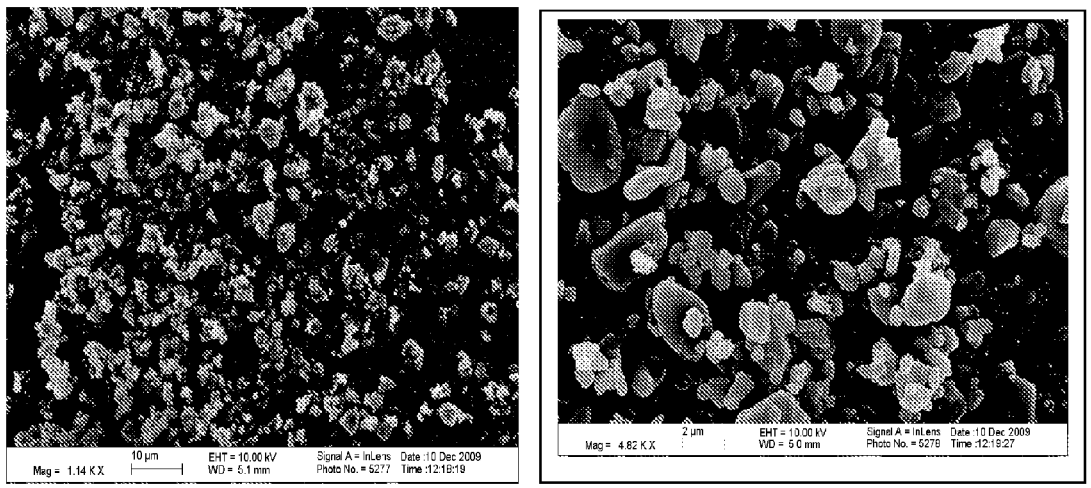
Figure 50:
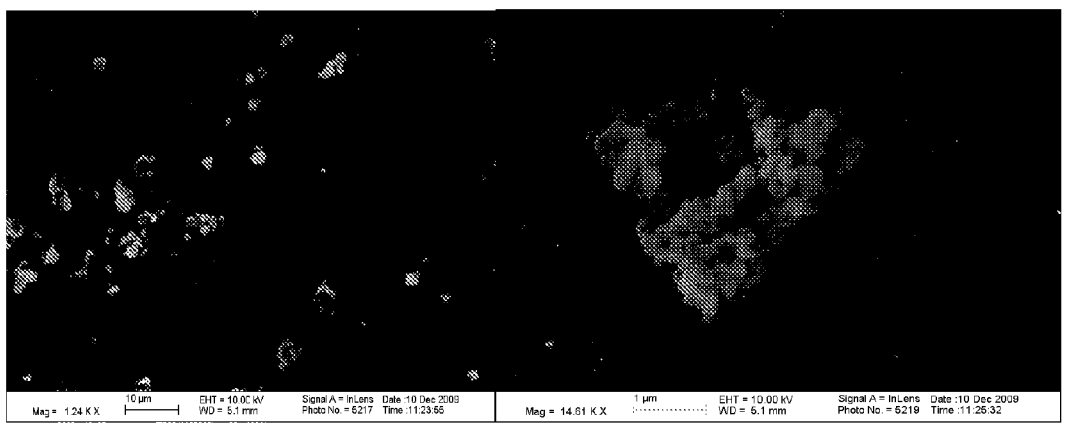
Figure 51:
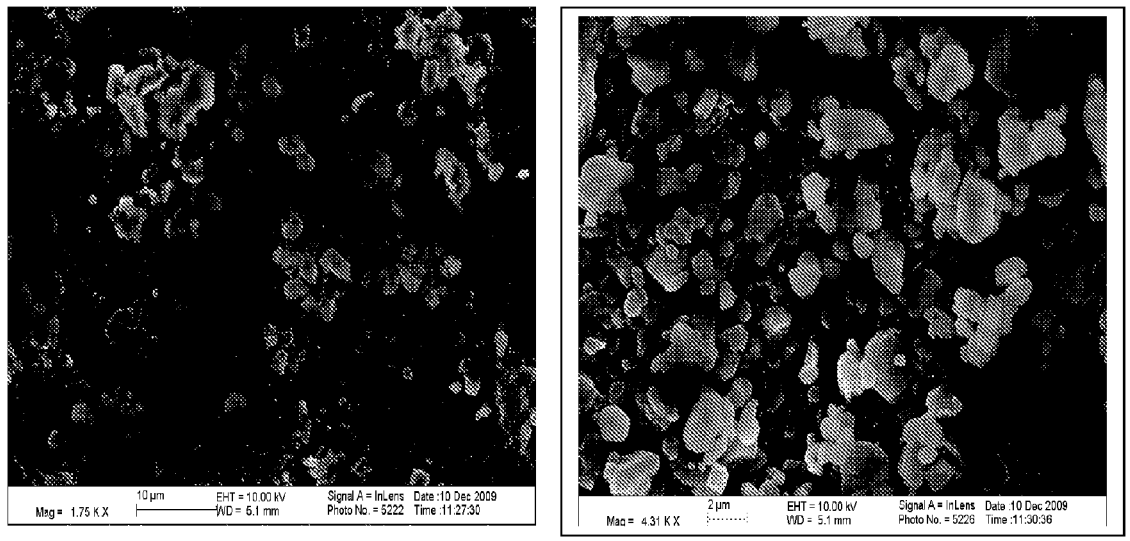
Figure 52:
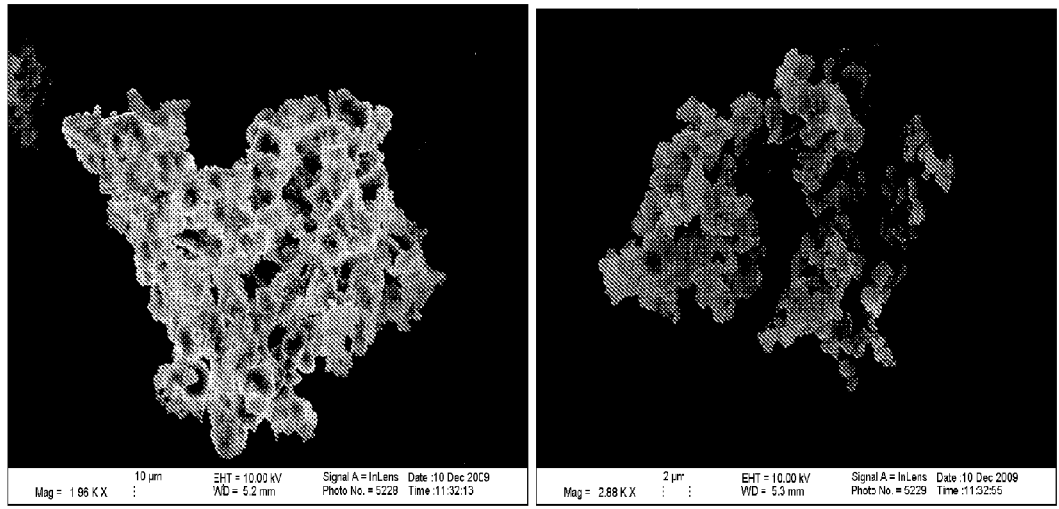
Figure 53:
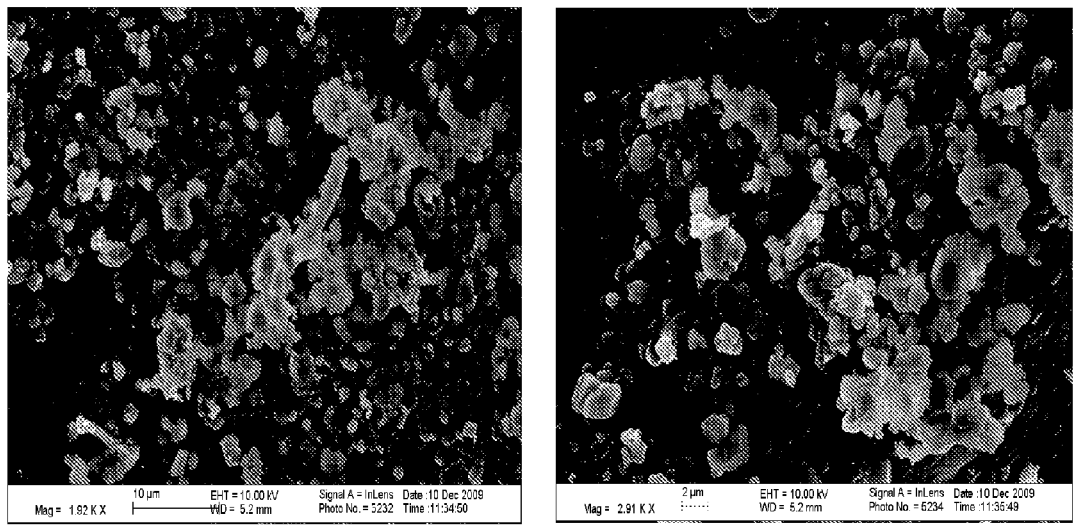
Figure 54:
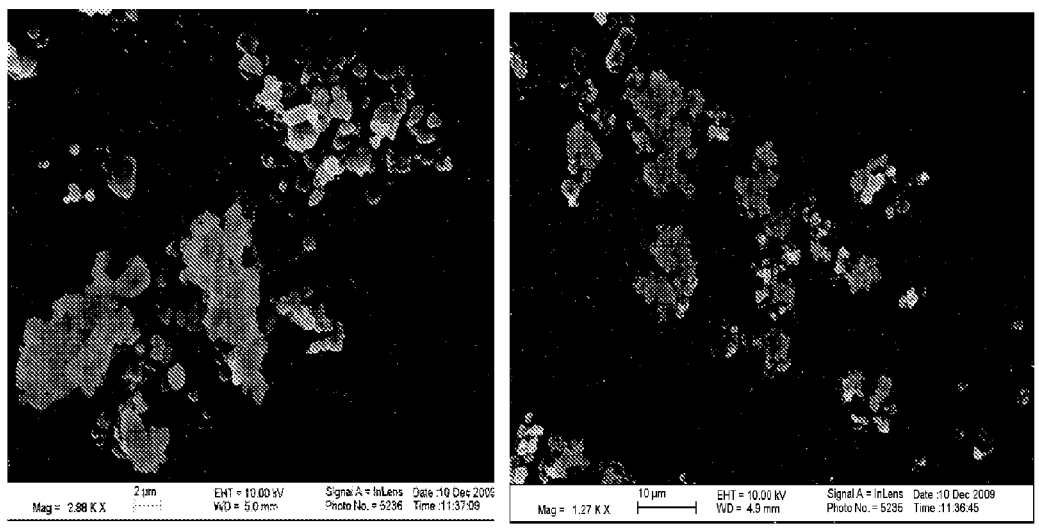
Figure 55:
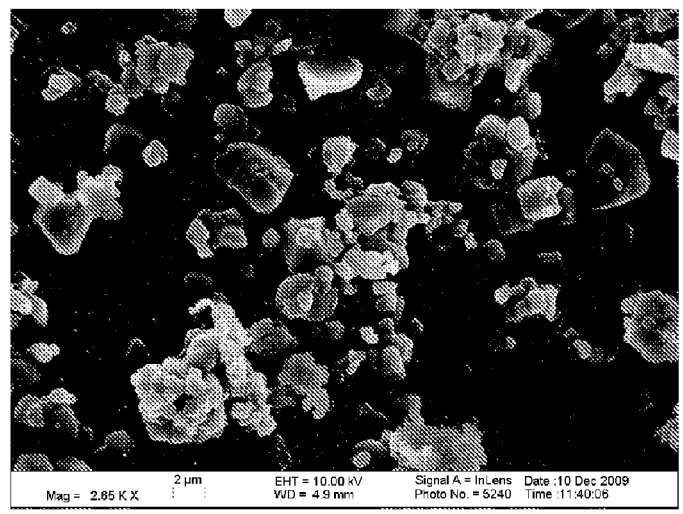
Figure 56:
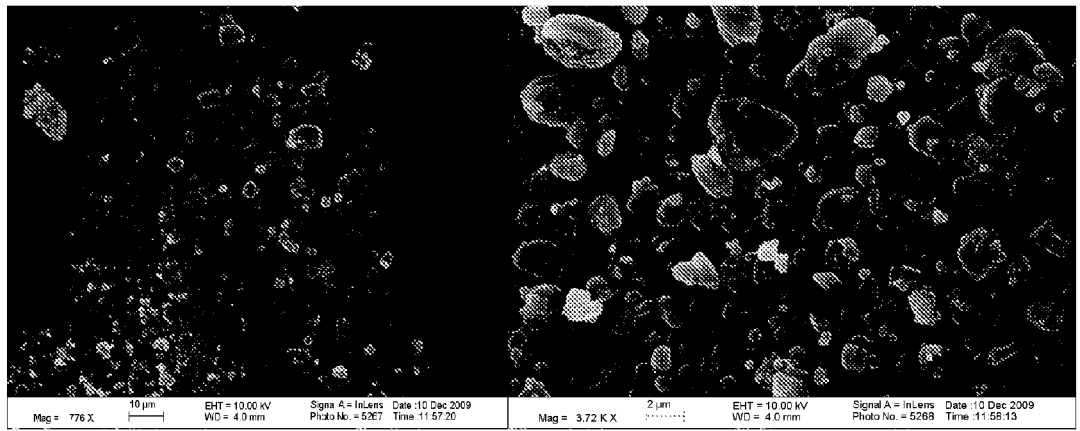
Figure 60:
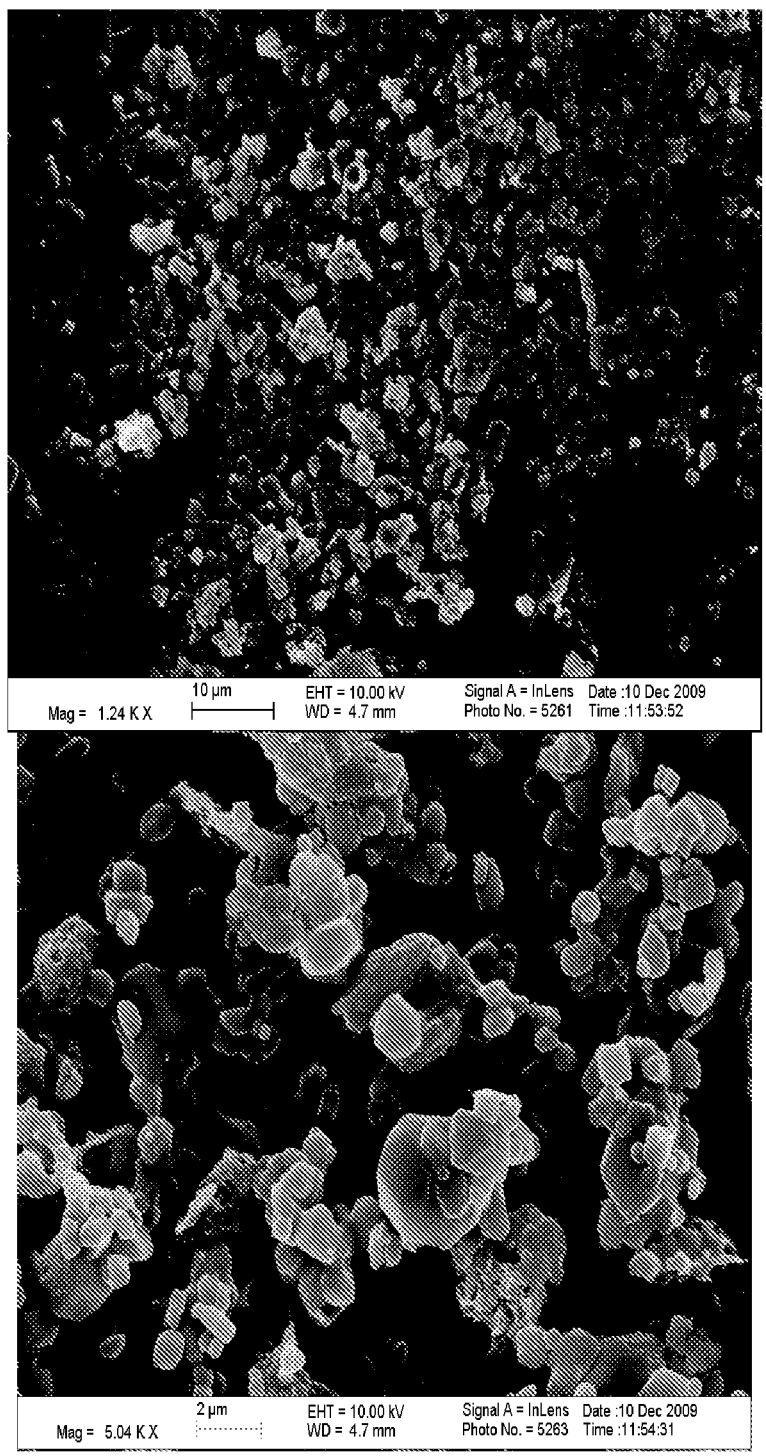

FIG. 46. Rifampicin as received.
FIG. 47. Rifampicin/acetone/water system.
FIG. 48. Rifampicin/ethanol/water system.
FIG. 49. Drug as received.
FIG. 50. SEM of SV 4-7.
FIG. 51. SEM of SV 5-7.
FIG. 52. SEM of SV 3-3.5.
FIG. 53. SEM of SV 4-3.5.
FIG. 54. SEM of SV 2-3.5.
FIG. 55. SEM of LV 2-3.5.
FIG. 56. SEM of LV 2-3.5/1% Lecithin.
FIG. 57. SEM of LV 2-3.5/0.1% oleic acid.
FIG. 58. SEM of SV 2-3.5/0.3% L-leucine.
FIG. 59. SEM of SV 2-3.5/0.7% L-leucine.
FIG. 60. SEM of SV 2-3.5/1% L-leucine.
FIG. 61. SEM of SV 2-3.5/0.3% Lactose.
FIG. 62. SEM of SV 2-3.5/0.7% Lactose.
FIG. 63. SEM of SV 2-3.5/1% Lactose.

Figure 64:
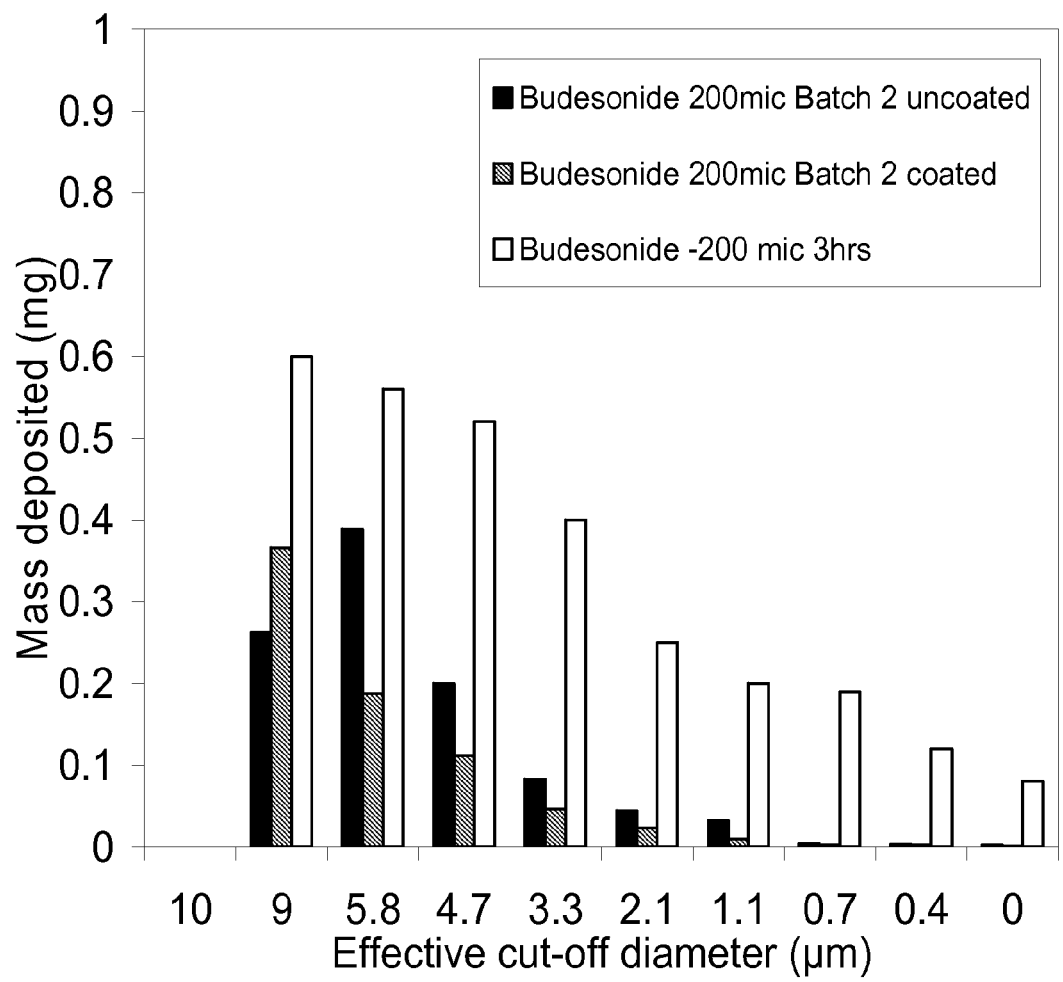

FIG. 64. The aerodynamic size distribution of budesonide NanoCluster powder of Batch 2 (200 mic), milled for 3 hours, at a rate of 30 L/min using Spinhaler and low feed.

Figure 65:
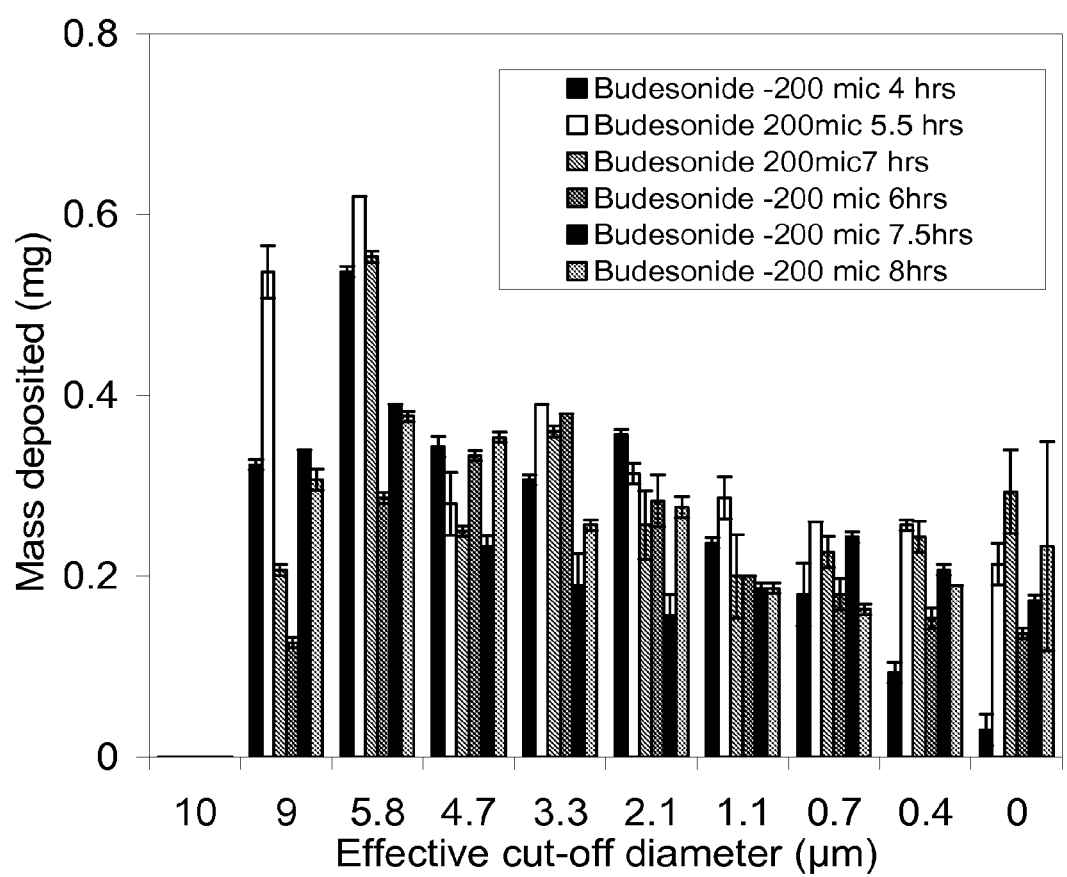

FIG. 65. The aerodynamic size distribution of budesonide NanoCluster powder of Batch 3 (200 mic), milled for 8 hours, at a rate of 30 L/min using Spinhaler and low feed.

Figure 67:
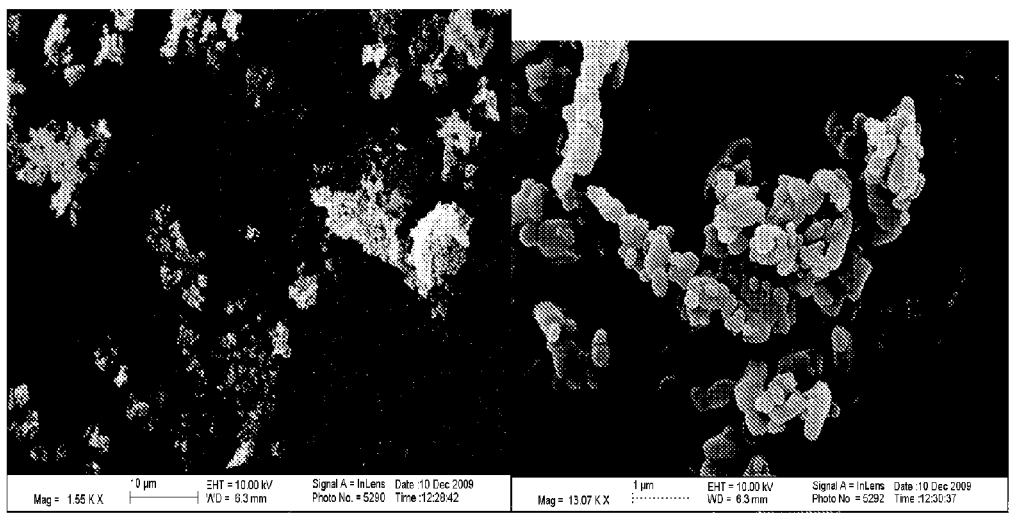
Figure 68:
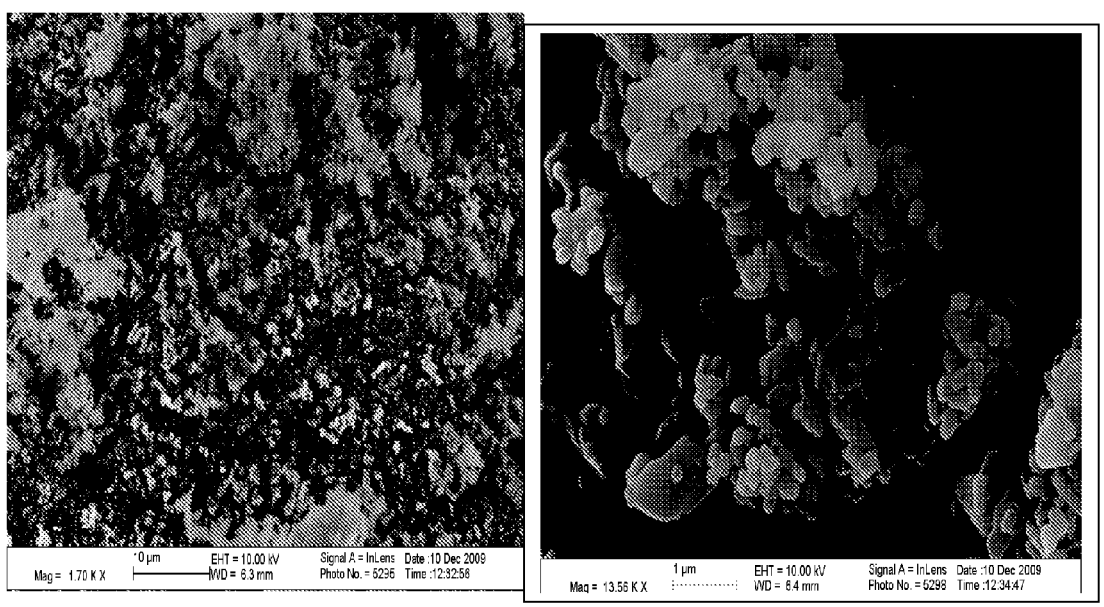
Figure 69:
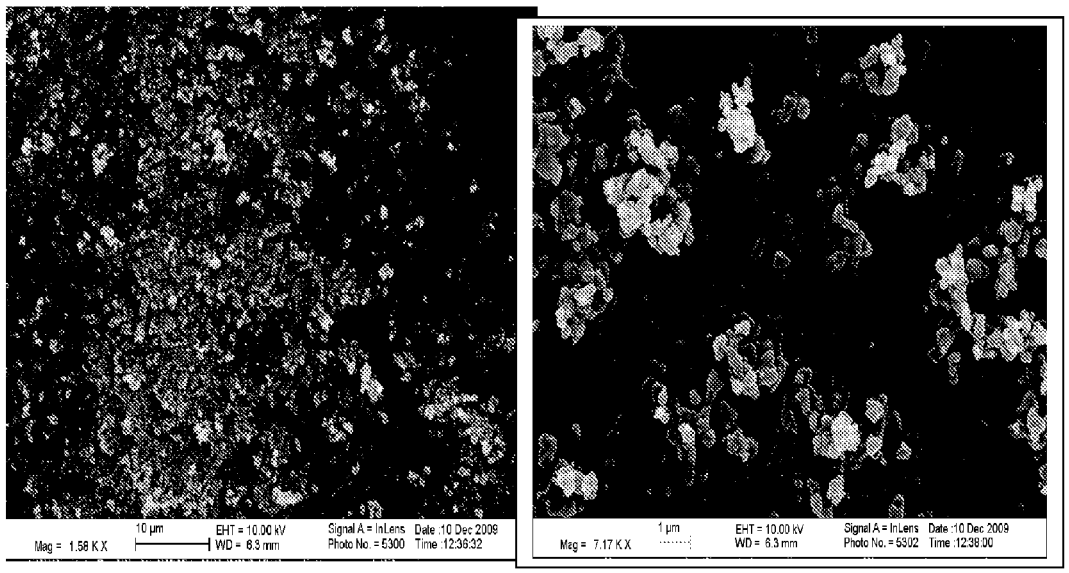
Figure 70:
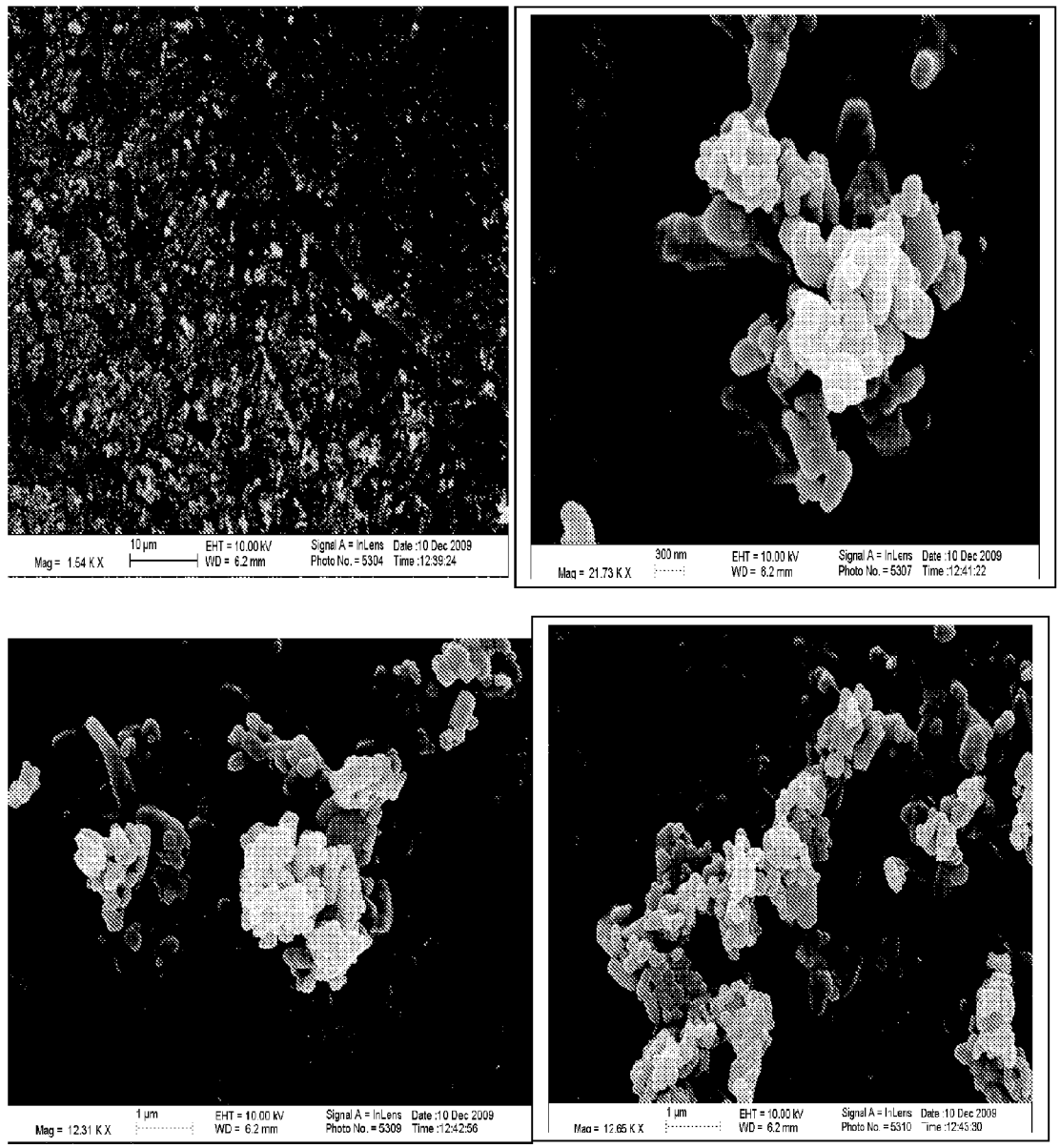
Figure 71:
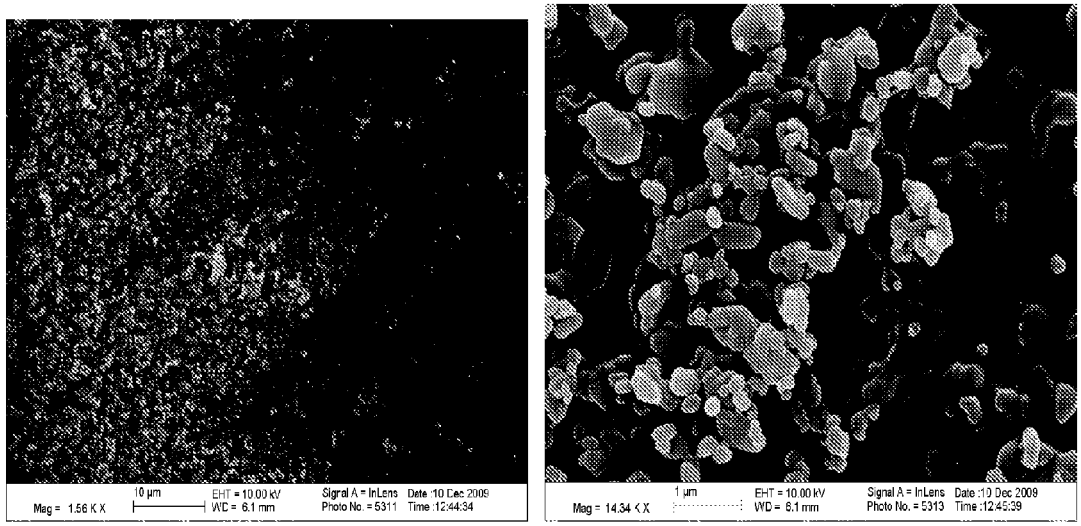
Figure 72:
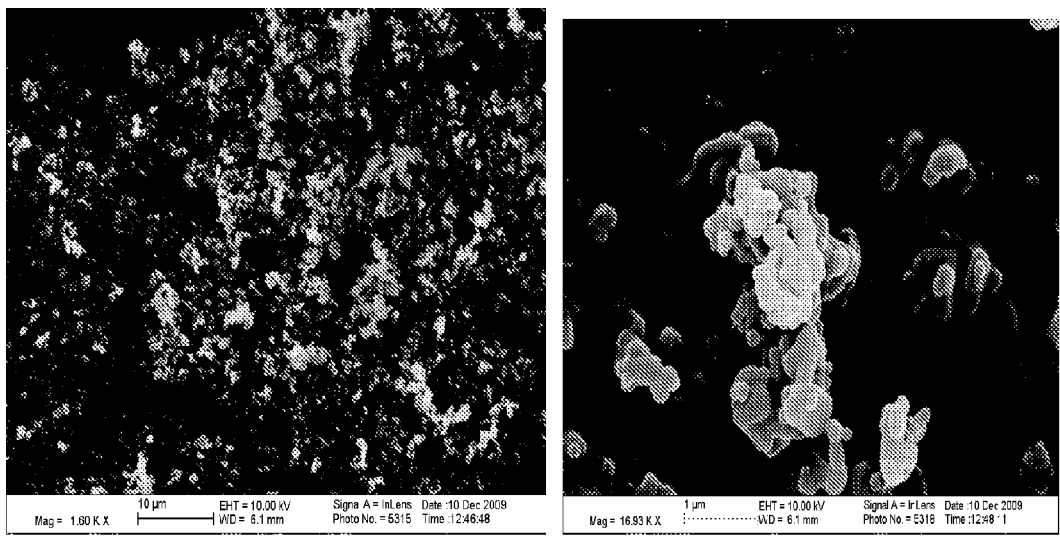
Figure 73:
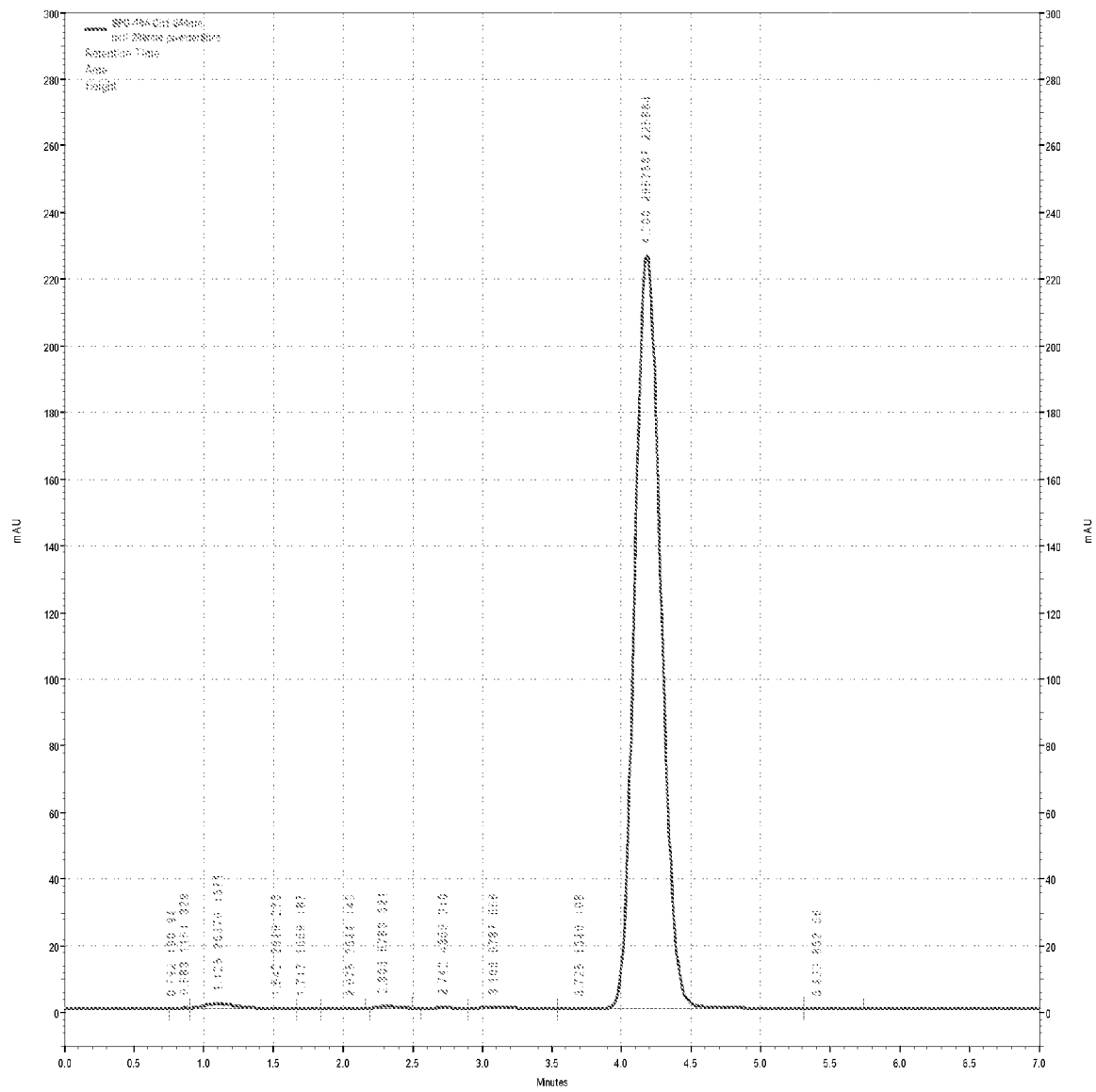
Figure 74:
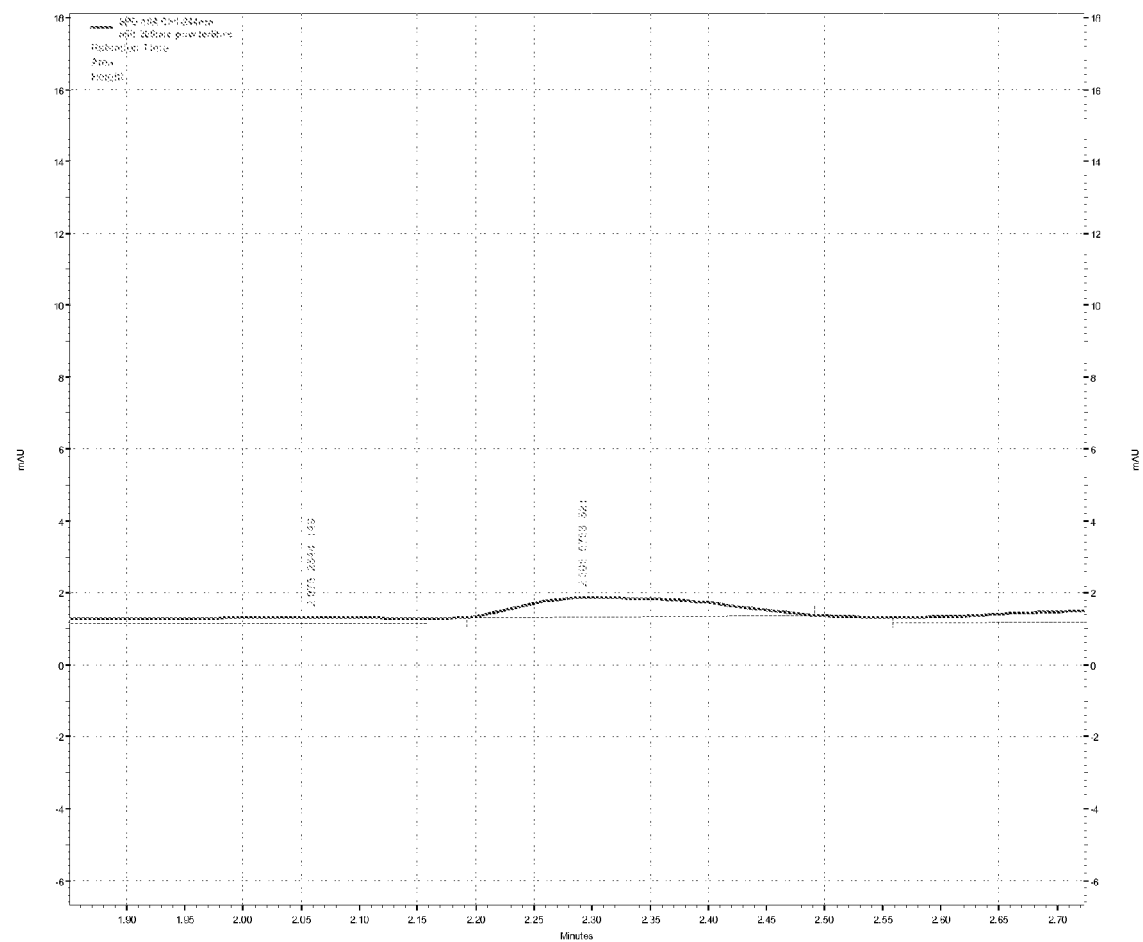
Figure 75:
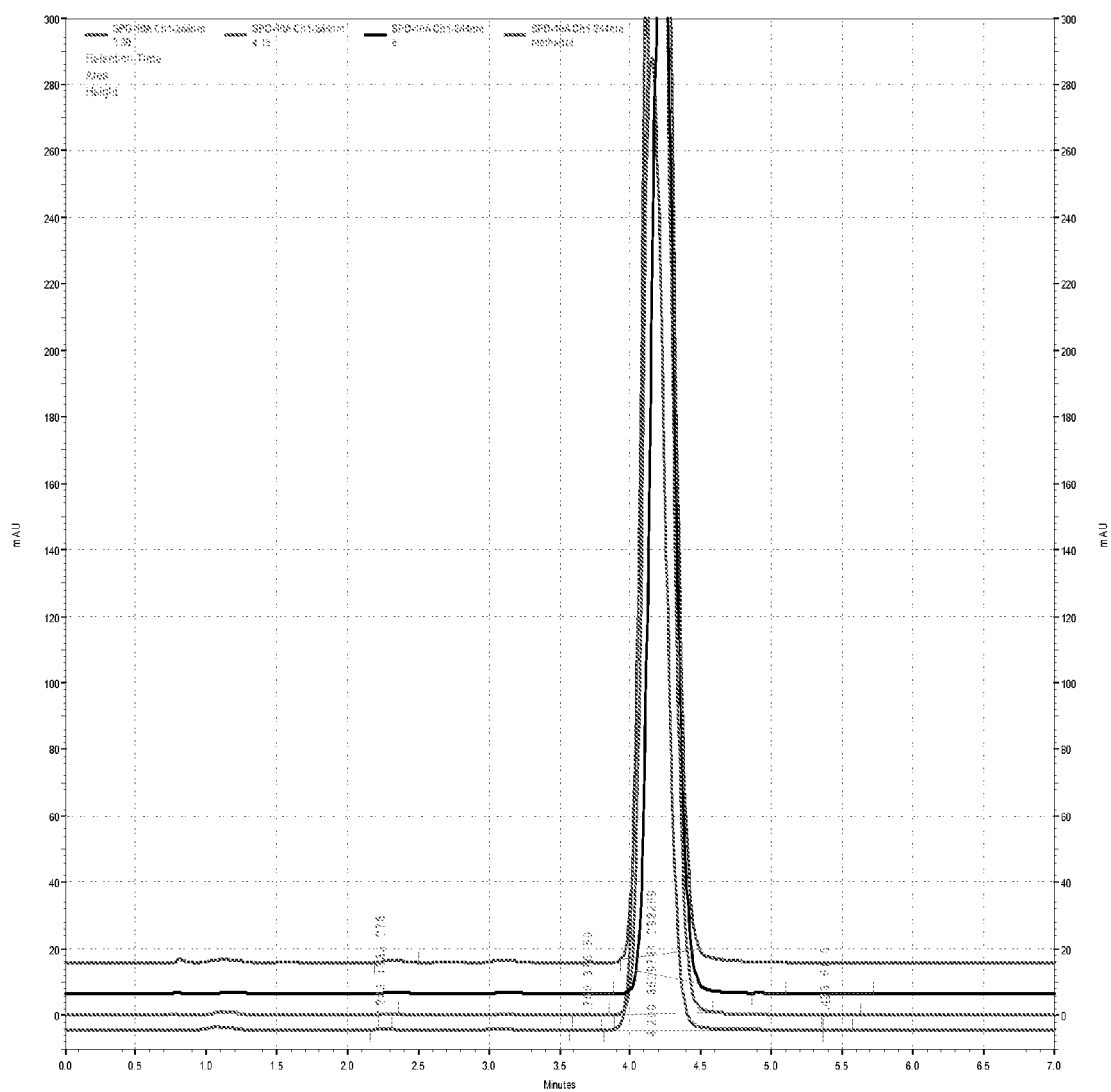
Figure 76:
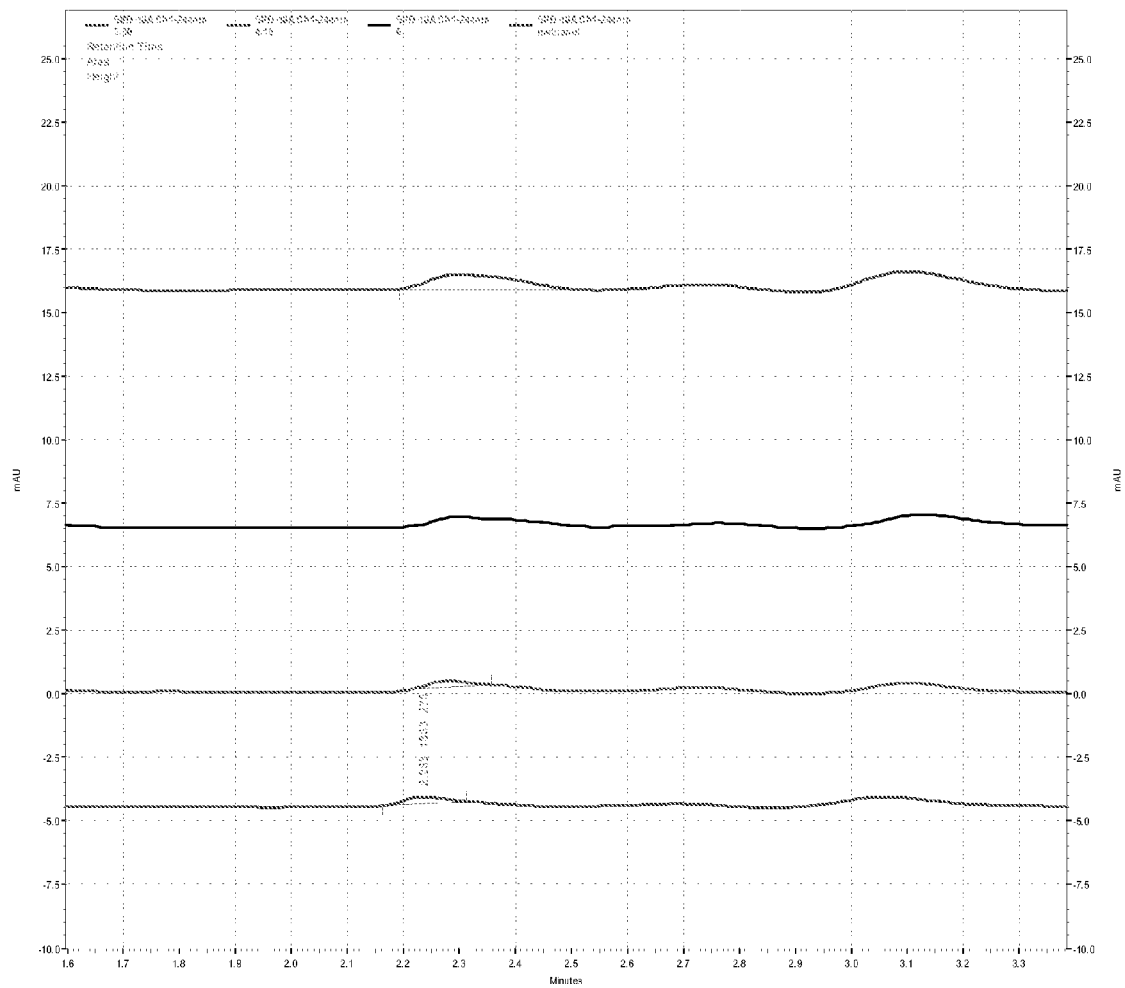
Figure 77:
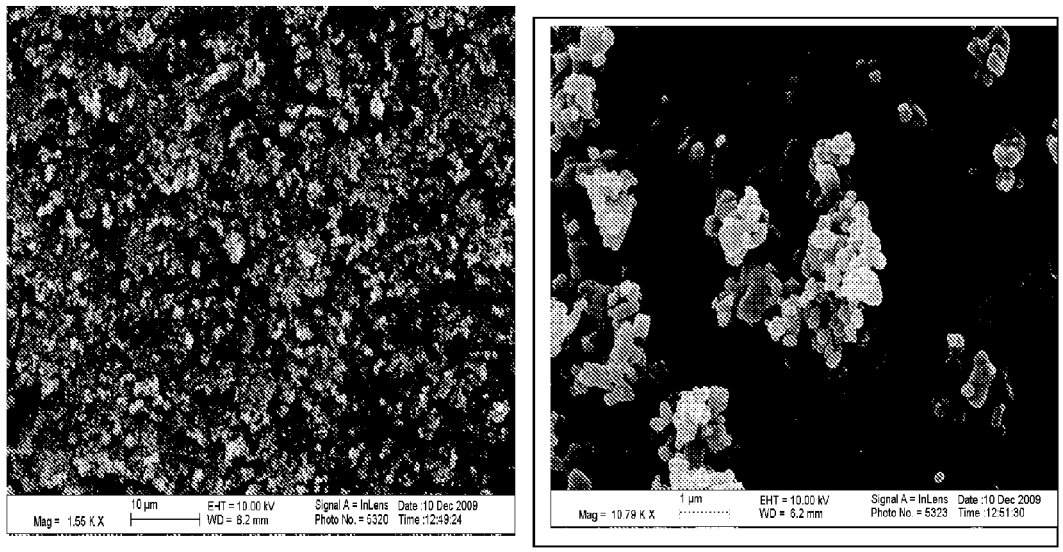
Figure 78:
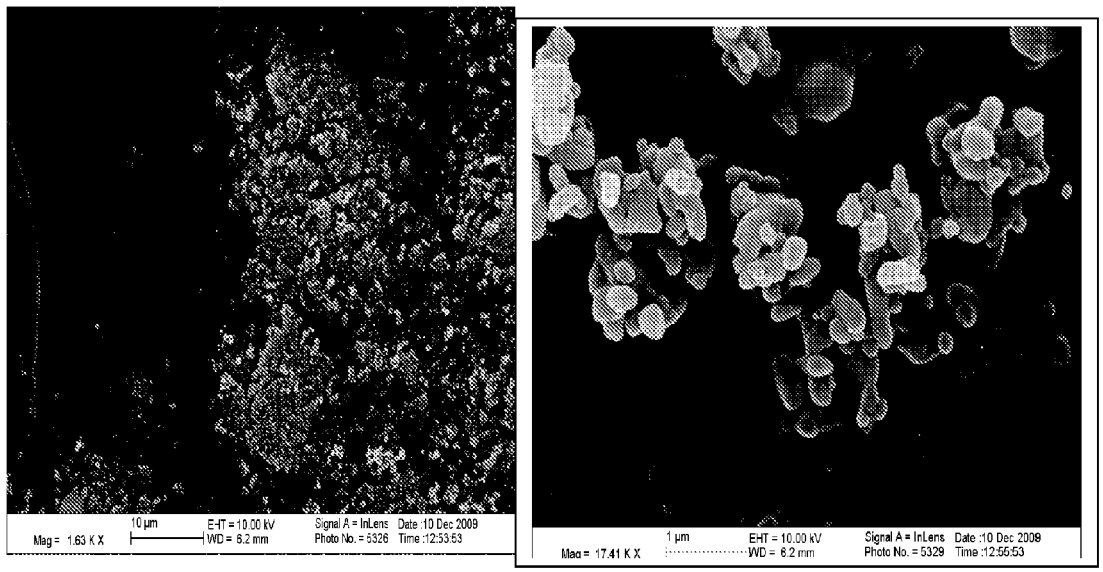
Figure 80:
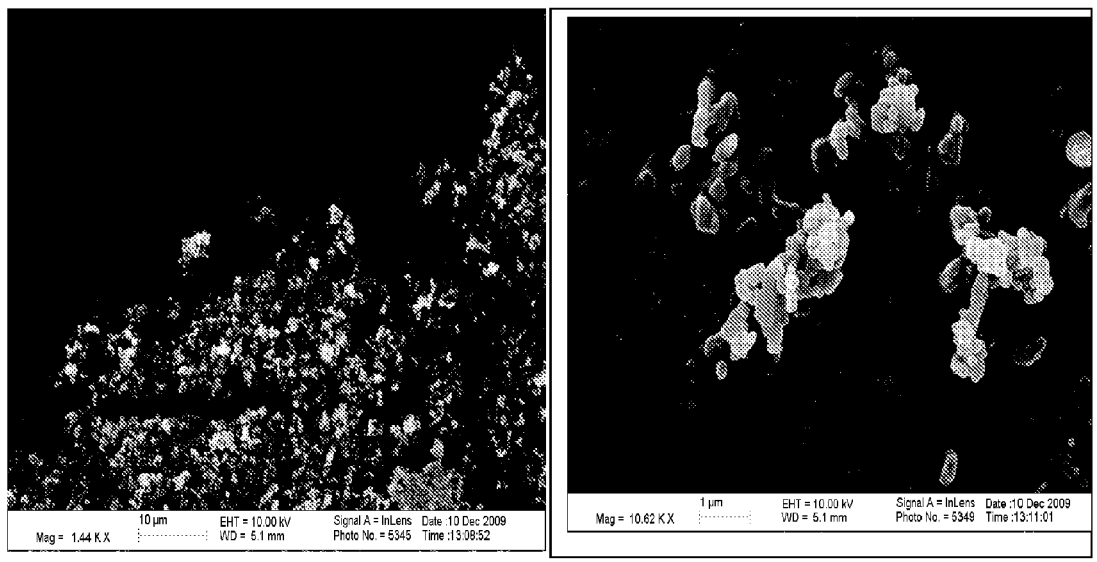

FIG. 66. SEM of milling with 200 micron media for 5 hrs.
FIG. 67. SEM of milling with 200 micron media for 5.5 hrs.
FIG. 68. SEM of milling with 200 micron media for 6 hrs.
FIG. 69. SEM of milling with 200 micron media for 6.5 hrs.
FIG. 70. SEM of milling with 200 micron media for 7 hrs.
FIG. 71. SEM of milling with 200 micron media for 7.5 hrs.
FIG. 72. SEM of milling with 200 micron media for 8 hrs.
FIG. 73. HPLC assay of 200 micron media batch 3 after 8 hrs milling.
FIG. 74. Focusing on the degradation peak of the samples.
FIG. 75. HPLC assay of 200 micron media batch 4 (the name methanol is sample at 10 hrs).
FIG. 76. Focus on the degradation peaks of 200 micron media batch 4 (the name methanol is sample at 10 hrs).
FIG. 77. Milling with 200 micron media for 9 hrs.
FIG. 78. Milling with 200 micron media for 10 hrs.
FIG. 79. Milling with 200 micron media for 10 hrs/0.3% w/w lactose.
FIG. 80. Milling with 200 micron media for 10 hrs/1% w/w lactose.
FIG. 81. Milling with 200 micron media for 10 hrs/0.3% w/w leucine.
FIG. 82. Milling with 200 micron media for 10 hrs/1% w/w leucine.
FIG. 83. Stability results for Concentration: 0.4 mg/ml at Time: 0 min.
FIG. 84. Stability results for Concentration: 0.4 mg/ml at Time: 1 hr.
FIG. 85. Stability results for Concentration: 0.4 mg/ml at Time: 4 days.
FIG. 86. Stability results for Concentration: 0.2 mg/ml at Time: 0 min.
FIG. 87. Stability results for Concentration: 0.2 mg/ml at Time: 3 days.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present disclosure relates to the delivery of therapeutic and diagnostic agents, and more particularly, in certain embodiments, to a nanocluster drug delivery platform.

Current drug delivery treatment options can often be ineffective due to inefficient delivery of an active ingredient to a targeted site. Many of the current drug delivery systems are limited in their ability or efficiency to access a specifically targeted site. Although nanoparticles offer several advantages for delivering drugs (e.g. improved dissolution of low solubility API, intracellular and transcellular transport, etc.), the use of nanoparticles, for example, can be hindered by the inability to deliver nanoparticles to the site of drug action (e.g. dried nanoparticles are too small to deposit efficiently in the lungs, can avoid detection by APCs, etc.). In addition, nanoparticles are often difficult to handle at an industrial scale and a controlled clustering process may ease handling and allow facile reconstitution and formulation of nanoparticles or nanoclusters for delivering drugs.

The nanoclusters of the present invention can be used to deliver active ingredients to a targeted site. The size and distribution of the disclosed nanoclusters can be designed for a desired route of administration and/or for the treatment of a particular disease or condition. In one aspect, for example, the nanoclusters provide an effective and efficient drug delivery system that can carry active ingredients to a targeted site via the nanocluster. In certain aspects, a nanocluster is maintained at the targeted site. In other aspects, a nanocluster can disperse the active ingredient at the targeted site. Additionally, the nanoclusters can be formulated with the appropriate properties to carry and controllably release active ingredients to a targeted site.

Nanoclusters

In general, the nanoclusters of the present disclosure comprise a plurality of nanoparticles having a core of nanoparticles arranged such that the surface of the nanoparticles contact one another to form a three dimensional structure, the nanoparticles may comprise a therapeutic or diagnostic agent. The nanoclusters of the present disclosure, among other things, provide the advantage of particle clusters appropriately sized for delivery of an active ingredient (e.g., lung, nasal passage, M-cells in the digestive tract, uptake by antigen presenting cells, etc.) with the benefits of improvements in, for example, drug solubility, aerosolization, bioavailability, transport through biological barriers, and intracellular delivery.

In certain embodiments, a nanocluster of the present disclosure may include an excipient. Excipients and the use of excipients are well known in the art. Excipients may be used as, among other things, dispersing agents, agglomerating agents, filling agents, buffering agents, and the like. Examples of suitable excipients include, but are not limited to, salts, amino acids, phospholipids, sugar alcohols, surfactants, and the like.

In certain embodiments, a nanocluster of the present disclosure may include nanoparticles from about 1% to about 99% by weight or volume. The nanocluster also may be completely made up of nanoparticles (i.e., 100%).

In certain embodiments, a nanocluster may have a mass median aerodynamic diameter of from about 0.25 μm to about 20 μm. In other embodiments a nanocluster may have a mass median aerodynamic diameter of from about 0.5 μm to about 10 μm. In other embodiments a nanocluster may have a mass median aerodynamic diameter of from about 3 μm to about 20 μm. In certain embodiments a nanocluster may have a mass median aerodynamic diameter of from about 0.5 μm to about 3 μm.

In certain embodiments, a nanocluster of the present disclosure has a mass median geometric diameter that is greater than the mass median aerodynamic diameter, as these particles have low bulk density.

In general, nanoclusters of the present disclosure are non-spherical and offer a non-continuous surface with irregular shape.

Nanoparticles

Nanoparticles are particles having features on a nanometer scale such as facets, cubes, angles, and the like. Conceptually, nanoclusters may be described as comprising nanoparticles; however, that is not to imply that the nanoclusters may only be formed by separate nanoparticles. Nanoclusters may be formed without first forming independently stable nanoparticles. In certain embodiments, a nanoparticle is a particle whose effective diameter measures less than 1,000 nm.

In general, the nanoparticles comprise a therapeutic or diagnostic agent (i.e., an active ingredient).

In general, the active ingredient is associated with the nanoparticle. For example, the active ingredient may be entangled, embedded, incorporated, encapsulated, bound to the surface, or otherwise associated with the nanoparticle. In other examples, the nanoparticle comprises an active ingredient such as a pure drug (e.g., drugs processed by crystallization or supercritical fluids, an encapsulated drug (e.g., polymers), a surface associated drug (e.g., drugs that are absorbed or bound to the nanoparticle surface), complexed drugs (e.g., drugs that are associated with the material used to form the nanoparticle). In certain embodiments, the nanoparticle consists essentially of active ingredient. The nanoparticles may have any type of structure.

In certain embodiments, a plurality of nanoparticles is capable of agglomerating together such that the surfaces of the nanoparticles effectively contact one another. Such agglomeration may occur through noncovalent interactions, such as van der Waals forces, hydrophobic interactions, Coulombic forces, and the like.

In addition to an active ingredient, the nanoparticles may include other materials, such as any organic or inorganic materials suitable for biological applications. Examples of these materials include, but are not limited to, surfactants, phospholipids, sugar alcohols, poly(orthoesters), poly(anhydrides), poly(phosphoesters), poly(phosphazenes), poly(lactic-co-glycolic acid) (PLGA), polyesters (such as poly(lactic acid), poly(L-lysine), poly(glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), copolymers of these monomers and the like), poly(anhydride-co-imides), poly(amides), poly(ortho esters), poly(iminocarbonates), poly(urethanes), poly(organophasphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, copolymers, polystyrene, and blends or co-polymers thereof. In certain embodiments, the nanoparticles include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, and the like, and their derivatives, co-polymers, and mixtures thereof. In certain embodiments the nanoparticles may include any inactive ingredient that is generally regarded as safe.

Active ingredients may include, but are not limited to, any component, compound, or small molecule that can be used to bring about a desired effect. Non-limiting examples of desired effects of the present invention include diagnostic and therapeutic effects. For example, a desired effect can include the diagnosis, cure, mitigation, treatment, or prevention of a disease or condition. An active ingredient may also affect the structure or function of body part or organ in a subject.

Active ingredients are known to those skilled in the art. Examples of active ingredients that may be used with the nanoclusters of the present disclosure include, but are not limited to, medical pharmaceuticals and specialties such as preventive agents, for example vaccines, diagnostic agents, for example tracers of various types and imaging enhancers, therapeutic agents, for example small molecules (e.g., nucleic acids, proteins, peptides, polypeptides, etc.), drugs, peptides, and radiation, immuno-modulators, vaccine and virus vectors, and combinations of these classes. Other suitable active ingredients include respirable non-medical specialties such as physiochemical agents, for example gas antidotes, biophysical modulators, for example paramagnetics, radioactive compounds for imaging, emitters, for example electromagnetic wave emitters, and imaging enhancers.

In certain embodiments, a nanocluster may include more than one active ingredient. For example, a nanocluster may include any combination of therapeutic agents or diagnostic agents, alone or in combination. For example, a nanocluster may include both a therapeutic agent and a diagnostic agent.

Examples of suitable active ingredients which may be included in the nanoclusters of the present disclosure include, but are not limited to, nucleic acids, proteins and peptides, hormones and steroids, chemotherapeutics, antineoplastic agents, NSAIDs, vaccine components, analgesics, antibiotics, CNS agents (e.g., anti-depressants, atypical antipsychotics, and benzodiazepines), calcium ion channel blockers (e.g., nifedipine), H1 antagonists (e.g., loratadine), and the like.

Examples of suitable nucleic acids that may be used include, but are not limited to, DNA, cDNA, RNA, iRNA, siRNA, anti-sense nucleic acid, peptide-nucleic acids, oligonucleotides, or nucleic acids that are modified to improve stability (e.g., phosphorothioates, aminophosphonates or methylphosphonates).

Examples of proteins and peptides that may be used include, but are not limited to, human growth hormone, bovine growth hormone, vascular endothelial growth factor, fibroblast growth factors, bone morphogenic protein, tumor necrosis factors, erythropoietin, thrombopoietin, tissue plasminogen activator and derivatives, insulin, monoclonal antibodies (e.g., anti-human epidermal growth factor receptor2 (Herceptin® (trastuzumab), anti-CD20 (rituximab), anti-CD 18, anti-vascular endothelial growth factor, anti-IgE, anti-CD 11a), and their derivatives, single-chain antibody fragments, human deoxyribonuclease I (domase alfa, Pulmozyme®), type-1 interferon, granulocyte colony-stimulating factor, leuteinizing hormone releasing hormone inhibitor peptides, leuprolide acetate, endostatin, angiostatin, porcine factor VIII clotting factor, interferon alfacon-1, pancrelipase (pancreatic enzymes), ovalbumin, and the like.

Examples of hormones and steroids (e.g., corticosteroids) that may be used include, but are not limited to, norethindrone acetate, ethinyl estradiol, progesterone, estrogen, testosterone, prednisone and the like.

Examples of antineoplastic agents that may be used include, but are not limited to, taxol (paclitaxel), vinblastine, cisplatin, carboplatin, tamoxifen, retanoids, enzyme inhibitors (e.g., COX, VEGF), and the like.

Examples of non-steroidal anti-inflammatory drugs (NSAIDs) that may be used include, but are not limited to, piroxicam, aspirin, salsalate (Amigesic®), diflunisal (Dolobid®), ibuprofen (Motrin®), ketoprofen (Orudis®), nabumetone (Relafen®), piroxicam (Feldene®), naproxen (Aleve®, Naprosyn®), diclofenac (Voltaren®), indomethacin (Indocin®), sulindac (Clinoril®), tolmetin (Tolectin®), etodolac (Lodine®), ketorolac (Toradol®), oxaprozin (Daypro®), and celecoxib (Celebrex®), and the like.

Examples of vaccine components that may be used include, but are not limited to, Hepatitis B, polio, measles, mumps, rubella, HIV, hepatitis A (e.g., Havrix), tuberculosis, and the like.

Examples of analgesics that may be used include, but are not limited to, aspirin, acetaminophen, ibuprofen, naproxen sodium, and the like.

Examples of antibiotics that may be used include, but are not limited to, amoxicillin, penicillin, sulfa drugs, erythromycin, streptomycin, tetracycline, clarithromycin, tobramycin, ciprofloxacin, terconazole, azithromycin, and the like.

Examples of anti-depressants that may be used include, but are not limited to, sertraline (Zoloft®), fluoxetine (Prozac®), paroxetine (Paxil®), citalopram, venlafaxine, fluvoxamine maleate, imipramine hydrochloride, lithium, nefazodone and the like.

Other examples of active ingredient that can be used that may be used include, but are not limited to, sildenafil, acyclovir, gancyclovir, fexofenidine, celecoxib, rofecoxib, androstenedione, chloroquine, diphenhydramine HCl, buspirone, doxazocin mesylate, loratadine, clomiphine, zinc gluconate, zinc acetate, hydrocortisone, warfarin, indinavir sulfate, lidocaine, novacaine, estradiol, norethindrone acetate, medroxyprogesterone, dexfenfluramine, dextroamphetamine, doxycycline, thalidomide, fluticasone, fludarabine phosphate, etanercept, metformin hydrochloride, hyaluronate, tetrazocin hydrochloride, loperamide, ibogaine, clonazepam, ketamine, lamivudine (3TC), isotretinoin, nicotine, mefloquine, levofloxacin, atorvastatin (LipitorZoloft), miconazole nitrate (MonistatZoloft), ritonavir, famotidine, simvastatin, sibutramine HCl monohydride, ofloxacin, lansoprozole, raloxifene, zanamivir, oseltamivir phosphate, 4-phenylbutyric acid sodium salt, chlorpromazine, nevirapine, zidovudine, and cetirizine hydrochloride.

Non-limiting examples of additional active ingredients can be found in Physician's Desk Reference 64th Edition, all of which are incorporated by reference.

Nanocluster Formulation Variables and Tunability

As mentioned above, the nanoclusters of the present disclosure may have various sizes. The size of a particular nanocluster may depend on, among other things, the nanoparticle type and/or size, excipients, and processing conditions. For example, varying processing conditions can be used to create nanoclusters with a broad or narrow size range. Controlling the droplet size in an emulsion, suspension, or solution sprayed from a nozzle can facilitate the formation of uniform nanoclusters. Varying the solvent and extraction phase, temperature, humidity, and other conditions, as well as the properties of the nanoparticles, can control the morphology of the nanocluster. Shear also may be used to control the morphology (e.g., size and/or shape) of nanoclusters. Varying processing times (e.g., hold times) also may lead to, for example, larger or smaller nanoclusters.

The tunability of the size of the nanocluster may be beneficial in several applications. For example, broadening the size distribution may improve the flow properties of a powder, thus facilitating manufacturing. Having a narrow distribution with a mass median aerodynamic size range of about 0.5 to about 3 micrometers may be useful in the delivery of drugs via the inhalation route to the distal lung. Changing the median aerodynamic size may favor deposition in a particular region of the pulmonary system. Optimizing the size and distribution of the nanocluster to achieve optimum dissolution, compactability, and strength of tablet formulations may be useful in the development of tablets for oral route of administration.

Methods for Preparing Nanoclusters

The present disclosure provides, in certain embodiments; methods for preparing a nanoclusters. In general, such methods comprise forming a nanocluster comprised of a core of nanoparticles arranged such that the surface of the nanoparticles contact one another, wherein the nanocluster has a mass median aerodynamic diameter of from about 0.25 μm to about 20 μm.

In certain embodiments, the nanoclusters may be formed using post-processing agglomeration followed by recovery of nanoclusters. In other embodiments, the nanoclusters may be formed using in-processing agglomeration followed by recovery of nanoclusters. Post-processing agglomeration generally comprises providing a colloidal dispersion of nanoparticles, agglomerating the nanoparticles, and recovering the nanoclusters. In-processing agglomeration generally comprises processing an active ingredient under conditions such that an agglomerate forms, where such agglomerate is already a nanocluster or from which a nanocluster may be recovered.

Post-Processing Agglomeration

As mentioned above, post-processing agglomeration generally comprises providing a colloidal dispersion of nanoparticles and agglomerating the nanoparticles.

In certain embodiments, the colloid dispersion of nanoparticles may be formed using attrition (e.g., size reduction of bulk solids) and/or precipitation (e.g., the formation of a suspension of nanoparticles from a solution).

Attrition may be accomplished using techniques such as milling (e.g., impact milling, jet milling, ball milling, wet milling, and the like), hydrodynamic cavitation, high shear fluid processing, homogenization, sonication, and the like. For example, in certain embodiments, unprocessed active ingredient may be processed to reduce particle size. In general, such embodiments comprise suspending unprocessed active ingredient in a suitable non-solvent to form a suspension and subjecting the unprocessed active ingredient to attrition to decrease the active ingredient's particle size. In some embodiments, the active ingredient's particle size may be reduced to an effective diameter less than 1,000 nm.

The non-solvent may be any liquid in which the active ingredient is substantially insoluble and/or which is capable of forming a suspension of active ingredient particles. Examples of suitable non-solvents include, but are not limited to water, acetone, methylene chloride, ethanol, hexane, and the like. The particular non-solvent chosen will depend upon, among other things, the solubility of the active ingredient and effect of solvent on surface energy.

The non-solvent also may include a material capable of changing the surface energy of the particles, for example, to allow the particles to agglomerate. Examples of such materials include agglomerating agents (e.g., surfactants, co-solvents, and salts). Such materials may be present in an amount sufficient to allow the particles to agglomerate and the amount may be tailored to achieve a desired size of the agglomerate. Examples of suitable surfactants include, but are not limited to, cetyl alcohol, PL, PVA, PVP K90, lecithin, leucine, Span 85, Pluronics, and other surfactants that are generally regarded as safe, and the like. Examples of suitable co-solvents include, but are not limited to, water, methanol, hexane, ethanol, acetone, acetonitrile, octanol, and the like. Examples of suitable salts include, but are not limited to, sodium chloride, calcium chloride, magnesium sulfate, and the like. The particular agglomerating agent chosen will depend upon, among other things, the solubility of the active ingredient and the affect of the agglomerating agent on the surface energy of the particles.

As mentioned above, precipitation may be used to form a colloid dispersion of nanoparticles. Precipitation may be accomplished using techniques such as solvent/anti-solvent, cryo-based precipitation, flash precipitation, sonoprecipitation, and the like. For example, in certain embodiments, an active ingredient may be dissolved to form a solution of the active ingredient and precipitated out of solution in a non-solvent to form a colloid suspension of active ingredient.

Once a colloid of active ingredient is formed it is at least partially agglomerated into nanoclusters. By way of explanation, agglomeration may occur as a result of a change in the surface energy of the particles that allows the particles in the colloid to agglomerate. In some embodiments, agglomeration may occur as a result of a change in particle size during processing. By way of explanation, smaller sized particles typically demonstrate an increase in surface energy and mobility, and these properties can drive assembly of particles into nanoclusters. In other embodiments, entropic effects such as water exclusion may be used to agglomerate a colloid of the active ingredient. In still other embodiments, desolvation of the colloid may be used to form agglomerates. In some embodiments, agglomerates may be formed through the action of a material capable of changing the surface energy of particles that may be present in the non-solvent (e.g., agglomerating agent). For example, an agglomerating agent may be added to a colloid.

In-Processing Agglomeration

As mentioned above, in-processing agglomeration generally comprises processing an active ingredient under conditions such that an agglomerate forms. In certain embodiments, the processing uses attrition and/or precipitation, as described above. In-processing differs from post-processing in that agglomerates form without first forming a stable colloid. In some embodiments, the change in surface energy of the colloid occurs during processing. In certain non-limiting examples, in-processing agglomeration may be the result of changes in surface energy of particles and/or a change in particle size.

Recovery of NanoClusters

In certain embodiments, it may be beneficial to recover the nanocluster from suspension.

In certain embodiments, in which a non-solvent is used, a nanocluster may be recovered by removing the non-solvent. Examples of techniques suitable for removing the non-solvent and recovering nanoclusters include, but are not limited to, evaporation, vacuum drying, spray-drying, freeze drying, spray freeze-drying, and lypholization.

In some embodiments, nanoclusters of the present disclosure may be formed through the action of shear. For example, nanoclusters may be formed by allowing a plurality of nanoparticles to agglomerate together and applying shear to the agglomerated nanoparticles to form a nanocluster. Examples of techniques suitable for applying shear include homogenization, sonication, wet milling, high shear flow processing, and the like. In certain embodiments, shear may be applied upon exiting a device for administration to a subject (e.g., an inhaler). For example, nanoclusters may be formed from agglomerated nanoparticles as they exit a metered dose inhaler and/or a dry powder inhaler.

The size of the resulting nanocluster also may be controlled by tailoring the recovery conditions. For example, more or less shear may be used to create nanoclusters in a desired size range. Similarly, a material capable of changing the surface energy of the particles (e.g., hydrophobicity) may be used to form nanoclusters in a desired size range.

The present disclosure provides, in certain embodiments, methods for preparing nanoclusters comprising: forming a nanocluster comprised of a core of nanoparticles arranged such that the surface of the nanoparticles contact one another, wherein the nanocluster has a mass median aerodynamic diameter of from about 0.25 µm to about 20 µm.

The present disclosure provides, in certain embodiments, methods for preparing nanoclusters comprising: providing a colloidal dispersion of nanoparticles, agglomerating at least a portion of the nanoparticles to form nanoclusters, and optionally recovering the nanoclusters.

The present disclosure provides, in certain embodiments, methods for preparing nanoclusters comprising: suspending unprocessed active ingredient in a non-solvent to form a suspension; attrition of the active ingredient to form a colloidal dispersion of nanoparticles; agglomerating at least a portion of the nanoparticles to form nanoclusters; and optionally recovering nanoclusters.

The present disclosure provides, in certain embodiments, methods for preparing nanoclusters comprising: suspending unprocessed active ingredient in a non-solvent to form a suspension; attrition of the active ingredient to form a colloidal dispersion of nanoparticles; and allowing nanoclusters to form in the suspension.

The present disclosure provides, in certain embodiments, methods for preparing nanoclusters comprising: precipitating active ingredient in a suitable non-solvent; obtaining a colloidal suspension of precipitated active ingredient particles; agglomerating at least a portion of the colloidal suspension of precipitated active ingredient particles to form nanoclusters; and recovering the nanoclusters.

The present disclosure provides, in certain embodiments, methods for preparing nanoclusters comprising: precipitating active ingredient in a suitable non-solvent; obtaining a colloidal suspension of precipitated active ingredient particles; and allowing nanoclusters to form in the suspension.

In certain embodiments, methods for preparing a nanocluster comprising include: precipitating active ingredient particles in a suitable non-solvent; and allowing at least a portion of the precipitated active ingredient particles to agglomerate into nanoclusters.

In certain embodiments, it is contemplated that the nanoclusters may be prepared in a solution without using spray and/or freeze dry techniques. It is also contemplated that the nanoclusters may be recovered from the solution by using freeze dry or spray dry techniques that are known to those of skill in the art. As noted throughout this disclosure, the nanocluster can be included within a composition. The composition can be formulated into a suspension, a liquid, a spray, an aerosol, a dry powder, or solid dosage form, among other things.

The present disclosure provides, in certain embodiments, methods for preparing a nanocluster comprising: (i) obtaining a plurality of nanoparticles; (ii) obtaining a dispersion material (when desired); and (iii) admixing the products of steps (i) and (ii), wherein the admixture is formulated into a nanocluster. In certain embodiments, obtaining a plurality of nanoparticles comprises: (i) obtaining an aqueous suspension of nanoparticles; (ii) emulsifying the suspension into a non-aqueous phase; (iii) allowing water in the aqueous suspension to absorb into the non-aqueous phase; (iv) allowing the nanoparticles to agglomerate together; and (v) retrieving the agglomerated nanoparticles. In other embodiments, obtaining a plurality of nanoparticles includes: (i) obtaining a non-aqueous suspension of nanoparticles; (ii) emulsifying the suspension into an aqueous phase; (iii) allowing liquid in the non-aqueous suspension to absorb into the aqueous phase; (iv) allowing the nanoparticles to agglomerate together; and (v) retrieving the agglomerated nanoparticles. For example, a colloidal suspension of nanoparticles may also be obtained in deionized water which is subsequently emulsified into octanol. Water in the dispersed droplets may then absorb into the octanol phase. Nanoparticles can pack together as water is extracted from individual droplets until an agglomerate of nanoparticles remains. The size of the droplet, in certain embodiments, may serve as a template for controlling the size of the resulting nanoclusters depending on the concentration of nanoparticles within the droplet.

As noted throughout this disclosure, the nanocluster can be included within a composition. The composition can be formulated into a liquid, a spray, an aerosol, a suspension, and a dry powder, among other things. For example, the composition may be formulated for use in a dry powder inhaler (DPI) or a pressurized metered dose inhaler (pMDI).

In certain embodiments, nanoclusters of the present disclosure may be formed into a dry powder formulation. For example, nano-suspensions of an active ingredient may be prepared using precipitation techniques known in the art from a solution of the drug. Agglomerates may then be prepared by adding an agglomerating agent and allowing the suspension to incubate for a period of time. Following the agglomeration, the solvent may be evaporated. The dry nanoclusters are then placed into a freezer dryer to remove the last of the solvent. This process allows the lyophilized powder to be conveniently stored for subsequent use.

Once the dry powder has been formulated, the drug may be administered in its existing form with a dry powder inhaler (DPI). However, one feature of the present disclosure is that the same dry powder may be resuspended and administered as a nebulized solution. The resuspension of the dry powder in the present disclosure simply requires the addition of water. In certain embodiments, the dry powder may be resuspended in a ratio of about 50 mg of lyophilized powder to about 10 mL of water. In other embodiments, the dry powder may be resuspended in any other ratio such that it is suitable for nebulization.

Once resuspended, the solution of dry powder in water may be nebulized according to techniques known in the art. Suitable nebulizers include, but are not limited to, jet nebulizers, vibrating mesh, and sonicating. In certain embodiments, the nebulized solution comprises droplets in the desired respirable range usually but not limited to between 0.5-4.0 μm.

Pharmaceutical Compositions and Routes of Administration

In another embodiment, the present disclosure provides a composition comprising a nanocluster. In certain embodiments, the composition (e.g., pharmaceutical composition) may comprise a plurality of nanoclusters; and, the nanoclusters may be identical to similar nanoclusters or the nanoclusters may be nanoclusters with different characteristics (e.g., different active ingredients attached, different shapes, different sizes, and the like). The compositions comprising nanoclusters may be formulated with a pharmaceutically acceptable carrier.

Certain embodiments of the present disclosure include methods of treating, preventing, or diagnosing a particular disease or condition by administering the disclosed nanoclusters to a subject. In many instances, the nanoclusters are administered alone or can be included within a pharmaceutical composition. An effective amount of a pharmaceutical composition, generally, is defined as that amount sufficient to ameliorate, reduce, minimize or limit the extent of the disease or condition. More rigorous definitions may apply, including elimination, eradication, or cure of the disease or condition.

Pharmaceutical Compositions

Pharmaceutical compositions of the present disclosure can include a nanocluster of the present disclosure. The phrases "pharmaceutical or pharmacologically acceptable" may include, but is not limited to, molecular entities and compositions that do not produce an adverse, allergic or other untoward reaction when administered to a subject, such as, for example, a human. The preparation of a pharmaceutical composition is generally known to those of skill in the art. Moreover, for animal (e.g., human) administration, it is preferred that the preparations meet sterility, pyrogenicity, general safety and purity standards as required by FDA Office of Biological Standards.

"Therapeutically effective amounts" are those amounts effective to produce beneficial results in a subject. Such amounts may be initially determined by reviewing the published literature, by conducting in vitro tests, and/or by conducting metabolic studies in healthy experimental animals. Before use in a clinical setting, it may be beneficial to conduct confirmatory studies in an animal model, preferably a widely accepted animal model of the particular disease to be treated.

The actual dosage amount of a composition of the present disclosure administered to a subject can be determined by physical and/or physiological factors such as body weight, severity of condition, the type of disease being treated, previous or concurrent therapeutic interventions, idiopathy of the patient, and on the route of administration. The practitioner responsible for administration will, in any event, determine the concentration of active ingredient(s) in a composition and appropriate dose(s) for the individual subject.

The compositions of the present invention may include different types of pharmaceutically acceptable carriers depending on whether it is to be administered in solid, liquid, or aerosol form, and whether it needs to be sterile for such routes of administration as injection. "Pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes), propellants, and combinations thereof. The proper fluidity can be maintained, for example, by the use of a coating, such as lecithin and/or leucine; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols, or inhalants in the present invention. Such compositions are generally designed to be compatible with the target tissue type. For example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example, peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

Routes of Administration

The pharmaceutical compositions of the present disclosure can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, intrathecally, topically, intratumorally, intramuscularly, intraperitoneally, subcutaneously, subconjunctival, intravesicularlly, mucosally, intrapericardially, intraumbilically, intraocularally, orally, locally, inhalation (e.g., aerosol inhalation), nebulization, injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art.

Combination Therapies

In order to increase the effectiveness of a treatment with the nanoclusters of the present invention, it may be desirable to combine these nanoclusters with other therapies effective in the treatment of a particular disease or condition. The pharmaceutical compositions of the present disclosure, for example, can precede or follow the other agent treatment by intervals ranging from minutes to weeks.

Nanoclusters for Pulmonary Administration

Pharmaceutical compounds are delivered to the lungs for a variety of reasons. Certain compounds are administered to the lungs for their therapeutic effect; other compounds are administered for diagnostic purposes. Delivery to the peripheral lung is important for effective use of many therapeutic and diagnostic agents. A major deterrent to utilizing the lung for systemic drug delivery is the inability to efficiently deliver drugs to the lung periphery (alveolar region) where free exchange with the circulatory system occurs. Current techniques (e.g. milling or spray drying) often produce broad particle size distributions, which translates into poor pulmonary deposition efficiency. Over the past 30 years, researchers have found that about 2 μm particles deposit with high efficiency to the deep lung avoiding deposition in the oropharangyal cavity common for larger particles (>5 μm) and exhalation common for submicron particles. Unfortunately, particles around this size and smaller suffer from a propensity to agglomerate; therefore, researchers have developed low density particles as a method to effectively deliver drugs to the deep lung. These particles possess large geometric diameters, but due to their low density, exhibit much smaller aerodynamic diameters as described by the equation, $d_{aero}=d_p[(\rho/\rho_{ref})/\gamma]0.5$, where $d_{aero}$ is the aerodynamic particle diameter, $d_p$ is the geometric particle diameter, $\rho$ is the particle density, $\rho_{ref}$ is a reference density (typically 1 g/cm$^3$) and $\gamma$ is a shape factor (typically 1 for a sphere). Large, low density particles possessing geometric diameters greater than about 15 to 20 μm are able to avoid uptake and clearance by macrophages; however, these cells may still be recruited to the site of particle deposition.

Nanoclusters of the present disclosure may be introduced into the lung in one of several different ways. In certain embodiments, nanoclusters may be formulated into a dry powder that is inhaled into the lung. In other embodiments, nanoclusters may be dissolved into a solution that is subsequently nebulized, or converted into a fine mist, prior to inhalation. Such delivery modes for nanoclusters and nanocluster formulations may be useful for treating for example, cystic fibrosis, asthma, and lung cancer, as well as for delivering large immunoglobulins or genetic material systemically by crossing the lung epithelium.

Conventional nebulized suspensions consist of large insoluble particles >2 microns in aerodynamic size that cannot be carried by many of the smaller, more respirable droplets generated by a jet nebulizer. The nanocluster formulations of the present disclosure improve the mass of drug carried in the fine particle fraction of aerosolized droplets, improving delivery efficiency and carrying a greater mass of drug out of the nebulizer and into the lung. In this way, smaller drug doses may be capable of delivering a greater percentage of active ingredient in the respirable fraction of droplets generated using nebulization. Improving the fine particle fraction may provide significant therapeutic benefit, among other things, by distributing drug more uniformly throughout the central and peripheral lung areas.

Accordingly, in certain embodiments, the present disclosure relates to the pulmonary delivery of nanoclusters as either a dry powder or a nebulized solution. Embodiments of the present disclosure include particular nanoclusters of active ingredients that function essentially the same way in either formulation. This outcome can be achieved by preparing nanoparticles according the techniques described above, causing the nanoparticles to agglomerate into nano-clusters, dewatering the agglomerated nano-clusters into a dry powder, and optionally suspending the dry powder in a nebulization liquid. This dry powder may be conveniently stored and subsequently used in either its powder form or after being resuspended and nebulized. For example, such formulations may be used in dry powder inhalers, nebulizers, or in-line ventilators.

The pulmonary administration of a dry powder formulation is often limited by the physiological response of the respiratory tract, i.e., the cough reflex. Traditionally, 20 mg of dry powder is the largest amount of dry powder that is usually administered, although some research claims that 50 mg may be reached. By administering the nanoclusters of the present disclosure as a nebulized solution, 100 mg may be achieved. Additionally, nebulized solutions frequently face less regulatory hurdles than their dry powder analogs. By producing a formulation with the same characteristics as a dry powder or a nebulized solution, the present disclosure facilitates the development and pulmonary administration of the drugs.

The present disclosure, according to certain embodiments, also provides a single formulation that is optimized as a nebulized and dry powder formulation simultaneously. Such embodiments may allow the development of aerosol formulations where the preclinical and early stage clinical work done by nebulization is able to be used when the formulation is translated into a dry powder formulation.

In certain embodiments, a dry powder nanocluster formulation produced according to the methods of the present disclosure may be suitable for use in a dry powder inhaler, but may be reconstituted as a nebulized formation simply though the addition of a suitable solution (e.g., saline, deionized water, and the like). In certain embodiments, the addition of a dry powder nanocluster formulation does not substantially decrease the vapor pressure of the solution. The components of the formulation are largely insoluble and would not be substantially dissolved by the aqueous nebulization liquid as to not impact the colligative properties of the aqueous system. Similarly, the evaporation rate of the nebulized nanocluster formulation is similar to the solution without a drug. In some embodiments, the addition of the dry powder nanocluster formulation does not materially increase the viscosity of the solution. As with, for example, beta cyclodextrin enabled nebulized formulations, the beta cyclodextrins substantially dissolve in the aqueous liquid significantly increasing the viscosity of the solution.

In certain embodiments, nanoclusters of the present disclosure may be administered to a subject through medical tubing (e.g., ventilator tubing, endotracheal tubes, and the like).

In certain embodiments, the nanoclusters that are delivered to the lungs in the present disclosure may be consumed by macrophages. As these cells return to the lymph nodes, they carry the nano-cluster and facilitate a pulmonary delivery of drugs to the lymph nodes.

EXAMPLES

The following examples are included to demonstrate certain non-limiting aspects of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Nanoclusters with Responsive Dispersion

Nanocluster Formation: Nanoclusters of the present disclosure can be prepared by the following procedure: Two syringe pumps (Harvard Apparatus 4400 and Isco) are connected to the inner and outer ports of a coaxial nozzle to pass a colloidal suspension of nanoparticles (e.g. colloid suspension in aqueous solution and 1-octanol (Fisher Scientific) as droplet carrying liquid, respectively). The two immiscible liquids are injected at appropriate flows to produce monodisperse aqueous droplets, which contain the colloidal suspension of nanoparticles, in the octanol phase. The nanoclusters are formed after water in the droplets dissolves into 1-octanol resulting in packing of the nanoparticles into a spherical structure (FIG. 1). Nanoclusters are then washed with ethanol to remove residual 1-octanol and can be freeze dried for analysis. Similar results may be achieved by simply adding the nanoparticle suspension to the octanol phase and stirring to form a primary emulsion.

In one embodiment, the inventors coated silica nanoparticles coated with poly(N-vinylformamide) and cross-linked this polymer with a hydrolyzable cross-linker (2-bis[2,2'-di (N-vinylformamido)ethoxy]propane) to form nanoclusters that dispersed in response to a decrease in pH (FIG. 2). This set-up demonstrates the ability to disperse nanoclusters in response to environmental cues.

Figures 3A, 3B, 3C:
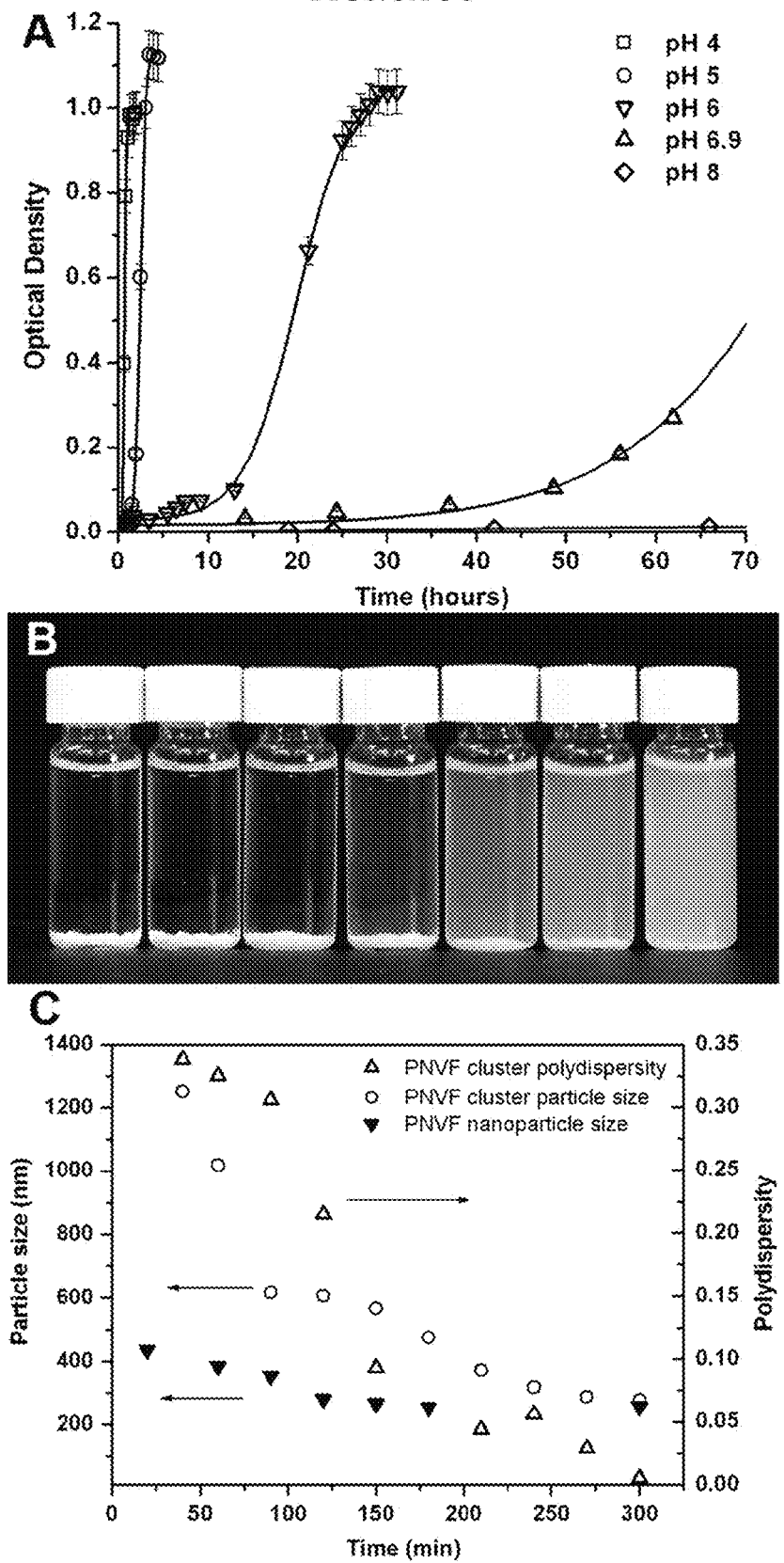

The clustered nanoparticles were slightly different in appearance due to the presence of the polymer, but the size distribution remained consistent with previous experiments. The nanoclusters were dispersed into aqueous solution as a function of time and pH (FIG. 3). A turbidity assay was used to measure optical density at 480 nm over time, the opacity of the solution indicating the relative dispersion of the clusters into constituent nanoparticles. The dispersion of the nanoclusters could also be visually tracked over time (FIG. 3B). Size analysis of the solution phase of dispersed nanoclusters via laser light scattering indicated that polydisperse agglomerates of nanoparticles were liberated. These agglomerates further dispersed into individual nanoparticles over time (FIG. 3C).

Example 2

Self-Assembled Nanoclusters

Nanoparticle Formation: PLGA nanoparticles were prepared by a modified emulsion/solvent extraction method using different polyelectrolyte coating materials to control surface charge (Table 1). Polyvinylamine (PV Am) was used as a cationic coating material and was synthesized according to methods known in the art. Polyethylene-alt-maleic acid (PEMA) was synthesized by hydrolysis of the anhydride from of this polymer as adapted from methods reported previously. The resulting polyelectrolyte-coated PLGA nanoparticles possessed excellent uniformity and high surface charge (Table 1). Each nanoparticle formulation was analyzed for size and zeta potential using dynamic light scattering and conductivity measurements (Brookhaven ZetaPALS), respectively, in the appropriate media (water or organic). Studies confirmed the maintenance of particle surface charge upon lyophilization and after more than one week of incubation at 37° C., pH 7.4 (data not shown). PVAm-coated nanoparticles were notably larger than PEMA-coated nanoparticles for this experiment; however, this size is readily controlled. Nanoparticles can be made by using reported techniques, for example; emulsion polymerization, emulsion solvent extraction, reverse emulsions of the same, precipitation, crystallization, freeze drying, spray freeze drying, salting out, and the like.

TABLE 1

PLGA nanoparticle properties

| PLGA Nanoparticle Size (nm) | Size (nm) | Zeta potential (mV) |
|---|---|---|
| PVAm-coated | 498.5 ± 8.4 | +30.7 ± 1.0 |
| PEMA-coated | 262.7 ± 11.3 | −52.3 ± 1.2 |

Nanocluster Formation: Nanoparticle clusters were produced by slow addition of 3 mL of PVAm-coated nanoparticles into 10 mL of PEMA-coated nanoparticles under gentle stirring. Nanocluster formation was induced by electrostatic self-assembly of the oppositely charged nanoparticles. Increasing the concentration of mixed nanoparticles resulted in a corresponding increase in the cluster diameter (FIG. 4A). The geometric size distribution of nanoclusters was determined in aqueous solution (Isoton) using a Coulter Multisizer III. Geometric size distributions were relatively broad exhibiting standard deviations that were 60-70% of the average geometric diameter. The aerodynamic size distributions were determined from freeze dried nanoclusters using time of flight measurements obtained by an Aerosizer LD. Nanocluster aerodynamic size distributions were narrower than the geometric size distributions as indicated by the increased volume percent (FIG. 4B) and decreased standard deviations (35-60% of the mean; Table 2). Free PEMA-coated nanoparticles were detected as a rising tail in the geometric size distributions, but were not detected in the aerodynamic size distributions. In addition, few free nanoparticles were observed in scanning electron micrographs (FIG. 4C) indicating that nanoparticles that were not associated with nanoclusters in solution bound to nanoclusters during lyophilization.

TABLE 2

Dependence of the size of nanocluster on the concentration of PLGA nanoparticles.

| | PLGA NP conc. (mg/ml) | | | | | | | |
|---|---|---|---|---|---|---|---|---|
| | (−)* | (+)** | (−) | (+) | (−) | (+) | (−) | (+) |
| | 0.68 | 0.72 | 1.36 | 1.44 | 2.04 | 2.16 | 2.72 | 2.82 |
| $d_{geo}$ (μm) | 7.4 ± 5.1 | | 8.7 ± 5.6 | | 9.4 ± 5.6 | | 13.7 ± 8.3 | |
| $d_{aero}$ (μm) | 2.4 ± 1.5 | | 3.0 ± 1.6 | | 3.4 ± 1.6 | | 4.4 ± 1.6 | |
| $d_{geo}/d_{aero}$ | 0.33 ± 0.29 | | 0.35 ± 0.29 | | 0.36 ± 0.29 | | 0.32 ± 0.19 | |
| Calculated ρ (g/cm³) | 0.11 ± 0.09 | | 0.12 ± 0.08 | | 0.13 ± 0.08 | | 0.10 ± 0.04 | |
| Fine Particle Fraction | 1.00 | | 0.80 | | 0.75 | | 0.50 | |

*(−): PLGA nanoparticles with negative surface charge (PEMA-coated)
**(+): PLGA nanoparticles with positive surface charge (PVAm-coated)
[1]Density calculated using $d_{geo} = d_p$, $\rho_{ref} = 1$ g/cm³ and γ = 1.
[2]Fine Particle Fraction defined as the fraction of dry particles with $d_{aero}$ (μm) < 5 μm.

Structural analysis of nanoclusters revealed a low density, web-like morphology. Scanning electron micrographs showed that freeze dried nanoparticle clusters possessed a large amount of porosity (FIG. 4C). The density of each nanocluster formulation was calculated from the geometric and aerodynamic diameters (Table 2). Although nanocluster size increased with increasing nanoparticle concentration, the calculated density was essentially the same for each. The calculated densities of nanoclusters were quite low (~0.15 g/cm$^3$) and yielded a very high fine particle fraction ($d_{aero}$<5 μm) for most formulations. The use of a hydrated geometric diameter, dehydrated aerodynamic diameter, and the assumed shape factor of γ=1 (i.e., a sphere) should be noted when interpreting this density calculation.

Laser scanning confocal microscopy was utilized to gain more insight into the nanocluster structure and formation mechanism. PVAm-coated nanoparticles were labeled with a green fluoroisothiocyanate (FITC) dye and PEMA-coated nanoparticles were labeled with a red rhodamine dye. Detailed analysis of two nanocluster particles indicated that both PVAm-coated (FIG. 5A and FIG. 5D) and PEMA-coated (FIG. 5B and FIG. 5E) nanoparticles were present throughout the entire nanocluster structure.

Example 3

Preparation of Nifedipine and Loratadine Nanoparticles

The following includes examples of preparing various non-limiting nifedipine and loratadine nanoparticles.

1020 nm Nifredipine nanoparticle—Nifedipine (50 mg) was dissolved in 3 ml of methylene chloride and rapidly mixed into 0.125% Cetyltrimethylammonium bromide (CTAB) solution (30 mL) and sonicated for 60 sec. The particle suspension was placed into a hood for two hours to evaporate the methylene chloride. The resulting nanoparticle had a particle size of 1020 nm and a polydispersity of 0.24.

660 nm Nifedipine nanoparticle—Nifedipine (50 mg) was dissolved in 3 ml of methylene chloride and rapidly mixed into 0.5% CTAB solution (30 mL) and sonicated for 60 sec. The particle suspension was placed into a hood for two hours to evaporate the methylene chloride. The resulting nanoparticle had a particle size of 660 nm and a polydispersity of 0.17.

480 nm Nifedipine nanoparticle—Nifedipine (50.2 mg) was dissolved in 3 ml of ethanol and rapidly mixed into 0.5% CTAB solution (30 mL) and sonicated for 60 sec. The particle suspension was placed into a hood for two hours to evaporate the ethanol. The resulting nanoparticle had a particle size of 480 nm and a polydispersity of 0.12.

2373 nm Nifedipine nanoparticle—Nifedipine (30 mg) was dissolved in 2 ml of ethanol and rapidly mixed into 0.3% Pluronic F-68 solution (30 mL) and homogenized at 15,000 rpm for 60 sec. The particle suspension was placed into a hood for two hours to evaporate the ethanol. The resulting nanoparticle had a particle size of 2373 nm and a polydispersity of 0.09.

897 nm Nifedipine nanoparticle—Nifedipine (30 mg) was dissolved in 2 ml of ethanol and rapidly mixed into 0.6% Pluronic F-68 solution (30 mL) and homogenized at 15,000 rpm for 60 sec. The particle suspension was placed into a hood for two hours to evaporate the ethanol. The resulting nanoparticle had a particle size of 897 nm and a polydispersity: 0.07.

639 nm Nifedipine nanoparticle—Nifedipine (30 mg) was dissolved in 2 ml of ethanol and rapidly mixed into 0.9% Pluronic F-68 solution (30 mL) and homogenized at 15,000 rpm for 60 sec. The particle suspension was placed into a hood for two hours to evaporate the ethanol. Resulting nanoparticle had a particle size of 639 nm and a polydispersity of 0.005.

391 nm Loratadine nanoparticle—Loratadine (10 mg) was dissolved in 1 ml of ethanol and rapidly mixed into 0.9% Pluronic F-68 solution (10 mL) and homogenized at 15,000 rpm for 60 sec. The particle suspension was placed into a hood for two hours to evaporate the ethanol. The resulting nanoparticle had a particle size of 391 nm and a polydispersity of 0.005.

Example 4

Preparation of Nifedipine Nanoparticle Clusters

This example provides a non-limiting embodiment of the present invention where the nanoparticle is pure nifedipine (a calcium channel blocker that treats high blood pressure). The nanoparticle is coated with a cationic surfactant (CTAB). A polyanion (sodium alginate) couples with the CTAB which induces nanocluster formation.

Preparation of nifedipine nanoparticles: Nifedipine (50 mg) was dissolved in methylene chloride (3 ml). The solution was poured completely into a CTAB concentration-known aqueous solution (Table 3). The solution was sonicated for 60 sec. Subsequently, the particle suspension was placed into a hood for two hours to evaporate the methylene chloride. The suspension was diluted to 1 mg/ml. FIG. 6 is a scanning electron microscope (SEM) image of a population of nifedipine nanoparticles.

Preparation of nanoparticles: PLGA nanoparticles were prepared using a modified emulsion-solvent evaporation technique (Kazzaz et al., 2000; Mainardes et al., 2005, both of which are incorporated by reference). A cationic surface charge was incorporated using the lipid 1,2-dioleoyl-3-trimethylammonium-propane (DOTAP; Avanti Polar Lipids, Inc.; Alabaster, Ala.) as the coating material. 3 mL PLGA (0.41 dL/g inherent viscosity; Lactel; Pelham, Ala.) dissolved in an acetone/methanol mixture (5/1) at 1.67% (w/v) was added to 25 mL DOTAP (50 μM) and sonicated at 50% power using a sonic dismembrator (Fisher Scientific; Pittsburgh, Pa.) for 60 sec on ice. This was repeated for a total of 6 batches. The batches were combined and stirred at moderate speed in the hood overnight to evaporate the solvent. The particles were crudely filtered through a KimWipe and washed three time's with ~15 mL distilled, deionized water using an Amicon Ultra-15 centrifugal filter unit (Millipore; Billerica, Mass.; F=863 g). The washed nanoparticles were sonicated in a water bath for 15 min and again filtered through a Kim Wipe to remove any large agglomerates. The resulting particles were then characterized using a Zeta Potential Analyzer (Brookhaven Instruments; Holtsville, N.Y.) to measure particle size and surface charge ($\zeta$): the nanoparticles had an average size of 343.0±8.6 (nm), a polydispersity of 0.232±0.022, and a zeta potential of 36.44±0.56 (mV). The nanoparticle suspension was diluted in 1 mM sodium nitrate solution for surface charge measurements.

TABLE 3

Geometric size and aerodynamic diameters of clusters*

| Conc. of CTAB (wt %) | $V_{nifedipine}/V_{algenic\ acid}$ | Geometric size (μm) | Aerodynamic diameter (before grinding) (mass median, μm) | Aerodynamic diameter (after grinding) (mass median, μm) |
|---|---|---|---|---|
| 0.125 | 2:1 | 28.11 ± 8.33 | 3.313 ± 1.868 | 3.321 ± 1.763 |
|  | 1:1 | 22.84 ± 11.64 | 3.814 ± 1.811 | 4.133 ± 1.829 |
|  | 1:2 | 29.27 ± 11.47 | 4.219 ± 1.597 | 4.234 ± 1.836 |
|  | 1:3 | 23.31 ± 13.4 | 3.397 ± 1.858 | 3.702 ± 1.844 |
| 0.25 | 2:1 | 27.24 ± 11.42 | 3.775 ± 1.804 | 3.467 ± 2.025 |
|  | 1:1 | 29.49 ± 12.36 | 3.98 ± 1.868 | 4.135 ± 1.803 |
|  | 1:2 | 23.36 ± 13.48 | 4.217 ± 1.874 | 4.312 ± 1.926 |
|  | 1:3 | 23.82 ± 10.50 | 3.520 ± 1.989 | 4.006 ± 1.903 |
| 0.4 | 2:1 | 26.39 ± 12.76 | 3.819 ± 1.786 | 4.715 ± 1.397 |
|  | 1:1 | 33.74 ± 13.85 | 4.156 ± 1.769 | 3.840 ± 1.942 |
|  | 1:2 | 30.97 ± 14.31 | 3.793 ± 1.866 | 3.973 ± 1.876 |
|  | 1:3 | 23.72 ± 15.70 | / | / |

*Concentration: particle suspension: 1 mg/ml; Algenic acid: 1 mg/ml $V_{nifedipine}/V_{algenic\ acid}$ Preparation of nifedipine nanoparticle clusters: Algenic acid aqueous solution (10 ml, 1 mg/ml) was poured into nifedipine nanoparticle aqueous suspension (10 ml, 1 mg/ml) and the mixture was homogenized with a homogenizer (about 2000 rpm) for 2 min. Dry Nifedipine nanoparticle clusters were obtained by freeze-drying. FIG. 7 is a SEM image of nifedipine nanoparticle clusters.

Example 5

Nanocluster Comprising Ovalbumin

This example provides a non-limiting embodiment of the present invention where the nanoparticle is a biodegradable polymer (PLGA) coated with a cationic lipid (DOTAP). Ovalbumin couples to the surface of the coated nanoparticle which induces nanocluster formation.

Spontaneous nanocluster formation of nanoparticles with ovalbumin: Ovalbumin was used as a model protein. Three solutions containing approximately 0.4, 1.5 and 2.5 mg/mL ovalbumin were prepared in phosphate buffered saline (PBS), and the exact concentration of each solution was determined using UV absorbance spectroscopy (Table 4). Using three labeled, 15 mL centrifuge tubes, 6 mL DOTAP nanoparticles and 1 mL ovalbumin solution were added. The samples were tumbled gently on an end-over-end tube rotator for 45 min at 4° C. The resulting nanoclusters were analyzed using a Multisizer 3 Coulter Counter (Beckman Coulter, Inc.; Fullerton, Calif.) to measure their geometric diameter. The nanoclusters were lyophilized using a Labconco bench-top lyophilizer (Kansas City, Mo.) and further characterized to determine the aerodynamic diameter (Aerosizer; Amherst Process Instruments Inc.) and morphology (SEM) (Table 5). FIG. 8 illustrates the geometric diameter of the DOTAP/PLGA nanoparticles with ovalbumin.

TABLE 4

Concentration of ovalbumin solutions as determined by UV absorbance spectroscopy

| Target Concentration (mg/mL) | Actual Concentration (mg/mL) |
|---|---|
| 0.4 | 0.371 ± 0.001 |
| 1.5 | 1.374 ± 0.003 |
| 2.5 | 2.236 ± 0.040 |

TABLE 5

Nanocluster sizes

| Target concentration of ovalbumin (mg/mL) | Mode Geometric Diameter* (μm) | Mean Aerodynamic Diameter (μm) |
|---|---|---|
| 0.4 | 6.25 | 2.384 ± 1.775 |
| 1.5 | 5.15 | 2.468 ± 1.931 |
| 2.5 | 5.10 | 2.447 ± 1.918 |

*See FIG. 8 for size distribution.

Scanning electron microscopy (SEM): The size and morphology of the nanoclusters were evaluated using a LEO 1550 field emission scanning electron microscope with secondary electron detection. The nanoclusters were coated on a platform and sputtered with gold prior to imaging at 4000 and 10,000 times magnification. FIG. 9 includes SEM images of the nanoclusters comprising DOTAP/PLGA nanoparticles and ovalbumin.

Example 6

Assessment of Dry Powder Performance In Vitro

A multi-stage liquid impactor (MSLI) fitted with a mouthpiece and throat assembly can be used to evaluate the deposition performance of various particle formulations administered from a dry powder inhaler. For administration through a dry powder inhaler (DPI) such as the Spinhaler®. Or Rotahaler®, particles are first encapsulated in a large, two-piece gelatin capsule. The capsule is placed into a small compartment in the DPI, which is then twisted to either separate or rupture the capsule immediately prior to breath actuation. Since no propellants or compressed gases are used for these DPIs, the breathing force of the patient, or in our case the volumetric flow rate through the MSLI, disperses the powder.

Using this experimental set-up, several important performance parameters can be evaluated, including the respirable fraction of a particle formulation, the mass depositing in the mouthpiece and throat assembly and the fractions of particles depositing at different stages throughout the MSLI (assessed by removing each section and weighing the collected particle mass). Particle batches depositing with high efficiency to the lower stages (~1-5 μm cut-off) of the MSLI will be deemed as "deep lung" formulations suitable for ciprofloxacin encapsulation experiments.

Example 7

Identification of Nanocluster Formulations that can Entrap, Deposit, and Release Ciprofloxacin Nanoclusters can be formulated for controlled release of ciprofloxacin for ~1 week. A complete analysis of nanoclus-ter physicochemical properties, dispersion and release of the drug can be prepared by the methods described throughout this specification. The nanoclusters, in one embodiment, can be made with nanoparticles of pure ciprofloxacin or ciprofloxacin encapsulated in PLGA nanoparticles. Ciprofloxacin is a broad spectrum antibiotic, especially effective against gram negative bacteria.

Nanocluster dispersability and ciprofloxacin release kinetics: Nanocluster formulations can be reformulated to determine controlled release of ciprofloxacin, taking care to maintain the same fabrication procedure and resulting structure designed for deep lung deposition. Ciprofloxacin (Sigma, Inc.) can be encapsulated by co-dissolving with the polymer phase and will be partially suspended in the polymer phase or dissolved in a co-solvent if low solubility in the polymer phase is an issue. Dissolution studies ascertain the release kinetics of ciprofloxacin. These studies are performed in phosphate buffered saline solution (pH 7.4) at physiological temperature (37° C.). Approximately 10-20 mg of each particle formulation is placed in 2 mL microcentrifuge tubes shaken at 150 rpm. Release samples will be tested by intermittently centrifuging samples to separate nanoparticles (15,000 rpm), collecting 1-1.5 mL of supernatant, replacing supernatant with fresh buffer and resuspending the samples. The supernatant will then be analyzed by spectrophotometry at ~350 nm to determine the concentration of ciprofloxacin at each time point while avoiding detection of polymer dissolution products. The release of ciprofloxacin from the various nanocluster formulations will be conducted in triplicate and the average and standard deviation is calculated. The initial loading of ciprofloxacin in nanocluster formulations is determined by dissolving ~10 mg of each formulation in triplicate in dimethylsulfoxide and measuring the absorbance at ~350 nm. Absorbance values for formulations of nanoclusters without ciprofloxacin are used as blanks. The calculated amount of ciprofloxacin per mass of polymer is termed the drug loading. This number can be divided by the mass of ciprofloxacin per mass of polymer entered into the experiment to calculate the drug encapsulation efficiency. The summed mass of ciprofloxacin released over time is then divided by the drug loading to arrive at the cumulative percent released. Analogous samples of nanoclusters can be prepared to determine the dispersion kinetics based on measuring the turbidity of the sample solution at 480 nm.

Reformulation and optimization of controlled release: Generating a near constant release of ciprofloxacin for ~1 week may include reformulation of nanoclusters. If drug "bursting" (rapid initial release) occurs or increased duration of release is desired, higher molecular weight PLGA or PLGA with a higher lactide content will be used as each of these prolong degradation of the polymer phase. In addition, increasing the size of constituent nanoparticles to decrease the rate of ciprofloxacin release can be used. The maintenance of small (e.g., <200 nm) nanoparticles can be used as a way to avoid phagocytosis or other clearance mechanisms from the lung epithelium.

Example 8

Paclitaxel Nano-Agglomerates as Dry Powder for Pulmonary Delivery

Paclitaxel (PX), L-a-phosphatidylcholine (lecithin; Lec), cetyl alcohol (CA), L-leucine (Leu), polyvinylpyrrolidone (PVP K90, Mw~36,000) and sodium chloride were purchased from Sigma Chemicals Co, U.S.A. Pluronic F-127 (PL, Mw~12,220) was purchased from BASF, The Chemical Company, U.S.A. Polyvinyl alcohol (PVA; Mw=22,000, 88% hydrolyzed) was purchased from Acros Organics, N.J., U.S.A. Potassium dihydrogen phosphate, disodium hydrogen phosphate, acetone, ethanol and acetonitrile were purchased through Fisher Scientific. Floatable dialysis membrane units (Mw cut-off=10,000 Da) were obtained from Spectrum Laboratories Inc., U.S.A. A549 cells were obtained from the American Type Culture Collection (ATCC, Rockville, Md.). The cell culture medium (Ham's F-12 Nutrient Mixture, Kaighn's modified with L-glutamine) was purchased through Fisher Scientific. Fetal bovine serum (FBS) was purchased from Hyclone. Penicillin-streptomycin was purchased from MB Biomedical, LLC. Trypsin-EDTA was purchased through Gibco. MTS reagent [tetrazolium compound; 3-(4, 5-dimethylthiazol-2-yl)-5-(3-carboxymethoxyphenyl)-2-(4-sulfophenyl)-2H-tetrazolium, inner salt] was purchased from Promega, U.S.A. Double-distilled water was used throughout the study, provided by an EASYpure® RODI (Barnstead International, Model # D13321).

Fabrication and Characterization of Paclitaxel Nanoparticles.

Nanosuspensions were prepared using a precipitation technique. The drug was precipitated by direct injection of acetone solution of paclitaxel, 0.1% w/v, in waters at a rate of 1 mL/min under sonication (Fisher Scientific, Sonic Dismembrator) with an amplitude of 46%. The chosen surfactants for the study included hydrophobic (cetyl alcohol), hydrophilic (PL, PVA and PVP K90) and amphoteric (lecithin). The hydrophobic and amphoteric surfactants were added to the drug organic solvent solution and the contents were allowed to stand at room temperature for 30 to 45 minutes with occasional vortexing to allow complete solubilization of the drug and the surfactants. Hydrophilic surfactants were added to the aqueous phase. Surfactants were used individually or in combination as reported.

The particle size and zeta potential of the nanosuspensions were determined by dynamic light scattering (Brookhaven, ZetaPALS). Zeta potential measurements were performed using 1 mM KCl solution. All measurements were performed in triplicate.

Preparation of Paclitaxel Nanoparticle Agglomerates

The paclitaxel nanoparticle agglomerates were prepared by addition of L-leucine powder to agglomerate nanoparticle suspensions followed by homogenization at 25,000 rpm for 30 sec. The amount of L-leucine added was adjusted to a drug:leucine ratio equal to 1:1. The size of paclitaxel nanoparticle agglomerates was measured in Isoton diluent using a Coulter Multisizer 3 (Beckman Coulter Inc.) equipped with a 100 mm aperture after three hours of incubation with the agglomerating agent. The suspensions were kept overnight at room temperature to allow evaporation of acetone and then frozen at −80° C. and transferred to a freeze dryer (Labconco, FreeZone 1). Drying lasted for 36 hours to remove all appreciable water content. Lyophilized powder was stored at room temperature for further characterization.

Characterization of the Prepared Nanoparticle Agglomerates

Determination of Particle Size Distribution

The particle size of the dispersed nanoparticle agglomerates as well as the resuspended lyophilized powder was measured using a Coulter Multisizer 3. The particle size distributions are shown in FIG. 10.

Flowability Characteristics

The flow properties of the nanoparticle agglomerates were assessed by angle of repose (tan θ=height/radius) measurement of the dried powders. The fixed-height cone method was used. A glass funnel with cut stem surface of 5 mm internal diameter was fixed at 2.5 cm height over a flat surface. The powders were allowed to flow gently through the funnel until a cone was formed and reached the funnel orifice. The flow of powder was then stopped and the average diameter of the formed cone (D) was measured. The area of the base of the cone was taken as a measure of the internal friction between the particles. The angle of repose was calculated by the equation: tan θ=height/radius.

In addition, the bulk density, Hausner ratio (Tapped density/bulk density) and Can's index (Ci) [(Tapped density−bulk density)/Tapped density×100%] were also determined for the dried powders. Ten mg of powders were weighed and poured into a 10 mL graduated measuring cylinder. The bulk volume occupied (Vb) was recorded. The measuring cylinder was tapped until a constant value was obtained and the tapped volume was recorded (Vt). The process was repeated at least three times and the average was taken in each case. The bulk and tapped densities of powder were calculated by dividing the weight by the corresponding bulk volume or tapped volume recorded.

Measurement of Aerodynamic Diameter

The aerodynamic size distributions of the agglomerate powders were measured directly from lyophilized powder by time-of-flight measurement using an Aerosizer LD (Amherst Instruments) equipped with a 700 mm aperture operating at 6 psi.

The theoretical mass-mean aerodynamic diameter ($d_{aero}$) of the nanoparticle agglomerates was determined from the geometric particle size and tapped density using the following relationship:

$$d_{aero} = \frac{d_{geo}}{\gamma}\sqrt{\rho/\rho_a}$$

Where $d_{geo}$=geometric diameter, γ=shape factor (for a spherical particle, γ=1; for aerodynamic diameter calculations, the particles in this study were assumed to be spherical), ρ=particle bulk density and $\rho_a$=water mass density (1 g/cm$^3$). Aerodynamic size distributions of paclitaxel nanoparticle agglomerates is shown in FIG. 11. Tapped density measurements underestimate particle bulk densities since the volume of particles measured includes the interstitial space between the particles. The true particle density, and therefore the aerodynamic diameter of a given powder, is expected to be slightly larger than reported.

Aerosolization Performance of Nano-Agglomerate Dry Powders

Aerodynamic characteristics of selected nanoparticle agglomerates were studied in vitro using a Tisch Ambient Cascade Impactor (Tisch Environmental, Inc., Ohio). The study was carried out by applying ~20 mg powder manually into the orifice of the instrument at an air flow rate of ~30 L/min. Cut-off particle aerodynamic diameters for each stage of the impactor were: pre-separator (10.00 mm), stage 0 (9.00 mm), stage 1 (5.8 mm), stage 2 (4.7 mm), stage 3 (3.3 mm), stage 4 (2.1 mm), stage 5 (1.1 mm), stage 6 (0.7 mm), stage 7 (0.4 mm) and filter (0 mm). Nanoparticle agglomerates deposited on each stage of the impactor were determined by measuring the difference in weight of filters placed on the stages. The mass median aerodynamic diameter, MMAD, and geometric standard deviation, GSD, were obtained by a linear fit of the cumulative percent less-than the particle size range by weight plotted on a probability scale as a function of the logarithm of the effective cut-off diameter. FIG. 12 shows the distribution of Paclitaxel powder as received and nanoparticle agglomerate formulations deposited on the stages of a cascade impactor at a flow rate of ~30 L/min.

Imaging of Particles by Transmission Electron Microscopy

Image data was used to corroborate the size of nanoparticles and nanoparticle agglomerates and to observe their morphological aspects. Transmission electron micrographs (TEM) were obtained for paclitaxel nanoparticles and nanoparticle agglomerates using a JEOL 1200 EXII transmission electron microscope. Initially, carbon-coated grids (Electron Microscopy Sciences) were floated on a droplet of the suspensions on a flexible plastic film (Parafilm), to permit the adsorption of the particles onto the grid. After this, the grid was blotted with a filter paper and air dried for 1 hr.

Determination of Process Yield and Loading Efficiency

The lyophilized powder for the prepared nanoparticle agglomerates was weighed and the yield was calculated using the following expression:

Paclitaxel loading efficiency was assessed by dispersing one mg of the lyophilized powder in 10 mL ethanol. The dispersion was sonicated in a bath-type sonicator (Branson 3510) for 30 min. Then the solution was centrifuged (Beckman, Avanti TM) at—15,000 rpm for 30 min to remove insoluble ingredients and the amount of drug in the supernatant was determined spectrophotomerically (Agilent C) at 228 nm.

Dissolution Studies

The dissolution of the prepared nanoparticles and nanoparticle agglomerates was determined and compared with the dissolution characteristics of the drug powder as received. The dissolution of paclitaxel was carried out at 37±0.5° C. in a 1 liter beaker. A known amount (~10 mg) of the lyophilized powder was suspended in 10 mL phosphate buffered saline (PBS, pH 7.4) and was placed into a floatable dialysis membrane unit (Mw cut-off=10,000 Da), and the unit was allowed to float in a 500 mL of PBS. The solution was stirred at a constant speed (100 rpm) using a magnetic stirrer (Barnstead, Thermolyne MIRAKTM). At predetermined time intervals for a total period of 8 hours, serial samples (1 mL) of the medium were withdrawn from the dialysis bag and centrifuged for 30 minutes at ~13,000 rpm. The nanoparticles-free supernatant was removed and extracted with 3 mL of ethanol. The ethanol extract was analyzed for paclitaxel concentration using a reverse-phase HPLC method. Studies were conducted in triplicate. A Shimadzu HPLC system including a solvent delivery pump (Shimadzu LC-10AT), a controller (Shimadzu SCL-10A), an autoinjector (Shimadzu SIL-10AxL), and a UV detector (Shimadzu SPD-10A) was used in this study. The peak areas were integrated using Shimadzu Class VP (Version 4.3). A 4.6 mm×100 mm long Zorbax SB C-8 column (Agilent C) with a particle diameter of 3.5 μm was used. During the assay, paclitaxel was eluted isocratically at a mobile phase flow rate of 0.9 mL/minute and monitored with a UV detector operating at 228 nm. The mobile phase for the assay consisted of an acetonitrile and water mixture (50:50 v/v). The run time for the assay was 20 minutes, and the retention time for paclitaxel was 10.7 minutes. FIG. 13 shows the in-vitro dissolution profiles of paclitaxel in PBS (pH 7.4) from pure paclitaxel powder and two different nanoparticle (NP) and nanoparticle agglomerate formulations (NA).

Cytotoxicity Assay

The cytotoxicity of selected nanoparticles and nanoparticle agglomerates was assessed using the CellTiter 96® Aqueous Cell Proliferation Assay (Promega) and compared with paclitaxel powder as received, lecithin, PVP K90, L-leucine, physical mixtures of these ingredients and blank nanoparticle agglomerates. In this experiment, 8×104 A549 cells/well were seeded in 96-well microtiter plates. At the end of the incubation period (12 h), 20 ml of MTS reagent solution was added to each well and incubated for 3 h at 37° C. The absorbance was measured at 490 nm using a microtiter plate reader (SpectraMax, M25, Molecular Devices Corp., CA). The percentage of viable cells with all tested concentrations was calculated relative to untreated cells. FIG. 14 shows the viability of A549 cells in the presence of formulation components as determined by an MTS assay.

TABLE 6

IC50 for Paclitaxel Formulations

| Formulation | $IC_{50}$ |
|---|---|
| Pure paclitaxel powder | 1.8 mg/ml |
| F1NP | 2.1 mg/ml |
| F1NA | 1.9 mg/ml |
| PM1 | 1.5 mg/ml |
| Blank1 | 0.88 mg/ml |
| F2NP | 1.6 mg/ml |
| F2NA | 2.1 mg/ml |
| PM2 | 1.5 mg/ml |
| Blank2 | 1.8 mg/ml |

TABLE 7

Paclitaxel formulations used in the studies.

| Formulation | Paclitaxel (% w/v) | Lecithin (% w/v) | PVP K90 (% w/v) | Cetyl alcohol (% w/v) |
|---|---|---|---|---|
| F1 | 0.1 | 0.02 | 0.01 | |
| F2 | 0.1 | 0.02 | | |
| F3 | 0.1 | 0.02 | | 0.01 |

TABLE 8

Physical properties of Paclitaxel nanoparticles (values = average ± standard deviation).

| Formulation | Nanoparticle size (nm) | Zeta-potential (mV) | Polydispersity |
|---|---|---|---|
| F1[a] | 298.7 ± 10.3 | 25.1 ± 0.7 | 0.04 ± 0.03 |
| F2[b] | 339.1 ± 13.6 | 24.7 ± 1.5 | 0.18 ± 0.1 |
| F3[c] | 358.5 ± 8.1 | 22.4 ± 1.02 | 0.31 ± 0.1 |

[a]F1 = 0.1:0.02:0.01; PX:Lec:PVP K90
[b]F2 = 0.1:0.02; PX:Lec
[c]F3 = 0.1:0.02:0.01; PX:Lec:CA

TABLE 9

Characteristics of Paclitaxel nanoparticle agglomerates (values = average ± standard deviation.).

| Characteristics | Formulations | |
|---|---|---|
| | F1[a] | F2[b] |
| Geometric particle size (μm) of NA[c] before lyophilization | 2.8 ± 0.5 | 3.7 ± 0.9 |
| Geometric particle size (μm) of lyophilized NA[c] | 4.8 ± 1.3 | 5.4 ± 1.6 |
| $MMAD_A$[d] of lyophilized NA[c] | 1.5 ± 0.08 | 1.7 ± 0.4 |

[a]F1 = 0.1:0.02:0.01; PX:Lec:PVP K90
[b]F2 = 0.1:0.02; PX:Lec
[c]NA: Nanoparticle agglomerates.
[d]MMAD: Mass median aerodynamic diameter obtained from Aerosizer.

TABLE 10

Yield, loading and dissolution behavior of Paclitaxel nanoparticle agglomerates (values = average ± standard deviation.).

| Characteristics | Formulations F1[a] | F2[b] |
|---|---|---|
| % Process yield of lyophilized NA[c] | 85.9 ± 2.7 | 89.8 ± 3.1 |
| Drug loading of lyophilized NA[c] | 85.1 ± 3.9 | 85.9 ± 8.7 |
| $Q_{8h}$[e]NP[d] | 66.4% ± 2.4 | 60.7% ± 13.04 |
| $Q_{8h}$[e] NA[c] | 43.6% ± 4.3 | 40.4% ± 2.9 |

[a]F1 = 0.1:0.02:0.01; PX:Lec:PVP K90
[b]F2 = 0.1:0.02; PX:Lec
[c]NA: Nanoparticle agglomerates.
[d]NP: Nanoparticles.
[e]$Q_{8h}$: % Paclitaxel dissolved after 8 hours.

TABLE 11

Cascade impaction results of lyophilized paclitaxel nanoparticle agglomerates (values = average ± standard deviation.).

| Characteristics of the lyophilized NA[c] | | | Formulations F1[a] | F2[b] | Paclitaxel as received |
|---|---|---|---|---|---|
| At flow | % EF[d] | | 71.9 ± 4.9 | 71.6 ± 15.4 | 68.3 ± 6.1 |
| rate of | % RF[e] | <5.7 | 95.7 ± 3.01 | 95.3 ± 4.1 | 0.39 ± 0.3 |
| ~30 | | <3.3 | 83.8 ± 2.8 | 79.55 ± 4.8 | 0 |
| L//min | MMAD[f] | | 1.5 ± 0.1 | 1.9 ± 0.4 | 0.08 ± 0.02 |
| | GSD[g] | | 2.26 ± 0.09 | 2.29 ± 0.05 | 2.2 ± 0.03 |

[a]F1 = 0.1:0.02:0.01; Px:Lec:PVP K90
[b]F2 = 0.1:0.02; Px:Lec
[c]NA: Nanoparticle agglomerates.
[d]% EF: Percent emitted fraction.
[e]RF: Percent respirable fraction.
[f]MMAD: Mass median aerodynamic diameter.
[g]GSD: Geometric standard deviation.

Example 9

Application of Budesonide Nanoparticles

Budesonide is a potent nonhalogenated corticosteroid with high glucocorticoid receptor affinity, airway selectivity and prolonged tissue retention. It inhibits inflammatory symptoms, such as edema and vascular hyperpermeability. Budesonide is already applied through dry powder inhalers (DPI, Pulmicort), metered dose inhalers (pMDI, Rhinocort) or ileal-release capsules (Entocort). This drug is considered one of the most valuable therapeutic agents for the prophylactic treatment of asthma despite its poor solubility in water (21.5 mg/ml under constant agitation).

This example demonstrates the translation of budesonide nanosuspensions into dry powder formulations capable of effective deposition and rapid dissolution. Different surfactants were used to create surface charge on the nanoparticles and charge interactions were leveraged to agglomerate nanoparticles into nanoparticle agglomerates exhibiting a particle size range of ~2-4 μm. Nanoparticle suspensions were evaluated by measuring particle size, polydispersity and zeta potential. Nanosuspensions were then agglomerated and lyophilized to obtain dry powders composed of micron-sized agglomerates. Nanoparticle agglomerates were characterized by the determination of particle size, aerolization efficiencies, flowability characteristics, process yield and loading efficiency. Finally, dissolution studies were performed for the selected nanoparticles and nanoparticle agglomerates, which were compared with the stock drug.

Materials and Methods

Budesonide (Bud), L-a-phosphatidylcholine (lecithin; Lec), cetyl alcohol (CA), L-leucine (Leu), polyvinylpyrrolidone (PVP), sorbitan tri-oleate (Span 85) and sodium chloride were purchased from Sigma Chemicals Co, U.S.A. Pluronic F-127 (PL, Mw~12,220) was purchased from BASF, The Chemical Company, U.S.A. Polyvinyl alcohol (PVA; Mw=22,000, 88% hydrolyzed) was purchased from Acros Organics, N.J., U.S.A. Potassium dihydrogen phosphate, disodium hydrogen phosphate, acetone, ethanol and acetonitrile were purchased through Fisher Scientific. Floatable dialysis membrane units (Mw cut-off=10,000 Da) were obtained from Spectrum Laboratories Inc., U.S.A. A549 cells were obtained from the American Type Culture Collection (ATCC, Rockville, Md.). The cell culture medium (Ham's F-12 Nutrient Mixture, Kaighn's modified with L-glutamine) was purchased through Fisher Scientific. Fetal bovine serum (FBS) was purchased from Hyclone. Penicillin-streptomycin was purchased from MB Biomedical, LLC. Trypsin-EDTA was purchased through Gibco. MTS reagent [tetrazolium compound; 3-(4,5-dimethylthiazol-2-yl)-5-(3-carboxymethoxyphenyl)-2-(4-sulfophenyl)-2H-tetrazolium, inner salt] was purchased from Promega, U.S.A. Double-distilled water was used throughout the study, provided by an EASYpure® RODI (Barnstead International, Model # D13321).

Preparation of Budesonide Nanosuspensions

Nanosuspensions were prepared using a precipitation technique. Briefly, solutions of budesonide in acetone were prepared at concentrations of 0.1 and 0.2% w/v and water was used as nonsolvent. To precipitate the drug, the solution of budesonide was directly injected into the non-solvent at a rate of 1 mL/min under sonication (Fisher Scientific, Sonic Dismembrator) with an amplitude of 46% in an ice bath. The selected surfactants for the study included hydrophobic (cetyl alcohol and Span 85), hydrophilic (PL, PVA and PVP) and amphoteric (lecithin). The hydrophobic and amphoteric surfactants were added to the drug organic solvent solution and the contents were allowed to stand at room temperature for 30 to 45 minutes with occasional vortexing to allow complete solubilization of the drug and the surfactants. Hydrophilic surfactants were added to the aqueous phase. Surfactants were used individually or in combination as reported.

Agglomeration of Budesonide Nanoparticles

The budesonide nanoparticle agglomerates were prepared by slow addition of L-leucine solution (1% w/v) in water to agglomerate nanoparticle suspensions during homogenization at 25,000 rpm for 30 sec. The amount of L-leucine added was adjusted to a drug:leucine ratio equal to 1:1. The size of budesonide nanoparticle agglomerates was measured in Isoton diluent using a Coulter Multisizer 3 (Beckman Coulter Inc.) equipped with a 100 μm aperture after three hours of incubation with the agglomerating agent. The agglomerated suspensions were kept overnight at room temperature to allow evaporation of acetone and then frozen at −80° C. and transferred to a freeze dryer (Labconco, FreeZone 1). Drying lasted for 36 hours to remove all appreciable water content. Lyophilized powder was stored at room temperature for further characterization.

Characterization of the prepared nanoparticles and nanoparticle agglomerates.

Particle Size Analysis and Zeta Potential Measurement of the Selected Nanosuspensions.

The size and zeta potential of the nanosuspensions were determined by dynamic light scattering (Brookhaven, Zeta- PALS). Zeta potential measurements were performed using 1 mM KCl solution. All measurements were performed in triplicate.

Determination of Particle Size Distribution and Aerodynamic Diameter of the Prepared Nanoparticle Agglomerates.

The particle size of the dispersed nanoparticle agglomerates as well as the resuspended lyophilized powder was measured using a Coulter Multisizer 3. The aerodynamic size distributions of the agglomerate powders were measured directly from lyophilized powder by time-of-flight measurement using an Aerosizer LD (Amherst Instruments) equipped with a 700 μm aperture operating at 6 psi.

Aerosolization of Nanoparticle Agglomerates

Aerodynamic characteristics of selected nanoparticle agglomerates were studied in vitro using a Tisch Ambient Cascade Impactor (Tisch Environmental, Inc., Ohio). The study was carried out by applying ~20 mg powder manually into the orifice of the instrument at three air flow rates; ~15 L/min, ~30 L/min and ~60 L/min. Cut-off particle aerodynamic diameters at 30 L/min for each stage of the impactor were: pre-separator (10.00 μm), stage 0 (9.00 μm), stage 1 (5.8 μm), stage 2 (4.7 μm), stage 3 (3.3 μm), stage 4 (2.1 μm), stage 5 (1.1 μm), stage 6 (0.7 μm), stage 7 (0.4 μm) and filter (0 μm). Nanoparticle agglomerates deposited on each stage of the impactor were determined by measuring the difference in weight of filters placed on the stages. The mass median aerodynamic diameter, MMAD, and geometric standard deviation, GSD, were obtained by a linear fit of the cumulative percent less-than the particle size range by weight plotted on a probability scale as a function of the logarithm of the effective cut-off diameter.

Transmission Electron Microscopy (TEM)

Image data was used to corroborate the size of nanoparticles and nanoparticle agglomerates and to observe their morphological aspects. Transmission electron micrographs (TEM) were obtained for budesonide nanoparticles and nanoparticle agglomerates using a JEOL 1200 EXII transmission electron microscope. Initially, carbon-coated grids (Electron Microscopy Sciences) were floated on a droplet of the suspensions on a flexible plastic film (Parafilm), to permit the adsorption of the particles onto the grid. After this, the grid was blotted with a filter paper and air dried for 1 hr.

SSNMR Analysis

All 13C spectra were collected using a Chemagnetics CMX-300 spectrometer using ramped amplitude cross-polarization (RAMP), magic-angle spinning (MAS), and SPINAL-64 decoupling. Samples were packed in 7 mm zirconia rotors using Teflon® end caps, and spun at 4 kHz in a 7 mm spin module from Revolution NMR.

All spectra are the sum of 2,000-48,000 transients collected using a 1-1.5 sec pulse delay, a contact time of 0.5-2 ms, and a 1H 90° pulse width of 3-4.5 μs. The free induction decays consisted of 512-2048 points with a dwell time of 33.3 μs. The spectra were externally referenced to tetramethylsilane using the methyl peak of 3-methylglutaric acid at 18.84 ppm.

The assignment of the peaks in the $^{13}C$ spectrum of the "as received" budesonide was performed using the modified spectral editing methods of Hu et al. and the $^{13}C$ solution predictions from ChemBioDraw Ultra (version 11.0) from CambridgeSoft and ACD/CNMR Predictor (version 7.09) from ACD/Labs. The spectral editing subspectra were collected using the parameters given in Table 12. These parameters were optimized using 3-methylglutaric acid.

TABLE 12

Parameters used to collect $^{13}C$ spectral editing subspectra.*

| Subspectra | Pulse Sequence | $t_{CP}$ (μs) | $t_{PI}$ (μs) | $t_{DD}$ (μs) | $t_{SL}$ (μs) | Number of Transients |
|---|---|---|---|---|---|---|
| All | (+) | 1500 | 0.2 | — | 133 | 800 |
| C + $CH_3$ | (+) | 1500 | 0.2 | 130 | 3 | 800 |
| C | (−) | 400 | 135 | 130 | 3 | 8,000 |
| CH | (+) | 40 | 24 | — | 133 | 6,000 |
| | (−) | 37 | 0.2 | 130 | 1 | 6,000 |
| $CH_2$ | (+) | 80 | 39 | — | 133 | 6,000 |
| | (−) | 78 | 0.2 | 147 | 1 | 6,000 |

*= All subspectra were collected with a 1.5 sec pulse delay, a $^1H$ 90° pulse width of 3.1 μs, 1024 acquisition points with a dwell time of 33.3 μs, and a magic-angle spinning rate of 4 kHz.

Determination of Process Yield

The lyophilized powder for the prepared nanoparticle agglomerates was weighed and the yield was calculated using the following expression:

$$\% \text{ Process yield} = \frac{\text{Recovered mass}}{\text{Mass entered into the experiment}} \times 100$$

Budesonide Loading Efficiency Measurement

Budesonide loading efficiency was assessed by dispersing one mg of the lyophilized powder in 10 mL ethanol. The dispersion was sonicated in a bath-type sonicator (Branson 3510) for 2 hours and then kept overnight at room temperature to allow complete dissolution of the drug by ethanol. Then the solution was centrifuged (Beckman, Avanti TM) at ~15,000 rpm for 30 min to remove insoluble surfactants and L-leucine and the amount of drug in the supernatant was determined spectrophotometrically (Agilent C) at 243 nm. Drug loading was defined as follows:

Flowability Characteristics

The flow properties of the nanoparticle agglomerates were assessed by angle of repose (tan θ=height/radius) measurement of the dried powders. The fixed-height cone method was used. A glass funnel with cut stem surface of 5 mm internal diameter was fixed at 2.5 cm height over a flat surface. The powders were allowed to flow gently through the funnel until a cone was formed and reached the funnel orifice. The flow of powder was then stopped and the average diameter of the formed cone (D) was measured. The area of the base of the cone was taken as a measure of the internal friction between the particles. The angle of repose was calculated by the equation: tan θ=height/radius.

In addition, the bulk density, Hausner ratio (Tapped density/bulk density) and Carr's index (Ci) [(Tapped density−bulk density)/Tapped density×100%] were also determined for the dried powders. Five mg of powders were weighed and poured into a 10 mL graduated measuring cylinder. The bulk volume occupied ($V_b$) was recorded. The measuring cylinder was tapped until a constant value was obtained and the tapped volume was recorded ($V_t$). The process was repeated at least three times and the average was taken in each case. The bulk and tapped densities of powder were calculated by dividing the weight by the corresponding bulk volume or tapped volume recorded.

Dissolution Studies

The dissolution of the prepared nanoparticles and nanoparticle agglomerates was determined and compared with the dissolution characteristics of the stock drug. The dissolution of budesonide was carried out at 37±0.5° C. in a 400 mL beaker. A known amount (~10 mg) of the lyophilized powder was suspended in 10 mL phosphate buffered saline (PBS, pH 7.4) and was placed into a floatable dialysis membrane unit (Mw cut-off=10,000 Da), and the unit was allowed to float in a beaker containing 300 mL of PBS. The solution was stirred at a constant speed (100 rpm) using a magnetic stirrer (Barnstead, Thermolyne MIRAKTM). At predetermined time intervals for a total period of 8 hours, aliquots (5 ml) of the medium were removed and fresh medium was immediately added to continue the dissolution study. Studies were conducted in triplicate. The budesonide concentration was analyzed using a reverse-phase HPLC method. A Shimadzu HPLC system including a solvent delivery pump (Shimadzu LC-10AT), a controller (Shimadzu SCL-10A), an autoinjector (Shimadzu SIL-10AxL), and a UV detector (Shimadzu SPD-10A) was used in this study. The peak areas were integrated using Shimadzu Class VP (Version 4.3). A 4.6 mm×100 mm long Zorbax SB C-18 column (Agilent C) with a particle diameter of 3.5 μm was used. During the assay, budesonide was eluted isocratically at a mobile phase flow rate of 0.6 mL/minute and monitored with a UV detector operating at 254 nm. The mobile phase for the assay consisted of an acetonitrile and water mixture (45:55 v/v). The run time for the assay was 20 minutes, and the retention time for budesonide was 14.01 minutes.

Cytotoxicity Assay

The cytotoxicity of selected nanoparticles and nanoparticle agglomerates was assessed using the CellTiter 96® Aqueous Cell Proliferation Assay (Promega) and compared with stock budesonide, lecithin, leucine, physical mixtures of these ingredients and blank nanoparticle agglomerates. In this experiment, 8×104 A549 cells/well were seeded in 96-well microtiter plates. At the end of the incubation period (12 h), 20 ml of MTS reagent solution was added to each well and incubated for 3 hours at 37° C. The absorbance was measured at 490 nm using a microtiter plate reader (SpectraMax, M25, Molecular Devices Corp., CA). The percentage of viable cells with all tested concentrations was calculated relative to untreated cells.

Results and Discussion

Fabrication of Budesonide Nanoparticles

Various methods have been reported for generating nanoparticles of poorly water soluble drugs. A precipitation method was selected to produce budesonide nanoparticles. Different concentrations of the drug and various types and ratios of surfactants, individually or in combination, were evaluated as a means to control the particle size and surface charge. Surfactants were chosen from excipients regarded as suitable for inhalation that have been designated as safe for human use. Formulations prepared using PVP and PVA in different ratios produced very large particle sizes even when combined with other surfactants. The mean particle size of formulations containing lecithin, cetyl alcohol, Span 85 and/or PL ranged from ~130 to 323 nm. Formulations containing Span 85 alone or in combination with lecithin yielded the smallest particle size but since Span is liquid at room temperature, it was not suitable for use in dry powder formulations.

Attempts to generate budesonide nanoparticles using PL alone or in combination with lecithin yielded reasonable particle sizes (~129-270 nm) but offered very low nanoparticle yields and high polydispersity values. Selected surfactant combinations for preparing budesonide nanosuspensions in acetone were designated F1 (0.1% w/v Bud+0.02% w/v Lec), F2 (0.1% w/v Bud+0.02% w/v CA+0.01% w/v PL) and F3 (0.2% w/v Bud+0.04% w/v CA+0.02% w/v PL) as reported in Table 13. These surfactant combinations demonstrated small particle size and could be used in dry powder formulations. A small change in zeta potential was observed with different types of surfactants and the values ranged from 22.5-25.1 mV (Table 14). The charged surface of the nanoparticles provided the potential for destabilizing this colloid via interaction with a agglomerating agent to form nanoparticle agglomerates.

TABLE 13

Composition of the selected formulations.

| Formulation | Budesonide (% w/v) | Lecithin (% w/v) | Cetyl alcohol (% w/v) | Pluronic F127 (% w/v) |
|---|---|---|---|---|
| F1 | 0.1 | 0.02 | | |
| F2 | 0.1 | | 0.02 | 0.01 |
| F3 | 0.2 | | 0.04 | 0.02 |

TABLE 14

Physical properties of budesonide nanoparticle (values = average ± standard deviation.).

| Formulation | Nanoparticle size (nm) | Zeta-potential (mV) | Polydispersity |
|---|---|---|---|
| F1[a] | 160.9 ± 15.6 | 25.1 ± 1.3 | 0.41 ± 0.1 |
| F2[b] | 188.8 ± 26.3 | 24.2 ± 1.1 | 0.34 ± 0.02 |
| F3[c] | 232.2 ± 11.2 | 22.5 ± 0.5 | 0.33 ± 0.02 |

[a]F1 = 0.1:0.02; Bud:Lec
[b]F2 = 0.1:0.02:0.01; Bud:CA:PL
[c]F3 = 0.2:0.04:0.02; Bud:CA:PL

Agglomerated Budesonide Nanoparticles Yielded Desirable Aerosol Characteristics

The mechanism to control nanoparticle agglomeration is mainly driven by leveraging the competitive processes of attraction (van der Waals force) and repulsion (electrostatic repulsive force or steric hindrance barrier or both). If particles are mainly stabilized electrostatically, disruption of the electrostatic double layer surrounding the particles will result in the agglomeration of nanoparticles. The addition of agglomerating agents has also been speculated to decreases the cohesion between particles. It is thought that these agents may interfere with weak bonding forces between small particles, such as van der Waals and Coulomb forces. These agents may act as weak links or "chain breakers" between the particles which are susceptible to disruption in the turbulent airstream created during inhalation. The amino acid, L-leucine, used as a agglomerating agent in these studies may also act as an anti-adherent material to yield a high respirable fraction of the agglomerated budesonide nanoparticles.

Agglomeration of nanoparticles resulted in the formation of agglomerates within the micrometer or sub-micrometer scale consisting of closely-packed nanoparticles. Nanoparticle agglomerates were prepared through the slow incorporation of a agglomerating agent (L-leucine) during homogenization (25,000 rpm) for 30 sec. The geometric size distribution of the prepared nanoparticle agglomerates was measured in Isoton diluent using a Coulter Multisizer 3. The size average of the three selected nanoparticle agglomerate formulations ranged from ~2-4 μm (Table 15). The size distributions of resuspended lyophilized powders were slightly broader and the average particle size was slightly increased, when compared to the nanoparticle agglomerates prior to lyophilization (Table 15 and FIG. 15). This may be due to the deposition of nanoparticles on agglomerates during lyophilization or to cohesion between agglomerates as a result of drying. The key physical parameter that predicts the site of aerosol deposition within the lungs for particles larger than several hundred nanometers is the aerodynamic diameter ($d_{aero}$). The aerodynamic diameter of the agglomerated nanoparticles, measured by an Aerosizer LD, was smaller than the geometric diameter and the aerodynamic size distribution was narrower than the geometric size distribution (Table 15 and FIG. 16). When compared to the geometric diameter, the lower aerodynamic diameter was likely due to the low density of nanoparticle agglomerates.

TABLE 15

Characteristics of budesonide nanoparticle agglomerates
(values = average ± standard deviation.).

| Characteristics | Formulations | | |
|---|---|---|---|
| | F1[a] | F2[b] | F3[c] |
| Geometric particle size (μm) of NA[d] before lyophilization | 2.8 ± 0.4 | 2.7 ± 0.4 | 3.2 ± 0.7 |
| Geometric particle size (μm) of lyophilized NA[d] | 3.1 ± 0.6 | 3.3 ± 0.7 | 3.9 ± 1.1 |
| MMAD[f] of lyophilized NA[d] | 1.4 ± 1.7 | 2.1 ± 1.8 | 1.9 ± 1.8 |
| % Process yield of lyophilized NA[d] | 95.5 ± 4.9 | 92.7 ± 3.1 | 89.7 ± 3.6 |
| Loading Efficiency of lyophilized NA[d] | 95.9 ± 3.6 | 86.5 ± 6.0 | 92.5 ± 6.6 |
| $Q_{8h}{}^g$NP[e] | 61.5% ± 1.6 | 75.5% ± 9.9 | 88.9% ± 3.0 |
| $Q_{8h}{}^g$NA[d] | 41.8% ± 4.6 | 51.2% ± 5.1 | 63.1% ± 5.1 |

[a]F1 = 0.1:0.02; Bud:Lec
[b]F2 = 0.1:0.02:0.01; Bud:CA:PL
[c]F3 = 0.2:0.04:0.02; Bud:CA:PL
[d]NA: Nanoparticle agglomerates.
[e]NP: Nanoparticles.
[f]MMAD: Mass median aerodynamic diameter obtained from Aerosizer.
[g]$Q_{8h}$: % budesonide dissolved after 8 hours.

The theoretical mass-mean aerodynamic diameters (daero) of the nanoparticle agglomerates, determined from the geometric particle size and tapped density, was found to be 2, 2.1 and 2.5 μm for F1, F2 and F3, respectively as calculated from the relationship:

$$d_{aero} = \frac{d_{geo}}{\gamma}\sqrt{\rho/\rho_a}$$

Where $d_{geo}$=geometric diameter, $\gamma$= shape factor (for a spherical particle, $\gamma=1$; for aerodynamic diameter calculations, the particles in this study were assumed to be spherical), $\rho$= particle bulk density and $\rho_a$= water mass density (1 g/cm$^3$). Tapped density measurements underestimate particle bulk densities since the volume of particles measured includes the interstitial space between the particles. The true particle density, and therefore the aerodynamic diameter of a given powder, is expected to be slightly larger than reported. Particles with a $d_{aero}$ between 1 and 5 μm that are inhaled via the mouth are capable of efficient alveolar deposition, whereas $d_{aero}$ between 4 and 10 μm are more likely to deposit primarily in the tracheobronchial region of the lungs. Therefore, the budesonide nanoparticle agglomerates with daero in the 2-2.5 μm range are expected to deposit primarily in the alveolar region of the lungs.

Aerosizer results and theoretical MMAD calculations were corroborated by cascade impaction studies at air flow rates of ~15 L/min, ~30 L/min and ~60 L/min (FIG. 17). At these flow rates, most nanoparticle agglomerates were deposited in stages 6 and 7 of the cascade impactor which was suggestive of efficient aerosolization and a high fine particle fraction. The aerosolization efficiency of nanoparticle agglomerates was represented by the percent emitted fraction (% EF), percent respirable fraction (RF), mass-median aerodynamic diameter (MMAD) and geometrical standard deviation (GSD). The percent emitted fraction was determined from the following equation:

$$\% \text{ Emitted fraction } (\% \text{ } EF) = \frac{\text{Total particle mass collected from the stages of the impactor}}{\text{Total particle mass entered into the impactor}} \times 100$$

The high emitted fraction of nanoparticle agglomerates obtained at the tested flow rates suggested efficient aerosolization of the powder (Table 16). The percent respirable fraction (RF), referred to also as the fine particle fraction of the total dose (FPFTD), was calculated as the percentage of aerosolized particles that reached the lower seven stages of the impactor (corresponding to aerodynamic diameters below 5.8 μm), or the lower five stages (corresponding to aerodynamic diameters below 3.3 μm) according to the following equation:

$$\% \text{ Respirable fraction } (RF) = \frac{\text{Powder mass recovered from terminal stages of the impactor}}{\text{Total particle mass recovered in the impactor}} \times 100$$

The results of the respirable fraction also suggested the efficient aerosolization of nanoparticle agglomerate powders (Table 16). The geometric standard deviation (GSD) of the nanoparticle agglomerates was determined from the following equation:

$$GSD = \left(\frac{d_{84.13\%}}{d_{15.87\%}}\right)^{1/2}$$

Where $d_n$ is the diameter at the nth percentile of the cumulative distribution. The mass-mean geometric size of nanoparticle agglomerates ranged between 3 and 4 μm with a GSD of ~2.3 μm (Table 16). Typical GSD values for aerosol particles are between 1.3-3.0.17 The mass-mean aerodynamic diameter (MMAD) of the selected nanoparticle agglomerates, as calculated from the cascade impaction results (Table 16) was close to that obtained from the Aerosizer (Table 15) although it was slightly smaller than the theoretical density values calculated from the tapped density indicating the suitability of the prepared nanoparticle agglomerate powders for peripheral lung deposition (i.e., <3 μm).

TABLE 16

Cascade impaction results of lyophilized budesonide nanoparticle agglomerates (values = average ± standard deviation).

| Characteristics of the lyophilized NA[d] | | | Formulations | | |
|---|---|---|---|---|---|
| | | | F1[a] | F2[b] | F3[c] |
| At flow rate of ~15 L//min | % EF[e] | | 74.9 ± 6.1 | 69.3 ± 5.5 | 86.5 ± 8.6 |
| | % RF[f] | <5.7 | 96.3 ± 1.8 | 97.5 ± 1.3 | 97.9 ± 0.3 |
| | | <3.3 | 77.6 ± 3.9 | 81.2 ± 5.2 | 75.3 ± 1.7 |
| | MMAD[g] | | 1.7 ± 0.1 | 1.5 ± 0.1 | 1.9 ± 0.3 |
| | GSD[h] | | 2.4 ± 0.2 | 2.3 ± 0.1 | 2.3 ± 0.3 |
| At flow rate of ~30 L//min | % EF[e] | | 75.3 ± 7.3 | 70.2 ± 4.1 | 81.2 ± 12.9 |
| | % RF[f] | <5.7 | 97.1 ± 0.2 | 96.8 ± 1.5 | 96.9 ± 1.4 |
| | | <3.3 | 84.3 ± 3.9 | 87.7 ± 1.5 | 82.3 ± 4.2 |
| | MMAD[g] | | 1.3 ± 0.2 | 1.2 ± 0.04 | 1.6 ± 0.3 |
| | GSD[h] | | 2.3 ± 0.3 | 2.3 ± 0.4 | 2.3 ± 0.1 |
| At flow rate of ~60 L//min | % EF[e] | | 77.4 ± 6.6 | 72.2 ± 5.9 | 82.9 ± 12.7 |
| | % RF[f] | <5.7 | 95.8 ± 0.2 | 95.9 ± 1.5 | 95.7 ± 1.7 |
| | | <3.3 | 87.1 ± 2.3 | 89.3 ± 2.5 | 83.6 ± 2.8 |
| | MMAD[g] | | 1.1 ± 0.2 | 1.1 ± 0.1 | 1.3 ± 0.2 |
| | GSD[h] | | 2.3 ± 0.1 | 2.3 ± 0.2 | 2.3 ± 0.1 |

[a]F1 = 0.1:0.02; Bud:Lec
[b]F2 = 0.1:0.02:0.01; Bud:CA:PL
[c]F3 = 0.2:0.04:0.02; Bud:CA:PL
[d]NA: Nanoparticle agglomerates.
[e]% EF: Percent emitted fraction.
[f]RF: Percent respirable fraction.
[g]MMAD: Mass median aerodynamic diameter.
[h]GSD: Geometric standard deviation.

Electron microscopy was used to study the morphology of budesonide nanoparticle and nanoparticle agglomerate formulations. Transmission electron micrographs (TEM) of F1 nanoparticles (FIG. 18A) depicted slightly elongated nanoparticles with smooth surfaces and a particle size around 170 nm. TEM images of F1 nanoparticle agglomerates (FIG. 18B) show that the nanoparticles were agglomerated into micron sized agglomerates with irregular structure and some sharp edges.

FIG. 19 shows the $^{13}C$ spectra of budesonide by itself and in formulations. Both the budesonide as received and the leucine exhibit relatively narrow lines (several tens of hertz), indicating that these samples are crystalline. Lecithin also had narrow lines, which is consistent with it being a crystalline form of phosphatidylcholine; however, it is a semi-solid and therefore cannot be crystalline. Conversely the budesonide that was melt quenched had significantly broader lines (several hundreds of hertz) indicating that the budesonide is consistent with it being amorphous. In the nanoparticles, the peaks for budesonide are similar to the peaks in the budesonide that was melt quenched, although the peak at ~180 ppm shows that there is a small amount of crystalline budesonide in the nanoparticles. The tall, sharp peaks in the spectrum of the nanoparticle agglomerates align with the peaks in the leucine spectrum and showed that the leucine in the formulation has undergone phase separation and has crystallized to some extent. The peak at 180 ppm showed that the amount of crystalline budesonide had increased in the formulation of the nanoparticle agglomerates. This was consistent with the shape of several other budesonide peaks in the spectrum.

Budesonide consists of 25 carbons (FIG. 20); however, the spectrum of the budesonide as received had at least 27 resolved peaks and several peaks that may be the result of several overlapping peaks. The extra peaks did not seem to be due to splitting, as would be expected if there were more than one molecule in the asymmetric unit cell.

The budesonide is a racemic mixture of both epimers that have been shown to pack differently in the crystal lattice. Therefore, spectral editing was used in an attempt to assign the peaks in the spectrum to determine if the differences in the two epimers could be used to explain the "extra" peaks. The spectral editing experiment allowed the assignment of carbon type (C, CH, CH2, or CH3) to a peak, these assignments could then be combined with predictions to assign the peaks to specific carbons within the molecule. The carbon type of most of the peaks could be assigned from these experiments (FIG. 21) with the exception of a few of the aliphatic peaks (particularly ~30--40 ppm). These results were then compared with predictions of the solution state chemical shifts from two different software programs and the resulting assignments are shown in Table 17.

TABLE 17

$^{13}C$ peak assignments for budesonide as received.

| Assignment | As Received | ACD/Labs* | ChemBioDraw* |
|---|---|---|---|
| 20 | 209.0 | 207.0 | 211.2 |
| 3 | 185.4 | 186.2 | 185.7 |
| 5 | 170.6 | 170.3 | 168.1 |
| 1 | 156.7 | 156.5 | 158.4 |
| 2 | 122.5 and 128.2 | 127.5 | 128.3 |
| 4 | | 122.1 | 124.2 |
| 22 | 104.5 and 107.3** | 105.1 | 102.0 |
| 17 | 99.8 | 94.4 | 105.0 |
| 16 | 83.0 | 77.3 | 86.7 |
| 11 | 67.4 and 70.7 | 68.0 | 69.0 |
| 21 | | 67.0 | 66.6 |
| 9 | 49.7 and 53.6 | 54.1 | 59.0 |
| 14 | | 48.8 | 44.0 |
| 13 | 44.6 and 47.4 | 47.0 | 44.7 |
| 10 | | 42.6 | 44.1 |
| 12 | 32.2, 33.9, 34.7, | 41.0 | 40.4 |
| 23 | 38.1, 39.0, and | 35.3 | 36.5 |
| 7 | 40.2 | 33.4 | 32.0 |
| 6 | | 31.9 | 32.9 |
| 15 | | 31.9 | 32.7 |
| 8 | 31.6 | 32.3 | 34.6 |
| 19 | 15.6, 18.7, and | 21.0 | 19.0 |
| 18 | 22.5 | 16.3 | 17.3 |
| 25 | | 14.0 | 14.4 |
| 24 | 17.2 | 18.4 | 13.1 |

*= Software predictions of chemical shifts in solution.

**= See text for explanation.

Chemical shifts for a compound in the solution and solid state can vary by as much as 10 ppm. For this reason, some assignments can be narrowed down to a few possibilities but an exact assignment was not possible with this data. For example, carbons 2 and 4 can be assigned to the peaks at 122.5 and 128.2, but it was not possible to definitively determine which carbon was associated with which peak. The solution predictions placed carbon 22 at ~103 ppm, while the spectral editing experiment showed that there are two peaks at 104.5 and 107.3 ppm that can be assigned to CH carbons. Additionally, carbon 22 is the chiral center of the epimers. Based on these observations and the fact that the two epimers have been shown to pack in different conformations, both peaks were assigned to carbon 22 with the interpretation that each peak represents one of the epimers. It is important to note that this interpretation assumes the budesonide is pure, which we have not confirmed. Additionally, there is always the possibility that these are different polymorphs; however, reports of polymorphism in budesonide have not been identified.

The process of agglomerating nanoparticles was evaluated to determine their yield. The results (Table 15) have shown that the process was efficient providing a high yield (~90-95%) and minimum batch variability. The loading efficiency of the drug in the prepared nanoparticle agglomerates was found to be between 85-95% (Table 16), thus demonstrating minimal loss of drug during formation.

The flow characteristics of the selected nanoparticle agglomerates were also determined (Table 18). Angle of repose, Hausner ratio and Carr's index are considered to be indirect methods for quantifying powder flowability. Budesonide nanoparticle agglomerates generally exhibited similar bulk densities and lower tapped densities than that of the stock drug powder. Nanoparticle agglomerates also demonstrated improved flow properties. This may be attributed to the reduced density of the nanoparticle agglomerates. In addition, L-leucine has been reported to reduce surface energy in dry powders and may improve flowability in this case. Formula F3 showed slightly better flowability compared to the others according to the Carr's index; however, all nanoparticle agglomerate powders possessed acceptable flowability.

TABLE 18

Flowability characteristics of budesonide nanoparticle agglomerates (values = average ± standard deviation).

| Formula No. | Angle of repose (θ) (flow-ability) | Bulk density (g/cm3) | Tapped density (g/cm3) | Carr's index ($C_i$ %) | Hausner ratio |
|---|---|---|---|---|---|
| F1[a] | 37.1 ± 2.6 | 0.34 ± 0.1 | 0.42 ± 0.03 | 21.8 ± 0.5 | 1.2 ± 0.03 |
| F2[b] | 39.1 ± 1.1 | 0.31 ± 0.1 | 0.40 ± 0.1 | 23.6 ± 0.6 | 1.3 ± 0.03 |
| F3[c] | 37.8 ± 2.1 | 0.29 ± 0.1 | 0.38 ± 0.1 | 18.6 ± 0.4 | 1.2 ± 0.1 |
| Stock budesonide | 43.5 ± 0.7 | 0.30 ± 0.04 | 0.47 ± 0.1 | 35.4 ± 2.1 | 1.5 ± 0.1 |

[a]F1 = 0.1:0.02; Bud:Lec
[b]F2 = 0.1:0.02:0.01; Bud:CA:PL
[c]F3 = 0.2:0.04:0.02; Bud:CA:PL

Budesonide Nanoparticle and Nanoparticle Agglomerates Showed Improved Dissolution Rates A dissolution study of budesonide was conducted for the prepared nanoparticles and nanoparticle agglomerates and compared to the unprocessed drug. The cumulative percentage of drug dissolved after 8 hours (Q8 h) was found to be slower than that of the nanoparticles and faster than that of the stock budesonide (Table 15). This finding was the expected result of increasing the surface area by decreasing the particle size. F2 and F3 nanoparticle and nanoparticle agglomerate formulations showed faster drug dissolution than F1 which may be due to the incorporation of the hydrophilic surfactant, PL (FIG. 22). In addition, increasing the concentration of this surfactant (F3) led to even faster dissolution. Linear regression analysis of the dissolution data concluded that the drug was released by the Higuchi diffusion mechanism in all cases. A two-way Analysis of Variance (ANOVA) was performed to determine the significance of differences in dissolution kinetics. Significant differences (α=0.05) existed between nanoparticles, nanoparticle agglomerates and stock budesonide. No significant differences existed between different nanoparticles or nanoparticle agglomerate formulations. A significant improvement (P<0.05) in the dissolution behavior of the nanoparticles and nanoparticle agglomerates was also observed when these were individually compared to the stock budesonide.

Formulation Components Exhibited Minimal Cytotoxicity

The cytotoxicity of the different budesonide formulations were compared to stock budesonide, lecithin, leucine, physical mixtures of F1 components and blank F1 nanoparticle agglomerates (FIG. 23). Stock budesonide, excipients and physical mixtures of F1 components up to 5 mg/mL did not show any significant cytotoxicity in A549 cells at the end of 12 hours. Blank F1 nanoparticle agglomerates did induce a very low level of cytotoxicity where the IC50 was found to be 0.97 mg/mL. Additionally, F1 nanoparticles and nanoparticle agglomerates also induced very low level of cytotoxicity with IC50 values equal to 1.67 mg/mL and 1.91 mg/mL, respectively. The IC50 values occurred at higher concentrations than the maximum daily dose of inhaled budesonide currently prescribed. These results may suggest that lecithin was responsible for the cytotoxic effect.

Many current techniques to generate dry powder aerosols have a major disadvantage of poor control over the particle shape, size and size distribution. In addition, many pulmonary formulations may benefit from the improved bioavailability and rapid onset of action that may be achieved by using drug nanoparticles. In this work, budesonide nanosuspensions were successfully prepared yielding nanoparticles in the range of ~160-230 nm. This was accomplished by using surfactants proven to be safe for human use such as lecithin. Nanosuspensions were agglomerated using L-leucine and the resulting nanoparticle agglomerates were analyzed. Nanoparticle agglomerates were efficiently aerosolized and offered a high fine particle fraction suitable for accessing the peripheral lung. Nanoparticle agglomerates also exhibited significantly faster budesonide dissolution when compared to the stock powder. In conclusion, budesonide nanoparticle agglomerates demonstrated a desirable microstructure for efficient lung deposition and nanostructure for rapid dissolution of poorly water soluble drugs.

Example 10

Application of Nifedipine Nanoparticles

Nifedipine (NIF), stearic acid (SA), arachidonic acid (AA), sodium chloride and calcium chloride were purchased from Sigma Chemicals Co, U.S.A. and used as received in solid form. Acetone, methanol, ethanol, and phosphate buffered salts were purchased from Fisher Scientific and used as received. Dialysis membranes (MWCO=6-8 kDa) were purchased from Fisher Scientific. DI water was used throughout the study as obtained from a Millipore ultrapurification unit present on site.

Preparation of Nifedipine Nanoparticle Suspensions

Nanoparticles were prepared by the rapid mixing of ethanol with dissolved nifedipine and stearic acid into a larger aqueous volume, known as a solvent anti-solvent precipitation technique. Briefly, 10 mg of Nifedipine and 1 mg of stearic acid were completely dissolved in 1 ml of ethanol and allowed to stir overnight. Upon complete dissolution this solution was added to 29 ml of cold deionized water under probe sonication at 60% amplitude for 20 seconds. The resulting colloid was then immediately frozen and lyophilized, or stored in a 4° C. refrigerator until further processing into agglomerations. At this time, a small sample was taken from the solution for sizing and imaging. All solution vials and reaction vessels were kept covered from any light sources, as Nifedipine exhibits considerable photosensitivity from UV and visible light spectra.

Preparation of Nanoparticle Agglomerations

Nanoparticle colloids were destabilized via a largely understood combination of ionic and thermodynamic force interactions to produce stable agglomerations of nanoparticles. Briefly, 30 ml of the nanoparticle suspension was taken from refrigeration and solid salt crystals were added in various amounts. Directly after addition, the suspensions would be subject to vigorous mixing via a homogenization probe operating at 20,000 RPM. Three different salt species were tested for their ability to form agglomerations: sodium chloride, calcium chloride, and magnesium sulfate. Salts were commonly added in a 1:1 ratio of salt to NIF. Colloid stability was also tested under a range of salt molarities and agglomeration behaviors were observed under all conditions.

Nanoparticle Characterization

Nanoparticle size, polydispersity, and zeta potential were all measured in solution directly after synthesis and prior to agglomeration using a zetaPALS dynamic light scattering device. Size and polydispersity were first measured. Briefly, 1 ml of the solution was added to a standard cuvette and the remaining volume was filled with deionized water. Data were collected in three runs and combined to arrive at a final size for each solution. Measurements were taken at 90 degrees to the incident light source while assuming a viscosity and refractive index of pure water. After arriving at a combined size, a second cuvette was filled with 1 ml of our colloid solution and the remaining volume was filled with KCl. A known voltage was then applied to this solution and data were analyzed via online software to determine the zeta potential of the particles in solution.

Agglomerate Characterization

Agglomerated nanoparticles were studied in solution and as a dry powder. After the agglomeration event was complete, a small volume (~3 ml) of the solution was analyzed using a Beckman Coulter multisizer III. Data were collected until the output graphs showed a stable shape and particle counts were above 100,000.

After lyophilization, dry powders of the agglomerates were first analyzed using an aerosizer. At this point, 5 mg of the powder was added to the aerosizer and data were collected until the output graphs showed a stable shape and the particle counts were above 100,000. Measurements were taken under medium shear and no regularization.

A cascade impactor was then used to collect data on powder performance in the lung. Briefly, eight filters were pre-weighed and set onto collection plates which were housed within eight airtight stages arranged serially and stacked on a level setting. Air was then pumped through the stages at 30 liters per minute via a vacuum pump and 10 mg of sample was introduced at the top of the impactor device. The powders were allowed to deposit amongst the stages for 20 seconds, after which time the air flow was stopped. Filters were then removed from the stages and weighed a second and final time.

Finally, the powders were characterized via two simple tests: a tap density test, and a test for angle of repose. The tap (bulk) density was determined by demarcating a small cuvette with known volumes, and then inserting a small mass of powder into the cuvette and tapping it vertically against a padded bench top 50 times. The density was tested in triplicate. The angle of repose was measured by placing a volume of powder on a glass slide and tilting the slide until the powder began to move down the slide, and recording the angle between the slide and the horizontal. This test was also performed in triplicate for each sample.

Particle Imaging

Nanoparticles, nanoclusters, and pure drug crystals were imaged via a scanning electron microscope. The samples were deposited onto mica slides in solution (or as received for the crystals) and allowed to evaporate over night. The slides were then coated with a 2 nm gold surface using a voltage controlled gold sputtering device and subject to a vacuum chamber whereby image data were subsequently collected.

Dissolution Studies

Dissolution events for the agglomerates, nanoparticles, and pure drug were observed and data were recorded using a Shimadzu SPD-10A UV-Vis detector set for detection at 240 nm. 45:55 (water:methanol) mixture buffered to pH 4.5 was used as mobile phase. Flowrates in the column were adjusted to 2 ml/hr and all injections were made at 50 µl. All studies were performed via the dialysis method in triplicate and sink conditions were maintained at a 30:1 volume ratio. Solutions were allowed to stir at 200 rpm without heating. Samples were introduced into dialysis bags with a molecular weight cut off of 6-8 kDa.

Results

The properties of our nanoparticle samples are shown in Table 19. It is hypothesized that including stearic acid in the formulation allows the polar lipids to migrate to the surface of the nanoparticles arranging their carbon chains to the core of the particles while allowing their hydroxyl groups to hydrogen bond with the surrounding water molecules. This behavior is observed from the greatly reduced zeta potential of the particles as compared with the pure drug nanoparticles (data not shown). Nifedipine is a characteristically non polar molecule, so any accumulation of charge on the surface of the nanoparticles may be attributed to the stearic acid. This reasoning is also aided by the observation that stearic acid is slightly more hydrophilic than nifedipine, so it likely acts as a surfactant between the nifedipine and the surrounding water molecules and thus migrates to the surface.

TABLE 19

Nanoparticle size, polydispersity, and zeta potential for an optimal formulation from an ethanol solution containing 1% w/v nifedipine and using stearic acid as a stabilizer in a ratio of 10:1 drug:acid.

| | |
|---|---|
| Effective Diameter (nm) | 732.1 |
| Polydispersity | 0.012 |
| Zeta Potential (mV) | −26.46 |
| Drug/Acid (mg/mg) | 10 |
| Vsolvent (mL) | 1 |
| Vantisol (mL) | 29 |

TABLE 20

Flowability parameters for three samples: Pure drug as received, a selected sample of nifedipine/stearic acid nanoparticles, and their corresponding agglomerates.

| Sample | Bulk Density (g/cm$^3$) | Tapped Density (g/cm$^3$) | Carr Index | Hausner Ratio |
|---|---|---|---|---|
| Pure Nif | 0.205 | 0.227 | 10.00 | 1.11 |
| Nif/SA NP | 0.103 | 0.123 | 16.67 | 1.20 |
| Nif/SA Floc | 0.073 | 0.097 | 25.00 | 1.33 |

It was observed that a main design constraint, nanoparticle size, could not be easily controlled by manipulating operating conditions during the formation of the colloid (data not shown). This is probably due to dominating thermodynamic force interactions in the suspension. The rate of particle precipitation is strongly dependent on the relative solubilities of the drug in both phases (water and ethanol), and this effect dominates other potential factors in particle formation such as mixing energy and time. As long as there is sufficient mixing of these two solvents, which can be achieved via ultrasonication at low to moderate amplitudes, the nucleation and growth kinetics will be able to proceed as governed by the unique interfacial force balances within the system.

Size distributions for a sample of nanoparticle agglomerations are shown in FIG. 24. This data reveals the particle size distribution from a sample of nanoparticles (geometric diameter: 421.7+/−26.2 nm, zeta potential: −32.16+/−3.75) before and after homogenization at 25,000 RPM for 30 seconds. The data were collected in solution, and as such it is not ideal data for studying the powder characteristics of the agglomerates.

However, it is important at this stage in the synthesis to verify agglomeration, as it is well known that particles can agglomerate upon lyophilization and we wanted to verify that this is not the case in our experiments. The samples reveal a fairly monodisperse distribution of sizes between about 2 and 20 microns, with an average diameter of about 10 microns. More so, the data reveals very stable microstructure in the agglomerates. Their distributions are barely altered after intense homogenization, and they maintain their shape almost entirely.

To begin powder characterization, particle samples were tested on an aerosizer via time of flight measurements. Only agglomerates were used in the aerosizer. FIG. 25 shows a typical aerodynamic size distribution as collected via this method. The theoretical mass-mean aerodynamic diameter ($d_{aero}$) of the nanoparticles was determined from the geometric particle size and tapped density using the following relationship:

$$d_{aero} = \frac{d_{geo}}{\gamma} \sqrt{\rho/\rho_a}$$

Where $d_{geo}$=geometric diameter, $\gamma$=shape factor (for a spherical particle, $\gamma$=1; for aerodynamic diameter calculations, the particles in this study were assumed to be spherical), $\rho$=particle density and $\rho_a$=water mass density (1 g/cm$^3$). As one can see from the variables, if the particle density is lower than that for water, then the aerodynamic diameter will be some fraction of the geometric diameter. This is the case for our agglomerate samples. Their geometric diameters are shown to be much larger, on average, than the aerodynamic diameters.

FIG. 26 shows SEM micrographs of the nanoparticles, agglomerates and pure drug. These images further validate the data collected, thus far. The nanoparticles are shown to bear an elliptical morphology with an average diameter somewhere below one micron, but not as small as 100 nanometers. The agglomerate images reveal a highly textured morphology, with many small and similarly shaped lumps protruding from the surface. These features are indicative of the mechanism behind particle formation, as they are probably the result of nanoparticles grouped together during the agglomeration step. Also, we can see a somewhat porous assembly in the imaged marked 'C'. Finally, the pure drug is shown to bear a highly crystalline structure, and is received in crystals larger than 100 micrometers in some cases. This crystalline morphology is not seen in any of the other images, thus indicating the potential change in overall crystallinity.

DSC thermographs were used to further investigate the effects of processing on drug crystallinity, and to verify the overall content in each of our formulations. As we can see from FIG. 27, both stearic acid and nifedipine draw sharp endothermic troughs where they undergo a melting phenomenon upon heating. These troughs show up in all the other graphs, however their extent and exact shape undergo changes. Firstly, it can be seen that the area between the curves and the baseline decrease for all processed samples. This may be due to experimental error, as small samples (<5 mg) were used to collect data for all particles. This was due, in part, to their very low density and the difficulties of handling the powders within the small sampling trays. However, it may be noted that since the particles have such a large surface area per mass, they will be much more susceptible to heating and thus will not require as much heat to induce a state transition. This difference would then show up as smaller troughs in the DSC endotherms. It is also worth noticing the consistently changed shape of the nifedipine peak for the nanoparticle samples. They reveal an exothermic peak indicative of a crystallization event, or some other energy producing phenomena. It may be surmised that the stearic acid and nifedipine interact upon melting of the nifedipine, whereby they arrange with respect to each other into a semi crystalline state of lower energy than just the randomly organized fluids initially present. No other theories for these exotherms have been presented at this point.

Dissolution studies were conducted to measure the relative ease of nifedipine dissolution from the various forms of processed drug as seen in FIG. 28. Drug was mostly dissolved from all samples within 8 hours, or the kinetics simply slowed to a considerable halt, as was the case with the pure nifedipine crystals. We can see here that the nanoparticles released the most drug in the least amount of time. This is to be expected as their smaller size allows for a greater surface area for the dissolution event to take place. The agglomerates outperformed the pure drug by a considerable margin, but no samples released 100% of their material into the bulk medium. This was due primarily to difficulties in the experimental apparatus, as nifedipine was inclined to adhere to the air water interfaces within the dissolution membrane and also to the membrane itself. Lack of proper dispersion prevented the pure drug samples from maintaining an optimal contact with the dissolution medium, and the same holds true for the other samples though to a lesser degree.

Finally, cascade impaction studies were performed to formalize our powder characterization for a pharmacological setting. The cascade impactor is a well known instrument devised in the 1950's for simulating aerosol performance in the human lungs. The stages are set up so that each of them (1-7 and F) represents a deeper layer of the pulmonary bed. Our data are shown in FIG. 29. Firstly, it should be noted that stage F is shown here as stage 8, simple to ensure a numerical ordering to the graph. The outputs reveal different behaviors for each of the samples. The pure drug mostly deposits in the earlier stages, 1-3. These stages represent the pharynx and primary bronchi and so it may be assumed that these powders would not enter the lungs whatsoever. The nanoparticles show the bulk of their deposition between stages 4-6 and these represent the secondary, and terminal bronchiolar and alveolar regions. The agglomerates show similar deposition patterns. Indeed, these are suitable regions for delivery of particles to the lungs and so it may be shown here that both the nanoparticle samples and their corresponding agglomerates are able to deposit efficiently to the lungs. The exact reasons for this similarity, given different processing steps, may be elusive for the time being. However, one may consider that the nanoparticles are able to agglomerate upon lyophilization and hence bear similar structural properties to the agglomerates. However, this similarity does not necessarily detract from the advantages of the agglomeration since the agglomerated particles are more likely able to be harvested directly from solution without the expensive processing step of lyophilization.

Stearic acid stabilized pure drug nanoparticles of nifedipine were synthesized via ultrasonication in a pure aqueous solution. These colloids were destabilized under different salt molarities and/or salt:drug mass ratios to induce particle agglomeration and subsequent microstructure formation. Nifedipine changes morphology upon processing with and without stearic acid. Nanoparticles revealed enhanced dissolution kinetics when compared to the pure drug and agglomerated samples. The resulting dried powders exhibited suitable flowability characteristics and size distributions for pulmonary drug delivery.

Throughout the course of preparing samples for the primary study, data were collected to help optimize the formulation and gain understanding of the processes at work. The results of these studies are shown here, with a brief discussion concerning their significance.

TABLE 21

Nanoparticle size, polydispersity, and zeta potential under various operating conditions.

| Sample | size(nm) | polydispersity | zeta(mV) | drug/acid | disp. vol. (ml) | cont. vol. (ml) | son. time(s) |
|---|---|---|---|---|---|---|---|
| A | 235.10 | 0.03 | −20.93 | 50.00 | 1.50 | 30.00 | 90.00 |
| B | 259.60 | 0.01 | −27.38 | 10.00 | 1.50 | 25.00 | 90.00 |
| C | 262.90 | 0.24 | −30.44 | 0.71 | 5.00 | 50.00 | 60.00 |
| D | 264.30 | 0.51 | n/a | 6.00 | 5.00 | 50.00 | 120.00 |
| E | 308.80 | 0.26 | −19.67 | 5.00 | 1.50 | 25.00 | 60.00 |
| F | 317.80 | n/a | −46.61 | 0.30 | 5.00 | 50.00 | 60.00 |
| G | 323.30 | n/a | −33.64 | 0.60 | 5.00 | 50.00 | 60.00 |
| H | 336.10 | n/a | −34.42 | 0.60 | 5.00 | 50.00 | 60.00 |
| I | 472.30 | 0.15 | n/a | 6.00 | 1.00 | 50.00 | 20.00 |
| J | 584.40 | 0.01 | n/a | 6.00 | 1.00 | 25.00 | 60.00 |
| K | 598.10 | n/a | n/a | 6.00 | 0.10 | 25.00 | 40.00 |
| L | 635.20 | 0.46 | n/a | 6.00 | 5.00 | 10.00 | 60.00 |
| M | 653.70 | 0.23 | n/a | 6.00 | 0.10 | 50.00 | 60.00 |

TABLE 22

Particle sizes under a range of sonication amplitudes. W/O = 25, D/A = 1, Vtot = 30 ml, Prepared with 0.1% nifedipine in ethanol and stearic acid as a stabilizer.

| Amplitude (%) | Effective Diameter (nm) | Polydispersity |
|---|---|---|
| 10 | 626.1 | 0.064 |
| 20 | 696.5 | 0.271 |
| 30 | 947.3 | 0.289 |
| 40 | 1057.5 | 0.005 |
| 50 | 1049.3 | 0.22 |
| 60 | 1303.7 | 0.005 |
| 70 | 689.8 | 0.354 |

TABLE 23

Particle sizes under a range of sonication times. W/O = 60, D/A = 10, Vtot = 30 ml, prepared with 1% nifedipine in ethanol.

| Time (seconds) | Effective Diameter (nm) | Polydispersity | Zeta Potential |
|---|---|---|---|
| 5 | 534.3 +/− 28.4 | 0.091 | (14.32) +− 0.82 |
| 10 | 507.1 +/− 39.0 | 0.154 | (12.47) +/− 0.69 |
| 15 | 553.8 +/− 16.5 | 0.166 | (15.65) +/− 1.25 |
| 30 | 507.0 +/− 20.1 | 0.184 | (17.63) +− 2.19 |
| 60 | 495.8 +/− 50.2 | 0.26 | (15.61) +/− .64 |

The dynamics of nanoparticle and agglomerate synthesis are somewhat elucidated from the previous tables and figures. Tables 21-23 show that nanoparticle formation does not show immediate dependence on either sonication amplitude or sonication time. However, it should be noted that both tests were carried out while holding all solution variables constant (solvent/anti-solvent volumes, drug concentration in the solvent phase, drug/acid ratio). It may be the case that the results could have shown stronger sonication amplitude and time dependencies if the solutions were altered.

Example 11

Application of Insulin Nanoparticles

This example describes a developed dry powder Zn-insulin formulation possessing appropriate microstructure to reach the deep lung that is processed without excipients (FIG. 30). Factors such as pH and insulin concentration were shown to have an effect on seed nanoparticle size. Circular dichroism (CD) and solid-state nuclear magnetic resonance (ssNMR) were used to show that irreversible secondary structure and crystallinity changes of the insulin did not occur as a result of processing. It has been demonstrated that excipient-free, insulin nanoclusters that are suitably sized for pulmonary delivery and have a high dissolution velocity can be produced with minimal processing steps.

Pure insulin nanoclusters with sizes within the respirable range were produced from the solvent-induced agglomeration of insulin nanoparticles. Nanoparticles were produced using titration and were shown to have a strong correlation between pH and particle size (FIG. 31). Nanoclusters were then produced using ethanol to displace the aqueous solvent and induce nanoparticle agglomeration.

Materials and Methods.

Materials.

Lyophilized insulin powder from bovine pancreas (0.5% zinc content) and phosphate buffered saline premix (PBS) were purchased from Sigma (St. Louis, Mo.). All other reagents were purchased from Fisher Scientific (Pittsburgh, Pa.) and used without further purification.

Fabrication of Insulin Nanoparticles

Approximately 100 mg of insulin stock powder was dissolved in 15 mL of 0.01 N HCl solution. The solution was then titrated drop-wise to a pH just below the isoelectric point (pI) of the native protein (5.3) with 0.01 N NaOH solution, at which point the solution became colloidal without fully precipitating. The mean geometric diameters and polydispersities of the nanoparticle suspension were measured using dynamic light scattering (Brookhaven Instruments Zeta Potential Analyzer, Holtsville, N.Y.). Nanoparticles were diluted in deionized $H_2O$ (100×) and three, 1 minute measurements were obtained at 25° C. for each sample. Mean size and polydisperity were determined by the method of cumulants. The same instrument was used to determine the zeta potential ($\zeta$) of the nanoparticles in 1 mM potassium chloride solution. Three runs of 15 cycles were acquired, and the mean zeta potential was recorded. Some samples were frozen at −80° C. and lyophilized using a Labconco bench top lyophilizer (Kansas City, Mo.) for further analysis.

A range of pH values near the pI of the native protein were determined in which the nanoparticle colloid was preserved. Particle sizes and zeta potentials were measured for each sample. Nanoparticle samples within this pH range (from 4.92 to 5.09) were centrifuged at 13,000 rpm for 10 minutes and the supernatant concentration of insulin was analyzed using UV absorbance spectroscopy (Agilent 8453). All pH values were measured in triplicate. The measured concentration was used to calculate the mass of insulin in the pellet from the original insulin mass and total volume.

Agglomeration of Insulin Nanoclusters.

5 mL aliquots of insulin nanoparticle suspensions were added to 15 mL of ethanol and stirred for 36 hours at 300 rpm under a fume hood. Nanoparticles with diameters of approximately 200 nm were selected for this step. The geometric diameters of the insulin nanoclusters were measured using a Coulter Multisizer™ 3 (Beckman Counter, Fullerton, Calif.). Samples were then frozen at −80° C. and lyophilized for further analysis.

Characterization of Aerosol Properties.

The aerodynamic diameters of the lyophilized powders were determined using an Aerosizer LD (Amherst Process Instruments Inc.). Data were collected over ~70 seconds under high shear force (−3.4 kPa) using a 700 μm nozzle.

Characterization of Particle Morphology.

The size and morphology of lyophilized samples were evaluated using a LEO 1550 field emission scanning electron microscope (SEM). All samples were sputter-coated with gold for 30 seconds prior to imaging.

Conformational Stability of Processed Insulin.

Post-processing secondary structural changes in samples were analyzed by dissolving particles in 0.01 N HCl solution and analyzing using circular dichroism spectroscopy (CD; Jasco J-810, Easton, Md.) to determine conformational differences between processed and unprocessed insulin, as well as thermal stability differences between groups. CD spectra were acquired in three accumulations from 260-195 nm with a scanning speed of 50 nm/min and 1.0 nm resolution. Thermal stability was determined at a wavelength of 210 nm from 10-80° C. with a scanning speed of 15° C./hr. Thermal stability spectra were acquired in triplicate. Insulin concentration in prepared solutions was determined by UV absorbance spectroscopy.

Crystallinity of Processed Insulin.

NMR: Spectra were collected using a Tecmag Apollo spectrometer operating at 300 MHz using ramped amplitude cross-polarization (RAMP), magic-angle spinning (MAS), and SPINAL-64 decoupling. Samples were packed in 4 mm o.d. Zirconia rotors using Teflon® endcaps, and spun at 8 kHz in a Chemagnetics™ Triple-Resonance HXY CP/MAS NMR probe configured to run in double-resonance mode using the H and X channels, and fitted with a 4 mm spin module from Revolution NMR. All spectra are the sum of 120,000 transients collected using a 1.5 sec pulse delay, a contact time of 2 ms, and a $^{1}H$ 90° pulse width of 2.3 μs. The free induction decays consisted of 256 points with a dwell time of 33.3 μs. The spectra were externally referenced to tetramethylsilane using the methyl peak of 3-methylglutaric acid at 18.84 ppm.

HPLC: The crystalline insulin content of the materials was determined using the method in the insulin zinc suspension monograph of the 2005 U.S. Pharmacopoeia National Formulary, with minor modifications. Buffered acetone TS was produced by dissolving 8.15 g of sodium acetate and 42 g of sodium chloride in 100 mL of water, to which 68 mL of 0.1 N hydrochloric acid and 150 mL of acetone were added, the mixture was then diluted with water to make 500 mL. Approximately 0.5 mg of insulin was placed in a 1.5 mL microcentrifuge tube and 33.3 pL of a 1:2 mixture of water and buffered acetone TS was added to the tube to extract any amorphous insulin. The sample was immediately centrifuged at 13,000 rpm for one minute, the supernatant was decanted, and the extraction was repeated. Additionally, ~0.5 mg of insulin was placed in another microcentrifuge tube to be used as a control. Both insulin samples were each dissolved in 33.3 pL of 0.01 N hydrochloric acid and analyzed by HPLC, with each sample being prepared in triplicate.

The HPLC was a Shimadzu system that consisted of an SCL-10A system controller, LC-10AT liquid chromatography pump, SIL-10A auto injector with a sample cooler, and SPD-10A UV-VIS detector with instrument control and data analysis performed through CLASS-VP software. Aqueous mobile phase was prepared by dissolving 28.4 g of anhydrous sodium sulfate in 1000 mL of water, to which 2.7 mL of phosphoric acid was added and the pH was adjusted to 2.3 with ethanolamine. The aqueous mobile phase was then mixed 74:26 with acetonitrile. The separation was performed on a 4.6×250 mm Symmetry® C18 column from Waters that was maintained at 40° C. Samples were maintained at 5° C. and 20 pL were injected for analysis, with a mobile phase flow rate of 1 mL/min and the detector set to 215 nm. Peak areas were normalized to the mass of insulin used to prepare the sample and the percent crystalline insulin was calculated with the following equation:

Dissolution of Insulin Particles.

Approximately 6 mg of each insulin particle sample was suspended in PBS (pH 7.4). The solution was placed in a 100,000 Dalton biotech grade cellulose ester dialysis tube (Spectrum Labs, Rancho Dominiguez, Calif.) and placed in PBS solution to a final volume of 45 mL. All samples were incubated at 37° C. and shaken at 50 rpm on a shaker table. 1 mL aliquots were taken at various time points up to 8 hours from the bulk solution and replaced with 1 mL of fresh PBS. The insulin concentration was measured using a Coomassie Plus colorimetric protein quantification assay (Thermo Fisher Scientific, Waltham, Mass.). A calibration curve was used to correlate the insulin concentration with the measured absorbance, with insulin concentrations ranging between 1 and 25 μg/mL used as the standard. Dissolved mass was calculated from the measured concentration, and was then normalized to the total loaded mass to determine the percent dissolved. All experiments were performed in triplicate. Analysis of variance (ANOVA) was used to determine statistically significant differences between groups ($p<0.05$). Comparisons among groups were done using a Fisher's F-test.

Estimation of Bulk Powder Density.

The bulk density of the dry powder was estimated using a micro-tap test approach, as defined in the U.S. Pharmacopoeia National Formulary, with slight modifications. Briefly, dry powder samples (unprocessed insulin, nanoparticles, and nanoclusters) were added to pre-weighed microcentrifuge tubes, and the tubes were weighed again to determine the mass of powder. The tubes were then tapped thirty times on the lab bench to compress the powder. The volume of the powder was approximated by comparing the height of the compressed powder to that of a volume of water in an identical pre-weighed microcentrifuge tube. The tube containing the water was then weighed to determine the volume of water (assuming a density of 1 g/mL). The powder density was calculated by dividing the mass of powder by the volume of water. All samples were analyzed in triplicate. Analysis of variance (ANOVA) was used to determine statistically significant differences between groups (p<0.05). Comparisons among groups were done using a Fisher's F-test.

Results

Characterization of Insulin Nanoparticles.

Zn insulin nanoparticles were created by titrating dissolved insulin to the pI of the native protein, which resulted in a colloidal suspension of nanoparticles. Particle sizes and zeta potentials were analyzed over a pH range of 4.92 to 5.09, and ranged from 292.5 nm to 592.1 nm (Table 24). Zeta potentials ranged from 10.86 mV to 18.89 mV. Neither particle sizes nor zeta potentials correlated strongly with the pH of the solution.

TABLE 24

Characteristics of nanoparticles at various pH values.

| pH | Diameter (nm) | Polydisperity | ζ-Potential (mV) |
|---|---|---|---|
| 4.92 | 292.5 ± 42 | 0.384 ± 0.015 | 10.86 ± 2.44 |
| 4.94 | 535.5 ± 60.1 | 0.364 ± 0.008 | 18.89 ± 1.27 |
| 4.97 | 345.1 ± 15.5 | 0.342 ± 0.02 | 15.6 ± 1.05 |
| 4.98 | 439.8 ± 57.6 | 0.357 ± 0.025 | 17.95 ± 1.27 |
| 5.09 | 592.1 ± 61.8 | 0.349 ± 0.012 | 17.62 ± 0.27 |

The mass fraction of insulin remaining in solution after nanoparticle precipitation was determined using LTV absorbance spectroscopy. These values were used to determine the mass fraction of total insulin contained in the nanoparticles. The results suggest a positive correlation between the particle size and the total mass of the insulin nanoparticles in suspension.

Characterization of Insulin Nanoclusters.

Insulin nanoclusters were produced from insulin nanoparticle suspensions through solvent displacement. This was achieved by adding aliquots of insulin nanoparticle suspension to ethanol and stirring overnight. The geometric diameter of the insulin nanoclusters was determined to be 3.408±1.35 μm. No correlation was determined to exist between insulin nanoparticle size and nanocluster size (FIG. 32). SEM imaging revealed differences in the morphology of the unprocessed insulin and the insulin nanoclusters (FIG. 33). The unprocessed insulin agglomerates appear to have a more regular structure, while the nanoclusters have more of a leaf-like morphology. This leaf-like shape could aid in the aerosolizability of the insulin nanoclusters, and would suggest a shape factor, γ, of less than 1.

Aerosol Properties of Insulin Particles.

The aerodynamic diameters of the unprocessed insulin powder, lyophilized insulin nanoparticles, and lyophilized insulin nanoclusters were measured with an Aerosizer LD and are shown in Table 25. The smaller aerodynamic diameter of the insulin nanoclusters compared to the geometric diameter of the nanoclusters was expected because of the lower density of the insulin nanoclusters (FIG. 34).

TABLE 25

Particle sizes

| Sample | $d_{geo}$ (μm) | $d_{aero}$ (μm) |
|---|---|---|
| Unprocessed | N/A | 4.117 ± 1.852 |
| Nanoparticles | N/A | 3.649 ± 2.069 |
| Nanoclusters | 3.408 ± 1.35 | 2.32 ± 1.974 |

Conformational Stability of Processed Insulin.

Circular dichroism (CD) was employed to analyze the secondary structure and thermal stability of processed insulin powders. Isothermal scans of dissolved, unprocessed insulin powder, dissolved nanoparticles, and dissolved nanoclusters reveal near-identical spectra with minima at 210 nm, suggesting that any changes in secondary structure that might occur during processing were reversible upon dissolution (FIG. 35). This overlap was also reflected in the thermal stability CD scans, which show a slight change in molar ellipticity from 10-80° C. starting at about 50° C. for all samples.

Crystallinity of Processed Insulin.

The crystallinity of the insulin particles was examined using $^{13}$C CP/MAS NMR (FIG. 36). The spectra display differences in the aliphatic region (–0 to 75 ppm), although these differences are difficult to correlate with the physical state of insulin. More obvious differences between the samples arise in the carbonyl (–175 ppm) and aromatic (–137 ppm) regions. The peak at –137 ppm in the unprocessed insulin seems to be narrower and better resolved than peaks at –129 ppm. These same lines in the other samples are broader, to the point where peaks at –129 ppm cannot be resolved. The peak at –175 ppm in the unprocessed insulin is more narrow, with two very clear shoulders at –180 ppm and –173 ppm. Other samples only show one broad peak at –175 ppm.

Crystallinity of the insulin particles was also examined using the buffered acetone method described in the U.S. Pharmacopoeia National Formulary. The results suggest that the unprocessed insulin particles are between 80% and 88% crystalline; much greater than both the nanoparticles and nanoclusters, which were estimated to be between 2% and 8% crystalline, and between 17% and 24% crystalline, respectively (FIG. 37).

Dissolution of Insulin Particles.

The concentration of insulin was measured over time in PBS solution to determine the dissolution rate of the different powders (FIG. 38). The unprocessed insulin follows Higuchi dissolution kinetics, and the nanoparticles and nanoclusters appear to show a burst dissolution phenomenon after 15 minutes. The dissolved masses of nanoparticles and nanoclusters were both significantly different from the dissolved mass of unprocessed powder after 15 minutes (p=0.0021 and p=0.0054, respectively). The dissolved masses of neither the nanoparticles nor the nanoclusters were significantly different from the dissolved mass of the unprocessed insulin after 8 hours.

Bulk Powder Density.

The tap test method was used to determine the bulk density of the insulin powders before and after processing. Density of the unprocessed insulin powder was determined to be 0.48±0.08 mg/μL (FIG. 34). The nanoparticle bulk density was determined to be 0.28±0.04 mg/μL, and the bulk density of the insulin nanoclusters was determined to be 0.063±0.004 mg/μL. Analysis of variance revealed a p-value of 0.00025 (p<0.05), indicating a statistically significant difference between the bulk densities of each group.

Discussion

The sizes of the nanoclusters were independent of the size of the nanoparticles used, and had a mean aerodynamic diameter that was roughly between 0.436 μm and 4.294 μm. This range of particle sizes is similar to other dry powder insulin formulations, such as Exubera (3.5 μm), and a formulation based on the Spiros technology (2-3 μm). Additionally, these particles were smaller than those produced using AIR technology (5-30 μm). Based on the relationship between geometric and aerodynamic diameters, our data suggest a mean shape factor equal to 0.135 (assuming a $p_{ref}$ of 1 mg/μL and $\mu_{tap}=\rho_{partide}$). This value is much less than 1, indicating that our particles are aspherical and highly irregular in morphology, thus making them good candidates for inhalation. This observation is further corroborated by SEM imaging (FIG. 33).

Circular dichroism was used to determine changes in the secondary structure of insulin that might occur as a result of particle processing. The data suggest that there are no irreversible changes that occur as a result of processing, and that the thermal stability of the insulin processed into nanoclusters and nanoparticles is neither enhanced nor diminished (FIG. 35).

The crystallinity of the insulin particles was first examined using $^{13}$C CP/MAS NMR (FIG. 36). Due to their highly ordered nature, crystalline materials will have relatively narrow lines in a $^{13}$C CP/MAS spectrum, while disordered or amorphous materials have relatively broad lines. Insulin consists of 51 amino acids and therefore the spectrum will be quite complicated because every amino acid will have at least an amide and a carbon, each of which will have slightly different conformations and thus different chemical shifts. Because of this, even the $^{13}$C CP/MAS spectrum of a crystalline protein will appear to have broad lines even though it of many narrow lines with slightly different chemical shifts. Therefore, it would be expected that there would be very few differences between the $^{13}$C CP/MAS spectra of amorphous and crystalline proteins, and any differences may be subtle. The sharply resolved peaks of the unprocessed insulin would suggest that it is crystalline while all of the other samples appear to be amorphous, which is corroborated by the dissolution testing. However, at this time nothing can be said about the purity of each form because there could be some crystalline insulin in the samples that appears to be amorphous.

Crystallinity was also determined by dissolution testing, as defined by the 2005 U.S. Pharmacopoeia National Formulary, with modifications. Buffered acetone TS was used to dissolve the amorphous insulin from each sample, the concentration of which was then determined and used to estimate the crystallinity of the particles. The unprocessed insulin was shown to be about 17 times more crystalline than the nanoparticles, and 4 times more crystalline than the nanoclusters (FIG. 37). The dissolution rate of both the nanoclusters and the nanoparticles exhibited a burst effect over the first few minutes when compared to the unprocessed insulin (FIG. 38). This burst may be due to the rapid dissolution of amorphous material deposited on the surface of the particles during processing or possibly during lyophilization. In the case of the nanoparticles, it is probable that the large total surface area of the particles also plays a significant role in increasing the dissolution rate. This may be beneficial in a pulmonary insulin formulation if the desired therapeutic effect is rapid control of spikes in glucose levels. This type of formulation may be adjusted for sustained control of glucose over long periods of time, or for postprandial glucose control.

Example 12

Formulation of Diatrozic Acid Nanoclusters

Diatrizoic acid has been validated as an effective and safe CT contrast agent for use in the lung as evidenced in both preclinical and clinical reports in the literature. Effective delivery to the peripheral lung is imperative to access regional lymph nodes and enable the use of diatrizoic acid in staging lung cancer. Our original proposal reviewed the value of this compound for this indication and demonstrated a nanotechnology approach to create dry powders capable of accessing the lung periphery. Several drug compounds (e.g. budesonide) were formulated to illustrate the fine powders enabled by this approach. Here, we demonstrate that diatrizoic acid can indeed be formulated as a dry powder or as a nebulized suspension. Both formulations show a high fine particle fraction, which strongly suggests that the diatrizoic acid will be effectively delivered to the lung periphery. In addition, the low solubility of this compound will result in phagocytic uptake and trafficking to the regional lymphatics to aid in diagnosis of developing lesions. The data presented here validates that our formulation of diatrizoic acid yields very fine particles that will access the lung periphery whether delivered as a dry powder or, alternatively, as a nebulized suspension.

Nanoparticles of diatrizoic acid. Nanosuspensions were prepared by precipitating diatrizoic acid dissolved in ethanol into water. The particle size and zeta potential of the nanosuspensions were determined by dynamic light scattering (Brookhaven, ZetaPALS). Particles as small as 136 nm were reproducibly fabricated (Table 26). Zeta potential measurements showed that the particles were positively charged. The solvent/non-solvent ratio of 1:10 generated the smallest diatrizoic acid nanoparticles. Zeta potential values ranged from 22-26 mV. The charged surface of the nanoparticles provided the potential for destabilizing this colloid via interaction with a agglomerating agent to form nanoparticle agglomerates.

TABLE 26

Properties of diatrizoic acid nanoparticles.
(values = average ± standard deviation).

| Solvent/non-solvent ratio | Nanoparticle size (nm) | Zeta-potential (mV) |
| --- | --- | --- |
| 1:3 | 217 ± 20 | 26 ± 1 |
| 1:10 | 136 ± 36 | 22 ± 1 |
| 1:14 | 316 ± 18 | 26 ± 1 |
| 1:29 | 188 ± 38 | 27 ± 3 |

Low density powders of diatrizoic acid. Low density nanoclusters are capable of accessing the peripheral lung. Our approach is to use the nanoparticles in suspension as building blocks to create low density nanoclusters. Diatrizoic acid nanoparticles were assembled into low density nanoclusters by addition of L-leucine. L-leucine destabilizes the colloid and causes the nanoparticles to assemble. The amount of L-leucine added was adjusted to a drug:leucine ratio equal to 1:1. The size of nanoparticle agglomerates was measured using a Coulter Multisizer 3 (Beckman Coulter Inc.). The diatrizoic acid nanoparticle agglomerates were kept overnight at room temperature to evaporate ethanol, frozen at −80° C., then freeze dried (Labconco, FreeZone 1). Drying lasted for 36 hours to remove all appreciable water content. The lyophilized powder was stored at room temperature for further characterization.

Low density particles were made by assembling 136 nm diatrizoic acid nanoparticles in suspension using the methods above. The particle size was determined from the lyophilized powder using particle time-of-flight analysis. The particle mass mean aerodynamic diameter indentified using this analytical method was 1.0±0.1 µm, which is an ideal particle size for accessing the lung periphery.

FDA requires characterization of aerosols using cascade impaction, which determines aerosol particle size; indicative of the probable deposition site in the lung. The nanoparticle agglomerate formulation described above was studied using a Tisch Ambient Cascade Impactor. The study was carried out by applying ~20 mg powder manually into the orifice of the instrument at an air flow rate of ~30 L/min. Alternatively, the dry powders were suspended in water and applied into the cascade impactor through a nebulizer equipped with an LC Star atomizer. The suspension was nebulized for ~30 minutes at the same cascade impactor flow rate. Cut-off particle aerodynamic diameters at 30 L/min for each stage of the impactor were: pre-separator (10.00 µm), stage 0 (9.00 µm), stage 1 (5.8 µm), stage 2 (4.7 µm), stage 3 (3.3 µm), stage 4 (2.1 µm), stage 5 (1.1 µm), stage 6 (0.7 µm), stage 7 (0.4 µm) and filter (0 µm). Diatrizoic acid nanoparticle agglomerates deposited on each stage of the impactor were determined by measuring the difference in weight of filters placed on the stages. The percent emitted fraction (% EF) and fine particle fractions of the total dose (FPFTD) were then calculated. In addition, the mass median aerodynamic diameter, MMAD, and geometric standard deviation, GSD, were obtained by a linear fit of the cumulative percent less-than the particle size range by weight plotted on a probability scale as a function of the logarithm of the effective cut-off diameter.

Most nanoparticle agglomerates were deposited in stages 5-7 of the cascade impactor which was indicative of efficient aerosolization and a high fine particle fraction capable of reaching the peripheral lung. Notably, using the nebulizer for delivering the resuspended dry powder achieved a higher total mass deposition (FIG. 39). The fine particle fraction of the total dose (FPFTD) was calculated as the percentage of aerosolized particles that reached the lower seven stages of the impactor (corresponding to aerodynamic diameters below 5.8 µm), or the lower five stages (corresponding to aerodynamic diameters below 3.3 µm): Cascade impaction data suggested that the anticipated total lung deposition (i.e. FPFTD<5.8 µm) was about 93-96% and deep lung deposition (i.e. FPFTD<3.3 µm) was ~80% for diatrizoic acid aerosol formulations.

The aerosolization efficacy was represented by the percent emitted fraction (% EF). The high emitted fraction of nanoparticle agglomerates obtained at the tested flow rate (~76-88%) suggested efficient aerosolization of the powder (Table 27). The mass-mean geometric size of nanoparticle agglomerates was ~1.5 µm with a GSD of ~2.2 µm (Table 27). Importantly, the process to agglomerate nanoparticles consistently achieved a high yield (~86%), which indicated efficient processing with minimum batch variability.

TABLE 27

Cascade impaction results of lyophilized diatrizoic acid nanoparticle agglomerates (values = average ± standard deviation).

| Characteristics of the lyophilized nanoparticle agglomerates | | Formulations | | | |
|---|---|---|---|---|---|
| | | Suspension | Dry powder | Diatrizoic acid (suspen.) | Diatrizoic acid (powder) |
| At flow rate of ~30 L//min | % EF[e] | 88 ± 1 | 76 ± 4 | 75 ± 5 | 70 ± 1 |
| | % <5.7 | 96 ± 0.3 | 93 ± 1 | 33 ± 6 | 21 ± 2 |
| | FPF[f] <3.3 | 81 ± 0.2 | 82 ± 1 | 10 ± 7 | 4 ± 2 |
| | MMAD[g] | 1.6 ± 0.02 | 1.4 ± 0.04 | 7 ± 1 | 9 ± 0.1 |
| | GSD[h] | 2.2 ± 0.2 | 2.3 ± 0.1 | 2 ± 0.1 | 2 ± 0.1 |

[e]% EF: Percent emitted fraction.
[f]FPF: Fine particle fraction.
[g]MMAD: Mass median aerodynamic diameter obtained from cascade impactor.
[h]GSD: Geometric standard deviation Example 13

Formulation of Moxifloxacin Nanoclusters

Various concentrations of moxifloxacin suspensions in acetone were prepared under ultrasonication operating with an amplitude of 48% or under homogenization at 25,000 rpm for 15 or 30 minutes, as shown in Table 28. The particle size was measured using a dynamic light scattering instrument (Table 28).

A concentrated solution of L-leucine was then added to the selected nanosuspension while homogenizing it at 25,000 rpm for 30 s to agglomerate and form moxifloxacin nanoparticle agglomerates. The amount of L-leucine added was adjusted to a drug:leucine ratio ranging from 1:0.1 to 1:1. The agglomerated suspension was allowed to stand for 30 min. A Coulter Multisizer 3 (Beckman Coulter Inc.) equipped with a 100-µm aperture was used to determine the geometric size distribution of the nanoparticle agglomerate suspensions. In addition, a pure moxifloxacin nanosuspension was kept without leucine. All samples were snap-frozen and lyophilized to remove final traces of acetone and form a porous dry powder.

Aerodynamic size distribution of the lyophilized powder was obtained by analyzing the time of flight measurements from an Aerosizer LD (Amherst Instruments) equipped with a 700 µm and operating 4 psi. The size distribution of the moxifloxacin nanoparticle suspension is shown in FIG. 40.

TABLE 28

Composition and characterization of the prepared moxifloxacin nanoparticles (values = average ± standard deviation).

| Formula No. | Conc. (mg %) | Process[1] | Time (min.) | Nanoparticle size (nm) | Polydispersity |
|---|---|---|---|---|---|
| M1 | 20 | H | 15 | 26,493.9 ± 14 | 0.61 ± 1 |
| M2 | 20 | H | 30 | 366.9 ± 4 | 0.29 ± 0.2 |

TABLE 28-continued

Composition and characterization of the prepared moxifloxacin nanoparticles (values = average ± standard deviation).

| Formula No. | Conc. (mg %) | Process[1] | Time (min.) | Nanoparticle size (nm) | Polydispersity |
|---|---|---|---|---|---|
| M3 | 100 | S | 15 | 331.4 ± 9 | 0.10 ± 0.1 |
| M4 | 100 | S | 30 | 418.9 ± 11 | 0.005 ± 0.01 |
| M5 | 100 | H | 15 | 175.8 ± 8 | 0.059 ± 0.1 |
| M6 | 100 | H | 30 | 269.9 ± 12 | 0.05 ± 0.3 |

[1]S: sonication process,
H: homogenization process

TABLE 29

Characterization of Ciprofloxacin nanoparticle agglomerates (values = average ± standard deviation).

| Nanoparticle agglomerate Formulas | Drug:L-leucine ratio | Nanoparticle size (nm) | Geometric particle size (μm) of lyophilized NA[b] | MMAD[c] of lyophilized NA[b] |
|---|---|---|---|---|
| [a]M5-1 | Pure drug | 175.8 ± 8 | 5.08 ± 1.77 | 2.125 ± 1.77 |
| M5-2 | 1:0.1 | 175.8 ± 8 | 3.77 ± 1.146 | 1.795 ± 1.89 |
| M5-3 | 1:0.5 | 175.8 ± 8 | 2.97 ± 0.88 | 1.724 ± 1.88 |
| M5-4 | 1:1 | 175.8 ± 8 | 3.675 ± 1.01 | 1.35 ± 1.93 |

[a]M5 = 25 mg moxifloxacin/25 mg acetone; 100 mg %
[b]NA: Nanoparticle agglomerates.
[c]MMAD: Mass median aerodynamic diameter obtained from Aerosizer.

Example 14

Formulation of Ciprofloxacin Nanoclusters

Preparation of Dry Agglomerated nanoCipro Powder

A homogenous suspension of nanoCipro was prepared by sonicating a colloidal solution of ciprofloxacin in acetone. Initial concentration of ciprofloxacin in acetone was varied between 20 mg % w/v, 40 mg % w/v and 100 mg % w/v. Different amplitudes of sonication ranging from 46% to 96% were tried. The time required for sonication was also varied between 15 min, 30 min, 45 min and 60 min. A solution of L-leucine was then added to the selected nanoCipro suspensions while homogenizing it at 25,000 rpm for 30 s to agglomerate and form ciprofloxacin nanoagglomerates. The amount of L-leucine added was adjusted to a drug:leucine ratio ranging from 1:0.1 to 1:1. Due to poor solubility of leucine in acetone, the desired amount of leucine was dissolved by sonication in minimal amount of water prior to injection in the nanosuspension. The agglomerated solution was allowed to stand for 30 min and was then left at room temperature to evaporate the acetone. The solution was then frozen at −80° C. and lyophilized to remove final traces of acetone and form a porous dry powder.

Particle Size Analysis

Particle size and zeta potential of nanoCipro suspensions was determined using a dynamic light scattering instrument (Brookhaven, ZetaPALS). In a standard cuvette, 1 mL of the nanosuspension was taken and the remaining volume was filled with deionized water for particle size analysis and 1 mM KCl for zeta potential analysis. Measurements were taken at an angle of 90° to the incident light source. A Coulter Multisizer 3 (Beckman Coulter Inc.) equipped with a 100-μm aperture was used to determine the geometric size distribution of the nanoparticle agglomerate suspensions and the resuspended lyophilized powder. Approximately 2 mL of dispersed ciprofloxacin nanoagglomerate solution and a pinch of the lyophilized powder were resuspended in ~3 mL isotonic solution respectively for the measurements.

Mass-Mean Aerodynamic Diameter and Tap Density Measurements.

The tap density of the dry powder was estimated using a micro-tap test approach, as defined in the U.S. Pharmacopoeia National Formulary, with slight modifications. Briefly, lyophilized nanoagglomerate powder was added to pre-weighed microcentrifuge tube, and the tubes were weighed again to determine the mass of powder. The tube was then tapped thirty times on the lab bench to compress the powder. The volume of the powder was approximated by comparing the height of the compressed powder to that of the volume of water in an identical pre-weighed microcentrifuge tube. The tube containing the water was then weighed to determine the volume of water (assuming a density of 1 g/cm$^3$). The powder density was calculated by dividing the mass of powder by the volume of water.

The tap density and the geometric particle size were then used to calculate the theoretical mass-mean aerodynamic diameter. Aerodynamic size distribution of the lyophilized powder was also obtained by analyzing the time of flight measurements from an Aerosizer LD (Amherst Instruments) equipped with a 700 μM and operating 4 psi.

In Vitro Aerosolization Performance.

To simulate inspiration in vitro, about 5 mg of the lyophilized powder was manually placed in the orifice of a Tisch Ambient Cascade Impactor (Tisch Environmental, Inc., Village of Cleves, Ohio, U.S.A.) operating at an air flow rate of 30 L/min for 20 s. Powders were collected from the eight different stages of the impactor. The cutoff particle aerodynamic diameter for each stage was provided by the manufacturer as follows: pre-separator (10.00 μm), stage 0 (9.00 μm), stage 1 (5.80 μm), stage 2 (4.70 μm); stage 3 (3.30 μm), stage 4 (2.10 μm), stage 5 (1.10 μm), stage 6 (0.70 μm), stage 7 (0.40 μm) and the filter (0.00 μm). Mass of the particles deposited on each stage was calculated by measuring the difference in the weights of the plates placed between the stages. Then, the emitted fraction (EF) was calculated to determine the amount of inhalable particles in the lyophilized powder using the following equation:

The fine particle fraction of the total dose (FPFTD) which would determine the amount of particles reaching the deep lung was calculated by measuring the percentage of aerosolized particles reaching the lower seven stages of the impactor (corresponding to aerodynamic diameters below 5.8 μm) as follows:

$$\% \text{ Fine particle fraction } (FPF_{TD}) = \frac{\text{Powder mass recovered from terminal stages of the impactor}}{\text{Total particle mass recovered in the impactor}} \times 100$$

Additionally, mass median aerodynamic diameter (MMAD) and geometric standard deviation (GSD) was calculated from a linear regression model of cumulative mass plotted as a function of the logarithm of the effective cut-off diameter.

Particle Imaging

Surface morphology of nanoparticle suspension, nanoagglomerates and pure drug crystals were investigated via transmission electron microscopy. Transmission electron micrographs were obtained using a JEOL 1200 EXIT transmission electron microscope. Initially, carbon-coated grids (Electron Microscopy Sciences) were coated by a droplet of the suspensions of nanoparticles, nanoagglomerates and the drug crystals respectively on a flexible plastic film (Parafilm), to facilitate the adsorption of the particles onto the grid. The grid was then blotted with a filter paper and air dried for 1 h prior to taking the micrographs.

Determination of Percent Yield and Drug Loading

The percent yield for lyophilized powder was calculated using the following equation:

$$\% \text{ Yield} = \frac{M_{lyophilized}}{M_{initial}} \times 100$$

Where, $M_{lyophlize}$ is the mass of powder obtained after lyophilization of the nanoagglomerates and $M_{initial}$ is the initial mass of solids introduced in acetone including the mass of pure drug crystals and the agglomerating agent added.

The drug loading efficiency was analyzed by dispersing 10 mg of the lyophilized powder in 100 mL of PBS. The solution was then sonicated in a water bath sonicator for 2 hrs and was centrifuged at 15,000 rpm for 30 min. to remove any extra amount of L-leucine. The amount of drug in the supernatant was determined spectrophotometrically at 270 nm. Drug loading was defined by the following equation:

$$\% \text{ Loading} = \frac{\text{Recovered ciprofloxacin mass}}{\text{Total mass}} \times 100$$

Drug Dissolution Studies

The in vitro dissolution of Cipro from the prepared nanoparticles and nanoparticle agglomerates was determined under sink condition and compared with the dissolution characteristics of the drug powder as received. An accurately weighed amount of the lyophilized powder equivalent to 1 mg ciprofloxacin was dispersed in 10 mL phosphate buffered saline (PBS, pH 7.4) and was suspended into a floatable dialysis membrane unit (Mw cut-off=10,000 Da). The unit was allowed to float in a beaker containing 150 mL PBS and the whole assembly was stirred at a constant speed (100 rpm) using a magnetic stirrer (Barnstead, Thermolyne MIRAK™) at 37±0.5° C. Aliquots were withdrawn from the dialysis bag and replaced with fresh medium at predetermined time intervals for a total period of 8 hours. Then, the drug content was measured spectrophotometrically at 270 nm. Studies were conducted in triplicate.

Results and Discussion

Fabrication of Ciprofloxacin Nanoparticles

Ciprofloxacin nanoparticles were fabricated by sonicating the drug in acetone. Different concentrations of the drug in acetone were sonicated at various amplitudes for different times yielded mean particle size ranging from ~68 nm to 722 nm (Table 30). Nanosuspensions with higher concentration of ciprofloxacin in acetone yielded very high particle size. Increasing the amplitude resulted in a polydispersive particle size distribution. Increasing the time required for sonication did not affect the particle size distribution much. The desired particle size of ~68 nm was obtained when a 20 mg % w/v solution of ciprofloxacin was sonicated at amplitude of 46% for 30 min.

Agglomeration of Ciprofloxacin Nanoparticles

The mechanism to control nanoparticle agglomeration is mainly driven by leveraging the competitive processes of attraction (van der Waals force) and repulsion (electrostatic repulsive force or steric hindrance barrier or both). L-leucine, used as a agglomerating agent in these studies may also act as an anti-adherent material to yield a high respirable fraction of the agglomerated ciprofloxacin nanoparticles.

Agglomeration of nanoparticles resulted in the formation of agglomerates within the micrometer or sub-micrometer scale consisting of closely-packed nanoparticles. Nanoparticle agglomerates were prepared through the slow incorporation of L-leucine during homogenization (25,000 rpm) for 30 sec. Different amount of this agglomerating agent ranging from a drug:leucine ratio of 1:0.1 to 1:1 was added to determine the effect on particle size distribution (Table 31). The geometric size distribution of the prepared nanoparticle agglomerate suspensions was measured in Isoton diluent using a Coulter Multisizer 3. The optimal geometric particle size of ~2.9 µm was obtained with a drug:leucine ratio of 1:0.5. Higher or lower ratios between the drug and leucine led to very wide size distribution or larger geometric size. The size distributions of resuspended lyophilized powders were slightly broader and the average particle size was increased to ~5.4 µm, when compared to the nanoparticle agglomerates prior to lyophilization as shown in FIG. 41. This may be due to the deposition of nanoparticles on agglomerates during lyophilization or to cohesion between agglomerates as a result of drying.

Agglomerated Ciprofloxacin Nanoparticles Yielded Desirable Aerosol Characteristics The aerodynamic diameter ($d_{aero}$) is used to estimate the site of aerosol deposition of nanoclusters within the lungs. The aerodynamic diameter of the agglomerated nanoparticles, measured by an Aerosizer LD, was smaller than the geometric diameter indicating the low density of nanoparticle agglomerates as shown in Table 31 and FIG. 42.

The theoretical mass-mean aerodynamic diameters ($d_{aero}$) of the nanoparticle agglomerates determined from the geometric particle size and tapped density was found to be 1.7 µm. Table 31. Tap density measurements underestimate particle bulk densities since the volume of particles measured includes the interstitial space between the particles. The true particle density, and therefore the aerodynamic diameter of a given powder, is expected to be slightly larger than reported. Ciprofloxacin nanoparticle agglomerates with $d_{aero}$~1.7 are expected to deposit primarily in the alveolar region of the lungs.

Cascade impaction studies were carried out to confirm the Aerosizer results and theoretical MMAD calculations (FIG. 43). Most nanoparticle agglomerates were deposited in stages 4 and 5 of the cascade impactor with a high portion of powder deposition in the lower stages. This was indicative of efficient aerosolization and a high fine particle fraction. Conversely, drug powder as received exhibited main deposition on stages 3 & 4 with a small amount of deposition in the lower stages. The high emitted fraction of nanoparticle agglomerates obtained at the tested flow rate (~78%) suggested efficient aerosolization of the powder (Table 32).

Cirofloxacin dry powder formulation showed an anticipated total lung deposition (i.e. $FPF_{TD}$<5.8 µm)~78% and deep lung deposition (i.e. $FPF_{TD}$<3.3 µm) about 52% (Table 32). However, drug powder as received demonstrated lower values than that found for the dry powders. This also was suggestive of better aerosol performance of the nanoagglomerates compared to the drug crystals.

The mass-mean geometric size of nanoparticle agglomerates was found to be ~5.4 with a GSD of ~2.1 μm (Table 32). Typical GSD values for aerosol particles are between 1.3-3.0. The mass-median aerodynamic diameter (MMAD) of the selected nanoparticle agglomerates, as calculated from the cascade impaction results (Table 32) was found to be 2.9 which is slightly higher than that obtained from the Aerosizer and the theoretical MMAD calculations however this diameter indicated good aerosolization efficiency of the prepared Cipro dry powder (Table 32).

Particle Imaging

Figure 44B:
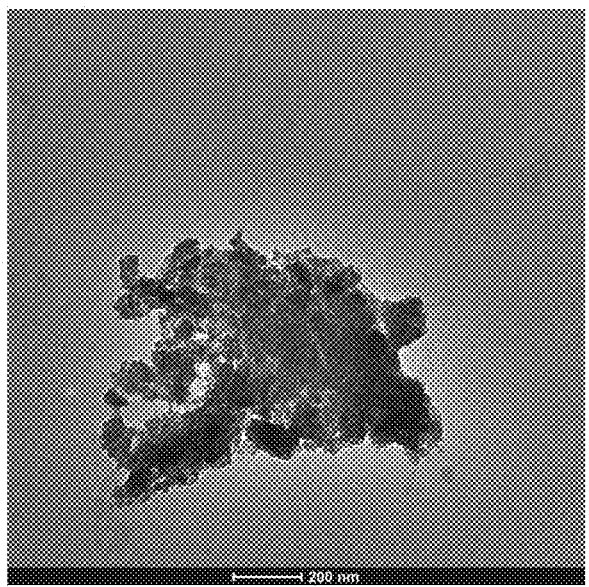

Electron microscopy was used to study the morphology of ciprofloxacin nanoparticles and nanoparticle agglomerate formulation (C1). Transmission electron micrographs (TEM) of Ciprofloxacin nanoparticles appeared to be very small elongated rods with smooth surface and a particle size ~100 nm. nanoparticles (FIG. 44A). TEM images of the nanoparticle agglomerates depicted that the nanoparticles were agglomerated into micron sized agglomerates resembling bundles of elongated Cipro particles as shown in FIG. 44B.

Process Yield and Drug Loading.

Cipro nanoparticle agglomerates consistently achieved a high yield (~81%), indicating the effectiveness of the agglomeration process. The loading efficiency of Ciprofloxacin in the prepared nanoparticle agglomerates (C1) was ~96% (Table 31), representing minimal loss of drug during powder preparation.

Dissolution Studies.

A dissolution study of Ciprofloxacin showed that the cumulative percentage of drug dissolved from nanoparticle agglomerates after 8 hours (Q8 h) was found to be ~60.7% which was slower than that of the nanoparticles that achieved ~72.8%, as shown in FIG. 45. However, nanoparticle agglomerates revealed faster dissolution compared to the stock Ciprofloxacin which exhibited ~44.3% of 8 hours. This finding indicated that Ciprofloxacin nanoparticles and nanoparticle agglomerates improved the dissolution rate of the drug.

TABLE 30

Composition and characterization of the prepared Cirofloxacin nanoparticles

| Formula No. | Conc. (mg %) | Amplitude | Time (min.) | Nanoparticle size (nm) | Zeta-potential (mV) | Polydispersity |
|---|---|---|---|---|---|---|
| C1 | 20 | 46% | 30 | 68 ± 20 | 0.9 ± 0.6 | 0.3 ± 0.1 |
| C2 | 20 | 72% | 15 | 85 ± 2 | 1.5 ± 1 | 0.6 ± 0.1 |
| C3 | 40 | 46% | 30 | 81 ± 21 | 0.4 ± 1 | 0.6 ± 0.02 |
| C4 | 40 | 46% | 60 | 301 ± 12 | 0.7 ± 4 | 0.3 ± 0.02 |
| C5 | 40 | 72% | 30 | 92 ± 7 | 1.6 ± 3 | 0.4 ± 0.3 |
| C6 | 40 | 72% | 60 | 97 ± 21 | 1.3 ± 1 | 0.3 ± 0.02 |
| C7 | 40 | 95% | 30 | 122 ± 21 | 0.8 ± 2 | 0.4 ± 0.1 |
| C8 | 100 | 46% | 30 | 722 ± 68 | 0.5 ± 3 | 0.2 ± 0.01 |

TABLE 31

Characterization of Ciprofloxacin nanoparticle agglomerates (values = average ± standard deviation).

| Characteristics | Formulation (C1[a]) |
|---|---|
| Geometric particle size (μm) of NA[b] before lyophilization | 2.9 ± 1 |
| Geometric particle size (μm) of lyophilized NA[b] | 5.4 ± 1 |
| Tab density (g/cm³) | 0.1 ± 0.01 |
| MMAD$_A$[c] of lyophilized NA[b] | 1.2 ± 3 |
| MMAD$_T$[d] of lyophilized NA[b] | 1.7 ± 0.1 |
| Process yield of lyophilized NA[b] | 81% ± 3 |
| Loading Efficiency of lyophilized NA[d] | 96% ± 4 |

[a]C1 = 5 mg Cipro/25 mg acetone; 20 mg %
[b]NA: Nanoparticle agglomerates.
[c]MMAD: Mass median aerodynamic diameter obtained from Aerosizer.
[d]MMAD: Theoretical mass mean aerodynamic diameter calculated from density measurements.

TABLE 32

Cascade impaction results of lyophilized Ciprofloxacin nanoparticle agglomerates (values = average ± standard deviation.).

| Characteristics of the lyophilized NA[b] | | | Formulations | |
|---|---|---|---|---|
| | | | C1 | Drug as received |
| At flow rate of ~30 L//min | % EF[c] | | 79 ± 4 | 69 ± 1 |
| | % FPF[d] | <5.7 | 79 ± 4 | 68 ± 0.1 |
| | | <3.3 | 52 ± 1 | 30 ± 0.2 |
| | MMAD[e] | | 2.9 ± 0.1 | 4.2 ± 0.03 |
| | GSD[f] | | 2.1 ± 0.1 | 2.3 ± 0.2 |

[a]C1 = 5 mg Cipro/25 mg acetone; 20 mg %
[b]NA: Nanoparticle agglomerates.
[c]% EF: Percent emitted fraction.
[d]FPF: Fine particle fraction.
[e]MMAD: Mass median aerodynamic diameter obtained from cascade impactor.
[f]GSD: Geometric standard deviation.

Example 15

Formulation of Anti-Tuberculosis Nanoclusters

Rifampicin

This drug is freely soluble in almost all organic solvent and has certain solubility in water ~2.5 mg/mL which still very high percent. This solubility in water has been achieved only at 25° C., so one method for preparing this drug as nanoparticles is to use the precipitation technique where the solvent can be acetone or ethanol and the anti-solvent is very cold water. The use of an ice bath helps.

The drug as received is shown in FIG. 46. Two formulae were prepared successfully by injecting 0.1% drug solution in acetone or ethanol into very cold water in an ice bath. For acetone as solvent, particle size was 269.6 nm (0.008). For ethanol as solvent, particle size was 347.5 nm (0.005).

Then the samples were lyophilized directly and the dry powder was analyzed by SEM imaging. It was clear that most of the formulated rifampicin dry powder, using acetone, was successfully agglomerated into nanocluster of ~2 microns consisting of nanoparticles of ~200 nm compared to using ethanol and the drug as received. However, there were some nanoparticles still unagglomerated. FIG. 47 depicts the suspension in the acetone solvent. FIG. 48 depicts the suspension in the ethanol solvent.

Streptomycin

By trying the solubility of streptomycin, it was found that it is freely water soluble which indicate that it is the sulfate salt of the compound. In addition, it was found that it is poorly soluble in acetone and ethanol. So the process recommended is the homogenization or sonication of the compound in these organic solvent using different concentrations of the drug and different times. Also precipitation technique was carried out using water as solvent and the organic solvent as anti-solvent.

| Drug conc. | Technique | Particle size |
|---|---|---|
| 0.1%-acetone-water | ppt | Very big |
| 0.1%-ethanol-water | ppt | Very big |
| 0.2% in ethanol | Sonic. 15 min | Very big |
| 0.2% in ethanol | Hom, 15 min | Very big |
| 0.2% in acetone | Sonic. 15 min | Very big |
| 0.2% in acetone | Soni, 15 min | Very big |
| 0.2% in acetone | Hom, 30 min | 511.5 nm (with some large particles) |
| 1% in acetone | Hom, 1 hrs | 15 min: 154.4 nm (with some large particles) |
| | | 30 min: 167.9 nm (0.005) monodisperse |
| | | 45 min: 238.7 nm (0.14) |
| | | 1 hr: 359.8 nm-611.1 nm (with some large particles) |

The samples after homogenization in acetone (0.2% and 1%) were lyophilized for analysis by SEM (data not shown).

Example 16

Budesonide Nanocluster Formulation

Milling with 50 Micron Grinding Media

Second preliminary small scale milling experiments had been done using 50 micron grinding media to determine the suitability of this procedure for the formulation of budesonide Nanoclusters.

However, all samples exhibited particle size ranging from 400 nm to 800 nm with no degradation over the 24 hrs of the experiment. SEM images showed that all most samples consisted of either separated particles of ~2 microns or agglomerates exceeding 5 microns. This may indicate the insufficient contact between the drug and the balls or crystallization of particles during filtration especially some samples showed particles absolutely similar to the drug as received (FIG. 49-63). In addition, incorporation of excipients had no great effect on the results.

Lead formulations were produced using the following conditions: 12 mg/mL budesonide, 7 mL 50 micron media and 4 mL water (FIGS. 50) and 25 mg/mL budesonide, 3.5 mL 50 micron media, 2 mL water (FIG. 55). These samples showed 3-4 micron agglomerates of small particle less than 1 micron.

FIG. 49 through FIG. 63 depict the various samples. In each figure's description, "SV" refers to small vials, "LV" refers to large vials, the first number is the mL of water and second number is mg of media.

Milling with 200 Micron Grinding Media

Four batches were carried out using the new 200 micron YTZ media. The first batch was run over 5 hours. The second batch was run over 3 hours. The third batch was run over 8 hours. The fourth batch was run over 10 hours. The final lyophilized powder was analyzed by cascade impactor, SEM, and HPLC.

Milling Using 200 Micron Media for Over 3 Hours

A cascade impaction test was carried out twice using 1.5 mg of drug and the Spinhaler for 5 sec. The analysis was done chemically using HPLC. In the first run, the plates were washed with 10 mL ethanol and injected into HPLC. In the second run, the plates were coated with silicon oil then after the run the plates were washed with 10 mL ethanol and injected into HPLC.

The results showed lower emitted fraction of the chemically analyzed samples with higher MMAD compared to the sample carried out by previous procedures (Table 33 & FIG. 64).

TABLE 33

Cascade impaction results of lyophilized budesonide mill batch 2-3 hours dry powder using 200 micron media (values = average ± standard deviation).

| | | Formulations | | |
|---|---|---|---|---|
| Characteristics of the lyophilized powder | | 200 mic 3 hrs Gravimetric analysis | 200 mic 3 hrs HPLC analysis | 200 mic 3 hrs HPLC analysis with coated plates |
| At flow rate of ~30 L//min | % EF$^b$ | 91 | 68 | 50 |
| | % <5.7 | 60 | 36 | 26 |
| | FPF$^c$ <3.3 | 29 | 8 | 5 |
| | MMAD$^d$ | 5.1 | 6.8 | 8.8 |
| | GSD$^e$ | 2.6 | 2.1 | 1.9 |

$^a$% EF: Percent emitted fraction.
$^b$FPF: Fine particle fraction.
$^c$MMAD: Mass median aerodynamic diameter obtained from cascade impactor.
$^d$GSD: Geometric standard deviation.

Milling Using 200 Micron Media for 8 Hours.

This experiment was carried out over 8 hrs using lower concentration of budesonide (2.5 grams/250 mL water). Samples were collected each 30 minutes after 4 hrs of starting the experiment to measure the particle size and appearance of degradation products. Also the samples were collected in sufficient amount and have been snap frozen directly to be lyophilized for 3 days and then put in the vacuum dryer for a day.

The size started to decrease more until 7 hours followed by increase again. These results were confirmed by both cascade impactor and SEM.

Cascade impaction test was carried out using ~3 mg of the powder for 5 seconds only and the Spinhaler was used for the delivery of the powder. In addition, filter paper was placed each run below the final plate to minimize the passage of the powder into the tubing of the instrument.

Cascade impaction results showed decrease in the MMAD until 7 hrs followed by gradual increase. The MMAD for 3 hrs was 5.1 microns and for 5 hours was 4.6 microns. It is obvious that 7 hours may be an optimal time for milling the drug using 200 microns. In all samples, the emitted fraction and FPF were high indicating the improvement of the powder aerosolization compared to the previous batches prepared. However the MMAD was still slightly high, it was better that the other pure drug batches (Table 34 & FIG. 65)

From SEM images, it was appeared that starting from 6 hours the size decreased until 7 hours then the particles became smaller even ~100 nm but agglomerated into larger agglomerates.

TABLE 34

Cascade impaction results of lyophilized budesonide mill dry powder batch 3-200 mic-8 hrs (values = average ± standard deviation).

| Characteristics of the lyophilized NA | | Formulations | | | | | |
|---|---|---|---|---|---|---|---|
| | | 4 hrs | 5.5 hrs | 6 hrs | 7 hrs | 7.5 hrs | 8 hrs |
| At flow rate of ~30 L//min | % EF[a] | 80 ± 2 | 99 ± 1 | 69 ± 2 | 84 ± 4 | 71 ± 2 | 78 ± 3 |
| | % <5.7 | 64 ± 1 | 63 ± 1 | 80 ± 0.1 | 72 ± 0.4 | 66 ± 1 | 71 ± 2 |
| | FPF[b] <3.3 | 37 ± 1 | 42 ± 0.2 | 45 ± 2 | 48 ± 1 | 46 ± 0.4 | 45 ± 3 |
| | MMAD[c] | 4.6 ± 0.7 | 4.1 ± 0.1 | 3.5 ± .4 | 3.2 ± 0.3 | 3.8 ± 0.1 | 3.9 ± 0.1 |
| | GSD[d] | 2.8 ± 1 | 3.6 ± 1 | 3.3 ± 0.3 | 3.5 ± 1 | 3.8 ± 0.1 | 4 ± 0.1 |

[a]% EF: Percent emitted fraction.
[b]FPF: Fine particle fraction.
[c]MMAD: Mass median aerodynamic diameter obtained from cascade impactor.
[d]GSD: Geometric standard deviation.

FIG. 66 through FIG. 72 depict SEM images of the samples.

The lyophilized powder after 8 hours was analyzed by HPLC. The powder was dissolved in acetonitrile and injected into HPLC. The results indicated that the degradation peak was negligible and the ratio of the degradation peak area to the characteristic peak area was ~0.2% however for the suspension the ratio was 0.4%, Table 35 & FIG. 73. FIG. 74 focuses on the degradation peak of the sample.

TABLE 35

Area under the curve (AUC) and peak height (PH) of the characteristic peak (CP) and degradation peak (DP) for the sample after 8 hrs of millings.

| Samples | Peak area of characteristic peak | Peak area of degradation peak | % degradation |
|---|---|---|---|
| 8 hrs (suspension) | 1076041 | 5083 | 0.4 |
| 8 hrs (powder) | 2957567 | 5783 | 0.2 |

Milling Using 200 Micron Media for 10 Hours

This experiment was carried out over 10 hrs using budesonide concentration of 5 grams/200 mL water. Samples were collected after different time intervals to measure the particle size and appearance of degradation products. Also the samples were collected after 9 and 10 hrs and snap frozen directly to lyophilized and used for further evaluation studies. Samples after 10 hrs of milling were divided into five portions, 1—pure drug
2—drug/0.3% leucine
3—drug/1% leucine
4—drug/0.3% lactose
5—drug/1% lactose The sample was lyophilized and the samples were places in vacuum dryer. Few of the powders were taken to carry out SEM. After 4 hrs, the size started to increase, which suggested the formation of Nanoclusters.

TABLE 36

Particle size analysis of the samples at different time intervals

| Samples | Particle size (nm) |
|---|---|
| 3.5 hrs | 632.5 |
| 4.15 hrs | 481.5 |
| 6 hrs | 1256.5 |
| 7.5 hrs | 2893.6 |

Chemical Analysis Using HPLC.

Samples at different time intervals (3.5 hr, 4.15 hr, 6 hr and 10 hrs) were analyzed by HPLC. All samples were diluted with acetonitrile without adjusting the concentration and measured in the same day of preparation. The results may indicate that there was no degradation peak or non-significant peak in all samples, FIG. 75 (and FIG. 76). The ratio of the peak area of the characteristic peak to the degradation peak was indicated in Table 37.

TABLE 37

Area under the curve (AUC) of the characteristic peak (CP) and degradation peak (DP) for all samples.

| Samples | Peak area of characteristic peak | Peak area of degradation peak | % degradation |
|---|---|---|---|
| 3.5 hrs | 3532298 | — | |
| 4.15 hrs | 5113106 | 1174 | 0.02 |
| 6 hrs | 3664129 | — | |
| 10 hrs | 6393427 | 2033 | 0.03 |

SEM of batch 4—200MIC FOR 10 HRS

All images indicated that milling of budesonide powder for 10 hrs using 200 micron media got very small particles (~400 nm) agglomerated into Nanoclusters of ~2-4 microns with the appearance of many separated nanoparticles. Addition of lactose monohydrate or leucine got the same results, however; increasing leucine concentration led to increase the Nanocluster size, shown in FIG. 77 through FIG. 82.

Continuous Precipitation

In continuing to optimize the conditions for continuous precipitation, more trials with acetone with varying concentrations, solvent injection rates, and non-solvent injection rates were performed. Table 38 shows all of the combinations studied.

TABLE 38

Varying conditions to create particles by continuous precipitation.

| Budes. (mg/mL) | Solvent Injection (mL/min) | Non-Solvent Injection (mL/min) | Sonication (%) | Particle Size (nm) | Polydispersity | Production Rate (mg/min) |
|---|---|---|---|---|---|---|
| 2 | 1 | 10 | 40 | 526.4 ± 135.7 | 0.474 ± 0.025 | 2 |
| 5 | 1 | 10 | 40 | 651.1 ± 102.0 | 0.148 ± 0.083 | 5 |
| 10 | 1 | 10 | 40 | 7638.8 ± 3080.4 | 1.066 ± 0.549 | 10 |
| 5 | 1 | 7.5 | 40 | 792.8 ± 94.7 | 0.314 ± 0.194 | 5 |
| 5 | 1 | 5 | 40 | 29104.4 ± 10282.3 | 2.316 ± 0678 | 5 |
| 5 | 0.5 | 7.5 | 40 | 11495.0 ± 1336.3 | 1.647 ± 0.181 | 2.5 |
| 5 | 0.5 | 10 | 40 | 565.3 ± 61.2 | 0.406 ± 0.101 | 2.5 |
| 2 | 1 | 7.5 | 40 | 399.7 ± 46.1 | 0.477 ± 0.043 | 2 |

Solvent: Acetone
Non-solvent: Water

Based on the particle size measurements alone, the conditions shown in bold may contain agglomerates.

The production rate of the various conditions studied is rather low with acetone. Using ethanol as the solvent can result in large particles rather than agglomerates. The use of surfactants may reduce particle size for conditions with increased production rates. several trials have been performed by adding lecithin to the solvent (Table 39). Since lecithin has low solubility in acetone, the solvent was switched to ethanol for these studies. Based on the particle size measurements, the addition of lecithin may increase the particle size.

TABLE 39

Addition of lecithin to create particles for continuous precipitation (Solvent: Ethanol; Non-solvent: Water).

| Budes. (mg/mL) | Solvent Injection (mL/min) | Non-Solvent Injection (mL/min) | Lecithin (%) | Particle Size (nm) | Polydispersity | Production Rate (mg/min) |
|---|---|---|---|---|---|---|
| 10 | 1 | 7.5 | 0 | 854.1 ± 198.9 | 0.154 ± 0.120 | 10 |
| 10 | 1 | 7.5 | 0.1 | 7801.1 ± 1776.7 | 0.466 ± 0.027 | 10 |
| 10 | 1 | 7.5 | 0.2 | 2233.6 ± 1001.3 | 0.378 ± 0.126 | 10 |

Example 17

Budesonide Nanoclusters as MDI Formulations

A trial run for determining the feasibility of budesonide nanoclusters as Metered Dose Inhaler formulations was performed. Budesonide nanoclusters and pure budesonide (milled) were dispersed in model propellant HPFP (2H,3H perfluoropentane) and their dispersion stability was analyzed. HPFP has similar physico-chemical properties to MDI propellants such as HFA134a and HFA227ea. Previous literature studies indicate that dispersion stability of therapeutic molecules is similar in both HPFP and HFA227ea.

The dispersion stability was assessed and the results are shown in FIG. 83 through FIG. 87. During the study, milled budesonide began creaming at around 5 min and a clearly visible layer was seen at 1 hr. The rate of creaming was slowed when budesonide was formulated as nanoclusters. However, the reason for the steric stability of these nanoclusters dispersions in HPFP is not yet fully understood.

The study demonstrates that Budesonide nanocluster dispersions are more stable in HPFP compared to the pure milled budesonide. The stability of nanoclusters are a function of concentration. As seen from FIG. 83 through FIG. 87, 0.4 mg/ml of budesonide nanocluster are more stable to 2 mg/ml. However, at both theses concentrations, complete creaming was seen for jet milled budesonide after 3 days. The reasons for the favorable solvation of nanocluster budesonide particles by the HPFP molecules are not yet clear. It is possible that individual primary nanocluster nanoparticles act as steric stabilizers for the nanoclusters or it can act similarly to hollow porous particles by allowing the HPFP molecules to enter the spaces within the nanoclusters and thereby reducing van der Waals forces. But this study indicates that these nanoclusters could be used as modified therapeutic APIs for inhalation using pMDIs.

Example 18

Process for Making NanoCluster Budesonide

The stock budesonide powder was suspended in water at a concentration of 5 μm/300 mL. The suspension was then introduced into a MiniCer (Netzsch Premier technologies, LLC) media mill containing ceramic grinding media of 200 micron diameter. Milling was conducted at 20° C. for 10 hours at 2700 RPM. The milled suspension was subsequently frozen and dried by lyophilization.

The dried powder was tested for particle size distribution in an Anderson Cascade Impactor (ACI) using a low resistance Monodose device (Plastiape S.p.a., Italy). The results are shown below in Table 40.

TABLE 40

NanoCluster Budesonide.

| Characteristics of NanoCluster | | Batch 1 | Batch 2 | Batch 3 |
|---|---|---|---|---|
| % EF[a] | | 85.6 | 83 | 71 ± 5 |
| % FPF[b] ED[e] | ≤5 | 76 | 69 | 55 ± 3 |
| | ≤3 | 60 | 54 | 48 ± 1 |

TABLE 40-continued

NanoCluster Budesonide.

| Characteristics of NanoCluster | Batch 1 | Batch 2 | Batch 3 |
|---|---|---|---|
| MMAD[c] | 1.9 | 1.9 | 1.5 ± 0.2 |
| GSD[d] | 2 | 2.9 | 3.2 ± 0.05 |

[a]% Emitted fraction = (ED/MD) * 100
[b]FPF: Fine particle fraction
[c]MMAD: Mass median aerodynamic diameter (50% on cumulative mass distribution plot)
[d]GSD: Geometric standard deviation
[e]ED: Emitted Dose Example 19

BET Surface Area Measurement of Budesonide Nanoclusters

The surface area difference between micronized budesonide and nanocluster budesonide was determined using BET Surface and is shown in Table 41. NC Batch 25 was made using the similar conditions as Batch 4 in Example 16.

TABLE 41

BET Surface area measurement

| Samples | Surface are (m$^2$/g) |
|---|---|
| Raw material | 4.315 ± 0.0676 |
| Budesonide NC Batch 25 | 65.54 ± 9.67 |

Therefore, the present disclosure is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A nanocluster comprising a plurality of nanoparticles having a core of nanoparticles arranged such that the surfaces of the nanoparticles contact adjacent nanoparticles, the nanoparticles comprise an active ingredient, and the nanocluster has a mass median aerodynamic diameter of from about 0.25 μm to about 20 μm.

2. The nanocluster of claim 1, wherein the mass median aerodynamic diameter is from about 0.5 μm to about 10 μm.

3. The nanocluster of claim 1, wherein the mass median aerodynamic diameter is from about 3 μm to about 20 μm.

4. The nanocluster of claim 1, wherein the active ingredient has solubility in water of less than 200 mg/ml.

5. The nanocluster of claim 1, wherein the nanocluster comprises at least 50% nanoparticles by weight.

6. The nanocluster of claim 1, wherein the active ingredient is an anti-inflammatory compound, a bronchodilator, an antimicrobial, a vaccine, an analgesic, an anxiolytic, a hypnotic, a vasodilator, a cytotoxic agent, an opiod, an anti-cancer agent, DNA, RNA, budesonide, vancomycin, moxifloxacin, mometazone, epinephrine, $^{13}$C labeled urea, atropine, or diatrizoic acid.

7. The nanocluster of claim 1, wherein the nanocluster is formulated into a dry powder, a suspension, an aerosol, a spray, a tablet, or a liquid.

8. The nanocluster of claim 1, wherein the nanocluster is formulated together with a pharmaceutically acceptable carrier.

9. The nanocluster of claim 1, wherein the nanoparticles consist essentially of the active ingredient.

* * * * *